United States Patent
Granot et al.

(10) Patent No.: US 10,975,385 B2
(45) Date of Patent: Apr. 13, 2021

(54) METHODS OF MODULATING STOMATA CONDUCTANCE AND PLANT EXPRESSION CONSTRUCTS FOR EXECUTING SAME

(71) Applicants: The State of Israel, Ministry of Agriculture & Rural Development, Agricultural Research Organization (ARO) (Volcani Center), Rishon-LeZion (IL); Yissum Research Development Company of the Hebrew University of Jerusalem Ltd., Jerusalem (IL)

(72) Inventors: David Granot, Jerusalem (IL); Gilor Kelly, Beit-Elazari (IL); Menachem Moshelion, Rechovot (IL)

(73) Assignees: The State of Israel, Ministry of Agriculture & Rural Development, Agricultural Research Organization (ARO) (Volcani Center), Rishon-LeZion (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 16/426,061

(22) Filed: May 30, 2019

(65) Prior Publication Data
US 2019/0284569 A1 Sep. 19, 2019

Related U.S. Application Data

(63) Continuation of application No. 14/364,359, filed as application No. PCT/IL2012/050519 on Dec. 11, 2012, now abandoned.

(60) Provisional application No. 61/569,251, filed on Dec. 11, 2011.

(51) Int. Cl.
*C12N 15/82* (2006.01)

(52) U.S. Cl.
CPC ..... *C12N 15/8273* (2013.01); *C12N 15/8218* (2013.01); *C12N 15/8241* (2013.01); *C12N 15/8261* (2013.01); *C12N 15/8279* (2013.01)

(58) Field of Classification Search
None
See application file for complete search history.

(56) References Cited

U.S. PATENT DOCUMENTS

| 6,653,535 B1 * | 11/2003 | Tarczynski | C12N 15/8245 800/320.1 |
|---|---|---|---|
| 7,423,203 B2 | 9/2008 | Cheikh et al. | |
| 2009/0222949 A1 | 9/2009 | Epel et al. | |
| 2009/0265812 A1 | 10/2009 | Granot et al. | |
| 2010/0299782 A1 | 11/2010 | Schroeder et al. | |
| 2014/0090116 A1 | 3/2014 | Ainley et al. | |
| 2014/0109259 A1 | 4/2014 | Abbitt et al. | |
| 2014/0345000 A1 | 11/2014 | Granot et al. | |

FOREIGN PATENT DOCUMENTS

| AU | 2005339717 | 7/2007 |
|---|---|---|
| CN | 101466838 | 6/2009 |
| EP | 1962577 | 9/2008 |
| WO | WO 2007/078280 | 7/2007 |
| WO | WO 2007/116394 | 10/2007 |
| WO | WO 2008/134571 A1 * | 11/2008 |
| WO | WO 2013/088438 | 6/2013 |
| WO | WO 2013/088446 | 6/2013 |

OTHER PUBLICATIONS

Karve et al., 2008, Expression and evolutionary features of the hexokinase gene family in *Arabidopsis*, Planta 228: 411-425.*
Granot, 2008, Putting plant hexokinases in their proper place, Phytochemistry 69: 2649-2654.*
Li et al., 2000, Regulation of Abscisic Acid-Induced Stomatal Closure and Anion Channels by Guard Cell AAPK Kinase, Science 287: 300-304.*
Sarowar et al., 2008, A Role of Hexokinases in Plant Resistance to Oxidative Stress and Pathogen Infection, Journal of Plant Biology 51: 341-364.*
Olsson et al., 2003, A Novel Type of Chloroplast Stromal Hexokinase Is the Major Glucose-phosphorylating Enzyme in the Moss Physcomitrella patens, The Journal of Biological Chemistry 278: 44439-44447.*
Cárdenas et al., 1998, Evolution and regulatory role of the hexokinases, Biochimica et Biophysica Acta 1401: 242-264.*
Keskin et al., 2004, A new, structurally nonredundant, diverse data set of protein—protein interfaces and its implications, Protein Science 13: 1043-1055.*
Guo et al., 2004, Protein tolerance to random amino acid change, Proceedings of the National Academy of Sciences USA 101: 9205-9210.*
Thornton et al., 2000, From structure to function: Approaches and limitations, Nature Structural Biology, structural genomic supplement, Nov. 2000: 991-994.*
Tester and Bacic, 2005, Abiotic Stress Tolerance in Grasses. From Model Plants to Crop Plants, Plant Physiology 137: 791-793.*

(Continued)

*Primary Examiner* — Bratislav Stankovic

(57) ABSTRACT

A method of regulating plant stomata conductance is provided. The method comprises modulating in the plant the level and/or activity of a type B hexokinase in a guard cell specific manner, thereby regulating plant conductance.

5 Claims, 18 Drawing Sheets
(12 of 18 Drawing Sheet(s) Filed in Color)
Specification includes a Sequence Listing.

(56) References Cited

OTHER PUBLICATIONS

Requisition by the Examiner dated Dec. 17, 2019 From the Innovation, Science and Economic Development Canada, Canadian Intellectual Property Office Re. Application No. 2,860,011. (3 Pages).
Advisory Action Before the Filing of an Appeal Brief dated Aug. 10, 2018 From the US Patent and Trademark Office Re. U.S. Appl. No. 14/364,359. (3 pages).
Advisory Action Before the Filing of an Appeal Brief dated Jul. 11, 2017 From the US Patent and Trademark Office Re. U.S. Appl. No. 14/364,359. (5 Pages).
Applicant-Initiated Interview Summary Dated Jul. 23, 2018 From the US Patent and Trademark Office Re. U.S. Appl. No. 14/364,359. (3 pages).
Communication Pursuant to Article 94(3) EPC dated Feb. 24, 2016 From the European Patent Office Re. Application No. 12858594.0.
Communication Pursuant to Article 94(3) EPC dated Sep. 29, 2016 From the European Patent Office Re. Application No. 12858594.0.
Decision to Grant a Patent dated Oct. 25, 2017 From the State Intellectual Property Service of Ukraine, State Enterprise Ukranian Institute for Industrial Property Re. Application No. a 2014 07796 and Its Translation Into English. (5 Pages).
Examination Report dated Aug. 3, 2017 From the Australian Government, IP Australia Re. Application No. 2012354054. (5 Pages).
Examination Report Dated Oct. 3, 2016 From the Instituto Mexican de la Propiedad Industrial, IMPI Re. Application No. MX/a/2014/006966 and Its Translation Into English. (6 Pages).
Examination Report dated May 4, 2017 From the Instituto Mexicano de la Propiedad Industrial, Direction Divisional de Patentes, IMPI Re. Application No. MX/a/2014/006966 and Its Translation Into English. (6 Pages).
Examination Report Under Sections 12 & 13 of the Patents Act, 1970 and the Patents Rules, 2003 dated Oct. 23, 2018 From the Government of India, Intellectual Property India, Patents, Designs, Trade Marks, Geographical Indications Re. Application No. 2,860,011. (5 Pages).
Examination Report Under Sections 12 & 13 of the Patents Act, 1977 and the Patents Rules, 2003 dated Feb. 11, 2019 From the Government of India, Intellectual Property India, Patents, Designs, Trade Marks, Geographical Indications Re. Application No. 1398/MUMNP/2014. (8 Pages).
International Preliminary Report on Patentability dated Feb. 5, 2013 From the International Bureau of WIPO Re. Application No. PCT/IL2012/050519.
International Search Report and the Written Opinion dated Feb. 5, 2013 From the International Searching Authority Re. Application No. PCT/IL2012/050519.
Notice of Panel Decision from Pre-Appeal Brief Review dated Apr. 12, 2019 From the US Patent and Trademark Office Re. U.S. Appl. No. 14/364,359. (2 pages).
Notification of Office Action and Search Report dated Nov. 16, 2015 From the State Intellectual Property Office of the People's Republic of China Re. Application No. 201280069314.6.
Notification of Office Action dated Dec. 6, 2017 From the State Intellectual Property Office of the People's Republic of China Re. Application No. 201280069314.6 and Its Translation Into English. (4 Pages).
Notification of Office Action dated May 17, 2017 From the State Intellectual Property Office of the People's Republic of China Re. Application No. 201280069314.6 and its Summary into English. (4 Pages).
Notification of Office Action dated Sep. 20, 2016 From the State Intellectual Property Office of the People's Republic of China Re. Application No. 201280069314.6 and Its Summary in English.
Office Action dated Mar. 28, 2017 From the Israel Patent Office Re. Application No. 233076 and Its Translation Into English. (4 Pages).
Official Action dated Oct. 1, 2018 From the US Patent and Trademark Office Re. U.S. Appl. No. 14/364,359. (33 pages).

Official Action dated Nov. 15, 2017 From the US Patent and Trademark Office Re. U.S. Appl. No. 14/364,359. (24 pages).
Official Action dated Feb. 24, 2017 From the US Patent and Trademark Office Re. U.S. Appl. No. 14/364,359. (25 pages).
Official Action dated Jul. 28, 2016 From the US Patent and Trademark Office Re. U.S. Appl. No. 14/364,359.
Official Action dated Apr. 30, 2018 From the US Patent and Trademark Office Re. U.S. Appl. No. 14/364,359. (32 pages).
Preliminary Report on Patentability dated Jan. 25, 2017 From the State Intellectual Property Service of Ukraine, State enterprise 'Ukarinian Institute for Industrial Property' Re. Application No. a 2014 07796 and Its Translation Into English. (11 Pages).
Request for Examination dated Nov. 28, 2017 From the ROSPATENT, Federal Government Institution, Federal Institute of Industrial Property of the Federal Service for Intellectual Property, Patent and Trademarks of the Russian Federation Re. Application No. 2014128294 and Its Translation Into English. (6 Pages).
Request for Examination dated Nov. 30, 2016 From the ROSPATENT, Federal Government Institution, Federal Institute of Industrial Property of the Federal Service for Intellectual Property, Patent and Trademarks of the Russian Federation Re. Application No. 2014128294 and Its Translation Into English. (13 Pages).
Restriction Official Action dated Apr. 28, 2016 From the US Patent and Trademark Office Re. U.S. Appl. No. 14/364,359.
Supplementary European Search Report and the European Search Opinion dated Jun. 17, 2015 From the European Patent Office Re. Application No. 12858594.0.
Translation Dated Dec. 14, 2015 of Notification of Office Action dated Nov. 16, 2015 From the State Intellectual Property Office of the People's Republic of China Re. Application No. 201280069314.6.
Blum "Drought Resistence, Water-Use Efficiency, and Yield Potential—Are They Compatible, Dissonant, or Mutually Exclusive?", Australian Journal of Agricultural Research, 56(11): 1159-1168, Nov. 29, 2005.
Cardenas et al. "Evolution and Regulatory Role of the Hexokinases", Biochimica et Biophysica Acta, (BBBA)-Molecular Cell Research, 1401(3): 242-264, Mar. 5, 1998.
Cho et al. "Structure, Expression, and Functional Analysis of the Hexokinase Gene Family in Rice ( *Oryza sativa* L.)", Planta, 224(3): 598-611, Aug. 1, 2006.
Cominelli et al. "Transcription Factors Controlling Stomatal Movements and Drought Tolerance", Transcription, 1(1): 41-45, Jul./Aug. 2010.
Dai et al. "Overexpression of *Arabidopsis hexokinase* in Tomato Plants Inhibits Growth, Reduces Photosynthesis, and Induces Rapid Senescence", The Plant Cell, XP000827859, 11: 1253-1266, Jul. 1999.
Dai et al. "The Tomato Hexokinase LeHXK1 Cloning Mapping, Expression Pattern and Phylogenetic Relationships", Plant Science, 163: 581-590, 2002.
Gonzali et al. "*Arabidopsis* (HXK1 and HXK2) and Yeast (HXK2) Hexokinases Overexpressed in Transgenic Lines Are Characterized by Different Catalytic Properties", Plant Science, 163(5): 943-954, Nov. 30, 2002.
Granot et al. "Hexose Kinases and Their Role in Sugar-Sensing and Plant Development", Frontiers in Plant Science, 4(44): 1-17, Published Online Mar. 12, 2013.
Guo et al. "Protein Tolerance to Random Amino Acid Change." Proceedings of the National Academy of Sciences, 101(25): 9205-9210, Jun. 22, 2004.
Gupta et al. "Sugar Signalling and Gene Expression in Relation to Carbohydrate Metabolism Under Abiotic Stresses in Plants", Journal of Biosciences, 30(5): 761-776, Published Online Oct. 26, 2005.
Jang et al. "Hexokinase as a Sugar Sensor in Higher Plants", The Plant Cell, XP002078609, 1(9): 5-19, Jan. 5, 1997.
Karve et al. "Evolutionary Lineages and Functional Diversification of Plant Hexokinases", Molecular Plant, 3(2): 334-346, Mar. 2010.
Kelly et al. "Hexokinase Mediates Stomatal Closure", The Plant Journal, 75(6): 977-988, Sep. 1, 2013.
Kelly et al. "Hexokinase Mediates Stomatal Closure", The Plant Journal, XP055193054, 75(6): 977-988, Published Online Jun. 6, 2013.

(56) References Cited

OTHER PUBLICATIONS

Keskin et al. "A New, Structurally Nonredundant, Diverse Data Set of Protein—protein Interfaces and its Implications", Protein Science, 13(4): 1043-1055, Apr. 2004.
Kim et al. "Mitochondria-Associated Hexokinases Play a Role in the Control of Programmed Cell Death in Nicotiana Benthamiana", The Plant Cell, 18: 2341-2355, Sep. 2006.
Lawson et al. "Mesophyll Photosynthesis and Guard Cell Metabolism Impacts on Stomatal Behaviour", New Phytologist, XP055193053, 203(4): 1064-1081, Sep. 2014.
Moumeni et al. "Comparative Analysis of Root Transcriptome Profiles of Two Pairs of Drought-Tolerant and Susceptible Rice Near-Isogenic Lines Under Different Drought Stress", BMC Plant Biology, 11(174): 1-17, Dec. 2, 2011. p. 10, 2 Last Paras, Add. File 12.
Olsson et al. "A Novel Type of Chloroplast Stromal Hexokinase Is the Major Glucose-Phosphorylating Enzyme in the Moss Physcomitrella Patens", The Journal of Biological Chemistry, 278(45): 44439-44447, Published Online Aug. 26, 2003.
Plesch et al. "Involvement of TAAAG Elements Suggests a Role for Dof Transcription Factors in Guard Cell-Specific Gene Expression", The Plant Journal, 28(4): 455-464, Nov. 2001. Abstract.
Robey et al. "Mitochondrial Hexokinases, Novel Mediators of the Antiapoptotic Effects of Growth Factors and Akt", Oncogene, 25, 4683-4696, 2006.
Sarowar et al. "A Role of Hexakinases in Plant Resistance to Oxidative Stress and Pathogen Infection", Journal of Plant Biology, 51(5): 341-346, Sep. 2008. Abstract, Figs.2-5, Reference Mentioned in the Last Para of the 'Induction' Section, 1st Para of Section 'Material and Methods', p. 342, Right Col., p. 344-345.
Tester et al. "Abiotic Stress Tolerance in Grasses. From Model Plants to Crop Plants", Plant Physiology, 137(3): 791-793, Mar. 2005.
Thornton et al. "From Structure to Function: Approaches and Limitations" Nature Structural and Molecular Biology, 7: 991-994, Nov. 2000.
Search Report and Opinion dated Aug. 1, 2019 From the Serviço Publico Federal, Ministerio da Economia, Instituto Nacional da Propriedade Industrial do Brasil Re. Application No. BR112014014268-8 and Its Summay in English. (5 Pages).
Translation Dated Sep. 12, 2019 of Search Report and Opinion dated Aug. 1, 2019 From the Serviço Publico Federal, Ministerio da Economia, Instituto Nacional da Propriedade Industrial do Brasil Re. Application No. BR112014014268-8. (4 Pages).
Hearing Notice Dated Oct. 31, 2019 From the Government of India, Intellectual Property India, Patents, Designs, Trade Marks, Geographical Indications Re. Application No. 1398/MUMNP/2014. (2 Pages).

\* cited by examiner

FIG. 9
MCGFP
Tomato 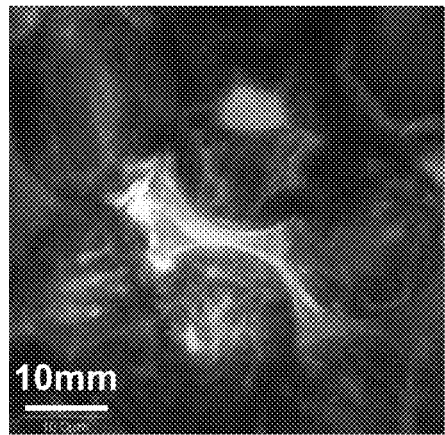 Arabidopsis 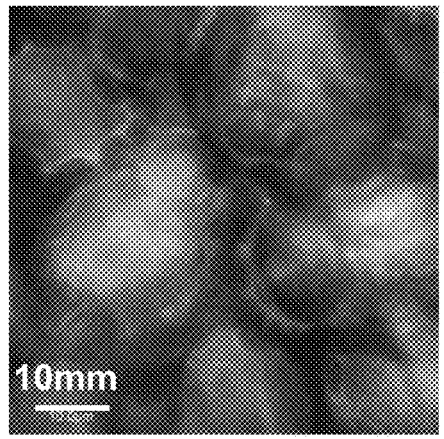

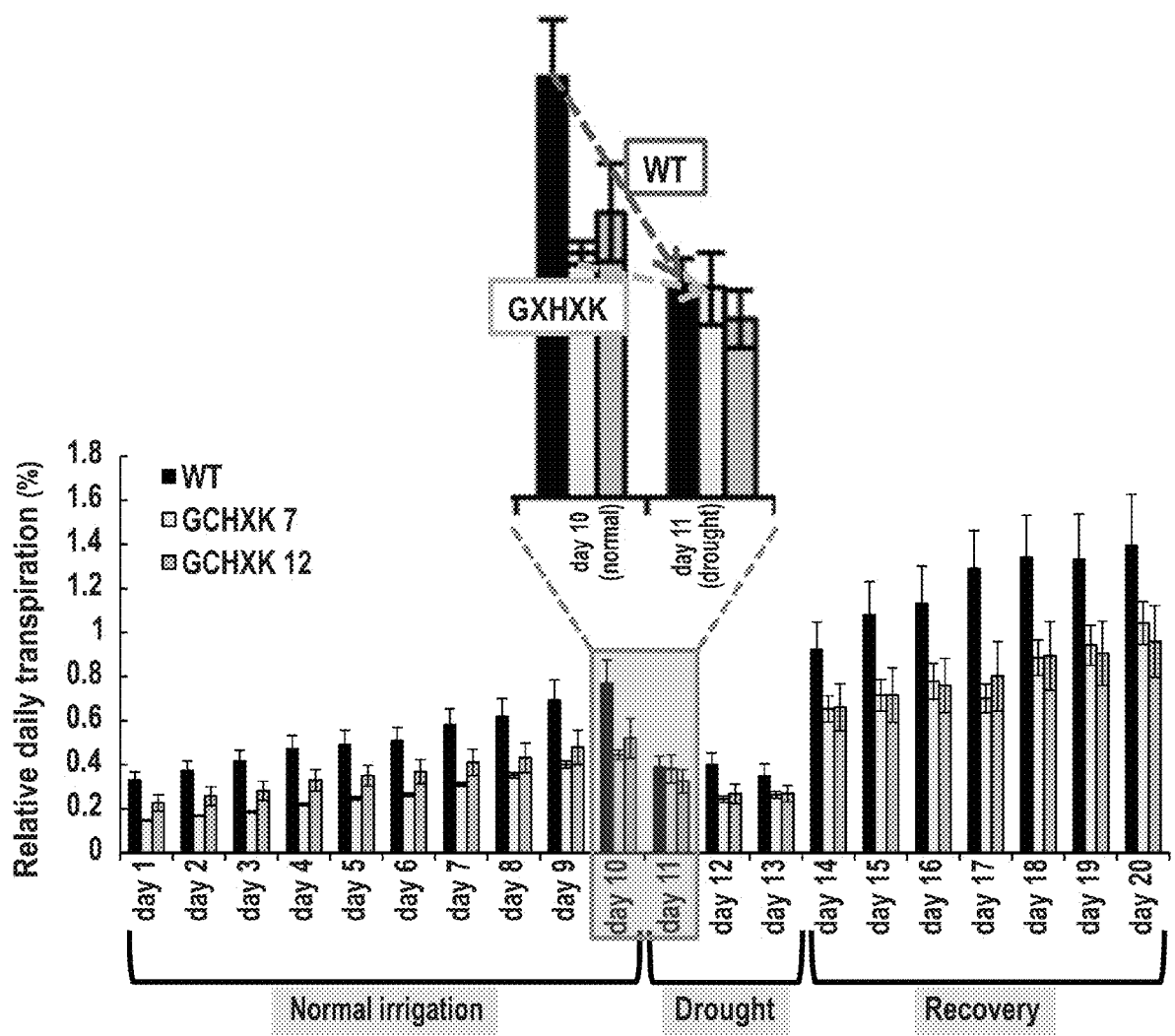
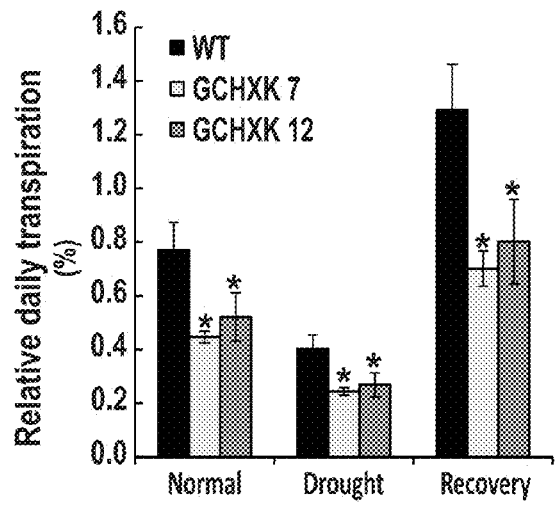
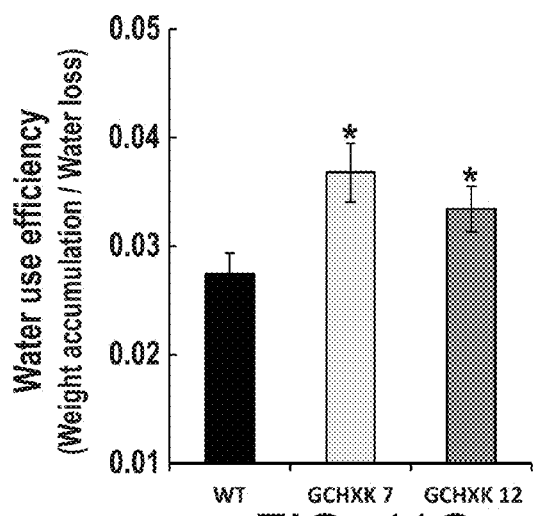
FIG. 11A
FIG. 11B
FIG. 11C

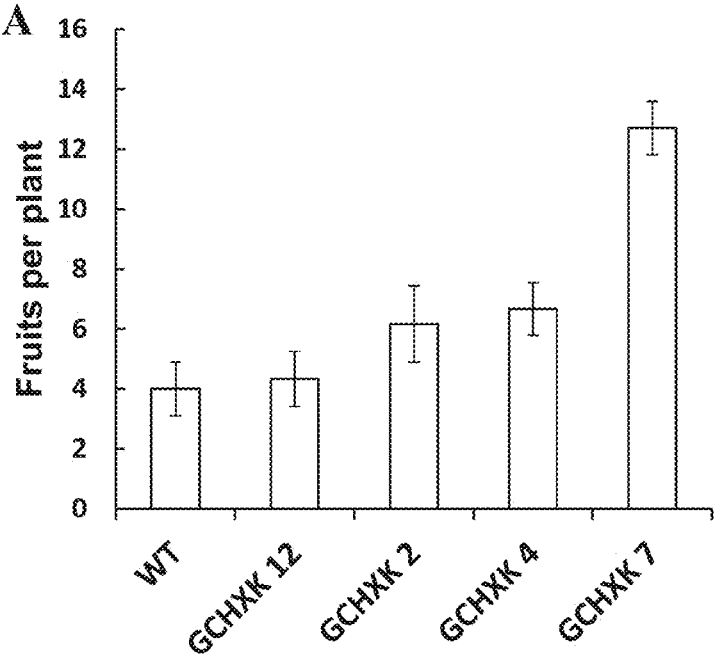
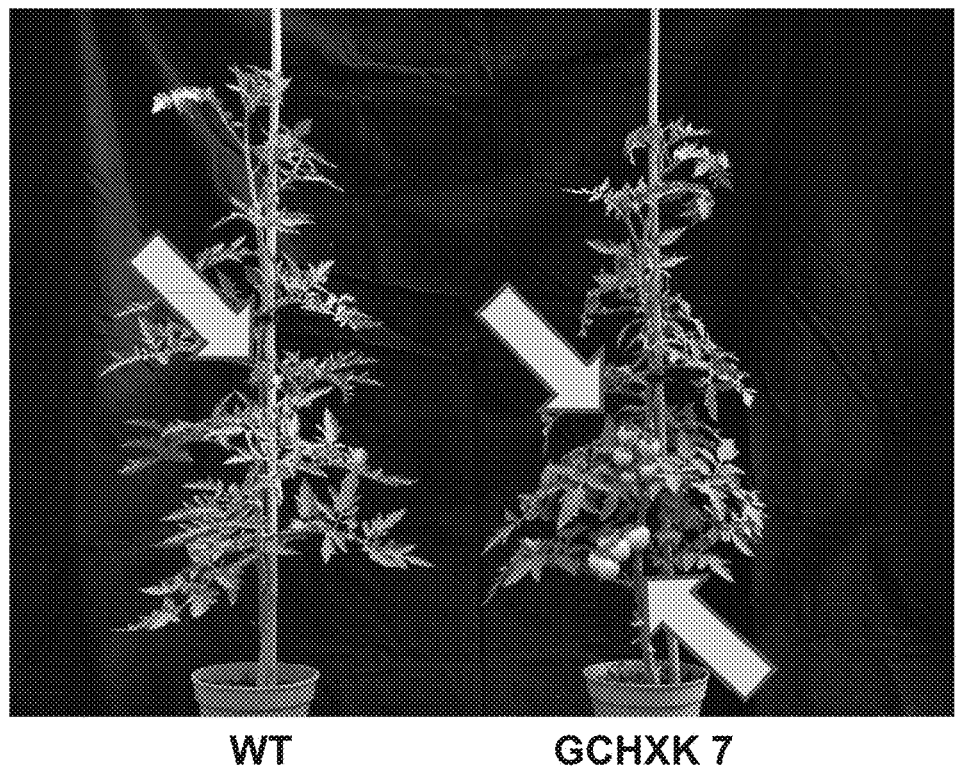

FIG. 15A
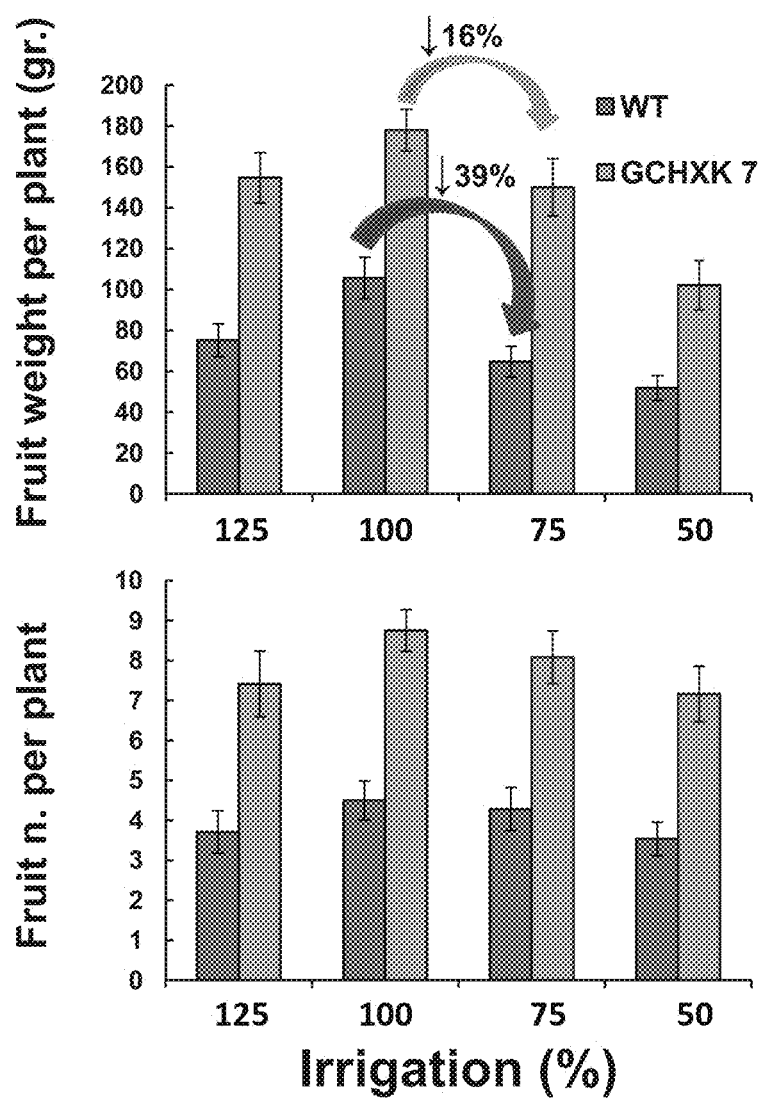
FIG. 15B
FIG. 15C

Arabidopsis:

METHODS OF MODULATING STOMATA CONDUCTANCE AND PLANT EXPRESSION CONSTRUCTS FOR EXECUTING SAME

RELATED APPLICATIONS

This application is a continuation of U.S. patent application Ser. No. 14/364,359 filed on Jun. 11, 2014, which is a National Phase of PCT Patent Application No. PCT/IL2012/050519 having International Filing Date of Dec. 11, 2012, which claims the benefit of priority under 35 USC 119(e) of U.S. Provisional Patent Application No. 61/569,251 filed on Dec. 11, 2011. The contents of the above applications are all incorporated by reference as if fully set forth herein in their entirety.

SEQUENCE LISTING STATEMENT

The ASCII file, entitled 77854SequenceListing.txt, created on May 30, 2019, comprising 333,589 bytes, submitted concurrently with the filing of this application is incorporated herein by reference.

FIELD AND BACKGROUND OF THE INVENTION

The present invention, in some embodiments thereof, relates to methods of modulating stomata conductance and plant expression constructs for executing same.

Stomata are dynamic pores in the impermeable protective cuticle that coats the aerial parts of land plants, which evolved primarily to save water. Stomata, which are comprised of two guard cells and the pore they circumscribe, open at dawn to allow the entry of atmospheric carbon dioxide ($CO_2$) for photosynthesis, at the cost of extensive transpirational water loss. The stomata close when carbon fixation and utilization are less efficient, in order to reduce the loss of water via transpiration (Assmann, 1993). At the mechanistic level, stomata open in response to increases in the osmolarity of the guard cells. These increases in osmolarity are followed by the movement of water into the guard cells, which increases their volume and opens the stomata (Taiz and Zeiger, 1998). Stomatal closure occurs in the opposite manner; as the osmolarity of guard cells is reduced, their volume decreases.

Water scarcity is a serious problem that will be exacerbated by global climate change. Abiotic stresses, especially drought and increased salinity, are primary causes of crop loss worldwide. Moreover, agriculture currently uses over 70% (86% in developing countries) of available freshwater. One of the approaches that may be adopted to save water in agriculture is the development of plants that use less water yet maintain high yields in conditions of water scarcity. As plants lose over 95% of their water via transpiration through stomata, the engineering of stomatal activity is a promising approach to reduce the water requirement of crops and to enhance productivity under stress conditions.

Cominelli et al. Transcription. 2010 Jul-Aug; 1(1): 41-45 reviews recent developments in the identification of transcription regulators controlling stomatal movements and involved in stomatal closure.

Additional background art includes:

U.S. Pat. No. 7,423,203 teaches a method of increasing plant yield by expressing fungal hexokinase under a seed-specific promoter.

U.S. Patent Application Publication No. 20090265812 teaches a method of increasing plant tolerance to high temperature stress by expressing hexokinase under a pollen specific promoter.

SUMMARY OF THE INVENTION

According to an aspect of some embodiments of the present invention there is provided a plant expression construct comprising a nucleic acid sequence encoding a hexokinase under a transcriptional control of a guard cell-specific cis-acting regulatory element.

According to an aspect of some embodiments of the present invention there is provided a plant expression construct comprising a nucleic acid sequence encoding a nucleic acid agent for silencing expression of a hexokinase, wherein expression of the nucleic acid agent is under a transcriptional control of a guard cell-specific cis-acting regulatory element.

According to some embodiments of the invention, the guard cell-specific cis-acting regulatory element is inducible.

According to some embodiments of the invention, the guard cell-specific cis-acting regulatory element is constitutive.

According to some embodiments of the invention, the guard cell-specific cis-acting regulatory element is a guard-cell specific promoter.

According to some embodiments of the invention, the guard-cell specific promoter is KST1 promoter.

According to an aspect of some embodiments of the present invention there is provided a method of regulating plant stomata conductance, the method comprising modulating in the plant the level and/or activity of a hexokinase in a guard cell specific manner, thereby regulating plant conductance.

According to some embodiments of the invention, the modulating is upregulating.

According to some embodiments of the invention, the upregulating is effected by introducing the nucleic acid construct of claim 1 into the plant.

According to some embodiments of the invention, the modulating is downregulating.

According to some embodiments of the invention, the downregulating is effected by introducing into the plant a nucleic acid silencing agent under a transcriptional control of a guard cell-specific cis-acting regulatory element.

According to an aspect of some embodiments of the present invention there is provided a method of decreasing plant stomata conductance, the method comprising introducing into a cell of a plant the nucleic acid construct, thereby decreasing the stomata conductance of the plant.

According to an aspect of some embodiments of the present invention there is provided a method of increasing water use efficiency of a plant, the method comprising introducing into a cell of the plant the nucleic acid construct, thereby increasing water use efficiency of the plant.

According to an aspect of some embodiments of the present invention there is provided a method of increasing tolerance of a plant to drought, salinity or temperature stress, the method comprising introducing into a cell of the plant the nucleic acid construct, thereby increasing tolerance of the plant to drought, salinity or temperature stress.

According to an aspect of some embodiments of the present invention there is provided a method of increasing biomass, vigor or yield of a plant, the method comprising introducing into a cell of the plant the nucleic acid construct, thereby increasing the biomass, vigor or yield of the plant.

According to an aspect of some embodiments of the present invention there is provided a method of increasing tolerance of a plant to biotic stress, the method comprising introducing into a cell of the plant the nucleic acid construct, thereby increasing tolerance of the plant to biotic stress.

According to an aspect of some embodiments of the present invention there is provided a transgenic plant or a part thereof comprising the plant expression construct.

According to an aspect of some embodiments of the present invention there is provided an isolated plant cell or a plant cell culture comprising the plant expression construct.

According to some embodiments of the invention, the part of the transgenic plant is a seed.

According to some embodiments of the invention, the part of the transgenic plant is a leaf.

According to some embodiments of the invention, the seed is a hybrid seed.

According to some embodiments of the invention, the method further comprises growing the plant under water deficient conditions.

According to some embodiments of the invention, the method further comprises growing the plant under salinity.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
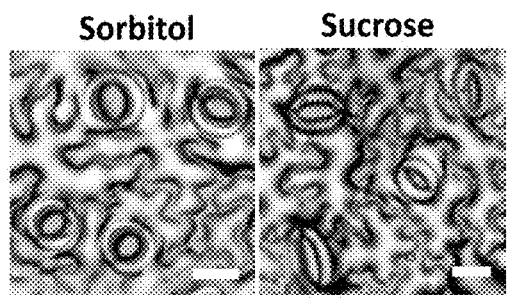
Figure 1B:
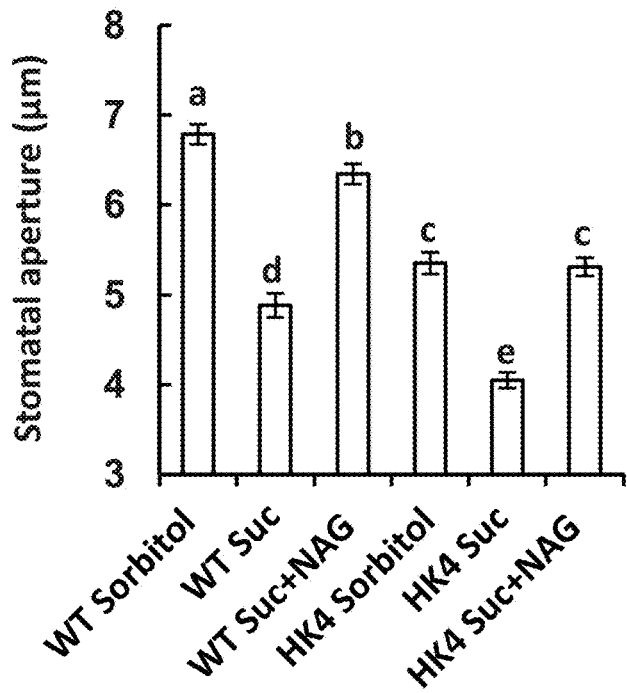
Figure 1C:
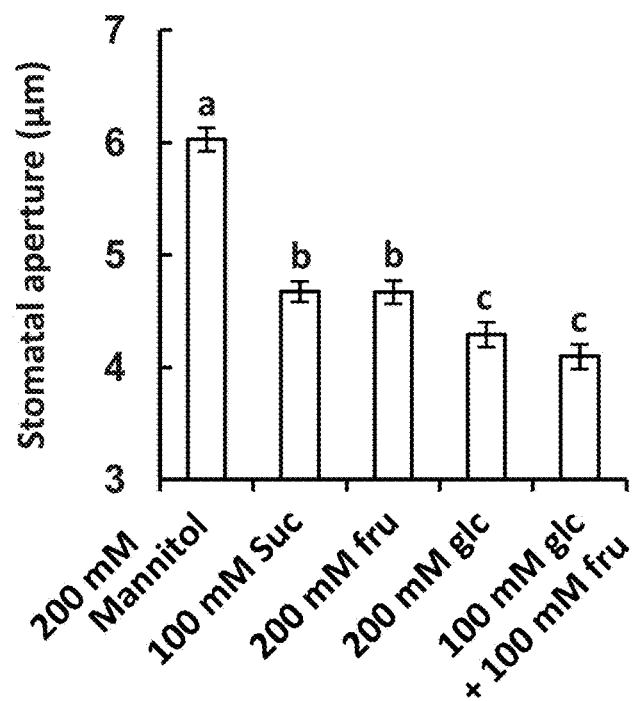

FIGS. 1A-1C are graphs showing that sucrose stimulates stomatal closure via hexokinase. FIG. 1A—Representative light microscopy images of stomata taken from epidermal imprints 3 h after treatment with 100 mM sorbitol or 100 mM sucrose (white bar=20 μm). B, Stomatal response to sucrose in wild-type (WT) and AtHXK1-expressing plants (HK4) was assayed with intact leaves immersed for 3 h in artificial apoplastic sap (Wilkinson and Davies, 1997) containing 100 mM sorbitol (as an osmotic control), 100 mM Suc or 100 mM sucrose together with 20 mM of the hexokinase inhibitor N-acetyl-glucoseamine (NAG). Epidermal imprints were then taken and stomatal aperture was measured. C, The stomatal responses of WT plants to the different sugar combinations were assayed as described in (FIG. 1B), with 200 mM mannitol serving as an additional osmotic control. The data shown in FIGS. 1B, 1C are means of 300 stomata from six independent biological repeats ±SE. Different letters indicate a significant difference (t test, P<0.05).

Figure 2A:
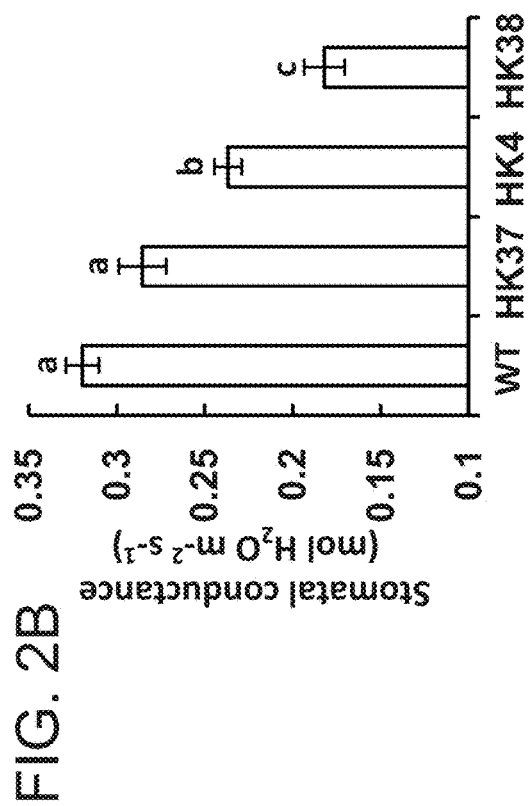
Figure 2B:
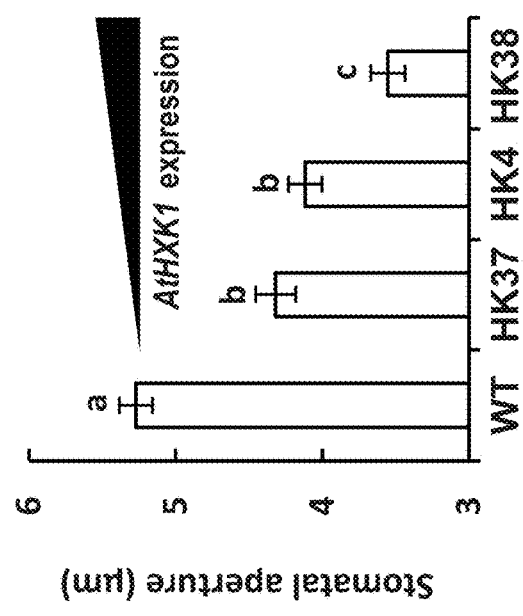
Figure 2C:
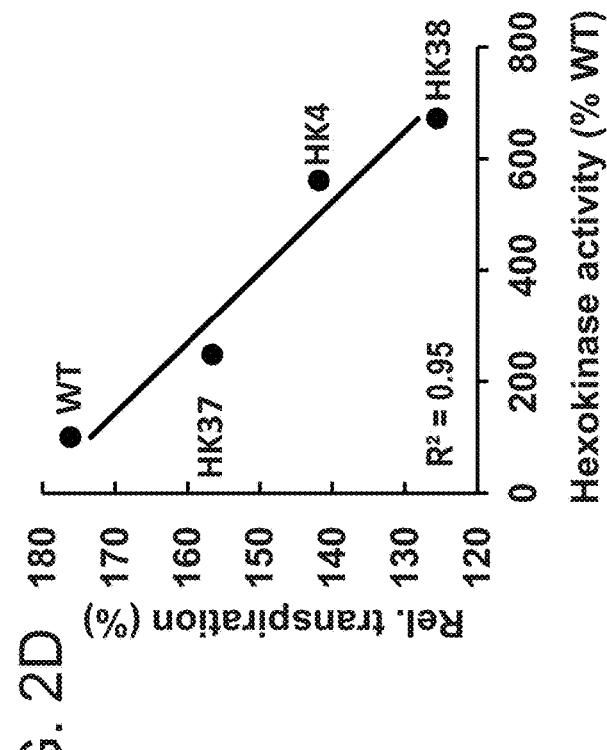
Figure 2D:
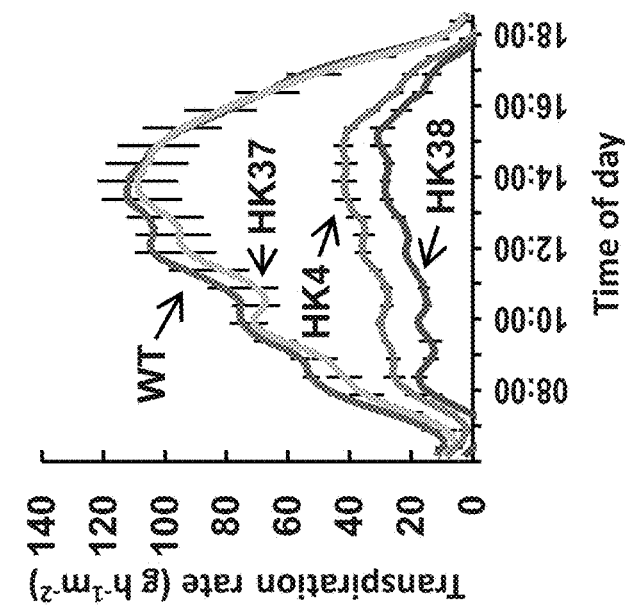

FIGS. 2A-2D show that elevated expression of hexokinase enhances stomatal closure and decreases transpiration. Stomatal aperture (FIG. 2A) and stomatal conductance (FIG. 2B) were determined for control (WT) and transgenic plants expressing different levels of AtHXK1 (HK38>HK4>HK37) (Dai et al., 1999). Aperture data are means of 200 stomata from four independent repeats ±SE. Stomatal conductance data are means of six independent repeats ±SE. Different letters indicate a significant difference (t test, P<0.05). FIG. 2C—The rate of transpiration normalized to the total leaf area was monitored simultaneously and continuously throughout the day and the data are given as the means ±SE for each $10^{th}$ sampling point (n=6). FIG. 2D-A negative correlation was observed between whole-plant relative daily transpiration and relative hexokinase-phosphorylation activity. The transpiration data were normalized to the total leaf area and the amount of water taken up by the neighboring submerged fixed-size wick each day, which was set to 100%. WT hexokinase activity was set to 100%.

Figure 3A:
Figure 3B:
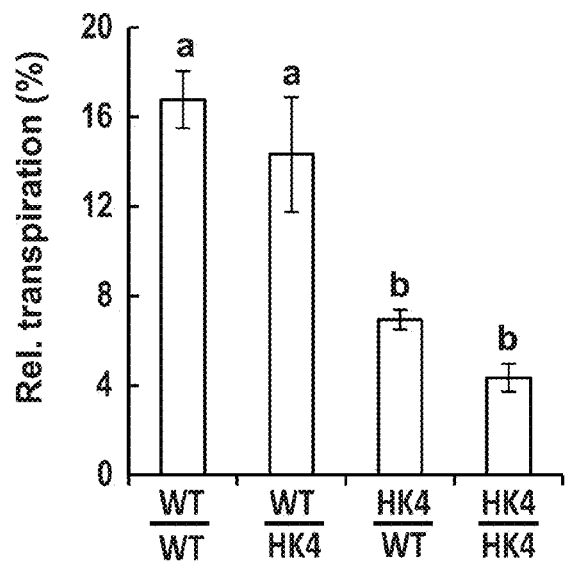
Figure 3C:
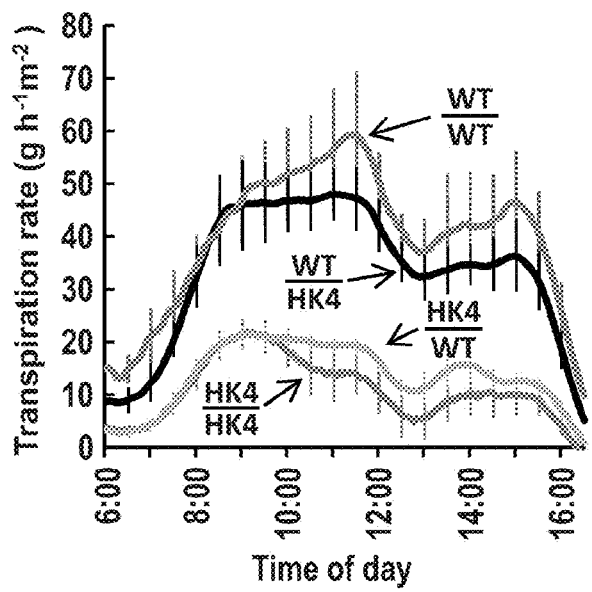
Figure 3E:
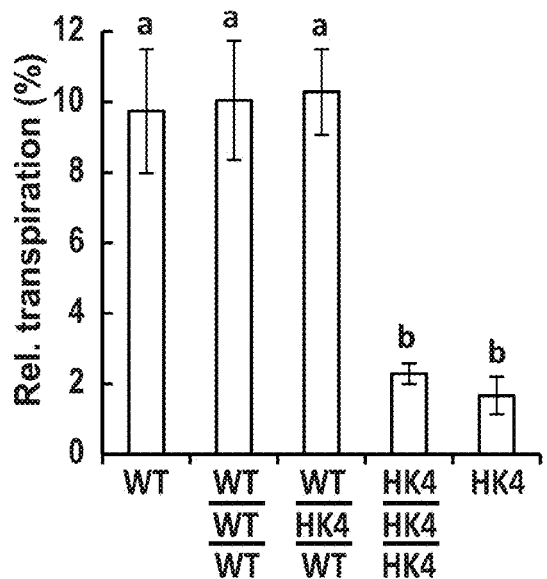

FIGS. 3A-3E show that AtHXK1 reduces transpiration primarily when expressed in leaves. Reciprocal grafting (FIG. 3A) and triple-grafting (FIG. 3D) procedures were performed at the seedling stage and plants were photographed and used for transpiration measurements about 4 weeks after grafting. The yellow arrows and brackets indicate the location of the grafts. FIG. 3B—Whole-plant relative daily transpiration of reciprocal-grafted plants. Data were normalized to the total leaf area and the amount of water taken up by the neighboring submerged fixed-size wick each day, which was set to 100%. Data are given as means of four independent repeats ±SE. Different letters indicate a significant difference (t test, P<0.05). FIG. 3C—Transpiration rate normalized to the total leaf area of reciprocal-grafted plants was monitored simultaneously and continuously throughout the day. The data are given as the means ±SE for each $10^{th}$ sampling point (n=4). FIG. 3E—Relative daily transpiration of whole triple-grafted plants calculated as in (FIG. 3B).

Figure 4A:
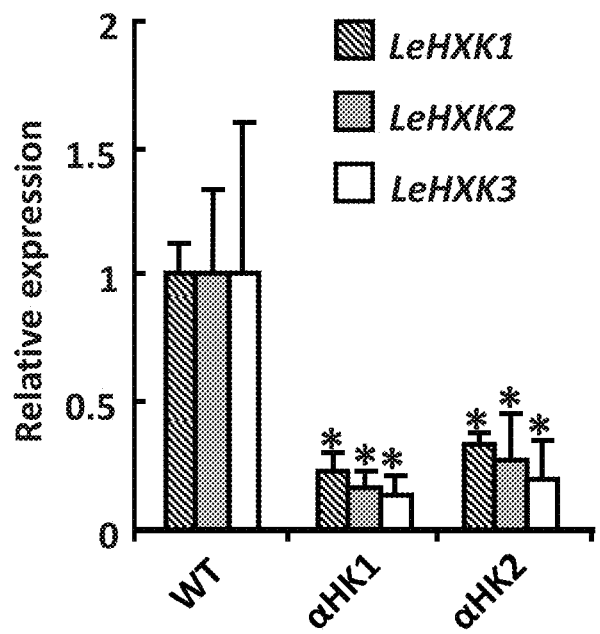
Figure 4B:
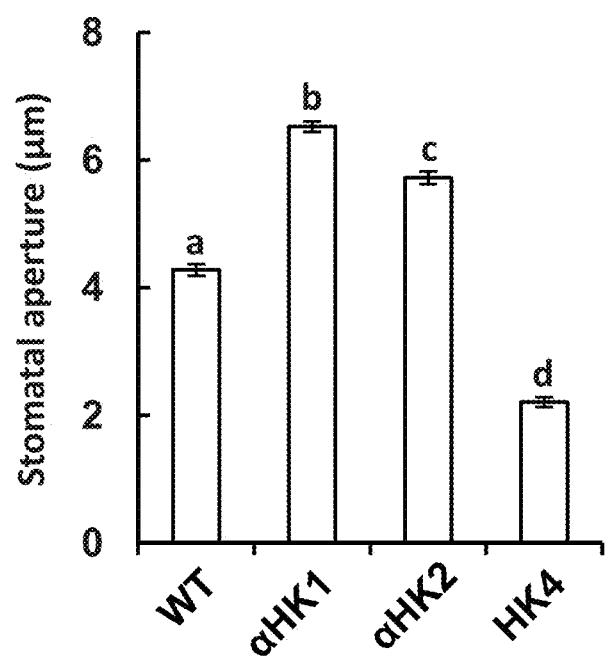

FIGS. 4A-4B are graphs showing that suppression of HXK inhibits stomatal closure in response to Suc. FIG. 4A—Quantitative measurements of the real-time expression of tomato LeHXK1-3 genes in wild-type tomato (WT) and in two independent tomato lines with antisense suppression of HXK, αHK1 and αHK2. Data are means of three independent biological repeats ±SE. Asterisks denote significant differences relative to the WT (t test, P<0.05). FIG. 4B—Stomatal response to Suc in WT, two antisense (αHK1 and αHK2) and AtHXK1-expressing (HK4) lines was assayed in intact leaves that were immersed in artificial apoplastic sap (Wilkinson and Davies, 1997) containing 100 mM Suc for 3 h. Data are given as means of 400 stomata from eight independent biological repeats ±SE. Different letters indicate a significant difference (t test, P<0.05).

Figure 5:
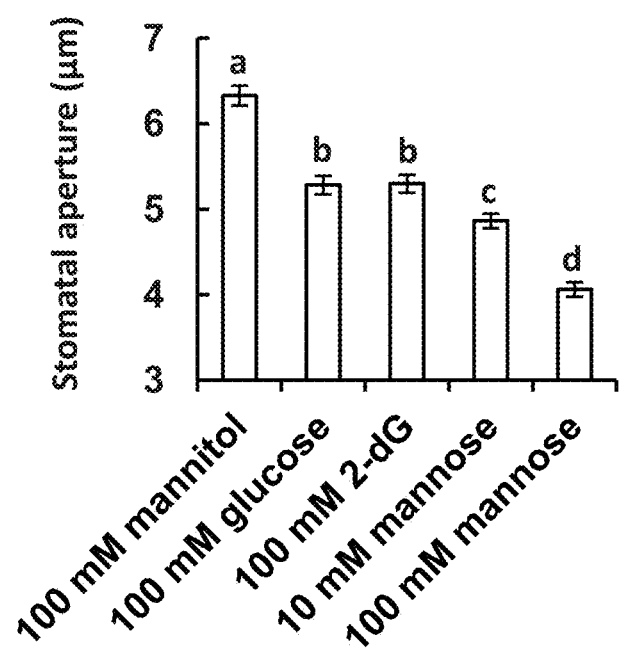

FIG. 5 is a graph showing that glucose (Glc) and sugars that can be phosphorylated, but not metabolized, stimulate stomatal closure. Stomatal responses to different sugars were assayed in intact leaves of wild-type plants. The leaves were immersed for 3 h in artificial apoplastic sap (Wilkinson and Davies, 1997) containing mannitol (as an osmotic control), Glc, 2-deoxyglucose (2-dG) or mannose. Epidermal imprints were then taken and stomatal aperture was measured. Data are given as means of 400 stomata from eight independent biological repeats ±SE. Different letters indicate a significant difference (t test, P<0.05).

Figure 6A:
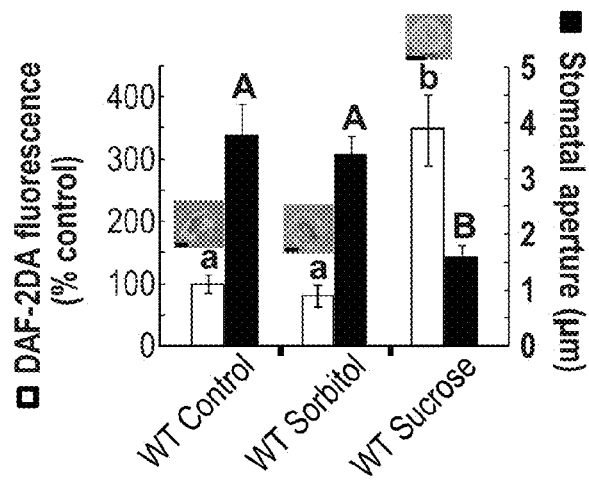
Figure 6B:
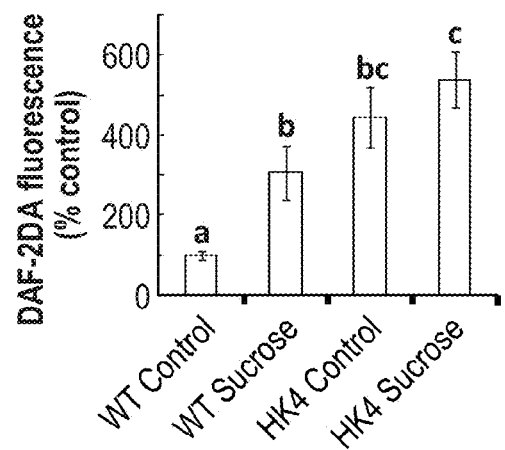
Figure 6C:
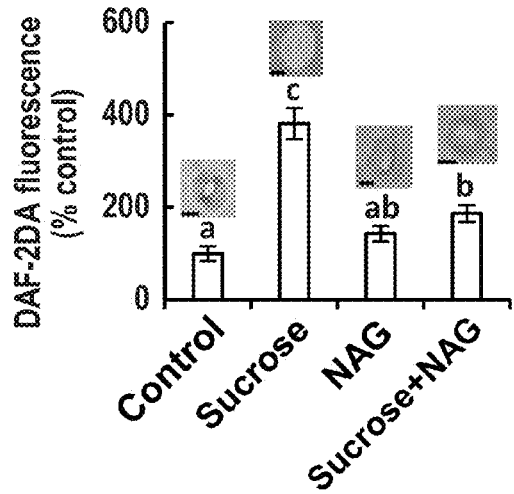
Figure 6D:
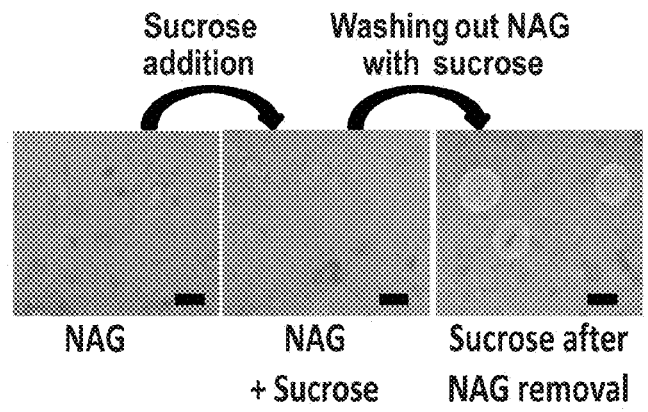
Figure 6E:
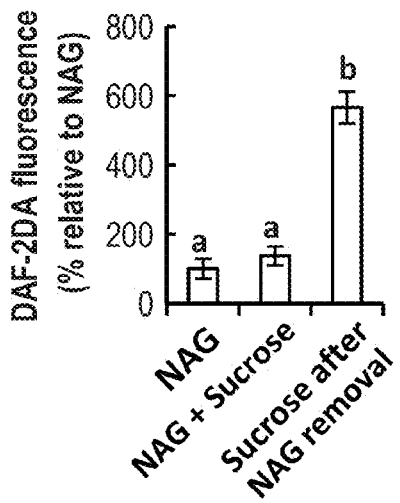
Figure 6F:
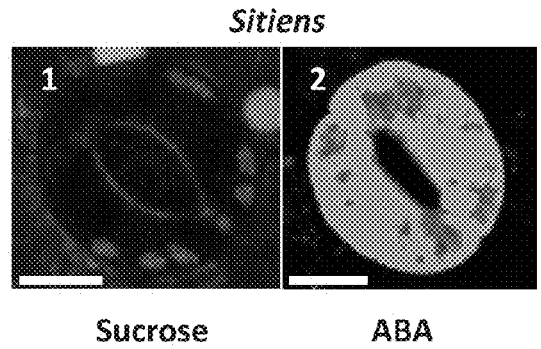

FIGS. 6A-6F show that Suc stimulates ABA-dependent NO production in guard cells that is mediated by HXK. FIGS. 6A-6B—Nitric oxide (NO) levels were monitored in guard cells from epidermal peels of wild-type (WT) and AtHXK1-expressing (HK4) plants using the fluorescent NO indicator dye DAF-2DA. Relative fluorescence levels of guard cells (white bars) and stomatal apertures (black bars) were determined after 30 min of treatment with MES buffer (control) or MES containing either 100 mM Suc or 100 mM sorbitol as an osmotic control. Representative fluorescence images are shown above the fluorescence columns (bar=10 µm). Data are given as means ±SE of 90 stomata (FIG. 6A) or 60 stomata (FIG. 6B) for each treatment with three to four independent biological repeats of each treatment. FIG. 6C—Relative fluorescence levels of WT guard cells were determined after 30 min of treatment with MES buffer (control), MES containing 20 mM of the hexokinase inhibitor N-acetyl-glucoseamine (NAG), or 100 mM Suc with or without 20 mM NAG. Representative fluorescence images are shown above the fluorescence columns (bar=10 µm). Data are given as means of 60 stomata from three independent biological repeats per treatment ±SE. FIG. 6D—Confocal images of NO production in guard cells of epidermal peels treated with 20 mM NAG only (left), 30 min after the addition of 100 mM Suc (middle) and 30 min after the NAG was washed out with 100 mM Suc (right). The assay was conducted as the same epidermal strip was being photographed (bar=20 µm). FIG. 6E—Relative fluorescence levels of guard cells from an epidermal strip treated as in (FIG. 6D). Data are given as means of 40-60 stomata ±SE. FIG. 6F—Confocal images of NO production in guard cells of epidermal peels of Sitiens (ABA-deficient mutants) after 30 min of treatment with MES buffer containing either 100 mM Suc (left) or 100 µM ABA (right); bar=10 µm. Different lower-case letters in (FIGS. 6A-6C, 6E) indicate a significant difference among the treatments with respect to the fluorescence data and different upper-case letters in (FIG. 6A) indicate a significant difference among the treatments with respect to the stomatal aperture data (t test, P<0.05).

Figure 7A:
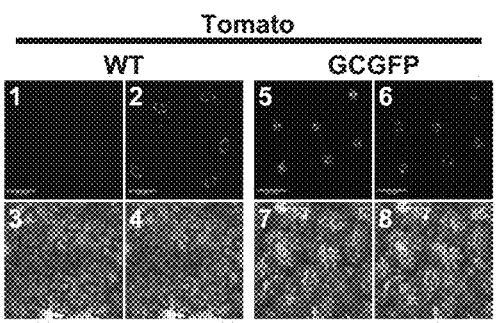
Figure 7B:
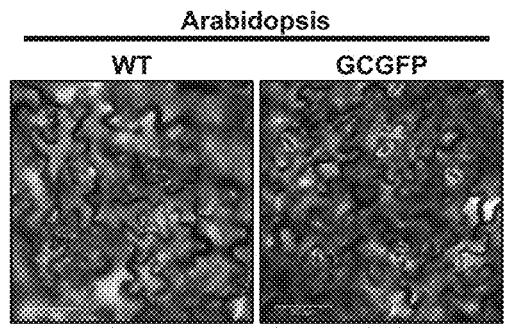
Figure 7C:
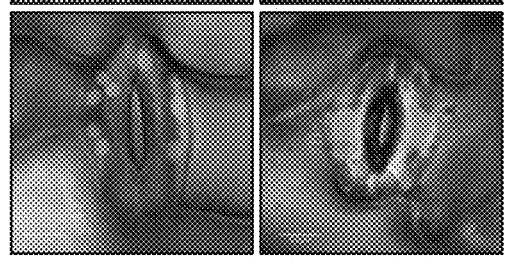
Figure 7D:
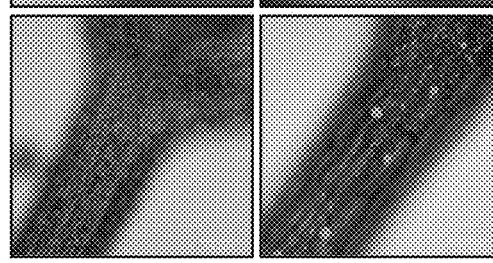
Figure 7E:
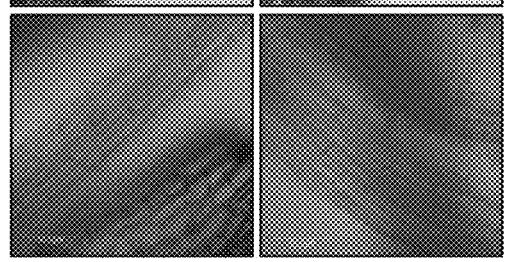

FIGS. 7A-7E show that GFP expression under the control of the KST1 promoter is specific to guard cells. FIG. 7A—Confocal images of wild-type (WT) (panels 1-4) and transgenic tomato leaves (panels 5-8) of plants with guard-cell specific expression of GFP (designated GCGFP) under the control of the KST1 promoter. Panels 1 and 5 are images of GFP fluorescence (stained green), panels 2 and 6 are chlorophyll autofluorescence (stained magenta), panels 3 and 7 are white light images and panels 4 and 8 are merged images. B-E, Confocal images of WT (left) and transgenic Arabidopsis GCGFP plants (right). Images were taken from leaves (FIGS. 7B and 7C, bars=50 µm and 5 µm, respectively), hypocotyls (FIG. 7D, bar=100 µm) and roots (FIG. 7E, bar=50 µm). All panels are merged images of white light, chlorophyll autofluorescence (magenta) and GFP fluorescence (green).

Figure 8A:
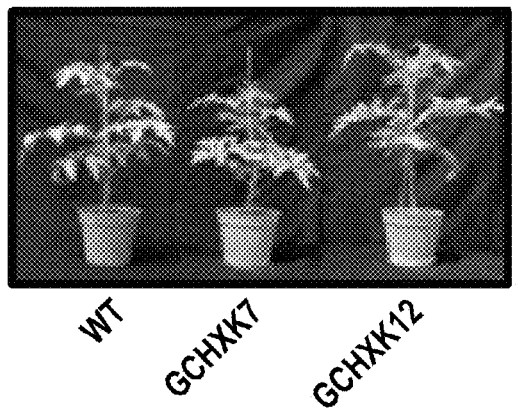
Figure 8D:
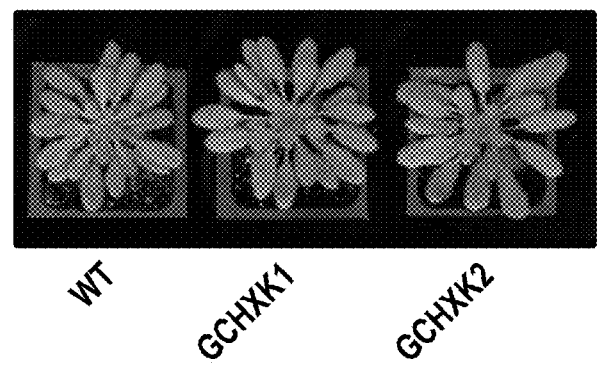
Figure 8B:
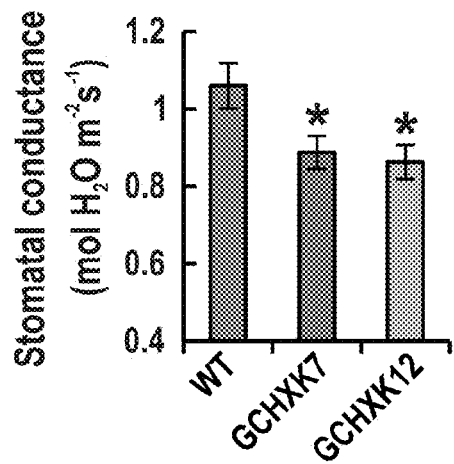
Figure 8E:
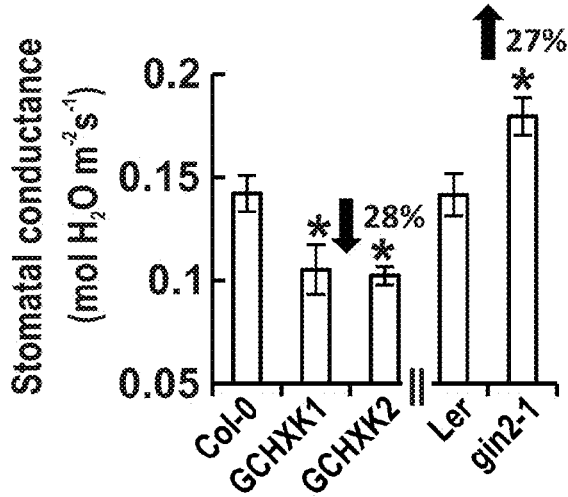
Figure 8C:
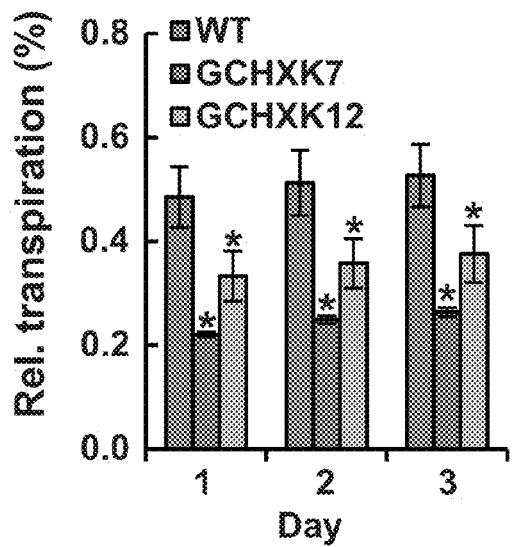
Figure 8F:
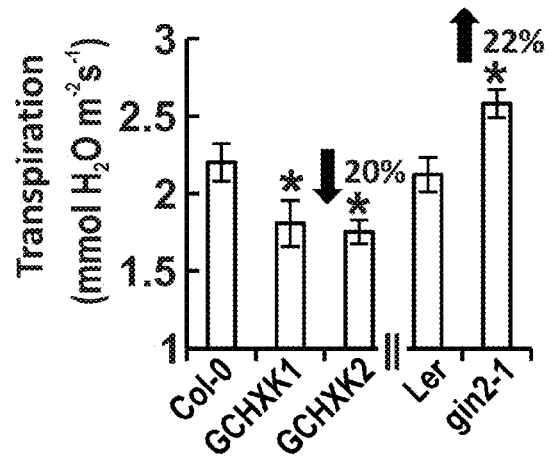

FIGS. 8A-8F show that guard cell-specific expression of AtHXK1 induces stomatal closure and reduces transpiration of tomato and Arabidopsis plants. FIG. 8A—Representative images of wild-type (WT) and two independent transgenic tomato lines expressing AtHXK1 specifically in guard cells (GCHXK7 and 12). FIGS. 8B and 8C—Stomatal conductance ($g_s$) and whole-plant relative daily transpiration of WT and two independent transgenic tomato lines (GCHXK7 and 12). Stomatal conductance data are given as means of four independent repeats ±SE. Transpiration data were normalized to the total leaf area and the amount of water taken up by the neighboring submerged fixed-size wick each day, which was set to 100%. Data from three consecutive days are presented. Data for each day are given as means of four independent repeats ±SE. FIG. 8D—Representative images of WT Arabidopsis (Col. ecotype) and two independent transgenic lines expressing AtHXK1 specifically in guard cells (GCHXK1 and 2). FIGS. 8E and 8F—Stomatal conductance and transpiration measurements of WT, two independent transgenic Arabidopsis lines, GCHXK1 and GCHXK2 (Col. ecotype), and of the gin 2-1 (AtHXK1 null mutant, Ler. ecotype). Arrows indicate increased or decreased conductance and transpiration relative to the WT. Data are given as means (±SE) of 8 and 12 independent repeats for the GCHXK and gin2-1 lines, respectively. Asterisks denote significant differences relative to the WT (t test, P<0.05).

FIG. 9 shows that GFP expression under the control of the FBPase promoter is specific to mesophyll cells. Confocal images of transgenic tomato and Arabidopsis leaves of plants with mesophyll specific expression of GFP (designated MCGFP) under the control of the FBPase promoter. Images are merge of GFP fluorescence (stained green) and white light images (bar=100 µm). Fluorescence is specific to mesophyll cells.

FIGS. 10A-10D are graphs showing that elevated expression of hexokinase in guard cells reduces transpiration while photosynthesis remains unchanged, thus improving instantaneous water use efficiency. Gas exchange analysis of GCHXK and WT plants was assayed using a Li-6400 portable gas-exchange system (LI-COR), stomatal conductance (FIG. 10A), transpiration (FIG. 10B), photosynthesis (FIG. 10C) and instantaneous water use efficiency (IWUE, FIG. 10D) were measured and calculated under favorable growth conditions. Data are mean ±SE (n=10 for WT and n=20 for 10 different transgenic lines, two measurements each). Star denotes significant difference (t test, P<0.05).

FIGS. 11A-11C show that elevated expression of hexokinase in guard cells reduces whole plant transpiration and increases water use efficiency. FIGS. 11A-11B—Whole plant relative daily transpiration (RDT) was analyzed using the large-scale lysimeter system as described in Example 1. WT and two GCHXK transgenic lines (GCHXK7, GCHXK12) were put on scales. Transpiration and total plant weight were documented every 3 minutes during the experiment in which plants were grown under normal conditions for 10 days, than subjected to drought stress for 3 days, followed by recovery irrigation process for additional 7 days. Data were normalized to the total plant weight and the amount taken up by the neighboring submerged fixed-size wick each day, which was set to 100% and served as a reference for the temporal variations in the potential transpiration. FIG. 11A—Day by day Relative daily transpiration during the whole experiment. Data are means of four independent repeats ±SEM FIG. 11B—Relative daily transpiration of selected days in each treatment. Data are means of four independent repeats ±SEM; Star denotes significant difference (t test, P<0.05). FIG. 11C—Water use efficiency was calculated by the ratio between plant weight accumulation and plant water loss, each day per each plant. Data are means of four independent repeats ±SEM; Star denotes significant difference (t test, P<0.05). (A-magnified) RDT of WT and GCHXK plants during the shift from normal irrigation (day 10) to drought conditions (day 11). Red and green arrows indicate RDT decline (represented by slope) of WT and GCHXK respectively after plants were exposed to drought.

Figure 12A:
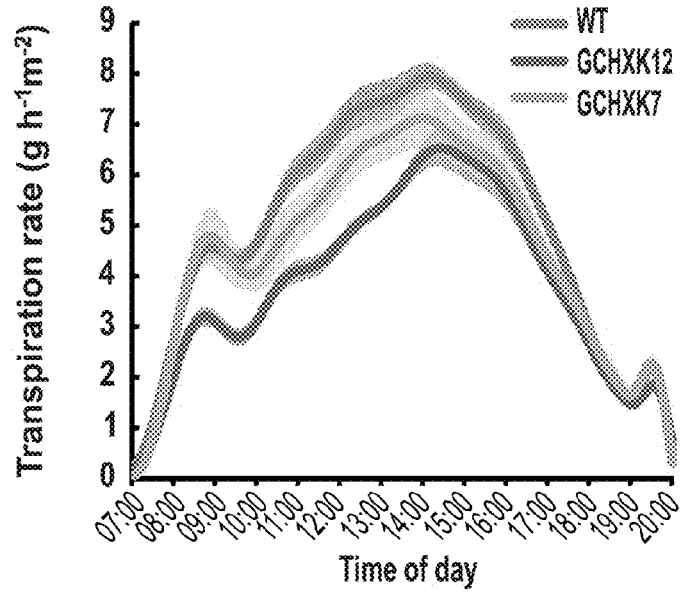
Figure 12B:
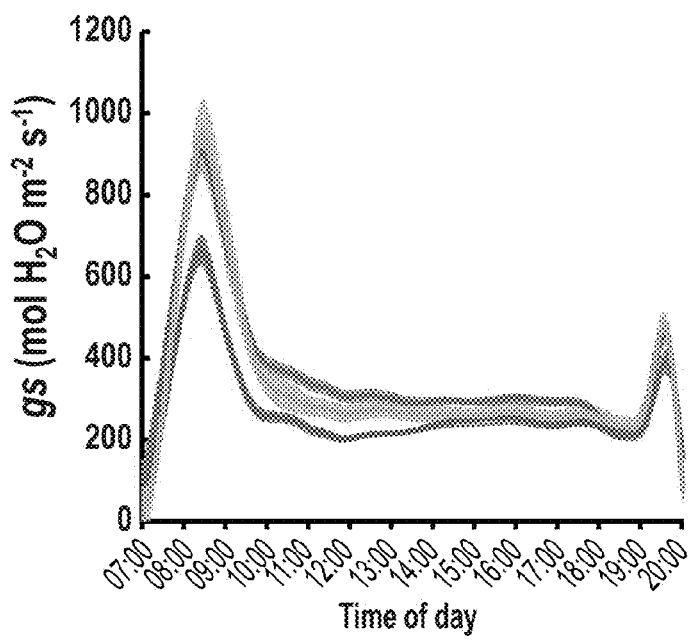
Figure 12C:
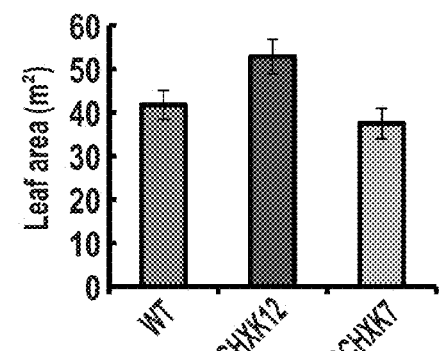
Figure 12D:
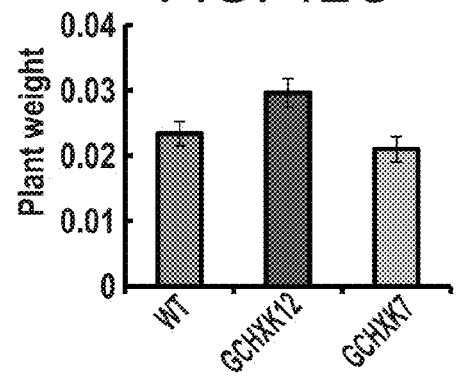
Figure 12E:
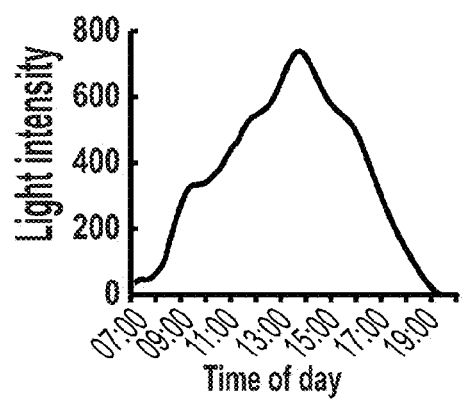
Figure 12F:
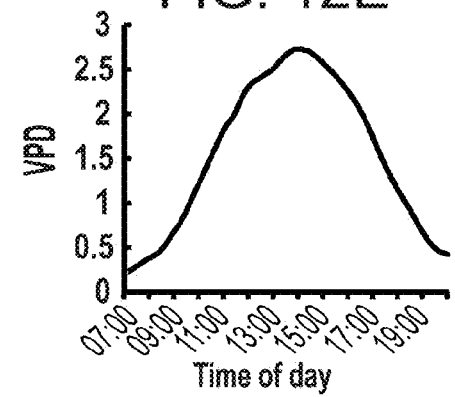

FIGS. 12A-12F show that elevated expression of hexokinase in guard cells reduces transpiration rate and stomatal conductance throughout the day, while displaying normal growth. Whole plant relative transpiration rate (FIG. 12A) and stomatal conductance ($g_s$, FIG. 12B) were analyzed using the large-scale lysimeter system as described in methods. WT and two GCHXK transgenic lines were put on scales. Transpiration rate, $g_s$, light intensity (FIG. 12E), vapor pressure deficit (VPD, FIG. 12F) were simultaneously documented every 3 minutes during the experiment in which plants were grown under normal conditions. Data for FIGS. 12A and B were normalized to the total leaf area and the amount taken up by the neighboring submerged fixed-size wick each day, which was set to 100% and served as a reference for the temporal variations in the potential transpiration. FIG. 12C—Total plant leaf area, FIG. 12D—Total plant weight.

Figure 13:
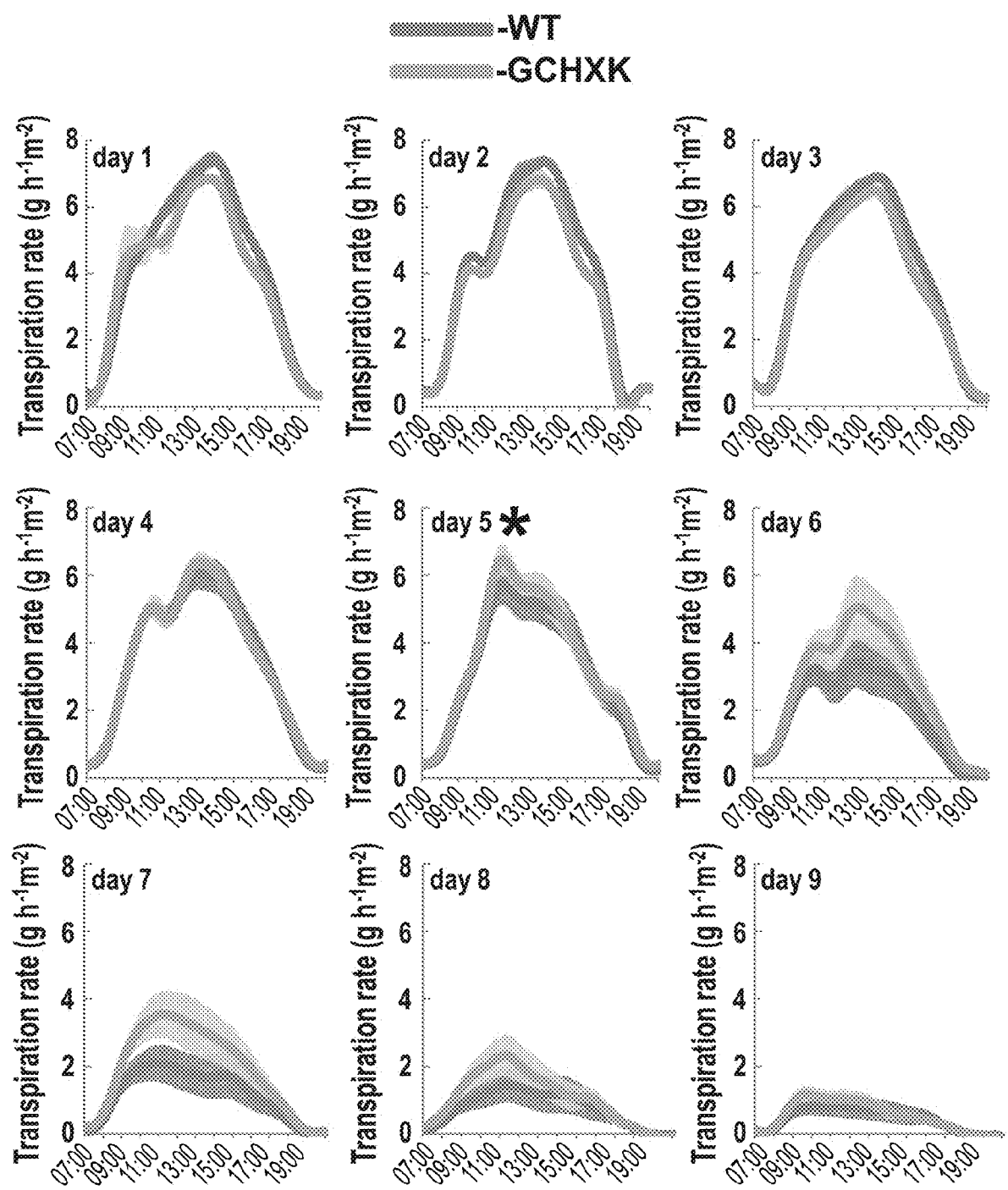

FIG. 13 shows the transpiration rate of WT and GCHXK plants under drought conditions. Whole plant transpiration rate was analyzed using the large-scale lysimeter system as described in Example 1. WT (blue) and GCHXK transgenic lines (green) were put on scales. Transpiration rates were documented for 9 days after exposing the plants to gradually increased—drought conditions, by fully stopping the irrigation. The rate of transpiration normalized to the total leaf area was monitored simultaneously and continuously throughout the day and the data are given as the means ±SE for each sampling point. Data were normalized to the total leaf area and the amount taken up by the neighboring submerged fixed-size wick each day, which was set to 100% and served as a reference for the temporal variations in the potential transpiration. Star denotes the day in which transpiration transition between WT and GCHXK had occurred.

FIGS. 14A-14B show the yield production of transgenic plants expressing hexokinase specifically in guard cells. FIG. 14A—Number of fruits collected from WT and GCHXK plants (4 independent lines). FIG. 14B—Representative images of wild-type (WT) and transgenic tomato plant expressing AtHXK1 specifically in guard cells (GCHXK7).

FIGS. 15A-15C show the yield production of transgenic plants expressing hexokinase specifically in guard cells, under limited water-supply conditions. FIG. 15A—Plants were grown under controlled commercial greenhouse conditions, following expert instructions with regard to growing procedures (Soil system, irrigation, fertilization etc.). Seedlings were planted in a mixed up order threw out the entire planting-row and the same order was kept in each row. Each row was irrigated differentially; either fully (100%) or partially (75%, 50% and 25% irrigation regimes). Since the initial fruit breaker stage, fruits were collected, counted and weighted for each individual plant for 4 weeks time. Cumulative fruit weight (FIG. 15B) and fruit number (FIG. 15C) of WT (blue) and GCHXK (green) plants were than averaged for each irrigation regime. Blue and green arrows indicates decreased fruit weight of WT and GCHXK plants respectively when shifting from 75% to 50% irrigation.

Figure 16A:
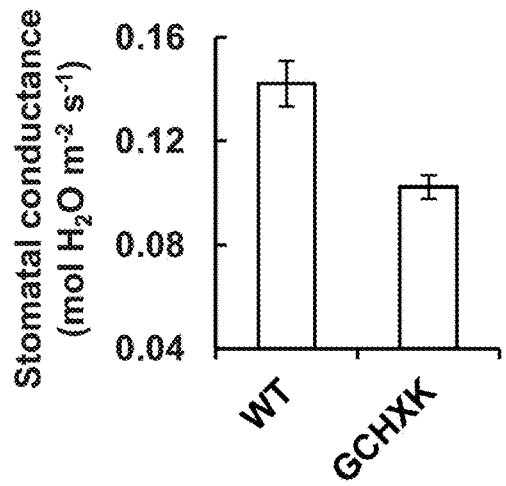
Figure 16B:
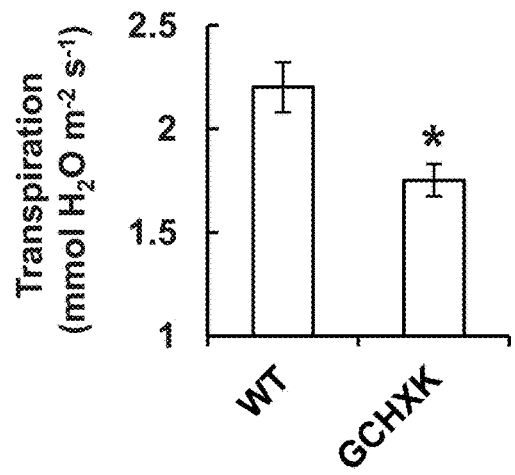
Figure 16C:
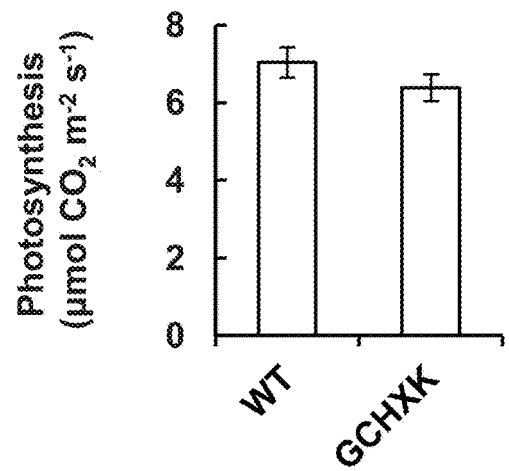
Figure 16D:
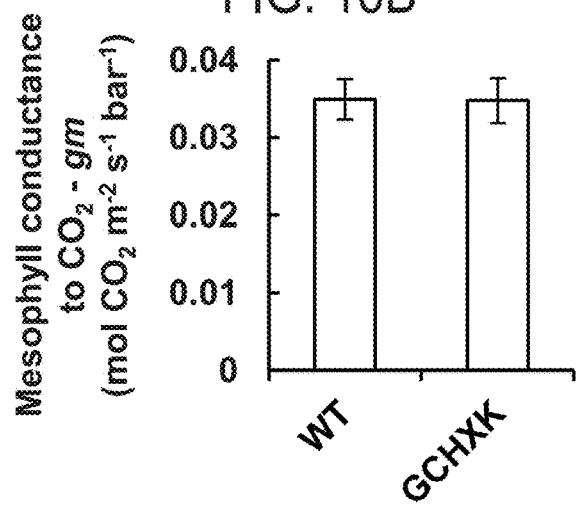
Figure 16E:
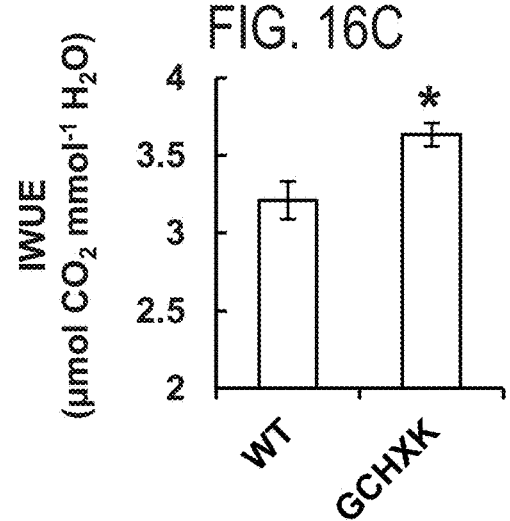
Figure 16F:
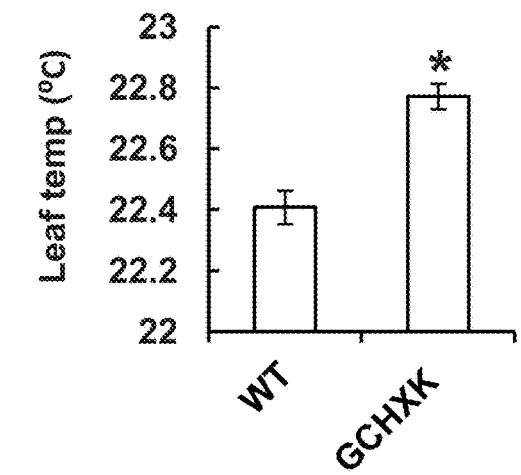

FIGS. 16A-16F show that guard cell-specific expression of AtHXK1 induces stomatal closure, reduces transpiration and increases leaf temperature without lowering photosynthesis or mesophyll conductance for $CO_2$, thus enhances water use efficiency of Arabidopsis plants. Stomatal conductance (FIG. 16A), transpiration (FIG. 16B), photosynthesis (FIG. 16C) and mesophyll conductance for $CO_2$ (gm, FIG. 16D) measurements of WT and transgenic Arabidopsis plants expressing AtHXK1 specifically in guard cells (GCHXK). FIG. 16E—instantaneous water use efficiency (IWUE) of WT and GCHXK plants. FIG. 16F—Leaf temperatures (warmer leaves—stomatal closure) of WT and GCHXK plants were determined using ThermaCam researcher pro 2.10 software. Data points are the means ±SE from 6 biological repeats in FIGS. 16A-E and of 12 biological repeats in FIG. 16F. An asterisk denotes a significant difference relative to the wild type (t test, P<0.05).

Figure 17A:
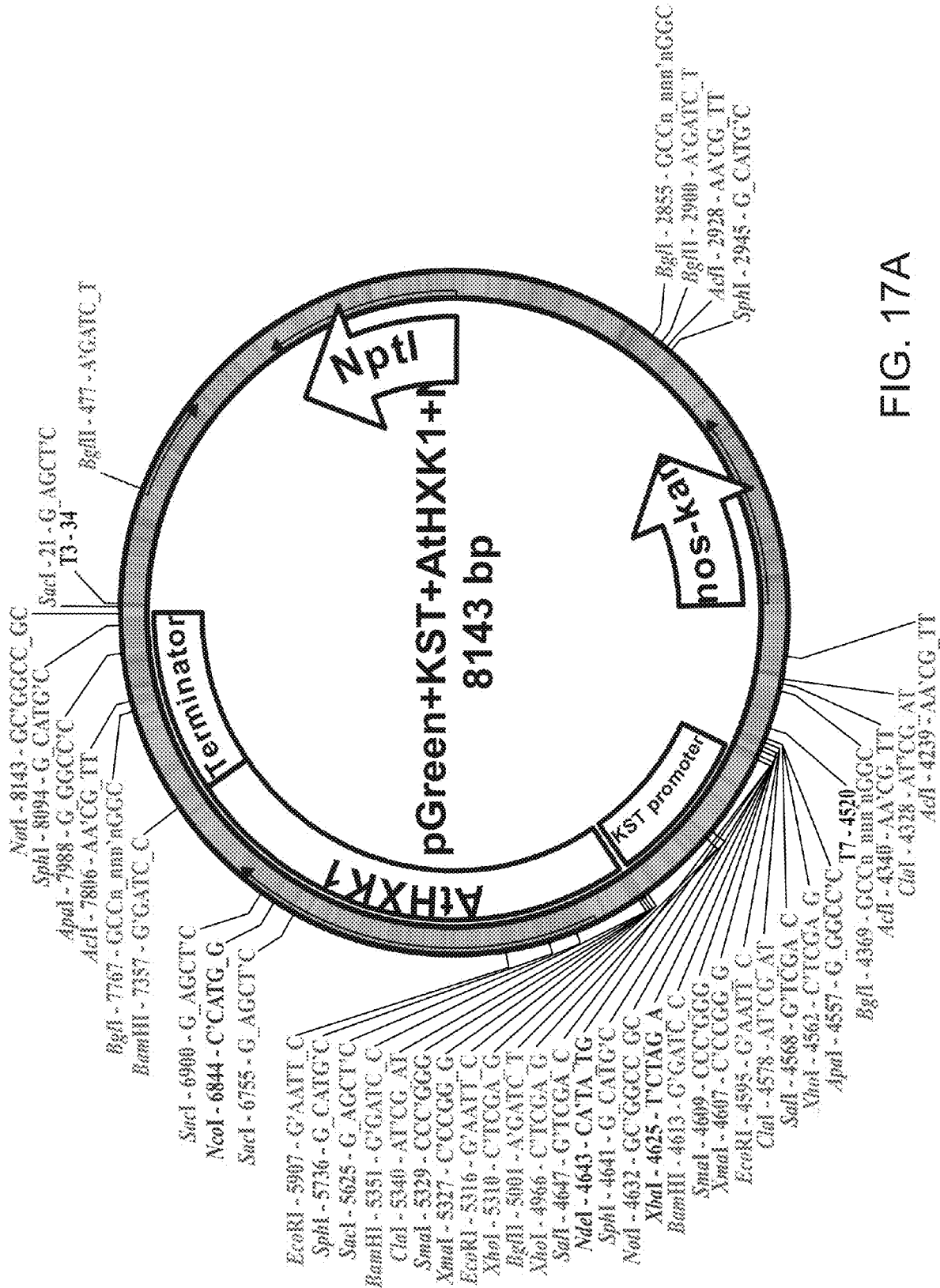
Figure 17B:
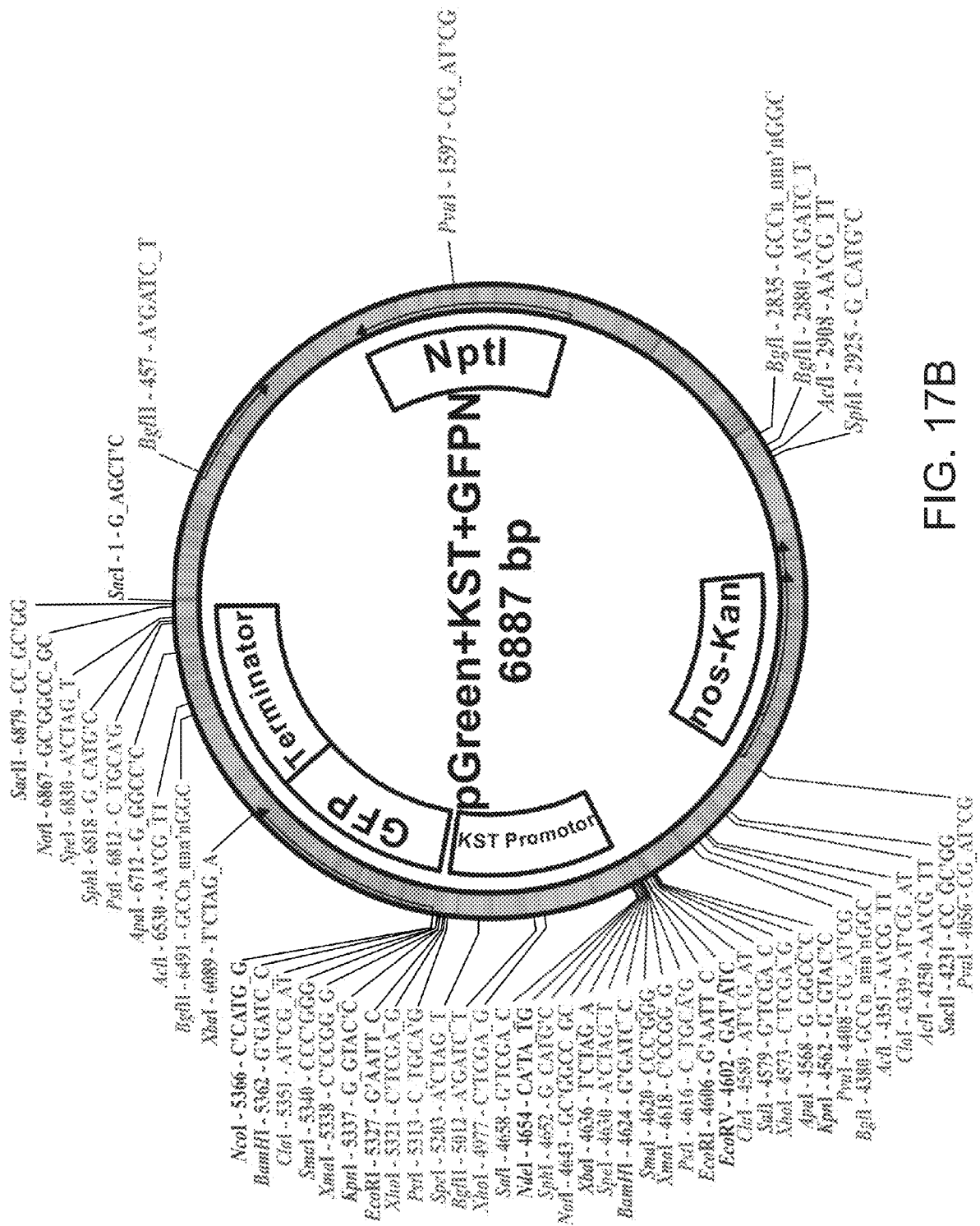

FIGS. 17A-17B are schematic maps of binary vector pGreen0029 containing KST1 promoter, AtHXK1 cDNA (FIG. 17A) or GFP (FIG. 17B) and a terminator: Vector also contains nos-Kan and neomycin phosphotransferase II (NptII) genes as selectable markers for bacteria and plant transformation.

DESCRIPTION OF SPECIFIC EMBODIMENTS OF THE INVENTION

The present invention, in some embodiments thereof, relates to methods of modulating stomata conductance and plant expression constructs for executing same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Water is the major factor limiting the growth and development of many land plants. Stomata, composed of two guard cells, are the chief gates controlling plants' water loss. Many environmental and physiological stimuli control stomatal opening, but they all function through the regulation of guard-cell osmolarity. Increased guard-cell osmolarity leads to the opening of the stomata and decreased osmolarity causes the stomata to close. The prevailing paradigm is that sucrose acts as an osmoticum in the guard cells, thereby contributing to the opening of the stomata.

While conceiving the present invention, the present inventors have found that contrary to the prevailing paradigm, sucrose closes stomata via a non-osmotic mechanism (see Example 2). Furthermore, the guard cells' response to sucrose is dependent on the sugar-sensing enzyme hexokinase (HXK), which triggers the abscisic acid-signaling pathway within the guard cells, leading to stomatal closure.

Thus, while reducing the present invention to practice, the present inventors have found that modulation of hexokinase activity or expression correlates with stomatal aperture.

As is illustrated herein below and in the Examples section which follows, the present inventors have overexpressed HXK in the stomata of tomato plants (in a guard-cell specific manner). Surprisingly, while photosynthesis remained unchanged (FIG. 10C), stomatal conductance (indicating stomatal aperture, FIG. 10B) and transpiration (FIG. 10A) were reduced. Similar results were obtained while monitoring the same parameters all day long (FIGS. 12A-12D). Importantly, by measuring total plant leaf area and weight (FIGS. 12C and 12D respectively), the present inventors discovered that even though plants have consumed less water (FIG. 12A), growth was not impaired, and was even improved. Saving water without affecting plant growth improves whole plant water use efficiency. Elevated expression of hexokinase in guard cells improves yield production (FIGS. 14A-14B) even under limited water supply (FIGS. 15A-15C). Similar results were observed in Arabidopsis. These results demonstrate that the same transgenic insertion of hexokinase under guard-cell specific promoter used in the case of Tomato (Solanaceae family) is universally applicable while affecting stomata and increases water use efficiency in the case of Arabidopsis (Brassicaceae family) as well, and that this technique could be implemented in other species as well.

Unlike previous studies, which relied on correlations between sucrose content and stomatal aperture, this study took a functional approach to the examination of the effects of sucrose and its cleavage products on stomatal behavior. It is now proven that sucrose stimulates a guard cell-specific response that is mediated by HXK and ABA and leads to stomatal closure. Without being bound to theory it is suggested that this response presents a natural feedback mechanism aimed at reducing transpiration and conserving water under excess of photosynthesis, thus coordinating between photosynthesis and transpiration.

Thus, according to an aspect of the invention there is provided a method of regulating plant stomata conductance, the method comprising modulating in the plant the level and/or activity of a hexokinase in a guard cell specific manner, thereby regulating stomata conductance and plant transpiration.

As used herein the phrase "stomata conductance" refers to gaseous exchange through the stomata pore complex. Stomata conductance is regulated by stomata aperture. Stomatal conductance affects plant transpiration and therefore the present methodology according to this aspect of the invention also regulated plant transpiration.

As used herein the phrase "regulating plant stomata conductance" refers to increase or decrease in stomata conductance. The increase or decrease may be by at least 2%, 5%, 10%, 20%, 30%, 40%, 50%, 60%, 70%, 80% or more say 90% or 100% (e.g., 20-40%).

As used herein the term "hexokinase", abbreviated as HXK, and referred to herein as "the transgene" or "the polypeptide", refers to the enzyme that typically phosphorylates hexoses (six-carbon sugars), forming hexose phosphate and having the E.C. Number 2.7.1.1. HXK as used herein also refers to hexokinase-like (HKL) protein that binds hexose and transmits a signal independent of its kinase (hexose phosphorylation) activity.

Hexokinases according to the present teachings may be about 100 kD in size as of most multicellular organisms (e.g., mammalian and plants). They consist of two halves (N and C terminal), which share much sequence homology. This suggests an evolutionary origin by duplication and fusion of a 50 kD ancestral hexokinase similar.

The hexokinase may be naturally occurring or may comprise/consist of a synthetic sequence (i.e., man-made) as long as it retains a hexokinase activity.

Due to their high conservation level, the hexokinase of the present invention can be of a plant- or an animal origin. According to a specific embodiment, the hexokinase is a plant hexokinase.

The hexokinases can be categorized according to their cellular localization. Thus, the HXKs may be associated with the mitochondria, associated with or within plastids or present in the cytosol. To date, all of the HXKs examined in eudicots have been found to have either a plastidic signal peptide (type A) or an N-terminal membrane anchor domain (type B), however, cytosolic hexokinases are also contemplated for use according to the present teachings. According to a specific embodiment, the hexokinase is a type B (mitochondrial associated) HXK.

As used herein "a hexokinase activity" refers to the ability of the enzyme to regulate stomata conductance. The enzyme may bind hexose and stimulate the abscisic acid (ABA) pathway which controls stomata conductance. The activity may be kinase independent.

Non limiting examples of hexokinases which are contemplated according to the present teachings are provided in Table 1 herein below.

TABLE 1

Hexokinase genes and their physiological function.

| Species | Gene | Accession no. (SEQ ID NO:) | Type/ Intracellular localization | Physiological function | References |
|---|---|---|---|---|---|
| Eudicots | | | | | |
| Arabidopsis thaliana | AtHXK1 | AT4G29130 (SEQ ID NOs: 11 and 12) | Type B M, N | Glc sensing PCD Mediates sugar and hormonal interactions Growth and development Photosynthetic gene repression Transpiration Actin filament reorganization Oxidative stress response Pathogen resistance Directional root growth Leaf senescence | (Jang et al., 1997; Dai et al., 1999; Yanagisawa et al., 2003; Moore et al., 2003; Leon and Sheen, 2003; Kim et al., 2006; Pourtau et al., 2006; Cho et al., 2006a; Rolland et al., 2006; Chen, 2007; Aki et al., 2007; Balasubramanian et al., 2007, 2008; Sarowar et al., 2008; Karve et al., 2008; Ju et al., 2009; Karve et al., 2010; Kushwah et al., 2011; Kelly et al., 2012) |
| | AtHXK2 | AT2G19860 (SEQ ID NOs: 13 and 14) | Type B M | Glc sensing PCD Photosynthetic gene repression | (Jang et al., 1997; Kim et al., 2006; Karve et al., 2008) |
| | AtHXK3 | AT1G47840 (SEQ ID NOs: 15 and 16) | Type A P | Glc sensing Abiotic stress response | (Claeyssen and Rivoal, 2007; Karve et al., 2008; Zhang et al., 2010) |

TABLE 1-continued

Hexokinase genes and their physiological function.

| Species | Gene | Accession no. (SEQ ID NO:) | Type/ Intracellular localization | Physiological function | References |
|---|---|---|---|---|---|
| | AtHKL1 | AT1G50460 (SEQ ID NOs: 17 and 18) | Type B M | Growth Root hair development Mediates Glc-ethylene crosstalk Abiotic stress response | (Claeyssen and Rivoal, 2007; Karve et al., 2008; Karve and Moore, 2009; Karve et al., 2012) |
| | AtHKL2 | AT3G20040 (SEQ ID NOs: 19 and 20) | Type B M | | (Karve et al., 2008) |
| | AtHKL3 | AT4G37840 (SEQ ID NOs: 21 and 22) | Type B M | Abiotic stress response | (Claeyssen and Rivoal, 2007; Karve et al., 2008) |
| Tomato (*Solanum lycopersicum*) | SlHXK1 | AJ401153 (SEQ ID NOs: 23 and 24) | Type B M | | (Damari-Weissler et al., 2006) |
| | SlHXK2 | AF208543 (SEQ ID NOs: 25 and 26) | Type B M | | (Menu et al., 2001; Damari-Weissler et al., 2006) |
| | SlHXK3 | DQ056861 (SEQ ID NOs: 27 and 28) | Type B M | | (Kandel-Kfir et al., 2006) |
| | SlHXK4 | DQ056862 (SEQ ID NOs: 29 and 30) | Type A P | | (Kandel-Kfir et al., 2006) |
| *Solanum chacoense* | ScHK2 | DQ177440 (SEQ ID NOs: 31 and 32) | ND | | (Claeyssen et al., 2006) |
| Potato (*Solanum tuberosum*) | StHXK1 | X94302 (SEQ ID NOs: 33 and 34) | ND | Glc sensing Leaves starch content | (Veramendi et al., 1999; Veramendi et al., 2002) |
| | StHXK2 | AF106068 (SEQ ID NOs: 35 and 36) | ND | Glc sensing | (Veramendi et al., 2002) |
| Tobacco (*Nicotiana tabacum/ benthamiana*) | NtHXK2 | AY553215 (SEQ ID NOs: 37 and 38) | Type A P | | (Giese et al., 2005) |
| | NbHXK1 | AY286011 (SEQ ID NOs: 39 and 40) | Type B M | Plant growth PCD Oxidative-stress resistance | (Kim et al., 2006; Sarowar et al., 2008) |
| Sunflower (*Helianthus annuus*) | HaHXK1 | DQ835563 (SEQ ID NOs: 41 and 42) | ND | Seed development | (Troncoso-Ponce et al., 2011) |
| *Populus trichocarpa* | PtHXK1 | XP_002325031 (SEQ ID NOs: 43 and 44) | Type B M | Glc sensing | (Karve et al., 2010) |
| Grape (*Vitis vinifera* L. cv. Cabernet Sauvignon) | VvHXK1 | JN118544 | ND | | (Yu et al., 2012) |
| | VvHXK2 | JN118545 | ND | | (Yu et al., 2012) |
| Spinach (*Spinacia oleracea*) | SoHXK1 | AF118132 (SEQ ID NOs: 45 and 46) | Type B M | | (Wiese et al., 1999; Damari-Weissler et al., 2007) |

Monocots

| Species | Gene | Accession no. (SEQ ID NO:) | Type/ Intracellular localization | Physiological function | References |
|---|---|---|---|---|---|
| Rice (*Oryza sativa*) | OsHXK1 | DQ116383 (SEQ ID NOs: 47 and 48) | C, N | | (Cho et al., 2006a; Cheng et al., 2011) |
| | OsHXK2 | DQ116384 (SEQ ID NOs: 49 and 50) | Type B M | | (Cheng et al., 2011) |
| | OsHXK3 | DQ116385 (SEQ ID NOs: 51 and 52) | Type B M | | (Cheng et al., 2011) |
| | OsHXK4 | DQ116386 (SEQ ID NOs: 53 and 54) | Type A P | | (Cho et al., 2006a; Cheng et al., 2011) |
| | OsHXK5 | DQ116387 (SEQ ID NOs: 55 and 56) | Type B M, N | Glc sensing Photosynthetic gene repression Shoot growth | (Cho et al., 2009a; Cheng et al., 2011) |

TABLE 1-continued

Hexokinase genes and their physiological function.

| Species | Gene | Accession no. (SEQ ID NO:) | Type/ Intracellular localization | Physiological function | References |
|---|---|---|---|---|---|
| | OsHXK6 | DQ116388 (SEQ ID NOs: 57 and 58) | Type B M, N | Glc sensing Photosynthetic gene repression Shoot growth | (Aki and Yanagisawa, 2009; Cho et al., 2009a; Cheng et al., 2011) |
| | OsHXK7 | DQ116389 (SEQ ID NOs: 59 and 60) | C, N | | (Cho et al., 2006a; Cheng et al., 2011) |
| | OsHXK8 | DQ116390 (SEQ ID NOs: 61 and 62) | C, N | | (Cheng et al., 2011) |
| | OsHXK9 | DQ116391 (SEQ ID NOs: 63 and 64) | Type B M | | (Cheng et al., 2011) |
| | OsHXK10 | DQ116392 (SEQ ID NOs: 65 and 66) | C and/or M | Pollen germination | (Xu et al., 2008; Cheng et al., 2011) |
| Sorghum (*Sorghum bicolor*) | SbHXK3 | XM_002459027 (SEQ ID NOs: 67 and 68) | Type B M | No Glc sensing role | (Karve et al., 2010) |
| | SbHXK8 | XM_002454982 (SEQ ID NOs: 69 and 70) | C | | (Karve et al., 2010) |
| Wheat (*Triticum aestivum*) | HXK | AY974231 (SEQ ID NOs: 71 and 72) | ND | Controls triose phosphate/phosphate translocation | (Sun et al., 2006) |
| Lycophytes | | | | | |
| Spike moss (*Selaginella mollendorffii*) | SmHXK3 | 26000047 * | C | Glc sensing | (Karve et al., 2010) |
| | SmHXK5 | 57.357.1 * | C | | (Karve et al., 2010) |
| Bryophytes | | | | | |
| Moss (*Physcomitrella patens*) | PpHXK1 | AY260967 (SEQ ID NOs: 73 and 74) | Type A P | Filamentous type and growth | (Olsson et al., 2003; Thelander et al., 2005) |
| | PpHXK2 | XM_001784578 (SEQ ID NOs: 75 and 76) | Type B M, P | | (Nilsson et al., 2011) |
| PpHXK3 | | XM_001784282 (SEQ ID NOs: 77 and 78) | Type B M, P | | Nilsson et al., 2011) |
| PpHXK4 | | XM_001760896 (SEQ ID NOs: 79 and 80) | Type C C, N | | (Nilsson et al., 2011) |
| PpHXK5 | | XM_001766381 (SEQ ID NOs: 81 and 82) | Type A P | | (Nilsson et al., 2011) |
| PpHXK6 | | XM_001762899 (SEQ ID NOs: 83 and 84) | Type A P | | (Nilsson et al., 2011) |
| PpHXK7 | | XM_001754096 (SEQ ID NOs: 85 and 86) | Type B M, P | | (Nilsson et al., 2011) |
| PpHXK8 | | XM_001752177 (SEQ ID NOs: 87 and 88) | Type B M, P | | (Nilsson et al., 2011) |
| PpHXK9 | | XM_001770125 (SEQ ID NOs: 89 and 90) | Type D M | | (Nilsson et al., 2011) |
| PpHXK10 | | XM_001776713 (SEQ ID NOs: 91 and 92) | Type D M | | (Nilsson et al., 2011) |
| PpHXK11 | | XM_001779426 (SEQ ID NOs: 93 and 94) | Type D M, P | | (Nilsson et al., 2011) |

Type A—localized in plastid stroma. Type B—associated with the mitochondria. Type C—localized in the cytosol and nucleus. Type D—associated with the mitochondria, different from type B in sequence. M—mitochondria associated. P—plastid. N—nucleus. C—cytosol. ND—not determined. PCD—programmed cell death. Glc—glucose.
* Joint Genome Institute—*Selaginella moellendorffii* v1.0.

As mentioned, the HXK sequence may be naturally occurring or artificially generated (e.g., codon-optimized) according to the intended use.

According to a specific embodiment, modulating the activity or expression of HXK refers to upregulating the activity or expression which results in reduction of stomatal conductance. Upregulating can be by at least 5%, 10%, 20, %, 30%, 40%, 50%, 60%, 70% 80% or more, say 90% or even 100%, as compared to hexokinase expression or activity in a similar cell of the same plant species, growth conditions and developmental stage (e.g., wild-type (WT) plant).

As mentioned, upregulation of hexokinase activity or expression in a guard-cell specific manner has a number of advantages in crop plants and vegetables farming.

Thus, the present inventors have shown that upregulation of HXK in a guard-cell specific manner decreases stomata aperture and conductance (without affecting photosynthesis), improves plant's water use efficiency, thereby increasing plant's tolerance to drought, and overall increases plants vigor, biomass or yield (under stress or optimal growth conditions). Likewise, plants expressing HXK in a guard-cell specific manner are tolerant to salinity stress. It is appreciated that Water are taken up (soaked) by plants as a result of the difference between water potential in the air and within the plants. This difference is termed vapor pressure deficit (VPD). The driving force of soaking water from the ground is the VPD. Higher VPD—the greater is the force. Yet, when the stomata are partially closed, the effect of VPD is lowered and less water is being taken up by the plant. In that case, the plant will take less salt from the ground and will be less affected. The present teachings have also an unprecedented impact on the tolerance of plants to biotic stress. Many human and plant pathogens such as bacteria and fungi, invade plants via the stomata (see for Example Kroupitski et al. Applied and Environmental Microbiology 2009 6076-6086 teaching that Salmonella enteric internalizes in leaves via open stomata). Not only does the stomata allow easy entrance, but also serve as good environment for attracting the pathogens by the accumulation of sugars near the guard cells when the stomata is open. Indeed, the present inventors have observed reduced fungi and bacteria infections in plants with high expression of HXK (not shown).

Alternatively or additionally, the present teachings can also be employed towards imparting the plant with a tolerance to temperature stress (heat or cold). For instance, plants expressing high levels of HXK in a guard cell specific manner are expected to exhibit extended heat and cold resistance with regard to fruit setting. Pollen development and germination are sensitive to heat and cold, most likely due to perturbation of sugar metabolism. It is suggested that during heat stress less sugars are being carried toward the pollen grains (and other sink tissues as well) since most of the water is transpired through the stomata. According to the present teachings, when less water is transpired through the stomata so then more water is available for sugar transport in the phloem. That may impart resistance to temperature stress (e.g., heat) thereby allowing production of viable pollen grains.

Alternatively or additionally, the present teachings can be employed towards prevention of blossom end rot (BER). BER is a visible physiological damage that affects many crops such as tomato, eggplants, pepper, melon and many more. BER happens mainly under heat and water stress. It is now suggested that under such conditions, most of the water is transpired and less water is available to carry sugars, minerals and ions toward the fruits. Accordingly, lowering transpiration may allocate more water carrying more sugars, minerals and ions toward the fruits and other sink tissues (Nikinma et al. 2012 Plant, Cell and Environment 2012 1-15). BER is determined by the percentage of fruits that exhibit visible or detectable rot (physical damage) on the fruit. BER prevention means lowering the percentage of fruits with BER.

Thus, according to an exemplary embodiment the present teachings can be used to increase biomass, vigor or yield of a plant.

As used herein the phrase "plant yield" refers to the amount (e.g., as determined by weight or size) or quantity (numbers) of tissues or organs produced per plant or per growing season. Hence increased yield could affect the economic benefit one can obtain from the plant in a certain growing area and/or growing time.

It should be noted that a plant yield can be affected by various parameters including, but not limited to, plant biomass; plant vigor; growth rate; seed yield; seed or grain quantity; seed or grain quality; oil yield; content of oil, starch and/or protein in harvested organs (e.g., seeds, fruits or vegetative parts of the plant); number of flowers (florets) per panicle (expressed as a ratio of number of filled seeds over number of primary panicles); harvest index; number of plants grown per area; number and size of harvested organs per plant and per area; number of plants per growing area (density); number of harvested organs in field; total leaf area; carbon assimilation and carbon partitioning (the distribution/allocation of carbon within the plant); resistance to shade; number of harvestable organs (e.g. seeds), seeds per pod, weight per seed; and modified architecture [such as increase stalk diameter, thickness or improvement of physical properties (e.g. elasticity)].

As used herein the phrase "seed yield" refers to the number or weight of the seeds per plant, seeds per pod, or per growing area or to the weight of a single seed, or to the oil extracted per seed. Hence seed yield can be affected by seed dimensions (e.g., length, width, perimeter, area and/or volume), number of (filled) seeds and seed filling rate and by seed oil content. Hence increase seed yield per plant could affect the economic benefit one can obtain from the plant in a certain growing area and/or growing time; and increase seed yield per growing area could be achieved by increasing seed yield per plant, and/or by increasing number of plants grown on the same given area.

The term "seed" (at times referred to as "grain" or "kernel") as used herein refers to a small embryonic plant enclosed in a covering called the seed coat (usually with some stored food), the product of the ripened ovule of gymnosperm and angiosperm plants which occurs after fertilization and some growth within the mother plant. The seed may be a hybrid seed or a homozygous line.

The phrase "oil content" as used herein refers to the amount of lipids in a given plant organ, either the seeds (seed oil content) or the vegetative portion of the plant (vegetative oil content) and is typically expressed as percentage of dry weight (10% humidity of seeds) or wet weight (for vegetative portion).

It should be noted that oil content is affected by intrinsic oil production of a tissue (e.g., seed, fruit, vegetative portion), as well as the mass or size of the oil-producing tissue per plant or per growth period.

In one embodiment, increase in oil content of the plant can be achieved by increasing the size/mass of a plant's tissue(s) which comprise oil per growth period. Thus, increased oil content of a plant can be achieved by increasing the yield, growth rate, biomass and vigor of the plant.

As used herein the phrase "plant biomass" refers to the amount (e.g., measured in grams of air-dry tissue) of a tissue produced from the plant in a growing season, which could also determine or affect the plant yield or the yield per growing area. An increase in plant biomass can be in the whole plant or in parts thereof such as aboveground (harvestable) parts, fruit biomass, vegetative biomass, roots and seeds.

As used herein the phrase "growth rate" refers to the increase in plant organ/tissue size per time (can be measured in cm$^2$ per day).

As used herein the phrase "plant vigor" refers to the amount (measured by weight) of tissue produced by the plant in a given time. Hence increased vigor could determine or affect the plant yield or the yield per growing time or growing area. In addition, early vigor (seed and/or seedling) results in improved field stand.

It should be noted that a plant yield can be determined under stress (e.g., abiotic stress) and/or non-stress (normal) conditions. It is contemplated herein that yield, vigor or biomass of the plant expressing the HXK in a guard cell-specific manner is increased as compared to that of wild-type plant (not expressing said HXK) under stress or non-stressed conditions.

As used herein, the phrase "non-stress conditions" (or normal or optimal as referred to herein) refers to the growth conditions (e.g., water, temperature, light-dark cycles, humidity, salt concentration, fertilizer concentration in soil, nutrient supply such as nitrogen, phosphorous and/or potassium), that do not significantly go beyond the everyday climatic and other abiotic conditions that plants may encounter, and which allow optimal growth, metabolism, reproduction and/or viability of a plant at any stage in its life cycle (e.g., in a crop plant from seed to a mature plant and back to seed again). Persons skilled in the art are aware of normal soil conditions and climatic conditions for a given plant in a given geographic location. It should be noted that while the non-stress conditions may include some mild variations from the optimal conditions (which vary from one type/species of a plant to another), such variations do not cause the plant to cease growing without the capacity to resume growth.

As mentioned increased yield can be under non-stress conditions or abiotic/biotic stress conditions.

The phrase "abiotic stress" as used herein refers to any adverse effect on metabolism, growth, reproduction and/or viability of a plant. Accordingly, abiotic stress can be induced by suboptimal environmental growth conditions such as, for example, salinity, water deprivation, flooding, freezing, low or high temperature (i.e., cold or heat), heavy metal toxicity, anaerobiosis, nutrient deficiency, atmospheric pollution or UV irradiation.

The phrase "abiotic stress tolerance" as used herein refers to the ability of a plant to endure an abiotic stress without suffering a substantial alteration in metabolism, growth, productivity and/or viability.

As used herein the phrase "water use efficiency (WUE)" refers to the level of organic matter produced per unit of water consumed by the plant, i.e., the dry weight of a plant in relation to the plant's water use, e.g., the biomass produced per unit transpiration.

Similarly "biotic stress" refers to stress that occurs as a result of damage done to plants by other living organisms, such as bacteria, viruses, fungi, parasites.

Upregulation of HXK in a guard-cell specific manner can be used to remedy any of the aforementioned conditions and to improve plants performance overall. Thus, upregulation of the HXK can be effected by expressing an exogenous polynucleotide encoding HXK in the plant in a guard-cell specific manner.

The phrase "expressing within the plant an exogenous polynucleotide encoding HXK" as used herein refers to upregulating the expression level of an exogenous polynucleotide encoding an HXK polypeptide within the plant by introducing the exogenous polynucleotide into a plant cell or plant and expressing by recombinant means, as further described herein below.

As used herein "expressing" refers to expression at the mRNA and polypeptide level. It will be appreciated that for silencing the expression is at the mRNA level alone (silencing mechanisms of HXK are described further hereinbelow).

As used herein, the phrase "exogenous polynucleotide" refers to a heterologous nucleic acid sequence which may not be naturally expressed within the plant or which overexpression in the plant is desired. The exogenous polynucleotide may be introduced into the plant in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the plant.

The term "endogenous" as used herein refers to any polynucleotide or polypeptide which is present and/or naturally expressed within a plant or a cell thereof.

According to the invention, the exogenous polynucleotide of the invention comprises a nucleic acid sequence encoding a polypeptide having an amino acid sequence of a hexokinase.

According to a specific embodiment the amino acid sequence of the HXK polypeptide (encoded from the exogenous polynucleotide) is at least about, 30%, 40% or 50%, or at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to the amino acid sequence selected from the group consisting of SEQ ID NOs: 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94, as long as its hexokinase activity is maintained as described above.

Homology (e.g., percent homology, identity+similarity) can be determined using any homology comparison software, including for example, the BlastP™ or TBLASTN™ software of the National Center of Biotechnology Information (NCBI) such as by using default parameters, when starting from a polypeptide sequence; or the tBLASTX™ algorithm (available via the NCBI) such as by using default parameters, which compares the six-frame conceptual translation products of a nucleotide query sequence (both strands) against a protein sequence database.

According to some embodiments of the invention, the term "homology" or "homologous" refers to identity of two or more nucleic acid sequences; or identity of two or more amino acid sequences.

Homologous sequences include both orthologous and paralogous sequences. The term "paralogous" relates to gene-duplications within the genome of a species leading to paralogous genes. The term "orthologous" relates to homologous genes in different organisms due to ancestral relationship.

One option to identify orthologues in monocot plant species is by performing a reciprocal BLAST™ search. This may be done by a first BLAST™ involving blasting the sequence-of-interest against any sequence database, such as the publicly available NCBI database which may be found at: Hypertext Transfer Protocol://World Wide Web (dot) ncbi (dot) nlm (dot) nih (dot) gov. If orthologues in rice were sought, the sequence-of-interest would be blasted against, for example, the 28,469 full-length cDNA clones from *Oryza sativa* Nipponbare available at NCBI. The BLAST™ results may be filtered. The full-length sequences of either the filtered results or the non-filtered results are then blasted back (second BLAST™) against the sequences of the organism from which the sequence-of-interest is derived. The results of the first and second BLAST™s are then compared. An orthologue is identified when the sequence resulting in the highest score (best hit) in the first BLAST™ identifies in the second BLAST™ the query sequence (the original sequence-of-interest) as the best hit. Using the same rational a paralogue (homolog to a gene in the same organism) is found. In case of large sequence families, the ClustalW program may be used [Hypertext Transfer Protocol://World Wide Web (dot) ebi (dot) ac (dot) uk/Tools/clustalw2/index (dot) html], followed by a neighbor-joining tree (Hypertext Transfer Protocol://en (dot) wikipedia (dot) org/wiki/Neighbor-joining) which helps visualizing the clustering.

According to some embodiments of the invention, the exogenous polynucleotide of the invention encodes a polypeptide having an amino acid sequence at least about 30%, 40%, 50%, 60%, 70% or at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% identical to the amino acid sequence selected from the group consisting of 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94 as long as the hexokinase activity of the protein (as described above) is maintained.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment e.g., from a plant cell.

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Nucleic acid sequences encoding the HXK polypeptides of the present invention may be optimized for expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1N[(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A Table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization Tables such as those provided on-line at the Codon Usage Database through the NIAS (National Institute of Agrobiological Sciences) DNA bank in Japan (Hypertext Transfer Protocol://World Wide Web (dot) kazusa (dot) or (dot) jp/codon/). The Codon Usage Database contains codon usage tables for a number of different species, with each codon usage Table having been statistically determined based on the data present in Genbank.

By using the above Tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

The term "plant" as used herein encompasses whole plants, ancestors and progeny of the plants and plant parts (those which comprise stomata but not necessarily), including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores.

According to some embodiments of the invention the plant is a dicotyledonous plant.

According to some embodiments of the invention the plant is a monocotyledonous plant.

Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present invention.

According to some embodiments of the invention, the plant used by the method of the invention is a crop plant such as rice, maize, wheat, barley, peanut, potato, sesame, olive tree, palm oil, banana, soybean, sunflower, canola, sugarcane, alfalfa, millet, leguminosae (bean, pea), flax, lupinus, rapeseed, tobacco, poplar and cotton.

According to some embodiments of the invention, the plant is a tomato or a banana.

According to some embodiments of the invention, expressing the exogenous polynucleotide of the invention within the plant is effected by introducing into a cell of the plant (e.g., transforming one or more cells of the plant) an exogenous polynucleotide encoding the HXK under a cis-acting regulatory element for driving expression of the HXK in a guard-cell specific manner, followed by generating a mature plant from the transformed cells and cultivating the mature plant under conditions suitable for expressing the exogenous polynucleotide within the mature plant.

Thus, there is provided a plant expression construct comprising a nucleic acid sequence encoding a hexokinase under a transcriptional control of a guard cell-specific cis-acting regulatory element and methods which make use of same.

There is also provided a method of decreasing plant stomata conductance, the method comprising introducing into a cell of a plant the above-described nucleic acid construct, thereby decreasing the stomata conductance of the plant.

Alternatively or additionally there is provided a method of increasing water use efficiency of a plant, the method comprising introducing into a cell of the plant the above-described nucleic acid construct, thereby increasing water use efficiency of the plant.

Alternatively or additionally there is provided a method of increasing tolerance of a plant to drought, salinity or temperature stress, the method comprising introducing into a cell of the plant the above-described nucleic acid construct, thereby increasing tolerance of the plant to drought, salinity or temperature stress.

Alternatively or additionally there is provided a method of increasing biotic stress tolerance of a plant, the method comprising introducing into a cell of the plant the above-described nucleic acid construct, thereby increasing biotic stress tolerance of the plant.

Alternatively or additionally there is provided a method of increasing biomass, vigor or yield of a plant, the method comprising introducing into a cell of the plant the nucleic acid construct, thereby increasing the biomass, vigor or yield of the plant.

According to some embodiments of the invention, the transformation is effected by introducing to the plant cell a nucleic acid construct which includes the exogenous polynucleotide of some embodiments of the invention encoding the HXK (as described above) and a guard cell-specific cis-acting regulatory element. Further details of suitable transformation approaches are provided hereinbelow.

As used herein "guard-cell specific cis-acting regulatory element" refers to the ability of a transcriptional element to drive expression of the nucleic acid sequence under its regulation (e.g., HXK) only in guard cells, leaving the rest of the tissues in the plant unmodified by transgene expression (e.g., more than 90% of the mRNA is expressed in the tissue of interest, as detected by RT-PCR). Tissue-specific cis-acting regulatory elements may be induced by endogenous or exogenous factors, so they can be classified as inducible promoters as well. In other cases they are constitutively expressed.

A coding nucleic acid sequence (e.g., HXK) is "operably linked" to a regulatory sequence (e.g., guard-cell specific promoter) if the regulatory sequence is capable of exerting a regulatory effect on the coding sequence linked thereto.

According to some embodiments of the invention the cis-acting regulatory element is a promoter.

As used herein, the term "promoter" refers to a region of DNA which lies upstream of the transcriptional initiation site of a gene to which RNA polymerase binds to initiate transcription of RNA. The promoter controls where (e.g., which portion of a plant) and/or when (e.g., at which stage or condition in the lifetime of an organism) the gene is expressed.

Examples of guard-cell specific promoters include, but are not limited to the promoters listed in Table 2 below and the KST1 promoter used in the Examples section (SEQ ID NO: 108).

TABLE 2

| | Promoter | Species | Accession n. | Verification method | Ref. | Comments |
|---|---|---|---|---|---|---|
| 1 | AtMYB61 promoter | Arabidopsis thaliana | AT1G09540 (SEQ ID NO: 95) | GFP | (Liang et al., 2005) | Specific expression in GC |
| 2 | At1g22690-promoter (pGC1) | Arabidopsis thaliana | At1g22690 (SEQ ID NO: 96) | GFP based calcium FRET reporter/ GUS | (Yang et al., 2008) | Specific expression in GC |
| 3 | AtMYB60 promoter | Arabidopsis thaliana | At1g08810 (SEQ ID NO: 97) | GUS, GFP | (Cominelli et al., 2005; Galbiati et al., 2008; Cominelli et al., 2011) | Specific expression in GC |
| 4 | R2R3 MYB60 transcription factor promoter | Vitis vinifera L. | ACF21938 (SEQ ID NO: 98) | GUS | (Galbiati et al., 2011) | Specific expression in GC |
| 5 | HIC (High carbon dioxide) promoter | Arabidopsis thaliana | AT2G46720 (SEQ ID NO: 99) | GUS | (Gray et al., 2000) | Specific expression in GC |
| 6 | CYTOCHROME P450 86A2 (CYP86A2) mono-oxygenase promoter (pCYP) | Arabidopsis thaliana | At4g00360 (SEQ ID NO: 100) | GFP | (Francia et al., 2008; Galbiati et al., 2008) | Specific expression in GC |
| 7 | ADP-glucose pyrophosphorylase (AGPase) Promoter | Solanum tuberosum | X75017 (Promoter seq.) (SEQ ID NO: 101) | GUS | (Muller-Rober et al., 1994) | 0.3 Kb 5'proximal promoter - exclusive GC expression |
| 8 | KAT1 promoter | Arabidopsis thaliana | AT5G46240 (gene), U25088 (promoter + gene seq.) (SEQ ID NO: 102) | GUS | (Nakamura et al., 1995) | Specific expression in GC. However, was detected also in vascular tissue of roots |
| 9 | Myrosinase-Thioglucoside glucohydrolase 1 (TGG1) promoter | Arabidopsis thaliana | At5g26000 (SEQ ID NO: 103) | GUS, GFP | (Husebye et al., 2002) | Specific expression in GC. Distinct expression in phloem |
| 10 | rha1 promoter | Arabidopsis thaliana | AT5G45130 (SEQ ID NO: 104) | GUS | (Terryn et al., 1993) | Mainly expressed (non-specific) in GC |
| 11 | AtCHX20 promoter | Arabidopsis thaliana | AT3G53720 (SEQ ID NO: 105) | GUS | (Padmanaban et al., 2007) | Specific expression in GC |

GC—guard cell.
GFP—green fluorescence protein.
GUS—β-glucoronidase reporter gene.

The nucleic acid construct of some embodiments of the invention can further include an appropriate selectable marker and/or an origin of replication. According to some embodiments of the invention, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

According to some embodiments of the invention, the method further comprising growing the plant expressing the exogenous polynucleotide under the biotic or abiotic stress (e.g., drought, water deprivation or temperature stress).

Thus, the invention encompasses (transgenic) plants, parts thereof or plant cells, exogenously expressing the polynucleotide(s)or the nucleic acid constructs of the invention.

Once expressed within the plant cell or the entire plant, the level of the polypeptide encoded by the exogenous polynucleotide can be determined by methods well known in the art such as, activity assays, Western blots using antibodies capable of specifically binding the polypeptide, Enzyme-Linked Immuno Sorbent Assay (ELISA), radio-immuno-assays (RIA), immunohistochemistry, immunocytochemistry, immunofluorescence and the like.

Methods of determining the level in the plant of the RNA transcribed from the exogenous polynucleotide are well known in the art and include, for example, Northern blot analysis, reverse transcription polymerase chain reaction (RT-PCR) analysis (including quantitative, semi-quantitative or real-time RT-PCR) and RNA-in situ hybridization.

The effect of the expressed HXK on plant stomata conductance (e.g., manifested by aperture), water use efficiency, water use efficiency and/or photosynthesis can be qualified using methods which are well known in the art. Stomata functionality assays are described in length in the Examples section which follows.

The effect of the exogenous polynucleotide encoding the HXK on abiotic stress tolerance can be determined using known methods such as detailed below and in the Examples section which follows.

Abiotic stress tolerance—Transformed (i.e., expressing the HXK) and non-transformed (wild type) plants are exposed to biotic or an abiotic stress condition, such as water deprivation or suboptimal temperature (low temperature, high temperature).

Cold stress tolerance—To analyze cold stress, mature (25 day old) plants are transferred to 4° C. chambers for 1 or 2 weeks, with constitutive light. Later on plants are moved back to greenhouse. Two weeks later damages from chilling period, resulting in growth retardation and other phenotypes, are compared between both control and transgenic plants, by measuring plant weight (wet and dry), and by comparing growth rates measured as time to flowering, plant size, yield, and the like.

Heat stress tolerance—Heat stress tolerance is achieved by exposing the plants to temperatures above 34° C. for a certain period. Plant tolerance is examined after transferring the plants back to 22° C. for recovery and evaluation after 5 days relative to internal controls (non-transgenic plants) or plants not exposed to neither cold or heat stress.

Water use efficiency—can be determined as the biomass produced per unit transpiration. To analyze WUE, leaf relative water content can be measured in control and transgenic plants. Fresh weight (FW) is immediately recorded; then leaves are soaked for 8 hours in distilled water at room temperature in the dark, and the turgid weight (TW) is recorded. Total dry weight (DW) is recorded after drying the leaves at 60° C. to a constant weight. Relative water content (RWC) is calculated.

Salinity tolerance assay—Transgenic plants with tolerance to high salt concentrations are expected to exhibit better germination, seedling vigor or growth in high salt. Salt stress can be effected in many ways such as, for example, by irrigating the plants with a hyperosmotic solution, by cultivating the plants hydroponically in a hyperosmotic growth solution (e.g., Hoagland solution), or by culturing the plants in a hyperosmotic growth medium [e.g., 50% Murashige-Skoog medium (MS medium)]. Since different plants vary considerably in their tolerance to salinity, the salt concentration in the irrigation water, growth solution, or growth medium can be adjusted according to the specific characteristics of the specific plant cultivar or variety, so as to inflict a mild or moderate effect on the physiology and/or morphology of the plants (for guidelines as to appropriate concentration see, Bernstein and Kafkafi, Root Growth Under Salinity Stress In: Plant Roots, The Hidden Half 3rd ed. Waisel Y, Eshel A and Kafkafi U. (editors) Marcel Dekker Inc., New York, 2002, and reference therein).

For example, a salinity tolerance test can be performed by irrigating plants at different developmental stages with increasing concentrations of sodium chloride (for example 50 mM, 100 mM, 200 mM, 400 mM NaCl) applied from the bottom and from above to ensure even dispersal of salt. Following exposure to the stress condition the plants are frequently monitored until substantial physiological and/or morphological effects appear in wild type plants. Thus, the external phenotypic appearance, degree of wilting and overall success to reach maturity and yield progeny are compared between control and transgenic plants.

Quantitative parameters of tolerance measured include, but are not limited to, the average wet and dry weight, growth rate, leaf size, leaf coverage (overall leaf area), the weight of the seeds yielded, the average seed size and the number of seeds produced per plant. Transformed plants not exhibiting substantial physiological and/or morphological effects, or exhibiting higher biomass than wild-type plants, are identified as abiotic stress tolerant plants.

Osmotic tolerance test—Osmotic stress assays (including sodium chloride and mannitol assays) are conducted to determine if an osmotic stress phenotype was sodium chloride-specific or if it was a general osmotic stress related phenotype. Plants which are tolerant to osmotic stress may have more tolerance to drought and/or freezing. For salt and osmotic stress germination experiments, the medium is supplemented for example with 50 mM, 100 mM, 200 mM NaCl or 100 mM, 200 mM NaCl, 400 mM mannitol.

The effect of the transgene on plant's vigor, growth rate, biomass, yield and/or oil content can be determined using known methods.

Plant vigor—The plant vigor can be calculated by the increase in growth parameters such as leaf area, fiber length, rosette diameter, plant fresh weight and the like per time.

Growth rate—The growth rate can be measured using digital analysis of growing plants. For example, images of plants growing in greenhouse on plot basis can be captured every 3 days and the rosette area can be calculated by digital analysis. Rosette area growth is calculated using the difference of rosette area between days of sampling divided by the difference in days between samples.

As mentioned, the present teachings are also directed at downregulating HXK activity or expression in a guard cell specific manner. This is effected to increase plant dehydration where needed. For example when there is a need to accelerate defoliation prior or after harvesting such as in cotton and other crops, or for dehydration of leaves and stems for straw for instance.

Downregulation (gene silencing) of the transcription or translation product of an endogenous HXK in a guard-cell specific manner can be achieved by co-suppression, anti-sense suppression, RNA interference and ribozyme molecules under the above mentioned cis-acting regulatory element active specifically in a guard cell.

Thus, there is provided a plant expression construct comprising a nucleic acid sequence encoding a nucleic acid agent for silencing expression of a hexokinase, wherein expression of said nucleic acid agent is under a transcriptional control of a guard cell-specific cis-acting regulatory element (as described above).

Co-suppression (sense suppression)—Inhibition of the endogenous gene can be achieved by co-suppression, using an RNA molecule (or an expression vector encoding same) which is in the sense orientation with respect to the transcription direction of the endogenous gene. The polynucleotide used for co-suppression may correspond to all or part of the sequence encoding the endogenous polypeptide and/or to all or part of the 5' and/or 3' untranslated region of the endogenous transcript; it may also be an unpolyadenylated RNA; an RNA which lacks a 5' cap structure; or an RNA which contains an unsplicable intron. In some embodiments, the polynucleotide used for co-suppression is designed to eliminate the start codon of the endogenous polynucleotide so that no protein product will be translated. Methods of co-suppression using a full-length cDNA sequence as well as a partial cDNA sequence are known in the art (see, for example, U.S. Pat. No. 5,231,020).

According to some embodiments of the invention, downregulation of the endogenous gene is performed using an amplicon expression vector which comprises a plant virus-derived sequence that contains all or part of the target gene but generally not all of the genes of the native virus. The viral sequences present in the transcription product of the expression vector allow the transcription product to direct its own replication. The transcripts produced by the amplicon may be either sense or antisense relative to the target sequence [see for example, Angell and Baulcombe, (1997) EMBO J. 16:3675-3684; Angell and Baulcombe, (1999) Plant J. 20:357-362, and U.S. Pat. No. 6,646,805, each of which is herein incorporated by reference].

Antisense suppression—Antisense suppression can be performed using an antisense polynucleotide or an expression vector which is designed to express an RNA molecule complementary to all or part of the messenger RNA (mRNA) encoding the endogenous polypeptide and/or to all or part of the 5' and/or 3' untranslated region of the endogenous gene. Over expression of the antisense RNA molecule can result in reduced expression of the native (endogenous) gene. The antisense polynucleotide may be fully complementary to the target sequence (i.e., 100% identical to the complement of the target sequence) or partially complementary to the target sequence (i.e., less than 100% identical, e.g., less than 90%, less than 80% identical to the comple- ment of the target sequence). Antisense suppression may be used to inhibit the expression of multiple proteins in the same plant (see e.g., U.S. Pat. No. 5,942,657). In addition, portions of the antisense nucleotides may be used to disrupt the expression of the target gene. Generally, sequences of at least about 50 nucleotides, at least about 100 nucleotides, at least about 200 nucleotides, at least about 300, at least about 400, at least about 450, at least about 500, at least about 550, or greater may be used. Methods of using antisense suppression to inhibit the expression of endogenous genes in plants are described, for example, in Liu, et al., (2002) Plant Physiol. 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal [See, U.S. Patent Publication No. 20020048814, herein incorporated by reference].

RNA interference—RNA interference can be achieved using a polynucleotide, which can anneal to itself and form a double stranded RNA having a stem-loop structure (also called hairpin structure), or using two polynucleotides, which form a double stranded RNA.

For hairpin RNA (hpRNA) interference, the expression vector is designed to express an RNA molecule that hybridizes to itself to form a hairpin structure that comprises a single-stranded loop region and a base-paired stem.

In some embodiments of the invention, the base-paired stem region of the hpRNA molecule determines the specificity of the RNA interference. In this configuration, the sense sequence of the base-paired stem region may correspond to all or part of the endogenous mRNA to be downregulated, or to a portion of a promoter sequence controlling expression of the endogenous gene to be inhibited; and the antisense sequence of the base-paired stem region is fully or partially complementary to the sense sequence. Such hpRNA molecules are highly efficient at inhibiting the expression of endogenous genes, in a manner which is inherited by subsequent generations of plants [See, e.g., Chuang and Meyerowitz, (2000) Proc. Natl. Acad. Sci. USA 97:4985-4990; Stoutjesdijk, et al., (2002) Plant Physiol. 129:1723-1731; and Waterhouse and Helliwell, (2003) Nat. Rev. Genet. 4:29-38; Chuang and Meyerowitz, (2000) Proc. Natl. Acad. Sci. USA 97:4985-4990; Pandolfini et al., BMC Biotechnology 3:7; Panstruga, et al., (2003) Mol. Biol. Rep. 30:135-140; and U.S. Patent Publication No. 2003/0175965; each of which is incorporated by reference].

According to some embodiments of the invention, the sense sequence of the base-paired stem is from about 10 nucleotides to about 2,500 nucleotides in length, e.g., from about 10 nucleotides to about 500 nucleotides, e.g., from about 15 nucleotides to about 300 nucleotides, e.g., from about 20 nucleotides to about 100 nucleotides, e.g., or from about 25 nucleotides to about 100 nucleotides.

According to some embodiments of the invention, the antisense sequence of the base-paired stem may have a length that is shorter, the same as, or longer than the length of the corresponding sense sequence.

According to some embodiments of the invention, the loop portion of the hpRNA can be from about 10 nucleotides to about 500 nucleotides in length, for example from about 15 nucleotides to about 100 nucleotides, from about 20 nucleotides to about 300 nucleotides or from about 25 nucleotides to about 400 nucleotides in length.

According to some embodiments of the invention, the loop portion of the hpRNA can include an intron (ihpRNA), which is capable of being spliced in the host cell. The use of an intron minimizes the size of the loop in the hairpin RNA molecule following splicing and thus increases efficiency of the interference [See, for example, Smith, et al., (2000) Nature 407:319-320; Wesley, et al., (2001) Plant J. 27:581-590; Wang and Waterhouse, (2001) Curr. Opin. Plant Biol. 5:146-150; Helliwell and Waterhouse, (2003) Methods 30:289-295; Brummell, et al. (2003) Plant J. 33:793-800; and U.S. Patent Publication No. 2003/0180945; WO 98/53083; WO 99/32619; WO 98/36083; WO 99/53050; US 20040214330; US 20030180945; U.S. Pat. Nos. 5,034,323; 6,452,067; 6,777,588; 6,573,099 and 6,326,527; each of which is herein incorporated by reference].

In some embodiments of the invention, the loop region of the hairpin RNA determines the specificity of the RNA interference to its target endogenous RNA. In this configuration, the loop sequence corresponds to all or part of the endogenous messenger RNA of the target gene. See, for example, WO 02/00904; Mette, et al., (2000) EMBO J 19:5194-5201; Matzke, et al., (2001) Curr. Opin. Genet. Devel. 11:221-227; Scheid, et al., (2002) Proc. Natl. Acad. Sci., USA 99:13659-13662; Aufsaftz, et al., (2002) Proc. Nat'l. Acad. Sci. 99(4):16499-16506; Sijen, et al., Curr. Biol. (2001) 11:436-440), each of which is incorporated herein by reference.

For double-stranded RNA (dsRNA) interference, the sense and antisense RNA molecules can be expressed in the same cell from a single expression vector (which comprises sequences of both strands) or from two expression vectors (each comprising the sequence of one of the strands). Methods for using dsRNA interference to inhibit the expression of endogenous plant genes are described in Waterhouse, et al., (1998) Proc. Natl. Acad. Sci. USA 95:13959-13964; and WO 99/49029, WO 99/53050, WO 99/61631, and WO 00/49035; each of which is herein incorporated by reference.

According to some embodiments of the invention, RNA interference is effected using an expression vector designed to express an RNA molecule that is modeled on an endogenous micro RNAs (miRNA) gene. Micro RNAs (miRNAs) are regulatory agents consisting of about 22 ribonucleotides and highly efficient at inhibiting the expression of endogenous genes [Javier, et al., (2003) Nature 425:257-263]. The miRNA gene encodes an RNA that forms a hairpin structure containing a 22-nucleotide sequence that is complementary to the endogenous target gene.

Thus, the present teachings provide for a transgenic plant or a part thereof comprising the plant expression construct as described herein as well as isolated plant cell or a plant cell culture comprising the plant expression construct as described herein.

The present teachings also relate to processed products produced from the plants, plant parts or plant cells of the present invention. Such processed products relate to food, animal feed, beverages, construction material, biofuel, biodiesel, oils, sauces, pastes, pastries, meal and the like.

It is expected that during the life of a patent maturing from this application many relevant hexokinases and guard cell specific cis-acting regulatory elements will be developed and the scope of the terms used herein are intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, cellular and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); all of which are incorporated by reference as if fully set forth herein. Other general references are provided throughout this document. The procedures therein are believed to be well known in the art and are provided for the convenience of the reader. All the information contained therein is incorporated herein by reference.

EXAMPLE 1

Materials and Methods

Plant Material and Growth Conditions

Experiments were conducted using WT tomato (*Solanum lycopersicum* cv. MP-1), isogenic independent transgenic homozygous tomato lines expressing different levels of the Arabidopsis AtHXK1 (35S::AtHXK1) [as previously described by Dai et al. (1999)], isogenic transgenic homozygous lines with antisense suppression of the tomato LeHXK1,2&3 genes, isogenic transgenic homozygous lines expressing GFP or AtHXK1 under the control of the KST1 promoter, and the ABA-deficient mutant Sitiens (Dai et al., 1999) (*S. lycopersicum* cv. Ailsa Craig).

Independent antisense-HXK tomato lines, αHK1 and αHK2, were generated following transformation of MP-1 with an antisense construct of StHXK1 (X94302) expressed under the 35S promoter. The potato StHXK1 shares over 80% sequence identity with LeHXK1,2&3 and conferred suppression of LeHXK1,2&3 (FIG. 4A). Arabidopsis (Col.) and tomato (MP-1) lines that express GFP or AtHXK1 specifically in guard cells (GCGFP and GCHXK lines, respectively) were generated following transformation with GFP or AtHXK1 expressed under the KST1 promoter (Muller-Rober et al., 1995). Independent transgenic homozygous lines for each construct were then identified. The tomato plants were grown in a temperature-controlled greenhouse under natural growth conditions and the Arabidopsis plants were grown in a walk-in growth chamber kept at 22° C., with an 8-h light/16-h dark photoperiod.

Stomatal Measurements

Stomatal aperture and density are determined using the rapid imprinting technique described by Geisler and Sack (2002). This approach allows to reliably score hundreds of stomata from each experiment, each of which is sampled at the same time. Light-bodied vinylpolysiloxane dental resin (Heraeus-Kulzer, Hanau, Germany) is attached to the abaxial leaf side and then removed as soon as it dries (1 min). The resin epidermal imprints are than covered with nail polish, which removed once it had dried out and serves as a mirror image of the resin imprint. The nail-polish imprints are put on glass cover slips and photographed under bright-field microscope. Stomata images are later analyzed to determine aperture size using the ImageJ software (World Wide Web (dot) rsb (dot) info (dot) nih (dot) gov/ij/) fit-ellipse tool or any other software that can process and analyze images. A microscopic ruler is used for the size calibration. Additional information can be obtained from the software such as stomata width, length, area, perimeter etc.

To assess stomatal responses, leaflets are cut and immediately immerse in artificial xylem sap solution (AXS) (Wilkinson and Davies, 1997) containing 100 mM sucrose (Duchefa Biochemie) with or without 20 mM N-acetyl glucosamine (NAG, Sigma-Aldrich), 100 mM or 200 mM glucose (Duchefa Biochemie), 100 mM or 200 mM fructose (Sigma-Aldrich), 100 mM 2-deoxyglucose (Sigma-Aldrich), 10 mM or 100 mM mannose (Sigma-Aldrich), 100 mM sorbitol (Sigma-Aldrich) or 100 mM or 200 mM mannitol (Duchefa Biochemie). The sorbitol and mannitol treatments serve as non-metabolic osmotic controls. Imprints are taken 3 h after immersion and stomatal aperture is analyzed. Different plant species can be used as well as, AXS solutions, treatment solutions and different timings to our decision.

Gas Exchange Analysis

Gas exchange measurements are assayed using a Li-6400 portable gas-exchange system (LI-COR). Plants are growing under favorable or stressed conditions, and measurements are conducted on fully expanded leaf, $5^{th}$-$6^{th}$ from top in the case of tomato. All measurements are conducted between 10:00 AM and 2:00 PM. We are inducing photosynthesis under saturating light (1000-1200 µmol $m^{-2}$ $sec^{-1}$) with 370 µmol $mol^{-1}$ CO2 surrounding the leaf (Ca). The amount of blue light is set to 15% photosynthetically active photon flux density to optimize stomatal aperture. The leaf-to-air VPD (Vapor pressure deficit) is kept at around 1 to 2.5 kPa and leaf temperature is kept at around 25° C., during all measurements. Once a steady state is reached, measurements are done. It is possible to tune each of the above mentioned parameters. Each measurement contains data of photosynthesis (µmol $CO_2$ $m^{-2}$ $s^{-1}$), transpiration (mmol $H_2O$ $m^{-2}$ $s^{-1}$), Stomatal conductance (mol $H_2O$ $m^{-2}$ $s^{-1}$), and calculated instantaneous water use efficiency (µmol $CO_2$ $mmol^{-1}$ $H_2O$). Additional data obtained from each measurement are mesophyll conductance for $CO_2$ (mol $CO_2$ $m^{-2}$ $s^{-1}$ $bar^{-1}$), electron transport rate, calculated from PS (photosystem) II quantum yield and internal $CO_2$ concentrations (Ci).

For stomatal conductance ($g_s$) measurements the leaf conductance steady-state porometer LI-1600 (LI-COR, Lincoln, Nebr.) is used according to manufacture instructions.

Whole-Plant Transpiration Measurements

Whole-plant transpiration rates and relative daily transpiration (RDT) are determined using a wide-screen lysimeter-scale system, which allows measurements of up to 160 plants simultaneously. Plants are planted in 3.9-L pots and grow under controlled conditions. Each pot is placed on a temperature-compensated load cell with digital output and is sealed to prevent evaporation from the surface of the growth medium. A wet vertical wick made of 0.15 $m^2$ cotton fibers partially submerged in a 1-L water tank is placed on a similar load cell and use as a reference for the temporal variations in the potential transpiration rate. The output of the load cells is monitored every 10 s and the average readings over 3 min are logged in a data logger for further analysis. The output data includes whole plant transpiration, plant weight, light intensity, vapor pressure deficit (VPD), temperature, stomatal conductance, water use efficiency and additional environmental and physiological parameters. The whole-plant transpiration rate is calculated by a numerical derivative of the load cell output following a data-smoothing process (Sade et al., 2010). The plant's daily transpiration rate is normalized to the total plant weight and the data for neighboring submerged wick and these figures are averaged for a given line over all plants (amount taken up by the wick daily=100%). Water use efficiency is calculated from the daily weight added against the daily water loss for each plant. Plants RDT is monitored under different growth conditions to our decision: Normal irrigation, drought, salt treatment and more. It is possible to shift growth conditions on a daily bases and to monitor plants responses.

RNA Extraction, cDNA Generation and Quantitative Real-Time PCR Expression Analysis (Based on Goren 2011, Kandel-Kfir 2006)

Tissue samples are snap-frozen and homogenize in liquid nitrogen. RNA is extracted using the EZ-RNA kit (Biological Industries, Kibbutz Bet Haemek, Israel), with up to 500 µl of frozen homogenized tissue per extraction tube. At least four independent extractions are performed for each tissue set. The extractions are carried out according to the manufacturer's protocol, including two optional washes in 2 M LiCl. RNA pellets are than suspended in 25 µl DEPC-treated $H_2O$ and treated with DNase (Ambion, Austin, Tex., USA) according to the manufacturer's instructions. RNA presence is confirmed by gel electrophoresis and DNA degradation is confirmed by PCR. RNA (≤1 µg) from each sample is than reverse-transcribed to cDNA using MMLV RT (ProMega, Madison, Wis., USA) in a 25-µl reaction, with 2 µl random primers and 1 µl mixed poly-dT primers (18-23 nt). All cDNA samples are diluted 1:8 in DEPC-treated water.

Real-time reactions are prepared using SYBR Green mix (Eurogentec S.A., Seraing, Belgium) in 10 µl volumes with 4 µl diluted cDNA per reaction, two replicates per cDNA sample. Reactions run in a RotorGene 6000 cycler (Corbett, Mortlake, New South Wales, Australia), 40 cycles per run, with sampling after each cycle. Following an initial preheating step at 95° C. for 15 min, there are 40 cycles of amplification consisting of 10 s at 95° C., 15 s at 55° C., 10 s at 60° C. and 20 s at 72° C. Results are than interpreted using RotorGene software, two duplicates per sample. Data are normalized using SlCyP as a reference gene (cyclophilin—accession no. M55019). Primers used for amplification: SlCyP—CGTCGTGTTTGGACAAGTTG (SEQ ID NO: 1) and CCGCAGTCAGCAATAACCA (SEQ ID NO: 2). The primers for SlHXKs (LeHXKs) are as follows: for SlHXK1- GACTTGCTGGGAGAGGAGT (SEQ ID NO: 3) and AAGGTACATTGAATGAGAGGCA (SEQ ID NO: 4); for SlHXK2-GTCCTCCCATCTTCCCTTG (SEQ ID NO: 5) and CCCAAGTACATACCAGAACAT (SEQ ID NO: 6); for SlHXK3-GCGATATTATCACCTCTCGTG (SEQ ID NO: 7) and CTGCTTCTCTCCGTCTTTAAA (SEQ ID NO: 8); and for SlHXK4-GCTGAGGACACCTGATATATG (SEQ ID NO: 9) and GATCGGATTTTACCCCAGCTA (SEQ ID NO: 10).

Protein Extraction and Analysis of Hexokinase Activity

Protein extraction from plant leaves is performed with 1 to 2 g of plant tissue homogenized in 4 volumes of extraction buffer (50 mM Hepes, pH 7.6, 1 mM EDTA, 15 mM KCl, 1 mM MgCl2, 1 mM phenylmethylsulfonyl fluoride, 3 mM diethyldithiocarbamic acid, and 0.2% PVP). The mixture is centrifuged for 25 min at 16,000 g at 48 C, and the supernatant is brought to 80% ammonium sulfate saturation. After centrifugation, the pellet is resuspended in 0.5 mL of washing buffer (50 mM Hepes, pH 7.5, 1 mM EDTA, and 1 mM DTT), desalted on a G-25 Sephadex column (55×11 mm), and used as a crude enzyme extract for subsequent enzymatic analysis.

Hexokinase activity is measured by enzyme-linked assay according to Schaffer and Petreikov (1997). The assays contain a total volume of 1 mL of 30 mM Hepes-NaOH, pH 7.5, 2 mM MgCl2, 0.6 mM EDTA, 9 mM KCl, 1 mM NAD, 1 mM ATP, and 1 unit of NAD-dependent glucose-6-phosphate dehydrogenase (G6PDH from Leuconostoc mesenteroides; Sigma). To assay glucose phosphorylation, the reaction is initiated with 2 mM glucose. Reactions are conducted at 37° C., and absorption at 340 nm is monitored continuously. (For additional information see Dai et al. 1999, Schaffer and Petreikov, 1997).

Monitoring Nitric Oxide Production in Guard Cells

Detection of nitric oxide (NO) levels in stomata is performed as follows: Epidermal peels are prepared and incubated in MES buffer [25 mM MES-KOH, pH=6.15 and 10 mM KCl (MES, 2-(N-morpholino)-ethane sulfonic acid; Sigma-Aldrich] with or without 20 mM NAG, for 2.5 h under steady light, and then loaded with 60 µM NO indicator dye, DAF-2DA (4, 5-diaminofluorescein diacetate; Sigma-Aldrich), diluted in MES buffer with or without 20 mM N-acetyl glucosamine (NAG, Sigma-Aldrich) and left for an additional 50 min. Then, the peels are washed with MES 3 times and re-incubated for 30 min in the buffer (control, set as 100% fluorescence) or in 100 mM sorbitol, 100 mM sucrose and 20 mM NAG. The peels are then photographed under a microscope (see Materials and Methods, "Confocal microscopy imaging"). Three to four biological repeats containing 20-30 stomata each are included in each experiment and each experiment is repeated several times. Images are analyzed using the ImageJ software histogram tool to evaluate fluorescence intensity and the fit-ellipse tool to determine stomatal aperture. It is possible to use epidermal strips from different species, use different treatments solutions and different timings, all to our decision.

Confocal Microscopy Imaging

Images are acquired using the OLYMPUS IX 81 (Japan) inverted laser scanning confocal microscope (FLUOVIEW 500) equipped with a 488-nm argon ion laser and a 60X1.0 NA PlanApo water immersion objective. Nitric oxide- DAF-2DA (4, 5-diaminofluorescein diacetate; Sigma-Aldrich) fluorescence is excited by 488-nm light and the emission is collected using a BA 505-525 filter. GFP is excited by 488-nm light and the emission is collected using a BA 505-525 filter. A BA 660 IF emission filter is used to observe chlorophyll autofluorescence. Confocal optical sections are obtained at 0.5-µm increments. The images are color-coded green for GFP and magenta for chlorophyll autofluorescence.

Thermal Imaging

Leaf temperature is a reliable tool for determine transpiration variation among different conditions and different plant species. High temperatures are associated with closed stomata and low transpiration, while low temperature points out for open stomata and high transpiration. For thermal imaging, leaves are imaged using a thermal camera (ThermaCAM model SC655; FLIR Systems). Pictures are later analyzed using the ThermaCAM researcher pro 2.10 software. The experiments are repeated several times. Data are means ±SE from five biological repeats per line; four leaves are analyzed per plant.

Use of KST1 as a Guard Cell Specific Promoter

The KST1 potassium channel in potato (*Solanum tuberosum* L.) has been shown to be expressed specifically in guard cells (Muller-Rober et al., 1995). Later, by GUS activity and staining assay it has been demonstrated that KST1 promoter segment can be used to express genes exclusively in guard cells (Plesch et al., 2001). Using this knowledge, transgenic tomato and Arabidopsis plants were generated overexpressing Arabidopsis hexokinase1 (KST::AtHXK1) or GFP (green fluorescence protein) (as a control for exclusive expression) specifically in guard cells in the following procedures:
1. Creation of binary vector containing an insert of AtHXK1 cDNA under KST1 promoter followed by terminator.
2. Creation of binary vector containing an insert of GFP gene under KST1 promoter followed by terminator.
3. Plant transformation.
4. Identification of plants containing KST1::AtHXK1 trait.

Creation of a Binary Vector Containing an Insert of AtHXK1 cDNA or GFP Under KST1 Promoter Followed by Terminator.

The binary vector pGreen0029 was used (Hellens et al., 2000b) for transformation into tomato and Arabidopsis plants. The KST1 promoter was ligated upstream the AtHXKl coding sequence (isolated by (Dai et al., 1995) or GFP followed by a terminator (See FIGS. 17A-17B).

EXAMPLE 2

Sucrose Stimulates Stomatal Closure

To examine the effect of Suc on stomata, intact wild-type (WT) tomato leaflets were immersed in artificial apoplastic solutions (Wilkinson and Davies, 1997) containing either 100 mM Suc or 100 mM sorbitol, a non-metabolic sugar used as an osmotic control, and measured stomatal aperture. Suc decreased stomatal aperture size by 29% relative to sorbitol (FIGS. 1A, 1B). Sucrose is a disaccharide that has to be cleaved. It may be cleaved by cell wall (apoplastic) invertases, yielding glucose (Glc) and fructose (Fm) in equal proportions (Granot, 2007) and resulting in additional extracellular osmolarities approaching 200 mOsm/L, as compared to the 100 mOsm/L of the original Suc added. We, therefore, compared the effects of 100 mM sucrose, 100 mM Glc+100 mM Fm and 200 mM Glc or Fm with the effect of 200 mM mannitol, which was used as an additional osmotic control. All of the sugar combinations decreased the size of stomatal apertures, as compared to the effect of 200 mM mannitol (FIG. 1C), supporting an osmotic-independent role for sugars in the regulation of stomatal closure.

EXAMPLE 3

Sucrose Stimulates Stomatal Closure Via Hexokinase

Sucrose may be cleaved by either apoplastic (extracellular) invertase or enter the cells via sucrose transporters and then be cleaved by intracellular sucrose-cleaving enzymes to yield the hexoses Glc and Fru. The hexoses Glc and Fru must be phosphorylated by hexose-phosphorylating enzymes (Granot, 2007). In plants, hexokinases (HXK) are the only enzymes that can phosphorylate Glc and may also phosphorylate Fm (Granot, 2007, 2008). HXKs are intracellular enzymes known to play both kinetic and sugar-signaling roles (Rolland et al., 2006). To examine whether Suc stimulates stomatal closure via HXK, the effect of Suc was tested in the presence of N-acetyl glucosamine (NAG), an efficient inhibitor of HXK activity (Hofmann and Roitsch, 2000). NAG almost completely abolished the effect of Suc and prevented stomatal closure, supporting a role for HXK in the regulation of stomatal closure (FIG. 1B).

EXAMPLE 4

Increased Expression of HXK Enhances Stomatal Closure

To further explore whether HXK mediates stomatal closure, the effect of Suc was examined on well-characterized transgenic tomato plants expressing the Arabidopsis HXK1 (AtHXK1) under the control of the global non-specific 35S promoter (Dai et al., 1999). The stomatal aperture of AtHXK1-expressing plants (the HK4 line, which has a level of HXK activity that is 5 times higher than that of WT plants) was reduced by 21% relative to the control plants even under the control conditions (100 mM sorbitol) (FIG. 1B), indicating that increased expression of HXK induces stomatal closure. The addition of Suc caused the stomata to close even further (FIG. 1B) and the HXK inhibitor NAG abolished the closing effect of Suc, further supporting a role for HXK in the regulation of stomatal closure (FIG. 1B).

EXAMPLE 5

Direct Correlation Between HXK Activity, Stomatal Closure and Reduced Transpiration To examine the effect of HXK on tomato stomata, the stomatal apertures and conductance of tomato lines expressing increasing levels of AtHXK1 were measured. (The HK37, HK4 and HK38 lines have levels of HXK activity that are 2, 5 and 6 times higher than those of WT plants, respectively) (Dai et al., 1999). The stomatal densities of the AtHXK1-expressing lines are similar to those of WT plants (Table S1), yet both stomatal aperture and conductance were significantly reduced, in direct correlation with the level of AtHXK1 expression (FIGS. 2A, 2B). Furthermore, continued measurement of transpiration over the course of the day revealed that AtHXK1 lowered the transpiration rate per unit leaf area in the AtHXK1-expressing lines, in correlation with the level of AtHXK1 expression (FIG. 2C), so that the cumulative whole-plant relative daily transpiration per unit leaf area (RDT) was clearly negatively correlated with HXK activity (FIG. 2D).

Figure 3D:
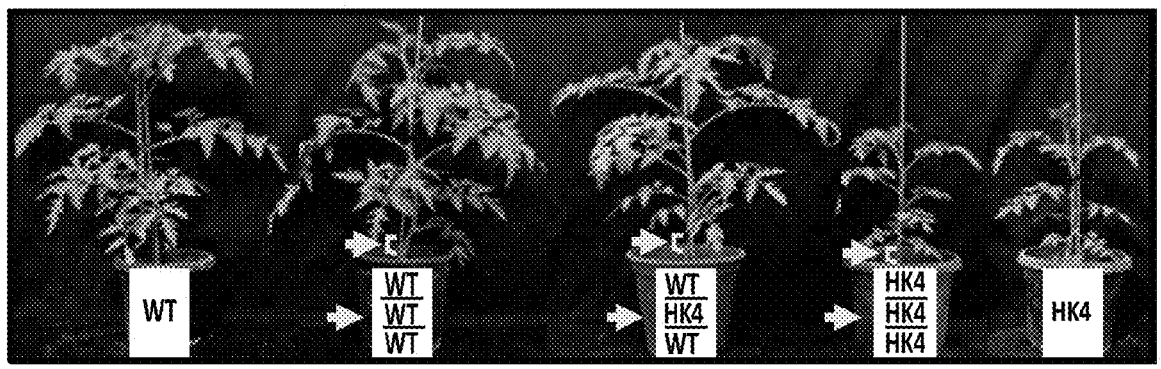

To rule out the possibility that the observed decrease in transpiration was the result of inhibitory effects of AtHXK1 on root water uptake or stem water transport, reciprocal grafting experiments were performed. HK4 shoots were grafted onto WT roots and WT shoots were grafted onto HK4 roots (FIG. 3A). Continued measurements of the transpiration rates and cumulative whole-plant relative daily transpiration per unit leaf area of the grafted plants indicated that decreased transpiration was generally associated with HK4 shoots, with the roots having only minor influence (FIGS. 3B, 3C). To further examine the effect of HK4 stems on transpiration, triple-grafted plants were generated in which HK4 interstock replaced a portion of the stem of WT plants (FIG. 3D). The HK4 interstock had no effect on RDT (FIG. 3E), indicating that the decreased transpiration of AtHXK1-expressing plants was the result of reduced transpiration by the leaves and not reduced water uptake by the roots or attenuated transport through the stem. The effect of AtHXK1 on leaf transpiration further indicates that HXK controls stomatal behavior that affects the transpiration of intact whole plants.

EXAMPLE 6

Suppression Of HXK Inhibits Stomatal Closure

The role of HXK in stomatal closure was further examined using tomato and Arabidopsis plants with antisense suppression and knockdown mutants of HXK, respectively. Four HXKs are known in tomato plants, three of which (LeHXK1,2 and 3) are mitochondria-associated HXKs similar to the sugar sensor AtHXK1 (Granot, 2007, 2008). Unlike the stomatal closure observed in tomato plants expressing high level of AtHXK1 (FIGS. 2A, 2B), stomatal closure in tomato lines (αHK1 and αHK2) with antisense suppression of LeHXK1,2&3 (FIG. 4A) was diminished in response to Suc treatments (FIG. 4B). Similarly, the Arabidopsis AtHXK1-knockout gin2-1 mutant had higher stomatal conductance and a higher transpiration rate, as compared to wild-type control plants (FIGS. 8E, 8F), supporting the hypothesis that HXK plays a role in the regulation of stomatal closure.

EXAMPLE 7

HXK Mediates Stomatal Closure Independent of Downstream Metabolism of the Phosphorylated Sugars To examine whether downstream metabolism of the phosphorylated sugars is required for stomatal closure, the effects of mannose (a glucose epimer at the second carbon atom) and 2-dexoxyglucose (2-dG—a glucose analog) were tested. Both of these sugars are phosphorylated by HXK, but 2-dG is not further metabolized and mannose is poorly metabolized (Klein and Stitt, 1998; Pego et al., 1999). Both mannose and 2-dG reduced stomatal aperture (FIG. 5). A lower concentration of mannose (10 mM) also reduced stomatal aperture more than 100 mM glucose (FIG. 5), in line with previous observations that mannose is more potent than glucose with regard to HXK-mediated sugar effects (Jang and Sheen, 1994; Pego et al., 1999). Moreover, the closure effect of 10 mM mannose further supports an osmotic-independent role of sugars in the stimulation of stomatal closure. The results with mannose and 2-dG suggest that HXK stimulates stomatal closure independent of downstream metabolism of the phosphorylated sugars.

EXAMPLE 8

Sucrose Stimulates an ABA-Signaling Pathway in Guard Cells

It has previously been shown that the sugar-signaling effects of HXK, such as the inhibition of photosynthesis and growth, are mediated by abscisic acid (ABA) [for an updated review see Rolland et al. (2006)], a well-known phytohormone that also induces stomatal closure. Therefore, it was speculated that Suc might modulate guard-cell aperture via the HXK and ABA within guard cells. ABA-signaling in guard cells is mediated by the rapid production of nitric oxide (NO), which is required for ABA-induced stomatal closure and serves as an indicator of stomatal-closure stimuli (Garcia-Mata et al., 2003; Neill et al., 2008). To examine the effect of Suc on the ABA-signaling pathway in guard cells, NO levels were monitored within guard cells in response to applications of Suc. Epidermal peels were incubated with Suc and monitored using the fluorescent NO indicator dye diaminofluorescein diacetate (DAF-2DA). Applications of 100 mM sorbitol had no effect on NO levels in guard cells (FIG. 6A). However, the application of 100 mM Suc resulted in a 3.5-fold increase in guard-cell fluorescence, indicating a rapid increase in NO levels, which was correlated with stomatal closure (FIG. 6A). The guard cells of untreated HK4 (AtHXK1-expressing line) epidermal peels exhibited high NO levels, similar to those of Suc-treated WT epidermal peels (FIG. 6B), and the addition of Suc to the peeled HK4 epidermis led to even more intense fluorescence (FIG. 6B).

To further examine the involvement of HXK in the production of NO in guard cells, the HXK inhibitor NAG was used with epidermal peels. NAG not only inhibited the effect of Suc and blocked stomatal closure (FIG. 1B), it also prevented the production of NO (FIG. 6C). Washing out NAG with 100 mM Suc led to the resumption of NO production within less than 30 min (FIGS. 6D, 6E). These results suggest that Suc elicits a guard cell-specific NO response via HXK.

To verify that ABA is indeed required for the stomatal NO response to Suc, the same experiments were conducted with the ABA-deficient tomato mutant Sitiens, whose stomata are always open (Neill and Horgan, 1985). Unlike what was observed for the WT plants, treating Sitiens epidermal peels with 100 mM Suc did not result in any increase in fluorescence or stomatal closure, indicating that there was no production of NO (FIG. 6F). However, treating Sitiens peels with externally supplied ABA did trigger the production of NO (FIG. 6F) and stomatal closure. These findings indicate that Sitiens's guard cells retain their ability to respond to externally supplied ABA by producing NO and that only the absence of ABA production in the Sitiens mutant prevents Suc-triggered NO production and stomatal closure. This observation confirms that Sitiens stomata do not respond to Suc due to this mutant's ABA deficiency and that ABA is a vital mediator of the stomatal response to Suc.

EXAMPLE 9

Guard-Cell Specific Expression of ATHXK1 Induces Stomatal Closure and Reduces Transpiration of Tomato and Arabidopsis Plants.

To examine the role of HXK specifically in guard cells, tomato and Arabidopsis plants were generated that express AtHXK1 under the KST1 guard-cell specific promoter (Muller-Rober et al., 1995). The specific expression of the KST1 promoter in tomato and Arabidopsis guard cells was verified by expression of GFP under the KST1 promoter (GCGFP lines, FIGS. 7A-7E). Expression of the KST1 promoter was specific to guard cells in all of the examined plant organs and was not detected in organs that do not have stomata, such as roots (FIG. 7E). Guard-cell specific expression was recorded from early seedling development, as observed in the hypocotyls of seedlings (FIG. 7D), through the stages in which leaves are fully expanded (FIGS. 7A-7C).

Unlike the expression of AtHXK1 under the 35S promoter (Dai et al., 1999; Kelly et al., 2012), the expression of AtHXK1 under the guard-cell specific KST1 promoter (GCHXK lines) had almost no negative growth effect (FIGS. 8A, 8D). Yet, expression of AtHXK1 under the KST1 promoter reduced both stomatal conductance and transpiration in both tomato and Arabidopsis plants (FIGS. 8B, 8C, 8E, 8F). These results strongly support the hypothesized specific role of HXK in guard cells, regulating stomatal closure.

EXAMPLE 10

GFP Expression Under the Control of the FBPase Promoter is Specific to Mesophyll Cells To discriminate between HXK effects in guard cells versus mesophyll cells the present inventors have created transgenic tomato and Arabidopsis plants expressing HXK under a mesophyll promoter FBPase (Peleg et al., 2007). The specific expression of FBPase promoter was demonstrated with transgenic tomato and Arabidopsis plants expressing GFP under control of this promoter (designated MCGFP, FIG. 9). Several independent homozygous Arabidopsis and tomato lines with high expression of FBPase:: AtHXK1 (named MCHXK plants) were identified.

EXAMPLE 11

Figure 10A:
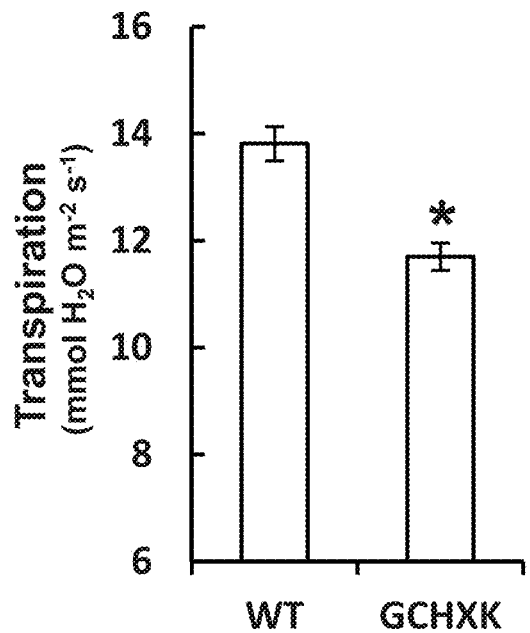
Figure 10C:
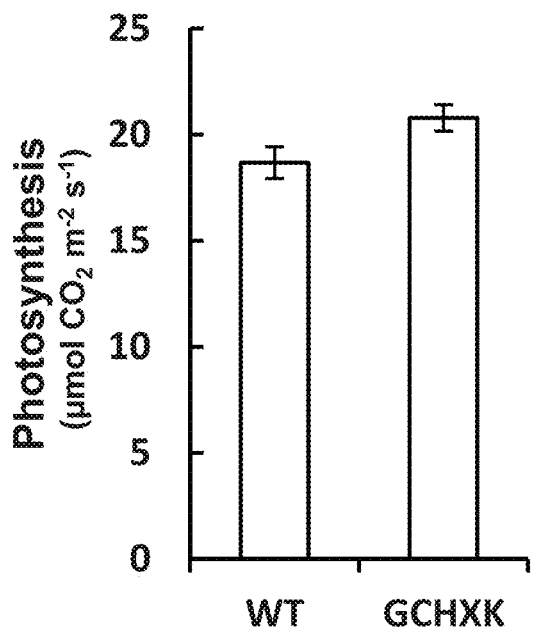
Figure 10B:
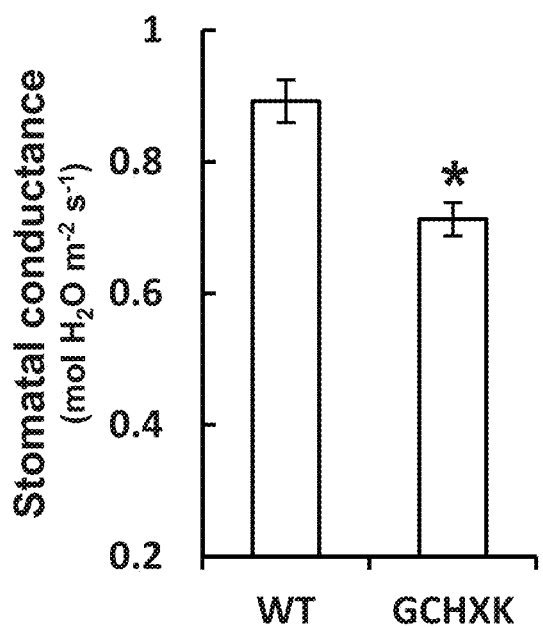
Figure 10D:
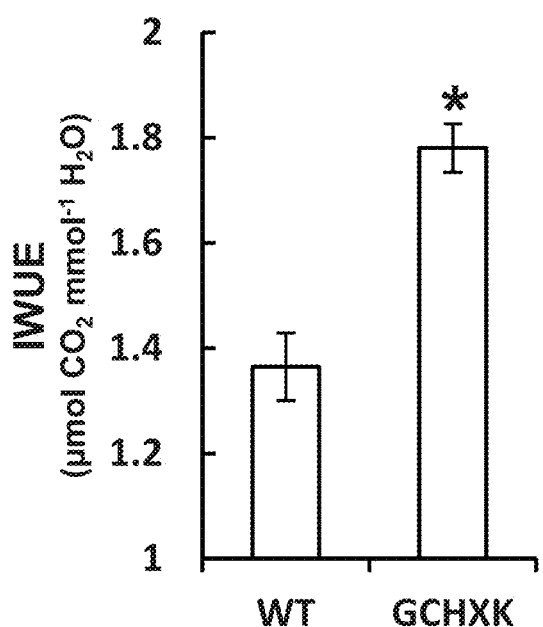

Elevated Expression of Hexokinase in Guard Cells Reduces Whole Plant Transpiration and Increases Water Use Efficiency, as Determined Using Gas Exchange Analysis System Using the LI-COR gas exchange system the present inventors have analyzed 10 GCHXK independent lines and discovered a striking increase in water use efficiency in those plants (FIGS. 10A-10D). Our data clearly shows that while photosynthesis remained unchanged (FIG. 10C), stomatal conductance (indicating stomatal aperture, FIG. 10B) and transpiration (FIG. 10A) were reduced by 20% and 15% respectively, thus improving water use efficiency from 1.36 in WT to 1.78 in GCHXK lines (FIG. 10D).

EXAMPLE 12

Elevated Expression of Hexokinase in Guard Cells Reduces Whole Plant Transpiration and Increases Water Use Efficiency, as Determined Using Lysimeter Scales System To evaluate water use efficiency in GCHXK plants the present inventors used the precise and sensitive lysimeter scales system, which measures plant weight accumulation and total plant water loss during long lasting experiments, and can monitor more than 160 plants simultaneously under varied irrigation treatments (FIGS. 11A-11C). Two independent GCHXK transgenic lines (that exhibited high WUE when measured by LI-COR (FIGS. 10A-D)) were analyzed. The present inventors have discovered that relative daily transpiration of these lines was lower than WT throughout the entire experiment (20 days) (FIGS. 11A-11C). Plant weight accumulation and growth were not affected. As a result, there was about 20%-30% increase in WUE in GCHXK lines compare to WT plants.

EXAMPLE 13

Elevated Expression of Hexokinase in Guard Cells Reduces Whole Plant Transpiration Rate and Stomatal Conductance, Without any Negative Effect on Growth, Thus Enhancing Water Use Efficiency Using lysimeter scales system we further analyzed water saving and WUE in GCHXK plants, which displayed high WUE when measured by LI-COR (FIGS. 10A-10D) and by lysimeter (FIGS. 11A-11C). Several parameters were monitored. Parameters for water loss: transpiration rate, stomatal conductance ($g_s$); parameters for growth: total plant weight, total plant leaf area and environmental parameters: light intensity, vapor pressure deficit (VPD). It was found that along the day, the transpiration rates normalized to total leaf area were correlated with environmental changes (light intensity and VPD, FIGS. 12E and 12F respectively). Transpiration rates of GCHXK plants were significantly lower compared with those of WT along the day (FIG. 12A). Accordingly, stomatal conductance was found to be reduced as well (FIG. 12B) proving that in GCHXK plants, water are saved and stomata are more closed. Moreover, by measuring total plant leaf area and weight (FIGS. 12C and 12D respectively), the present inventors discovered that even though plants have consumed less water (FIG. 12A) growth was not impaired, and was even improved as in the case of GCHXK 12 line. Saving water without affecting plant growth improves whole plant water use efficiency.

EXAMPLE 14

Elevated Expression of Hexokinase in Guard Cells Enhances Drought Tolerance

To monitor plants behavior under stress conditions the lysimeter scales system was used. After irrigation was fully stopped, plants were exposed to drought stress, which gradually increased each day throughout the experiment. Transpiration rates of WT and GCHXK plants were analyzed for nine consecutive days (FIG. 13). During the first 3 days GCHXK plants transpired less than WT, in line with normal conditions behavior (FIGS. 11A-11C; 12A-12F), indicating stress was only moderate at that time. However, in the following days (4 and 5), a transition between WT and GCHXK transpiration rates was observed (FIG. 13, *) and WT transpiration was steeply dropped compared with GCHXKs, indicating that WT plants are more sensitive to drought. As seen in moderate stress (days 5 and 6) as well as in severe stress conditions (days 7 and 8), GCHXK transpiration is less sensitive to water limitation compare to WT, displaying slower decline in transpiration throughout the experiment. These results indicate that GCHXK plants have better tolerance to water shortage and that under mild-stress conditions these plants can still function normally. Drought tolerance was also detected while monitoring relative daily transpiration (RDT) of WT and GCHXK plants under drought conditions (FIG. 11A). While shifting from irrigated to drought conditions (FIG. 11A, days 10-11, magnified), a steep reduction in transpiration was observed for WT plants (red arrow). However, GCHXK transpiration was only moderately affected when exposed to drought (green arrow), indicating that these plants have better tolerance to drought.

EXAMPLE 15

Elevated Expression of Hexokinase in Guard Cells Improves Yield Production

To examine the effect of GCHXK on yield, fruits number of GCHXK plants was monitored. Neither of the lines exhibited reduced yield, even though transpiration of these lines was found to be lower (FIGS. 10A-12F). On the contrary, in few lines fruit number was even higher than control (FIGS. 14A-14B).

EXAMPLE 16

Elevated Expression of Hexokinase in Guard Cells Improves Yield Production Under Limited Water Supply Conditions For a wide-range yield production assay, plants were grown in a controlled semi-commercial greenhouse under four different water stressed-irrigation regimes. Plants were irrigated either 25% above the recommended irrigation amount (125%), the recommended irrigation (100%) and deficit irrigation (75%, 50% irrigation regimes, FIG. 15A). Fruits were collected and cumulative fruit numbers and total fruit weight of each plant were documented (FIGS. 15B-15C). As clearly seen, GCHXK on yield was dramatic. Compare to WT, GCHXK plants had significantly higher yield (fruit number and total fruit weight under all irrigation regimes. Yet, deficit irrigation did not alter fruit number per plant but reduced fruit weight. Interestingly, GCHXK fruit weight under fully stressed conditions (50% irrigation) was higher than control plants at 100% irrigation. GCHXK plants have also better tolerance to water limitation. When lowering the irrigation from 100% to 75%, fruit weight of GCHXK plants was reduced by only 16% while that of WT control plants was reduced by 39%. Hence, in addition to more yield under normal (100%) irrigation conditions (FIGS. 14A-14B and FIG. 15B), GCHXK plants also have better tolerance (higher yield) to limited water supply. Together with the transpiration results (FIG. 13), these results indicate that specific expression of HXK in guard cells saves water, increases water use efficiency and improves yield production, not only under normal, but also under drought conditions as well.

EXAMPLE 17

Elevated Expression of Hexokinase in Guard Cells Reduces Whole Plant Transpiration, Induces Stomatal Closure and Increases Water Use Efficiency in Arabidopsis Thermal imaging and gas-exchange analysis were used to determine stomatal aperture, transpiration and WUE in Arabidopsis plants expressing HXK specifically in guard cells (GCHXK, FIGS. 16A-16F). The present inventors have discovered that in GCHXK plants, stomatal conductance and transpiration (FIG. 16A and 16B respectively, FIG. 8E-8F) are significantly reduced compare to WT. Additionally, by using thermal imaging technique, it was found that the leaf temperature of GCHXK plants was higher than WT, which indicates that stomata are more closed (FIG. 16F). In addition, while transpiration was reduced, photosynthesis rates (FIGS. 16C), as well as the mesophyll conductance to $CO_2$ (gm, FIG. 16D) were not affected. Moreover, growth was not affected as well (FIG. 8D). Overall, GCHXK plants had higher water use efficiency (FIG. 16E). These results demonstrate that the same transgenic insertion of hexokinase under guard-cell specific promoter used in the case of Tomato (Solanaceae family) is universally applicable while affecting stomata and increases water use efficiency in the case of Arabidopsis (Brassicaceae family) as well, and that this technique could be implemented in other species as well.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

LITERATURE CITED

Amodeo G, Talbott L D, Zeiger E (1996) Use of potassium and sucrose by onion guard cells during a daily cycle of osmoregulation. Plant Cell Physiol 37: 575-579

Arenas-Huertero F, Arroyo A, Zhou L, Sheen J, Leon P (2000) Analysis of Arabidopsis glucose insensitive mutants, gin5 and gin6, reveals a central role of the plant hormone ABA in the regulation of plant vegetative development by sugar. Genes Dev 14: 2085-2096

Assmann S M (1993) Signal transduction in guard cells. Annu Rev Cell Biol 9: 345-375

Baroli I, Price G D, Badger M R, von Caemmerer S (2008) The contribution of photosynthesis to the red light response of stomatal conductance. Plant Physiol 146: 737-747

Cheng W, Zhang H, Zhou X, Liu H, Liu Y, Li J, Han S, Wang Y (2011) Subcellular localization of rice hexokinase in the mesophyll protoplasts of tobacco. Biologia Plantarum 55: 173-177

Cho J I, Ryoo N, Eom J S, Lee D W, Kim H B, Jeong S W, Lee Y H, Kwon Y K, Cho M H, Bhoo S H, Hahn T R, Park Y I, Hwang I, Sheen J, Jeon J S (2009) Role of the rice hexokinases OsHXK5 and OsHXK6 as glucose sensors. Plant physiology 149: 745-759

Cho J I, Ryoo N, Ko S, Lee S K, Lee J, Jung K H, Lee Y H, Bhoo S H, Winderickx J, An G, Hahn T R, Jeon J S (2006) Structure, expression, and functional analysis of the hexokinase gene family in rice (*Oryza sativa* L.). Planta 224: 598-611

Christmann A, Hoffmann T, Teplova I, Grill E, Muller A (2005) Generation of active pools of abscisic acid revealed by in vivo imaging of water-stressed Arabidopsis. Plant Physiol 137: 209-219

Claeyssen E, Rivoal J (2007) Isozymes of plant hexokinase: occurrence, properties and functions. Phytochemistry 68: 709-731

Claeyssen E, Wally O, Matton D P, Morse D, Rivoal J (2006) Cloning, expression, purification, and properties of a putative plasma membrane hexokinase from *Solanum chacoense*. Protein Expr Purif 47: 329-339

Cominelli E, Galbiati M, Albertini A, Fornara F, Conti L, Coupland G, Tonelli C (2011) DOF-binding sites additively contribute to guard cell-specificity of AtMYB60 promoter. BMC plant biology 11: 162

Cominelli E, Galbiati M, Vavasseur A, Conti L, Sala T, Vuylsteke M, Leonhardt N, Dellaporta S L, Tonelli C (2005) A guard-cell-specific MYB transcription factor regulates stomatal movements and plant drought tolerance. Current biology : CB 15: 1196-1200

Cominelli E, Galbiati M, Tonelli C (2010) Transcription factors controlling stomatal movements and drought tolerance. Transcription 1: 41-45

Comstock J P (2002) Hydraulic and chemical signalling in the control of stomatal conductance and transpiration. J Exp Bot 53: 195-200

Dai N, Schaffer A, Petreikov M, Shahak Y, Giller Y, Ratner K, Levine A, Granot D (1999) Overexpression of Arabidopsis hexokinase in tomato plants inhibits growth, reduces photosynthesis, and induces rapid senescence. Plant Cell 11: 1253-1266

Damari-Weissler H, Kandel-Kfir M, Gidoni D, Mett A, Belausov E, Granot D (2006) Evidence for intracellular spatial separation of hexokinases and fructokinases in tomato plants. Planta 224: 1495-1502

Ewert M, Outlaw W, Zhang S, Aghoram K, Riddle K (2000) Accumulation of an apoplastic solute in the guard-cell wall is sufficient to exert a significant effect on transpiration in *Vicia faba* leaflets. Plant Cell Environ 23: 195-203

Francia P, Simoni L, Cominelli E, Tonelli C, Galbiati M (2008) Gene trap-based identification of a guard cell promoter in Arabidopsis. Plant signaling & behavior 3: 684-686

Galbiati M, Matus J T, Francia P, Rusconi F, Canon P, Medina C, Conti L, Cominelli E, Tonelli C, Arce-Johnson P (2011) The grapevine guard cell-related VvMYB60 transcription factor is involved in the regulation of stomatal activity and is differentially expressed in response to ABA and osmotic stress. BMC plant biology 11: 142

Galbiati M, Simoni L, Pavesi G, Cominelli E, Francia P, Vavasseur A, Nelson T, Bevan M, Tonelli C (2008) Gene trap lines identify Arabidopsis genes expressed in stomatal guard cells. The Plant journal: for cell and molecular biology 53: 750-762

Garcia-Mata C, Gay R, Sokolovski S, Hills A, Lamattina L, Blatt M R (2003) Nitric oxide regulates K+ and Cl− channels in guard cells through a subset of abscisic acid-evoked signaling pathways. Proc Natl Acad Sci USA 100: 11116-11121

Giese J O, Herbers K, Hoffmann M, Klosgen R B, Sonnewald U (2005) Isolation and functional characterization of a novel plastidic hexokinase from *Nicotiana tabacum*. FEBS Lett 579: 827-831

Geisler M J, Sack F D (2002) Variable timing of developmental progression in the stomatal pathway in Arabidopsis cotyledons. New Phytol 153: 469-476

Gotow K, Taylor S, Zeiger E (1988) Photosynthetic carbon fixation in guard cell protoplasts of *Vicia faba* L.: evidence from radiolabel experiments. Plant Physiol 86: 700-705

Granot D (2007) Role of tomato hexose kinases. Funct Plant Biol 34: 564-570

Granot D (2008) Putting plant hexokinases in their proper place. Phytochemistry 69: 2649-2654

Gray J E, Holroyd G H, van der Lee F M, Bahrami A R, Sijmons P C, Woodward F I, Schuch W, Hetherington A M (2000) The HIC signalling pathway links CO2 perception to stomatal development. Nature 408: 713-716

Hofmann M, Roitsch T (2000) The hexokinase inhibitor glucosamine exerts a concentration dependent dual effect on protein kinase activity in vitro. J Plant Physiol 157: 13-16

Husebye H, Chadchawan S, Winge P, Thangstad O P, Bones A M (2002) Guard cell-and phloem idioblast-specific expression of thioglucoside glucohydrolase 1 (myrosinase) in Arabidopsis. Plant physiology 128: 1180-1188

Jang J C, Sheen J (1994) Sugar sensing in higher plants. Plant Cell 6: 1665-1679

Jang J C, Leon P, Zhou L, Sheen J (1997) Hexokinase as a sugar sensor in higher plants. The Plant cell 9: 5-19

Kandel-Kfir M, Damari-Weissler H, German M A, Gidoni D, Mett A, Belausov E, Petreikov M, Adir N, Granot D (2006) Two newly identified membrane-associated and plastidic tomato HXKs: characteristics, predicted structure and intracellular localization. Planta 224: 1341-1352

Kang Y, Outlaw W H, Jr., Andersen P C, Fiore G B (2007) Guard-cell apoplastic sucrose concentration—a link between leaf photosynthesis and stomatal aperture size in the apoplastic phloem loader *Vicia faba* L. Plant Cell Environ 30: 551-558

Karve A, Rauh B L, Xia X, Kandasamy M, Meagher R B, Sheen J, Moore B D (2008) Expression and evolutionary features of the hexokinase gene family in Arabidopsis. Planta 228: 411-425

Karve R, Lauria M, Virnig A, Xia X, Rauh B L, Moore B D (2010) Evolutionary lineages and functional diversification of plant hexokinases. Mol Plant 3: 334-346

Kelly G, David-Schwartz R, Sade N, Moshelion M, Levi A, Alchanatis V, Granot D (2012) The pitfalls of transgenic selection and new roles of AtHXK1: a high level of AtHXK1 expression uncouples hexokinase1-dependent sugar signaling from exogenous sugar. Plant Physiol 159: 47-51

Kim M, Lim J H, Ahn C S, Park K, Kim G T, Kim W T, Pai H S (2006) Mitochondria-associated hexokinases play a role in the control of programmed cell death in *Nicotiana benthamiana*. Plant Cell 18: 2341-2355

Klein D, Stitt M (1998) Effects of 2-deoxyglucose on the expression of rbcS and the metabolism of *Chenopodium rubrum* cell suspension cultures. Planta 205: 223-234

Koiwai H, Nakaminami K, Seo M, Mitsuhashi W, Toyomasu T, Koshiba T (2004) Tissue-specific localization of an abscisic acid biosynthetic enzyme, AAO3, in Arabidopsis. Plant Physiol 134: 1697-1707

Kroupitski Y, Golberg D, Belausov E, Pinto R, Swartzberg D, Granot D, Sela S (2009) Internalization of *Salmonella enterica* in leaves is induced by light and involves chemotaxis and penetration through open stomata. Appl Environ Microbiol 75: 6076-6086

Lawson T (2009) Guard cell photosynthesis and stomatal function. New Phytol 181: 13-34

Lawson T, Lefebvre S, Baker NR, Morison J I, Raines C A (2008) Reductions in mesophyll and guard cell photosynthesis impact on the control of stomatal responses to light and CO2. J Exp Bot 59: 3609-3619

Leon P, Sheen J (2003) Sugar and hormone connections. Trends Plant Sci 8: 110-116.

Liang Y K, Dubos C, Dodd I C, Holroyd G H, Hetherington A M, Campbell M M (2005) AtMYB61, an R2R3-MYB transcription factor controlling stomatal aperture in Arabidopsis thaliana. Curr Biol 15: 1201-1206

Lloyd FE (1908) The physiology of stomata. Carnegie Inst Washington Yearbook 82: 1-142

Lu P, Outlaw W H, Smith B G, Freed G A (1997) A new mechanism for the regulation of stomatal aperture size in intact leaves—Accumulation of mesophyll-derived sucrose in the guard-cell wall of Vicia faba. Plant Physiol 114: 109-118

Lu P, Zhang S Q, Outlaw W H, Jr., Riddle K A (1995) Sucrose: a solute that accumulates in the guard-cell apoplast and guard-cell symplast of open stomata. FEBS Lett 362: 180-184

Melhorn V, Matsumi K, Koiwai H, Ikegami K, Okamoto M, Nambara E, Bittner F, Koshiba T (2008) Transient expression of AtNCED3 and AAO3 genes in guard cells causes stomatal closure in Vicia faba. J Plant Res 121: 125-131

Muller-Rober B, La Cognata U, Sonnewald U, Willmitzer L (1994) A truncated version of an ADP-glucose pyrophosphorylase promoter from potato specifies guard cell-selective expression in transgenic plants. The Plant cell 6: 601-612

Muller-Rober B, Ellenberg J, Provart N, Willmitzer L, Busch H, Becker D, Dietrich P, Hoth S, Hedrich R (1995) Cloning and electrophysiological analysis of KST1, an inward rectifying K+ channel expressed in potato guard cells. Embo J 14: 2409-2416

Menu T, Rothan C, Dai N, Petreikov M, Etienne C, Destrac-Irvine A, Schaffer A, Granot D, Ricard B (2001) Cloning and characterization of a cDNA encoding hexokinase from tomato. Plant Sci 160: 209-218

Nakamura R L, McKendree W L, Jr., Hirsch R E, Sedbrook J C, Gaber R F, Sussman M R (1995) Expression of an Arabidopsis potassium channel gene in guard cells. Plant physiology 109: 371-374

Neill S, Barros R, Bright J, Desikan R, Hancock J, Harrison J, Morris P, Ribeiro D, Wilson I (2008) Nitric oxide, stomatal closure, and abiotic stress. J Exp Bot 59: 165-176

Neill S J, Horgan R (1985) Abscisic acid production and water relations in wilty tomato mutants subjected to water deficiency. J Exp Bot 36: 1222-1231

Nikinmaa E, Holtta T, Hari P, Kolari P, Makela A, Sevanto S, Vesala T (2012) Assimilate transport in phloem sets conditions for leaf gas exchange. Plant, Cell & Environment doi: 10.1111/pce.12004

Nilsson A, Olsson T, Ulfstedt M, Thelander M, Ronne H (2011) Two novel types of hexokinases in the moss Physcomitrella patens. BMC Plant Biol 11: 32

Nylander M, Svensson J, Palva E T, Welin B V (2001) Stress-induced accumulation and tissue-specific localization of dehydrins in Arabidopsis thaliana. Plant molecular biology 45: 263-279

Olsson T, Thelander M, Ronne H (2003) A novel type of chloroplast stromal hexokinase is the major glucose-phosphorylating enzyme in the moss Physcomitrella patens. J Biol Chem 278: 44439-44447

Outlaw W H (2003) Integration of cellular and physiological functions of guard cells. Crit Rev Plant Sci 22: 503-529

Outlaw W H, Jr., De Vlieghere-He X (2001) Transpiration rate. An important factor controlling the sucrose content of the guard cell apoplast of broad bean. Plant Physiol 126: 1716-1724

Pandey S, Zhang W, Assmann S M (2007) Roles of ion channels and transporters in guard cell signal transduction. FEBS Lett 581: 2325-2336

Pego J V, Weisbeek P J, Smeekens S C (1999) Mannose inhibits Arabidopsis germination via a hexokinase-mediated step. Plant Physiol 119: 1017-1023

Padmanaban S, Chanroj S, Kwak J M, Li X, Ward J M, Sze H (2007) Participation of endomembrane cation/H+ exchanger AtCHX20 in osmoregulation of guard cells. Plant Physiol 144: 82-93

Poffenroth M, Green D B, Tallman G (1992) Sugar concentrations in guard cells of Vicia faba illuminated with red or blue light: analysis by high performance liquid chromatography. Plant Physiol 98: 1460-1471

Rennie E A, Turgeon R (2009) A comprehensive picture of phloem loading strategies. Proc Natl Acad Sci USA 106: 14162-14167

Ritte G, Rosenfeld J, Rohrig K, Raschke K (1999) Rates of sugar uptake by guard cell protoplasts of Pisum sativum L. related to the solute requirement for stomatal opening. Plant Physiol 121: 647-656

Roelfsema M R, Hedrich R (2005) In the light of stomatal opening: new insights into 'the Watergate'. New Phytol 167: 665-691

Rolland F, Baena-Gonzalez E, Sheen J (2006) Sugar sensing and signaling in plants: conserved and novel mechanisms. Annu Rev Plant Biol 57: 675-709

Sade N, Gebretsadik M, Seligmann R, Schwartz A, Wallach R, Moshelion M (2010) The role of tobacco Aquaporin1 in improving water use efficiency, hydraulic conductivity, and yield production under salt stress. Plant Physiol 152: 245-254

Schachtman D P, Goodger J Q (2008) Chemical root to shoot signaling under drought. Trends Plant Sci 13: 281-287

Schroeder J I, Allen G J, Hugouvieux V, Kwak J M, Waner D (2001) Guard cell signal transduction. Annu Rev Plant Physiol Plant Mol Biol 52: 627-658

Sun J Y, Chen Y M, Wang Q M, Chen J, Wang X C (2006) Glucose inhibits the expression of triose phosphate/phosphate translocator gene in wheat via hexokinase-dependent mechanism. Int J Biochem Cell Biol 38: 1102-1113

Taiz L, Zeiger E (1998) Plant Physiology, Ed. 2. Sinauer Associates, Sunderland, UK Tal M, Nevo Y (1973) Abnormal stomatal behavior and root resistance and hormonal imbalance in three wilty mutants of tomato. Biochem Genet 8: 291-300

Talbott LD, Zeiger E (1993) Sugar and organic acid accumulation in guard cells of Vicia faba in response to red and blue light. Plant Physiol 102: 1163-1169

Talbott LD, Zeiger E (1996) Central roles for potassium and sucrose in guard-cell osmoregulation. Plant Physiol 111: 1051-1057

Talbott LD, Zeiger E (1998) The role of sucrose in guard cell osmoregulation. J Exp Bot 49: 329-337

Tallman G, Zeiger E (1988) Light quality and osmoregulation in Vicia guard cells: evidence for involvement of three metabolic pathways. Plant Physiol 88: 887-895

Terryn N, Arias M B, Engler G, Tire C, Villarroel R, Van Montagu M, Inze D (1993) rha1, a gene encoding a small GTP binding protein from Arabidopsis, is expressed primarily in developing guard cells. The Plant cell 5: 1761-1769

Troncoso-Ponce M A, Rivoal J, Dorion S, Moisan M C, Garces R, Martinez-Force E (2011) Cloning, biochemical characterization and expression of a sunflower (Helianthus annuus L.) hexokinase associated with seed storage compounds accumulation. J Plant Physiol 168: 299-308

Veramendi J, Fernie A R, Leisse A, Willmitzer L, Trethewey R N (2002) Potato hexokinase 2 complements transgenic Arabidopsis plants deficient in hexokinase 1 but does not play a key role in tuber carbohydrate metabolism. Plant Mol Biol 49: 491-501

Veramendi J, Roessner U, Renz A, Willmitzer L, Trethewey R N (1999) Antisense repression of hexokinase 1 leads to an overaccumulation of starch in leaves of transgenic potato plants but not to significant changes in tuber carbohydrate metabolism. Plant Physiol 121: 123-134

Wasilewska A, Vlad F, Sirichandra C, Redko Y, Jammes F, Valon C, Frei dit Frey N, Leung J (2008) An update on abscisic acid signaling in plants and more. Mol Plant 1: 198-217

Wiese A, Groner F, Sonnewald U, Deppner H, Lerchl J, Hebbeker U, Flugge U, Weber A (1999) Spinach hexokinase I is located in the outer envelope membrane of plastids. FEBS Lett 461: 13-18

Wilkinson S, Davies W J (1997) Xylem sap pH increase: a drought signal received at the apoplastic face of the guard cell that involves the suppression of saturable abscisic acid uptake by the epidermal symplast. Plant Physiol 113: 559-573

Xu F Q, Li X R, Ruan Y L (2008) RNAi-mediated suppression of hexokinase gene OsHXK10 in rice leads to non-dehiscent anther and reduction of pollen germination. Plant Science 175: 674-684

Yang Y, Costa A, Leonhardt N, Siegel R S, Schroeder J I (2008) Isolation of a strong Arabidopsis guard cell promoter and its potential as a research tool. Plant Methods 4: 6

Yu F, Li L M, Yang P P, Wang X Q (2012) Hexokinase from grape berries: its prokaryotic expression, polyclonal antibody preparation and biochemical property analyses. J. Plant Biochem. Biotechnol. DOI 10.1007/s13562-012-0163-9

Zhu G H, Liu Y G, Ye N H, Liu R, Zhang J H (2011) Involvement of the abscisic acid catabolic gene CYP707A2 in the glucose-induced delay in seed germination and post-germination growth of Arabidopsis. Physiol Plant 143: 375-384

---

What is claimed is:

1. A method of increasing water use efficiency of a plant, the method comprising introducing into a cell of the plant a nucleic acid construct comprising a nucleic acid sequence encoding a plant type B mitochondrial—associated hexokinase (HXK) under a transcriptional control of a guard cell-specific cis-acting regulatory element, wherein said type B mitochondrial—associated hexokinase (HXK) controls stomata conductance, thereby increasing water use efficiency of the plant, wherein said type B mitochondrial—associated hexokinase (HXK) is at least 90% identical to SEQ ID NO: 12 or 24.

2. The method of claim 1, further comprising growing the plant under water deficient conditions or under salinity stress for the plant.

3. The method of claim 1, wherein said guard cell-specific cis-acting regulatory element is a guard-cell specific promoter.

4. The method of claim 1, wherein said type B mitochondrial—associated hexokinase (HXK) binds hexose.

5. The method of claim 1, wherein said type B mitochondrial—associated hexokinase (HXK) is at least 95% identical to SEQ ID NO: 12 or SEQ ID NO: 24.

* * * * *

SEQUENCE LISTING

```
<160> NUMBER OF SEQ ID NOS: 108

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
cgtcgtgttt ggacaagttg                                                      20

<210> SEQ ID NO 2
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 2
ccgcagtcag caataacca                                                       19

<210> SEQ ID NO 3
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 3
gacttgctgg gagaggagt                                                       19

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
aaggtacatt gaatgagagg ca                                                   22

<210> SEQ ID NO 5
<211> LENGTH: 19
<212> TYPE: DNA
<213> ORGANISM: Artificial sequence
<220> FEATURE:
<223> OTHER INFORMATION: Single strand DNA oligonucleotide
```

<400> SEQUENCE: 5
gtcctcccat cttcccttg                                                                    19

<210> SEQ ID NO 6
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 6
cccaagtaca taccagaaca t                                                                 21

<210> SEQ ID NO 7
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 7
gcgatattat cacctctcgt g                                                                 21

<210> SEQ ID NO 8
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 8
ctgcttctct ccgtctttaa a                                                                 21

<210> SEQ ID NO 9
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 9
gctgaggaca cctgatatat g                                                                 21

<210> SEQ ID NO 10
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 10
gatcggattt taccccagct a                                                                 21

<210> SEQ ID NO 11
<211> LENGTH: 2030
<212> TYPE: DNA
<213> ORGANISM: Arabidopsis thaliana

<400> SEQUENCE: 11
aagctctcgc ttacgtggtt tctacactgt ttttgacgaa cccaccaagc tcgagtagat         60
cggtattaga tccatcttag gtttctctaa tttctctcaa ttcactccaa aattttgatt        120
atttcttctt tctggcttgt caattttagt catttgtaat ccttgctttt gcgatcggaa        180

-continued

```
tcgtaaaaat ccgatctttc ttttagattc gttttgtttt tgattccaaa tcggaaaaat      240
gggtaaagta gctgttggag cgactgttgt ttgcacggcg gcggtttgtg cggtggctgt      300
tttggttgtt cgacgacgga tgcagagctc agggaagtgg ggacgtgttt tggctatcct      360
caaggccttt gaagaggatt gtgcgactcc gatctcgaaa ctgagacaag tggctgatgc      420
tatgaccgtt gagatgcatg ctggtcttgc atccgacggt ggtagcaaac tcaagatgct      480
tatcagctac gttgataatc ttccttccgg ggatgaaaag ggtctctttt atgcattgga      540 cctaggggggg acaaacttcc gtgtcatgcg tgtgcttctt ggcgggaagc aagagcgtgt      600
tgttaaacaa gaattcgaag aagtttcgat tcctcctcat ttgatgactg gtggttcaga      660
tgagttgttc aattttatag ctgaagctct tgcgaagttt gtcgctacag aatgcgaaga      720
ctttcatctt ccagaaggta gacagaggga attaggtttc actttctcgt ttcctgttaa      780
gcagacttct ctgtcctctg gtagtctcat caaatggaca aaaggctttt ccatcgaaga      840
agcagttgga caagatgttg ttggagcact taataaggct ctggaaagag ttggtcttga      900
catgcgaatc gcagcacttg ttaatgatac cgttggaaca ctagccggtg gtagatacta      960
taacccggat gttgttgctg ctgttatttt aggcactggg acaaacgcag cctatgttga     1020
gcgtgcaacc gcgatcccta aatggcatgg tctgcttcca aaatcaggag aaatggttat     1080
aaacatggaa tggggaaact tcaggtcatc acatcttcca ttaaccgagt ttgatcacac     1140
gctggatttc gagagtctga atccaggcga acagattctt gagaaaatca tttccggtat     1200
gtacttggga gagattttgc gaagagttct tctaaagatg gctgaagatg ctgctttctt     1260
tggcgataca gtcccatcta agctgagaat accattcatc attaggactc ctcacatgtc     1320
ggctatgcac aacgacactt ctccagactt gaagattgtt gggagcaaga ttaaggatat     1380
attggaggtc cctacaactt ctctgaaaat gagaaaagtt gtgatcagtc tctgcaacat     1440
catagcaacc cgaggagctc gtctctctgc tgctggaatc tatggtattc tgaagaaact     1500
gggaagagat actactaaag acgaggaggt gcagaaatcg gttatagcca tggatggtgg     1560
attgtttgag cattacactc agtttagtga gtgtatggag agctcactaa aagagttgct     1620
tggagatgaa gcttcaggaa gcgttgaagt cactcactcc aatgatggat caggcattgg     1680
agctgcgctt cttgctgctt ctcactctct ctaccttgaa gactcttaaa acctacccaa     1740
agagcgccat ttttcggtaa tttactgaaa gcttttcgct atcagaaaac gcctaagcca     1800
agttctaagg cgtcataaaa gaaagcattc catgttttta ctcttcccca agactttctt     1860
tgtagcaaat aagtttcctt gggagaaata tttgttttca tgttcttcaa aaataaaaga     1920
ctcagttctt cagattctgg gatttttatta taaccagata tgttgtaaaa actacaaatt     1980
caaagctcac ttcactggag ttctgagtat ataaagattt cattttttcct              2030
```

<210> SEQ ID NO 12  
<211> LENGTH: 496  
<212> TYPE: PRT  
<213> ORGANISM: Arabidopsis thaliana

<400> SEQUENCE: 12

Met Gly Lys Val Ala Val Gly Ala Thr Val Val Cys Thr Ala Ala Val  
1               5                   10                  15

Cys Ala Val Ala Val Leu Val Val Arg Arg Arg Met Gln Ser Ser Gly  
            20                  25                  30

Lys Trp Gly Arg Val Leu Ala Ile Leu Lys Ala Phe Glu Glu Asp Cys  
        35                  40                  45

```
Ala Thr Pro Ile Ser Lys Leu Arg Gln Val Ala Asp Ala Met Thr Val
 50                  55                  60

Glu Met His Ala Gly Leu Ala Ser Asp Gly Ser Lys Leu Lys Met
 65                  70                  75                  80

Leu Ile Ser Tyr Val Asp Asn Leu Pro Ser Gly Asp Glu Lys Gly Leu
                 85                  90                  95

Phe Tyr Ala Leu Asp Leu Gly Gly Thr Asn Phe Arg Val Met Arg Val
                100                 105                 110

Leu Leu Gly Gly Lys Gln Glu Arg Val Val Lys Gln Glu Phe Glu Glu
                115                 120                 125

Val Ser Ile Pro Pro His Leu Met Thr Gly Gly Ser Asp Glu Leu Phe
    130                 135                 140

Asn Phe Ile Ala Glu Ala Leu Ala Lys Phe Val Ala Thr Glu Cys Glu
145                 150                 155                 160

Asp Phe His Leu Pro Glu Gly Arg Gln Arg Glu Leu Gly Phe Thr Phe
                165                 170                 175

Ser Phe Pro Val Lys Gln Thr Ser Leu Ser Ser Gly Ser Leu Ile Lys
                180                 185                 190

Trp Thr Lys Gly Phe Ser Ile Glu Glu Ala Val Gly Gln Asp Val Val
            195                 200                 205

Gly Ala Leu Asn Lys Ala Leu Glu Arg Val Gly Leu Asp Met Arg Ile
            210                 215                 220

Ala Ala Leu Val Asn Asp Thr Val Gly Thr Leu Ala Gly Gly Arg Tyr
225                 230                 235                 240

Tyr Asn Pro Asp Val Val Ala Val Ile Leu Gly Thr Gly Thr Asn
                245                 250                 255

Ala Ala Tyr Val Glu Arg Ala Thr Ala Ile Pro Lys Trp His Gly Leu
                260                 265                 270

Leu Pro Lys Ser Gly Glu Met Val Ile Asn Met Glu Trp Gly Asn Phe
            275                 280                 285

Arg Ser Ser His Leu Pro Leu Thr Glu Phe Asp His Thr Leu Asp Phe
            290                 295                 300

Glu Ser Leu Asn Pro Gly Glu Gln Ile Leu Glu Lys Ile Ile Ser Gly
305                 310                 315                 320

Met Tyr Leu Gly Glu Ile Leu Arg Arg Val Leu Leu Lys Met Ala Glu
                325                 330                 335

Asp Ala Ala Phe Phe Gly Asp Thr Val Pro Ser Lys Leu Arg Ile Pro
                340                 345                 350

Phe Ile Ile Arg Thr Pro His Met Ser Ala Met His Asn Asp Thr Ser
            355                 360                 365

Pro Asp Leu Lys Ile Val Gly Ser Lys Ile Lys Asp Ile Leu Glu Val
370                 375                 380

Pro Thr Thr Ser Leu Lys Met Arg Lys Val Val Ile Ser Leu Cys Asn
385                 390                 395                 400

Ile Ile Ala Thr Arg Gly Ala Arg Leu Ser Ala Ala Gly Ile Tyr Gly
                405                 410                 415

Ile Leu Lys Lys Leu Gly Arg Asp Thr Thr Lys Asp Glu Glu Val Gln
                420                 425                 430

Lys Ser Val Ile Ala Met Asp Gly Gly Leu Phe Glu His Tyr Thr Gln
                435                 440                 445

Phe Ser Glu Cys Met Glu Ser Ser Leu Lys Glu Leu Leu Gly Asp Glu
                450                 455                 460

Ala Ser Gly Ser Val Glu Val Thr His Ser Asn Asp Gly Ser Gly Ile
```

465                 470                 475                 480
Gly Ala Ala Leu Leu Ala Ala Ser His Ser Leu Tyr Leu Glu Asp Ser
                485                 490                 495

<210> SEQ ID NO 13
<211> LENGTH: 1815
<212> TYPE: DNA
<213> ORGANISM: Arabidopsis thaliana

<400> SEQUENCE: 13

| | | | | | | |
|---|---|---|---|---|---|---|
| tttccaactt | tttttttat | taatttgggc | caacttttt | tggtttgaga | attgggcgag | 60 |
| ggagaaagat | gggtaaagtg | gcagttgcaa | cgacggtagt | gtgttcggtg | gcggtatgtg | 120 |
| cggcggcggc | gttgatagta | cggaggagaa | tgaaaagcgc | agggaaatgg | caagagtga | 180 |
| tagagatatt | gaaagccttt | gaagaagatt | gtgcaacgcc | aattgccaaa | ttgagacaag | 240 |
| tggctgatgc | tatgactgtt | gagatgcatg | ctggtcttgc | ttctgaaggt | ggcagcaagc | 300 |
| ttaagatgct | tattagctac | gttgataatc | ttccttctgg | ggatgagact | ggttttttct | 360 |
| atgcgttgga | tctaggcgga | acaaacttcc | gtgttatgcg | tgtgcttctt | ggtgggaagc | 420 |
| acgaccgtgt | tgttaaacga | gaattcaaag | aagaatctat | tcctcctcat | ttgatgaccg | 480 |
| ggaagtcaca | tgaattattc | gatttttatcg | ttgatgttct | tgccaagttt | gtcgctacag | 540 |
| aaggcgagga | ctttcatctc | ccacctggta | gacaacggga | actaggtttt | actttctcat | 600 |
| ttccggttaa | gcagctatct | ttatcctctg | gcactctcat | caactggacg | aagggctttt | 660 |
| ccattgacga | tacagttgat | aaagatgttg | ttggagaact | tgttaaagct | atggaaagag | 720 |
| ttgggctgga | catgcttgtc | gcagcgcttg | ttaatgatac | cattggaaca | cttgcgggtg | 780 |
| gtagatacac | taacccggat | gtcgttgtcg | cagttatttt | gggcaccggc | acaaatgcag | 840 |
| cctatgtcga | acgtgcacat | gcaattccca | aatggcatgg | tttgctaccc | aaatcaggag | 900 |
| aaatggtgat | caacatggaa | tggggaaact | tcaggtcatc | acatcttcca | ttgacagagt | 960 |
| acgaccactc | tctagatgtc | gatagtttga | atcctggtga | acagattctt | gagaaaatca | 1020 |
| tttccggaat | gtatctggga | gaaatcttgc | gtagagttct | tctgaagatg | gctgaagaag | 1080 |
| ctgccttctt | tggcgatatc | gtcccaccta | agctgaaaat | accattcatc | ataaggaccc | 1140 |
| cgaacatgtc | tgctatgcac | agtgatactt | ccccggattt | gaaggttgta | ggaagcaagt | 1200 |
| taaaagacat | attggaggtc | cagactagtt | ctctgaagat | gaggaaagtt | gtgatcagcc | 1260 |
| tatgtaacat | cattgcaagc | cgaggagctc | gtttatctgc | tgcggggatc | tatggaatcc | 1320 |
| tcaagaaaat | aggaagagac | gcaacaaaag | atggagaagc | tcagaaatct | gtgatagcga | 1380 |
| tggacggtgg | gctattcgag | cattacactc | agttcagtga | gtcgatgaag | agttcattga | 1440 |
| aagagttgct | tggagatgaa | gtttcagaga | gtgttgaagt | gatactgtcg | aatgatggtt | 1500 |
| caggtgttgg | agctgcatta | cttgctgctt | ctcactctca | gtatctcgaa | cttgaagatg | 1560 |
| actctgaaac | aagttaattt | taaaagcctt | ttttttgtgt | ttaaccttct | tctttgtttt | 1620 |
| gccgttaggg | tttaaacaaa | taaaaaaag | taagaaggta | aaaatgccct | tttgggaaat | 1680 |
| tttattttg | acaattttca | ggaacaataa | aacctggatt | cttcatcaaa | gctctgggaa | 1740 |
| attcaaacga | ccagccaatg | ttgtagaact | atacatatat | attcgagttc | tttctatgaa | 1800 |
| cgttcatttt | ttccc | | | | | 1815 |

<210> SEQ ID NO 14
<211> LENGTH: 502
<212> TYPE: PRT

-continued

<213> ORGANISM: Arabidopsis thaliana

<400> SEQUENCE: 14

```
Met Gly Lys Val Ala Val Ala Thr Thr Val Cys Ser Val Ala Val
1               5                   10                  15

Cys Ala Ala Ala Leu Ile Val Arg Arg Met Lys Ser Ala Gly
            20                  25                  30

Lys Trp Ala Arg Val Ile Glu Ile Leu Lys Ala Phe Glu Glu Asp Cys
        35                  40                  45

Ala Thr Pro Ile Ala Lys Leu Arg Gln Val Ala Asp Ala Met Thr Val
    50                  55                  60

Glu Met His Ala Gly Leu Ala Ser Glu Gly Ser Lys Leu Lys Met
65                  70                  75                  80

Leu Ile Ser Tyr Val Asp Asn Leu Pro Ser Gly Asp Glu Thr Gly Phe
                85                  90                  95

Phe Tyr Ala Leu Asp Leu Gly Gly Thr Asn Phe Arg Val Met Arg Val
            100                 105                 110

Leu Leu Gly Gly Lys His Asp Arg Val Val Lys Arg Glu Phe Lys Glu
        115                 120                 125

Glu Ser Ile Pro Pro His Leu Met Thr Gly Lys Ser His Glu Leu Phe
    130                 135                 140

Asp Phe Ile Val Asp Val Leu Ala Lys Phe Val Ala Thr Glu Gly Glu
145                 150                 155                 160

Asp Phe His Leu Pro Pro Gly Arg Gln Arg Glu Leu Gly Phe Thr Phe
                165                 170                 175

Ser Phe Pro Val Lys Gln Leu Ser Leu Ser Ser Gly Thr Leu Ile Asn
            180                 185                 190

Trp Thr Lys Gly Phe Ser Ile Asp Asp Thr Val Asp Lys Asp Val Val
        195                 200                 205

Gly Glu Leu Val Lys Ala Met Glu Arg Val Gly Leu Asp Met Leu Val
    210                 215                 220

Ala Ala Leu Val Asn Asp Thr Ile Gly Thr Leu Ala Gly Gly Arg Tyr
225                 230                 235                 240

Thr Asn Pro Asp Val Val Ala Val Ile Leu Gly Thr Gly Thr Asn
                245                 250                 255

Ala Ala Tyr Val Glu Arg Ala His Ala Ile Pro Lys Trp His Gly Leu
            260                 265                 270

Leu Pro Lys Ser Gly Glu Met Val Ile Asn Met Glu Trp Gly Asn Phe
        275                 280                 285

Arg Ser Ser His Leu Pro Leu Thr Glu Tyr Asp His Ser Leu Asp Val
    290                 295                 300

Asp Ser Leu Asn Pro Gly Glu Gln Ile Leu Glu Lys Ile Ile Ser Gly
305                 310                 315                 320

Met Tyr Leu Gly Glu Ile Leu Arg Arg Val Leu Leu Lys Met Ala Glu
                325                 330                 335

Glu Ala Ala Phe Phe Gly Asp Ile Val Pro Pro Lys Leu Lys Ile Pro
            340                 345                 350

Phe Ile Ile Arg Thr Pro Asn Met Ser Ala Met His Ser Asp Thr Ser
        355                 360                 365

Pro Asp Leu Lys Val Val Gly Ser Lys Leu Lys Asp Ile Leu Glu Val
    370                 375                 380

Gln Thr Ser Ser Leu Lys Met Arg Lys Val Val Ile Ser Leu Cys Asn
385                 390                 395                 400
```

```
Ile Ile Ala Ser Arg Gly Ala Arg Leu Ser Ala Ala Gly Ile Tyr Gly
                405                 410                 415

Ile Leu Lys Lys Ile Gly Arg Asp Ala Thr Lys Asp Gly Glu Ala Gln
            420                 425                 430

Lys Ser Val Ile Ala Met Asp Gly Gly Leu Phe Glu His Tyr Thr Gln
        435                 440                 445

Phe Ser Glu Ser Met Lys Ser Leu Lys Glu Leu Leu Gly Asp Glu
    450                 455                 460

Val Ser Glu Ser Val Glu Val Ile Leu Ser Asn Asp Gly Ser Gly Val
465                 470                 475                 480

Gly Ala Ala Leu Leu Ala Ala Ser His Ser Gln Tyr Leu Glu Leu Glu
                485                 490                 495

Asp Asp Ser Glu Thr Ser
            500

<210> SEQ ID NO 15
<211> LENGTH: 1653
<212> TYPE: DNA
<213> ORGANISM: Arabidopsis thaliana

<400> SEQUENCE: 15
tcttcgttct tacaaaacag aaccaaactt cgacaatgtc actcatgttt tcttcccctg      60
tcgtcacccc agcactcgga tctttcacct tctcatctcg accacgctcc aattacatcg     120
tgatgtccgc cgtccgatct aactctgctt cgacgtgtcc tatactgacc aagtttcaga     180
aagactgcgc cactcctaca ccgtacctac gcaacgtagc caacgccatt gctgatgaca     240
tgcgagatgg tctagctgtt gaaggaggag agatctcga gatgatcttg acttttgttg      300
acgctttgcc ttctgggaat gaggaagggt tgttctatgc attggattta ggaggtacaa     360
attttcgggt gcgtagcgtg caattaggag aaagaaaga gcgagtctta gctaccgaat      420
ctgaacaaat atctatttct caaaagctta tgattggtac aagtgaggag cttttcgggt     480
tcattgcttc aaagcttgca aattttgttg caaaggagaa gccaggtcgg tttcttttag     540
aagaagggag gaaagggag ttagggttta ccttttcatt ccctgtgaag caaacctcta      600
ttgattcagg cacattaagc aagtggacta aaggctttaa agtgtctgga atggaaggaa     660
aaaatgtggt tgcttgttta aatgaagcta tggaagcaca tggactcgat atgcgagttt     720
ctgctcttgt aaatgatgga gtgggaacat tagctggagc aaggtattgg gatgaggatg     780
tgatggtcgg tgtgattctt ggcactggga ccaatgcttg ttatgtagaa cagaaacatg     840
caattcctaa actccgaagc aaatcttctt ctggaacaac gatcataaac actgagtggg     900
gagggttctc taagattctt ccgcaaacca ttttgacct agagatggat gagacaagcc      960
tgaatcctgg tgaacattta tatgagaaga tgatctcagg gatgtacctt ggtgaaattg    1020
taaggagggt tttgctccat atgtgtgaaa ctagtgactt gtttggacac ttcgctcctg    1080
ccaaactctc cactcctttg gcactcagga ccgagcatct atgcaaaatg caagaggaca    1140
atacagatga tcttcgggat gttggatcaa tcctatacga cttttagat gtagaggcga     1200 atatgaatgc aaggaggaga gtggtggaag tgtgtgacac agtagtgaaa cgcggagggc    1260
gtctagcagg agctggtata gtggcaattc tggagaagat tgaaaagat accaaaagaa     1320 tgggttcagg taaagaacc gttgtggcta tggacggtgc actgtatgag aagtacccac     1380
aatatcgaca gtatatgcaa gacgcactag tcgagcttct tggccataag cttgcaagtc    1440
acgttgcgat caaacatacc aaagacgtgt ctgggctcgg tgctgctctt ttggcggcca    1500
```

```
ctaactccat ttactagtac ttggacctct acttcatgag tataggagga cttttggtcc    1560
atttgtttgt gtacatttat ataagatatc atatcaatat caataagatt gtaaagagga    1620
gcaacgaact agcagaagat tatgtcttgg acc                                  1653
```

<210> SEQ ID NO 16
<211> LENGTH: 493
<212> TYPE: PRT
<213> ORGANISM: Arabidopsis thaliana

<400> SEQUENCE: 16

```
Met Ser Leu Met Phe Ser Ser Pro Val Thr Pro Ala Leu Gly Ser
1               5                   10                  15

Phe Thr Phe Ser Ser Arg Pro Arg Ser Asn Tyr Ile Val Met Ser Ala
                20                  25                  30

Val Arg Ser Asn Ser Ala Ser Thr Cys Pro Ile Leu Thr Lys Phe Gln
            35                  40                  45

Lys Asp Cys Ala Thr Pro Thr Pro Tyr Leu Arg Asn Val Ala Asn Ala
50                  55                  60

Ile Ala Asp Asp Met Arg Asp Gly Leu Ala Val Glu Gly Gly Gly Asp
65                  70                  75                  80

Leu Glu Met Ile Leu Thr Phe Val Asp Ala Leu Pro Ser Gly Asn Glu
                85                  90                  95

Glu Gly Leu Phe Tyr Ala Leu Asp Leu Gly Gly Thr Asn Phe Arg Val
            100                 105                 110

Arg Ser Val Gln Leu Gly Gly Lys Lys Glu Arg Val Leu Ala Thr Glu
        115                 120                 125

Ser Glu Gln Ile Ser Ile Ser Gln Lys Leu Met Ile Gly Thr Ser Glu
130                 135                 140

Glu Leu Phe Gly Phe Ile Ala Ser Lys Leu Ala Asn Phe Val Ala Lys
145                 150                 155                 160

Glu Lys Pro Gly Arg Phe Leu Glu Glu Gly Arg Lys Arg Glu Leu
                165                 170                 175

Gly Phe Thr Phe Ser Phe Pro Val Lys Gln Thr Ser Ile Asp Ser Gly
            180                 185                 190

Thr Leu Ser Lys Trp Thr Lys Gly Phe Lys Val Ser Gly Met Glu Gly
        195                 200                 205

Lys Asn Val Val Ala Cys Leu Asn Glu Ala Met Glu Ala His Gly Leu
210                 215                 220

Asp Met Arg Val Ser Ala Leu Val Asn Asp Gly Val Gly Thr Leu Ala
225                 230                 235                 240

Gly Ala Arg Tyr Trp Asp Glu Asp Val Met Val Gly Val Ile Leu Gly
                245                 250                 255

Thr Gly Thr Asn Ala Cys Tyr Val Glu Gln His Ala Ile Pro Lys
            260                 265                 270

Leu Arg Ser Lys Ser Ser Gly Thr Thr Ile Ile Asn Thr Glu Trp
        275                 280                 285

Gly Gly Phe Ser Lys Ile Leu Pro Gln Thr Ile Phe Asp Leu Glu Met
290                 295                 300

Asp Glu Thr Ser Leu Asn Pro Gly Glu His Leu Tyr Glu Lys Met Ile
305                 310                 315                 320

Ser Gly Met Tyr Leu Gly Glu Ile Val Arg Arg Val Leu Leu His Met
                325                 330                 335

Cys Glu Thr Ser Asp Leu Phe Gly His Phe Ala Pro Ala Lys Leu Ser
            340                 345                 350
```

```
Thr Pro Leu Ala Leu Arg Thr Glu His Leu Cys Lys Met Gln Glu Asp
            355                 360                 365

Asn Thr Asp Asp Leu Arg Asp Val Gly Ser Ile Leu Tyr Asp Phe Leu
        370                 375                 380

Asp Val Glu Ala Asn Met Asn Ala Arg Arg Val Val Glu Val Cys
385                 390                 395                 400

Asp Thr Val Val Lys Arg Gly Arg Leu Ala Gly Ala Gly Ile Val
                405                 410                 415

Ala Ile Leu Glu Lys Ile Glu Lys Asp Thr Lys Arg Met Gly Ser Gly
            420                 425                 430

Lys Arg Thr Val Val Ala Met Asp Gly Ala Leu Tyr Glu Lys Tyr Pro
            435                 440                 445

Gln Tyr Arg Gln Tyr Met Gln Asp Ala Leu Val Glu Leu Leu Gly His
        450                 455                 460

Lys Leu Ala Ser His Val Ala Ile Lys His Thr Lys Asp Val Ser Gly
465                 470                 475                 480

Leu Gly Ala Ala Leu Leu Ala Ala Thr Asn Ser Ile Tyr
                485                 490

<210> SEQ ID NO 17
<211> LENGTH: 2074
<212> TYPE: DNA
<213> ORGANISM: Arabidopsis thaliana

<400> SEQUENCE: 17
aatccataaa tctcttcctc tctctctttc ttatttaatc gtcacttgac cgccggtaag      60
aaactcgaga gtttgaatcg tttttttaacc ctcgccggtg attattgact ggaaaacacc    120
aaacgaatcg aagcagttag tttacaggta gagcagtgac agctgagcaa aaaaaaaggc    180
ggcggaaaaa aagtagtag tagttgatga tgatgaagat ggtgaaacag attcgtatag     240
ggttttctaa tcggcggtgt tcgctgttcg tgaactcttt attggagtaa gtaaaaagcg    300
ccagagagag agatattgtg tatttgtctt tttggttctg ttttgggatg gggaaagtgg    360
cggttgcgtt tgcggcggtt gctgttgttg cggcttgttc tgttccgcg gtgatggttg    420 ggaggaggat gaagagtcgg aggaaatgga ggactgttgt tgagattttg aaagagttgg    480
aggatgattg tgatactccg gttgggaggt tgaggcaagt ggttgatgct atggccgtgg    540
agatgcacgc tggtttggct tctgaaggtg gctctaagct taaaatgctc ctcactttcg    600
tcgatgattt gcccactggg agggagaaag gtacttatta tgcacttcac cttggaggca    660
cttattttag gattttaagg gttcttctgg gtgatcaaag gtcttatcta gatgttcaag    720
atgttgaacg acacccaata ccttcacatt tgatgaatag caccagcgag gttcttttca    780
actttctcgc ctttccttg gaaaggttta ttgaaaagga ggaaaacggg tccgattcac    840
aaggtgttag aagggaactt gcatttacgt tctcattccc tgtcaagcat acttctatt     900 cttcaggagt tctaattaaa tggaccaaag gttttgagat tagtgaaatg gttgggcaag    960
atatagctga atgtctacaa ggagctctga acagaagagg cctagatatg catgttgcgg   1020
ctcttgtgaa tgatactgtt ggagccttgt cgcttggata ttatcacgat ccagatacgg   1080
ttgttgcggt tgtatttgga acaggtagta atgcatgtta cttggaaaga accgatgcca   1140
taatcaagtg tcagggtctg cttacaactt ctggaagcat ggtggtaaat atggagtggg   1200 gaaattttg gtcctctcat ttgcctagaa cttcgtatga cattgacttg gatgcagaga   1260
gttcaaatgc aaatgatatg ggatttgaga agatgatatc aggaatgtat ctgggtgaca   1320
```

```
ttgttcgtag agtaattctc cgcatgtcag aagattctga tatctttgga cccatctcgc   1380
ccgtgttatc tgagccttac gttctaagaa caaattcagt ctcagccata catgaagatg   1440
acacacctga gttacaagaa gtagcaagaa tcttgaaaga catagggta tcagatgtac    1500 cactgaaggt gagaaaacta gtggtgaaaa tatgcgatgt ggttacacga agagcaggga   1560
ggcttgcagc agcaggaata gcaggaatct tgaagaagat aggccgagat ggaagcgggg   1620
gaatcacgag cgggagaagc agaagtgaaa tccaaatgca gaaaagaaca gttgttgcgg   1680
tagaaggagg tttgtacatg aattaccaca tgtttaggga atacatggaa gaagctctcg   1740
tagagatact aggagaagaa gtgagtcaat acgtggtggt taaagccatg gaagatggtt   1800
ctagcattgg ctctgctctc ctcgttgcct ctttacagtc atgaatcatc atcgtcgtcg   1860
ttcgtattaa atggtgatat aattggttat gttcgtcctt gtgtgtgtat atagattatt   1920
caatatttgt ttgttgttaa ttataattat tattattcta tatagctttt gtgtaaatgc   1980
ttaggaaggt tttatgtatt ctttgtttct tctattcgta tgatgtgtac tggaaaatag   2040
gtactgggtt tttaagaaaa tgatttacac tgtc                               2074
```

<210> SEQ ID NO 18
<211> LENGTH: 498
<212> TYPE: PRT
<213> ORGANISM: Arabidopsis thaliana

<400> SEQUENCE: 18

```
Met Gly Lys Val Ala Val Ala Phe Ala Ala Val Ala Val Ala Ala
1               5                   10                  15

Cys Ser Val Ala Ala Val Met Val Gly Arg Arg Met Lys Ser Arg Arg
                20                  25                  30

Lys Trp Arg Thr Val Val Glu Ile Leu Lys Glu Leu Asp Asp Cys
            35                  40                  45

Asp Thr Pro Val Gly Arg Leu Arg Gln Val Val Asp Ala Met Ala Val
        50                  55                  60

Glu Met His Ala Gly Leu Ala Ser Glu Gly Gly Ser Lys Leu Lys Met
65                  70                  75                  80

Leu Leu Thr Phe Val Asp Asp Leu Pro Thr Gly Arg Glu Lys Gly Thr
                85                  90                  95

Tyr Tyr Ala Leu His Leu Gly Gly Thr Tyr Phe Arg Ile Leu Arg Val
            100                 105                 110

Leu Leu Gly Asp Gln Arg Ser Tyr Leu Asp Val Gln Asp Val Glu Arg
        115                 120                 125

His Pro Ile Pro Ser His Leu Met Asn Ser Thr Ser Glu Val Leu Phe
    130                 135                 140

Asn Phe Leu Ala Phe Ser Leu Glu Arg Phe Ile Glu Lys Glu Glu Asn
145                 150                 155                 160

Gly Ser Asp Ser Gln Gly Val Arg Arg Glu Leu Ala Phe Thr Phe Ser
                165                 170                 175

Phe Pro Val Lys His Thr Ser Ile Ser Ser Gly Val Leu Ile Lys Trp
            180                 185                 190

Thr Lys Gly Phe Glu Ile Ser Glu Met Val Gly Gln Asp Ile Ala Glu
        195                 200                 205

Cys Leu Gln Gly Ala Leu Asn Arg Arg Gly Leu Asp Met His Val Ala
    210                 215                 220

Ala Leu Val Asn Asp Thr Val Gly Ala Leu Ser Leu Gly Tyr Tyr His
225                 230                 235                 240
```

```
Asp Pro Asp Thr Val Ala Val Val Phe Gly Thr Gly Ser Asn Ala
            245                 250                 255

Cys Tyr Leu Glu Arg Thr Asp Ala Ile Ile Lys Cys Gln Gly Leu Leu
        260                 265                 270

Thr Thr Ser Gly Ser Met Val Val Asn Met Glu Trp Gly Asn Phe Trp
        275                 280                 285

Ser Ser His Leu Pro Arg Thr Ser Tyr Asp Ile Asp Leu Asp Ala Glu
        290                 295                 300

Ser Ser Asn Ala Asn Asp Met Gly Phe Glu Lys Met Ile Ser Gly Met
305                 310                 315                 320

Tyr Leu Gly Asp Ile Val Arg Arg Val Ile Leu Arg Met Ser Glu Asp
            325                 330                 335

Ser Asp Ile Phe Gly Pro Ile Ser Pro Val Leu Ser Glu Pro Tyr Val
            340                 345                 350

Leu Arg Thr Asn Ser Val Ser Ala Ile His Glu Asp Thr Pro Glu
            355                 360                 365

Leu Gln Glu Val Ala Arg Ile Leu Lys Asp Ile Gly Val Ser Asp Val
        370                 375                 380

Pro Leu Lys Val Arg Lys Leu Val Val Lys Ile Cys Asp Val Val Thr
385                 390                 395                 400

Arg Arg Ala Gly Arg Leu Ala Ala Ala Gly Ile Ala Gly Ile Leu Lys
            405                 410                 415

Lys Ile Gly Arg Asp Gly Ser Gly Gly Ile Thr Ser Gly Arg Ser Arg
            420                 425                 430

Ser Glu Ile Gln Met Gln Lys Arg Thr Val Val Ala Val Glu Gly Gly
        435                 440                 445

Leu Tyr Met Asn Tyr Thr Met Phe Arg Glu Tyr Met Glu Glu Ala Leu
        450                 455                 460

Val Glu Ile Leu Gly Glu Glu Val Ser Gln Tyr Val Val Val Lys Ala
465                 470                 475                 480

Met Glu Asp Gly Ser Ser Ile Gly Ser Ala Leu Leu Val Ala Ser Leu
            485                 490                 495

Gln Ser

<210> SEQ ID NO 19
<211> LENGTH: 2039
<212> TYPE: DNA
<213> ORGANISM: Arabidopsis thaliana

<400> SEQUENCE: 19
gcgtccttct tctgactctt accaaaattt tatcaatctc tccctcgccg cgccttttcg    60
ccggaaggac ataactttta ccgggatttg ttgtctacaa gggaacctcg agcgcaaggc   120
tgtttaatcg gaagaatctg gagtcacgga gaagcaaaaa tgaacaaaaa gagagaccct   180
ttatgctgag acggtttaat tttgtatctg tggttataga aaggaatcgt ttgcgatgaa   240
atggagcctt ataggggttat tctgatcggt ggttgaagcg ttgtcatttg catttcgtgt   300
cattctggtt atagactctg tttcaattgc ttctcgtcgt aaaggcgttt gcttttgtga   360
gtaatttatc tcgattcttc tgaaagacgt agaaagagag aaggttgtgt atagatattg   420
gaaatgggga aggttttggt gatgttgacg gcagctgcgg ctgtggtggc ttgttcagtg   480
gcgactgtga tggtgagaag gaggatgaaa gggaggagga aatggaggag ggtggtgggt   540
ttacttaagg atttggagga agcttgtgag acgcctttag gaaggttgag gcagatggtt   600
```

```
gatgccatag ctgtggagat gcaagctggt ttggtttctg aaggagggtc aaagcttaaa      660
atgttgctca cttttgttga tgatcttccc aatgggagcg agacaggaac ctattatgca      720
cttcatcttg gaggctccta ctttaggata ataaaggttc atctaggtgg tcaaagatca      780
tctcttgaag ttcaagatgt tgaacgacat tccataccaa catctttgat gaatagcact      840
agcgaggttc tcttcgactt tctcgcatca tccttgcaga ggtttattga aaagaaggg       900 aacgatttca gttgtcaca acctttaaaa agggaacttg cgtttacttt ttctttccca       960
gtcaagcaga catccatctc atcaggagtt ctaattaaat ggaccaaagg ttttgcaatt     1020
agtgaaatgg ctggggaaga cattgctgaa tgtctacaag gagcgttgaa caagagaggg     1080
ctagatattc gcgttgcagc tcttgtgaat gatactgttg gggctttatc ctttggacat     1140
tttcatgacc cagacacaat tgctgctgtt gtctttggaa caggtagtaa tgcatgttac     1200
cttgaacgaa ctgatgccat aatcaagtgt caaaatccac gcacgacttc tggaagcatg     1260
gtggtcaata tggagtgggg aaacttttgg tcatctcgtc tgccaagaac ttcatatgac     1320
cttgagttgg atgcagagag tatgaattca atgacatgg gctttgagaa gatgatagga     1380
gggatgtatc tgggcgacat tgtccgcaga gtaattcttc gaatgtcaca agagtccgac     1440
atctttggac ctatctcatc catttttatcc acgccttcg ttctgagaac aaattctgtc     1500
tcagcaatgc atgaagatga cacatccgag ttacaagaag tagcacgaat cttgaaagat     1560
ttaggggtgt cagaggtacc aatgaaggtg aggaaacttg tagtgaagat ctgcgatgta     1620
gtgacacgca gagcagctag gctagcagca gcaggaattg caggaatctt gaagaaggta     1680
gggagagatg ggagcggagg aggaaggaga agcgataagc agataatgag aagaacagtg     1740
gtggcagttg aaggaggtct gtatttgaac tacaggatgt tcagagaata tatggacgaa     1800
gctctgagag atatactggg agaagatgtg gctcaacacg tagtggtgaa ggccatggaa     1860
gatggttcca gcattggctc tgcattgttg ctggcttcgt cacaaagtgt tcaaacaata     1920
ccatccgtat gaataatttg tgtacatatt tacaatgtat atagccaatt gttttagaag     1980
catgtaggtt tgtgtaaata ttgtaggcac ttttttagttt cttctactca tgattaagt      2039
```

<210> SEQ ID NO 20
<211> LENGTH: 502
<212> TYPE: PRT
<213> ORGANISM: Arabidopsis thaliana

<400> SEQUENCE: 20

```
Met Gly Lys Val Leu Val Met Leu Thr Ala Ala Ala Val Val Ala
1               5                  10                  15

Cys Ser Val Ala Thr Val Met Val Arg Arg Arg Met Lys Gly Arg Arg
            20                  25                  30

Lys Trp Arg Arg Val Val Gly Leu Leu Lys Asp Leu Glu Glu Ala Cys
        35                  40                  45

Glu Thr Pro Leu Gly Arg Leu Arg Gln Met Val Asp Ala Ile Ala Val
    50                  55                  60

Glu Met Gln Ala Gly Leu Val Ser Glu Gly Gly Ser Lys Leu Lys Met
65                  70                  75                  80

Leu Leu Thr Phe Val Asp Asp Leu Pro Asn Gly Ser Glu Thr Gly Thr
                85                  90                  95

Tyr Tyr Ala Leu His Leu Gly Gly Ser Tyr Phe Arg Ile Ile Lys Val
            100                 105                 110

His Leu Gly Gly Gln Arg Ser Ser Leu Glu Val Gln Asp Val Glu Arg
        115                 120                 125
```

His Ser Ile Pro Thr Ser Leu Met Asn Ser Thr Ser Glu Val Leu Phe
    130                 135                 140

Asp Phe Leu Ala Ser Ser Leu Gln Arg Phe Ile Glu Lys Glu Gly Asn
145                 150                 155                 160

Asp Phe Ser Leu Ser Gln Pro Leu Lys Arg Glu Leu Ala Phe Thr Phe
                165                 170                 175

Ser Phe Pro Val Lys Gln Thr Ser Ile Ser Ser Gly Val Leu Ile Lys
                180                 185                 190

Trp Thr Lys Gly Phe Ala Ile Ser Glu Met Ala Gly Glu Asp Ile Ala
            195                 200                 205

Glu Cys Leu Gln Gly Ala Leu Asn Lys Arg Gly Leu Asp Ile Arg Val
210                 215                 220

Ala Ala Leu Val Asn Asp Thr Val Gly Ala Leu Ser Phe Gly His Phe
225                 230                 235                 240

His Asp Pro Asp Thr Ile Ala Ala Val Val Phe Gly Thr Gly Ser Asn
                245                 250                 255

Ala Cys Tyr Leu Glu Arg Thr Asp Ala Ile Ile Lys Cys Gln Asn Pro
                260                 265                 270

Arg Thr Thr Ser Gly Ser Met Val Val Asn Met Glu Trp Gly Asn Phe
            275                 280                 285

Trp Ser Ser Arg Leu Pro Arg Thr Ser Tyr Asp Leu Glu Leu Asp Ala
290                 295                 300

Glu Ser Met Asn Ser Asn Asp Met Gly Phe Glu Lys Met Ile Gly Gly
305                 310                 315                 320

Met Tyr Leu Gly Asp Ile Val Arg Arg Val Ile Leu Arg Met Ser Gln
                325                 330                 335

Glu Ser Asp Ile Phe Gly Pro Ile Ser Ser Ile Leu Ser Thr Pro Phe
                340                 345                 350

Val Leu Arg Thr Asn Ser Val Ser Ala Met His Glu Asp Asp Thr Ser
            355                 360                 365

Glu Leu Gln Glu Val Ala Arg Ile Leu Lys Asp Leu Gly Val Ser Glu
370                 375                 380

Val Pro Met Lys Val Arg Lys Leu Val Val Lys Ile Cys Asp Val Val
385                 390                 395                 400

Thr Arg Arg Ala Ala Arg Leu Ala Ala Ala Gly Ile Ala Gly Ile Leu
                405                 410                 415

Lys Lys Val Gly Arg Asp Gly Ser Gly Gly Arg Ser Asp Lys
            420                 425                 430

Gln Ile Met Arg Arg Thr Val Val Ala Val Glu Gly Leu Tyr Leu
            435                 440                 445

Asn Tyr Arg Met Phe Arg Glu Tyr Met Asp Glu Ala Leu Arg Asp Ile
450                 455                 460

Leu Gly Glu Asp Val Ala Gln His Val Val Lys Ala Met Glu Asp
465                 470                 475                 480

Gly Ser Ser Ile Gly Ser Ala Leu Leu Leu Ala Ser Ser Gln Ser Val
                485                 490                 495

Gln Thr Ile Pro Ser Val
            500

<210> SEQ ID NO 21
<211> LENGTH: 1482
<212> TYPE: DNA
<213> ORGANISM: Arabidopsis thaliana

<400> SEQUENCE: 21

```
atgaccagga aagaggtggt tctggccgtg acggctgcaa ccattacggc ggttgcagca      60
ggtgtactaa tgggtcggtg gatccggagg aaagagcggc ggttgaaaca tacgcagaga     120
attttgagga aattcgctag agaatgcgcc acgccggttt cgaagctttg gcggtggcg      180
gacgccttgg tcgccgacat gaccgcctct ttaaccgccg agtgttgcgg ttccctcaac     240
atgctcgttt cattcaccgg ttctctccct tccggtgatg agaaaggggt acactatgga     300
gtcaacttga gaggcaagga actattactg ttacgtggga cgctaggtgg taacgaagag     360
cctatttccg atgtacagaa gcatgagatt ccgatccctg acgatgtttt aaatggttct     420
ttcaaggagt tgtgcgattt catatcattg gagcttgtta aatttcttgc gatgaatccc     480
ggtggagaag cagaagaagt gaagaatctc gggtttacgt tgacgcgctc tgttgagcag     540
attgggtcac attcaatctc gtcgatacat aggaagagtt tagcaaatga cgatgatgag     600
aaggttttga agatttggt gaatgatatg aatgaatcac tggaaacaca cggtctgaaa     660
attcggatga acacagcgct ggtggataat actataggag aattggctgg aggaaggtat     720
tatcacaagg acactgtggc tgcagtatca ttaggtatgg gaaccaacgc tgcttacatt     780
gaacaagctc aagagatatc gaggtggaaa tctgcgatac gtgagccaca agagatcgtt     840
gttagcacag agtggggaga tttcagatct tgccatcttc ctataaccga gttcgatgct     900
tctcttgacg cggaaagctt gaatcccgga catcgaaat ttgagaagat ggtgtcagga     960
agatacttag gggagatagt aagaagagtg ttactaaaaa tgtctgaaga atctgctctc    1020
tttggagata cactacctcc aaaactcaca attccttaca ttttatggtc tccagatatg    1080
gctgcaatgc atcaagatat atccgaagaa cgggagactg taaacaaaaa gctcaaggaa    1140
gttttcggta taatggattc aactcttgcg gcgagagaag ttgtagttga agtatgcgat    1200
gtagtcgcgg aacgagcggc tcgtttagcg ggagcaggaa tagttgggat gataaagaag    1260
cttggaagat tagagaagaa aatgagcatt gtgatagttg aaggaggatt gtatgatcat    1320
tatagggtat ttagaaacta tcttcatagc agcgtttggg aaatgcttgg tgatgagtta    1380
tcagatcacg tcgtcattga gcattctcac ggtggatctg ctgccggagc tctcttcctt    1440
gccgcatgtg gcgacggtca tcaagattct gaaagcaagt ga                        1482
```

<210> SEQ ID NO 22
<211> LENGTH: 493
<212> TYPE: PRT
<213> ORGANISM: Arabidopsis thaliana

<400> SEQUENCE: 22

```
Met Thr Arg Lys Glu Val Val Leu Ala Val Thr Ala Ala Thr Ile Thr
1               5                   10                  15

Ala Val Ala Ala Gly Val Leu Met Gly Arg Trp Ile Arg Arg Lys Glu
            20                  25                  30

Arg Arg Leu Lys His Thr Gln Arg Ile Leu Arg Lys Phe Ala Arg Glu
        35                  40                  45

Cys Ala Thr Pro Val Ser Lys Leu Trp Ala Val Ala Asp Ala Leu Val
    50                  55                  60

Ala Asp Met Thr Ala Ser Leu Thr Ala Glu Cys Cys Gly Ser Leu Asn
65                  70                  75                  80

Met Leu Val Ser Phe Thr Gly Ser Leu Pro Ser Gly Asp Glu Lys Gly
                85                  90                  95

Val His Tyr Gly Val Asn Leu Arg Gly Lys Glu Leu Leu Leu Leu Arg
```

```
             100                 105                 110
Gly Thr Leu Gly Gly Asn Glu Glu Pro Ile Ser Asp Val Gln Lys His
            115                 120                 125

Glu Ile Pro Ile Pro Asp Asp Val Leu Asn Gly Ser Phe Lys Glu Leu
130                 135                 140

Cys Asp Phe Ile Ser Leu Glu Leu Val Lys Phe Leu Ala Met Asn Pro
145                 150                 155                 160

Gly Gly Glu Ala Glu Val Lys Asn Leu Gly Phe Thr Leu Thr Arg
            165                 170                 175

Ser Val Glu Gln Ile Gly Ser His Ser Ile Ser Ser Ile His Arg Lys
            180                 185                 190

Ser Leu Ala Asn Asp Asp Glu Lys Val Leu Lys Asp Leu Val Asn
            195                 200                 205

Asp Met Asn Glu Ser Leu Glu Thr His Gly Leu Lys Ile Arg Met Asn
210                 215                 220

Thr Ala Leu Val Asp Asn Thr Ile Gly Glu Leu Ala Gly Gly Arg Tyr
225                 230                 235                 240

Tyr His Lys Asp Thr Val Ala Ala Val Ser Leu Gly Met Gly Thr Asn
            245                 250                 255

Ala Ala Tyr Ile Glu Gln Ala Gln Glu Ile Ser Arg Trp Lys Ser Ala
            260                 265                 270

Ile Arg Glu Pro Gln Glu Ile Val Val Ser Thr Glu Trp Gly Asp Phe
            275                 280                 285

Arg Ser Cys His Leu Pro Ile Thr Glu Phe Asp Ala Ser Leu Asp Ala
290                 295                 300

Glu Ser Leu Asn Pro Gly His Arg Ile Phe Glu Lys Met Val Ser Gly
305                 310                 315                 320

Arg Tyr Leu Gly Glu Ile Val Arg Val Leu Leu Lys Met Ser Glu
            325                 330                 335

Glu Ser Ala Leu Phe Gly Asp Thr Leu Pro Pro Lys Leu Thr Ile Pro
            340                 345                 350

Tyr Ile Leu Trp Ser Pro Asp Met Ala Ala Met His Gln Asp Ile Ser
            355                 360                 365

Glu Glu Arg Glu Thr Val Asn Lys Lys Leu Lys Glu Val Phe Gly Ile
370                 375                 380

Met Asp Ser Thr Leu Ala Ala Arg Glu Val Val Glu Val Cys Asp
385                 390                 395                 400

Val Val Ala Glu Arg Ala Ala Arg Leu Ala Gly Ala Gly Ile Val Gly
            405                 410                 415

Met Ile Lys Lys Leu Gly Arg Leu Glu Lys Lys Met Ser Ile Val Ile
            420                 425                 430

Val Glu Gly Gly Leu Tyr Asp His Tyr Arg Val Phe Arg Asn Tyr Leu
            435                 440                 445

His Ser Ser Val Trp Glu Met Leu Gly Asp Glu Leu Ser Asp His Val
            450                 455                 460

Val Ile Glu His Ser His Gly Gly Ser Ala Ala Gly Ala Leu Phe Leu
465                 470                 475                 480

Ala Ala Cys Gly Asp Gly His Gln Asp Ser Glu Ser Lys
            485                 490

<210> SEQ ID NO 23
<211> LENGTH: 1862
<212> TYPE: DNA
<213> ORGANISM: Solanum lycopersicum
```

<400> SEQUENCE: 23

```
gaattcggca ccagctttga tccgatctcc tctctgtaat ttttattatt ctccttaaa    60
aaatcacaaa tctttacttt actcatttca ttttttctc agtggaccaa ctttttgcca   120
acctcaaatt ccggcaaaat gaagaaagtg acggtgggag tcgccgtggt tggtgcagct   180
gcggtgtgtg cagtggcggt gttaatagtg aatcaccgga tgcggaaatc tagtaaatgg   240
ggtcgtgcta tggctattct tcgtgaattt gaagaaaagt gtaagactca agatgcaaag   300
cttaagcaag ttgctgatgc tatgactgtt gagatgcacg ccggacttgc ttctgaaggc   360
ggcagtaagc tcaagatgct tatcacttat gtggataatc tacccactgg tgatgaagct   420
ggcgtcttct atgcgttgga tcttggtgga acaaattttc gagtattgcg agtgcaattg   480
ggtggaaaag atggtggtat tattcatcaa gaatttgctg aggcatcaat tcctccaagt   540
ttgatggttg ggacttcaga tgaactttt gattatattg cggctgagct tgcaaaattt   600
gttgctgcgg aagaggaaaa atttcatcaa cctcctggta agcagagaga actaggtttc   660
accttctcat tcccagtaat gcagacttca atcaactccg gaatattat gcggtggaca   720
aaaggcttct ctattgatga tgcggttggt caagatgttg ttggagaact cacaaaagct   780
atgaaaagaa aaggtgtcga tatgcgtgtc tcagctctgg tgaatgatac cgttggaacg   840
ttagctggtg gtaaatatac gcaaaaggat gtagctgttg ctgttatctt aggtacaggg   900
accaatgcag cttatgtgga acgggtgcag gcaattccaa agtggcatgg tcctgtgcca   960
aaatctggtg aaatggttat caatatggaa tggggtaatt ttaggtcatc ccatctgccg  1020
ttgacagagt atgatcatgc attggataat gagagtttaa atcctggtga acagatattt  1080
gagaagatga cttctggcat gtacttggga gaatttttac gcagagttct acttagggtg  1140
gctgaagaag ctggcgtttt tggtgatgag gtccctccaa agctcaagga accatttgtg  1200
ttaaggacac ctgatatgtc tgctatgcat catgacacat cctctgatct gaaagtggtt  1260
ggtgaaaagc tgaaggatat tttagagata tctaataact ccttgaagac gagaaaacta  1320
gtggttgagc tgtgcaatat cgttgccaca cgtggggcaa gacttgcagc tgcaggtgta  1380
ttgggcatct tgaaaaagat gggaagagat acgcctaagc agggtggttc agaaaggacg  1440
gttatagcca tggatggcgg gttgtatgag cactatacag aatacaggat gtgtttagag  1500
aactctttga aggacttgct gggagaggag ttagcaacga gcatcgtttt tgtgcactcc  1560
aatgatggtt ctggcattgg tgctgctctt cttgctgcct ctcattcaat gtaccttgaa  1620
gatcaagatg cttaggagtg tgacaaaagc catatcttgc tagagggaac tacctttaga  1680
ctcctctcta gcgttttcgg tattttctct cctttatgta ccatcaaaat gaaattaata  1740
atatctccag cagatacatt taactttat ctctaggaga gttttcctaa gagtgccttc  1800
ataaacacac aattttcatg gataaagagt ccttttacta cctgaaaaaa aaaaaaaaa  1860
aa                                                                 1862
```

<210> SEQ ID NO 24
<211> LENGTH: 498
<212> TYPE: PRT
<213> ORGANISM: Solanum lycopersicum

<400> SEQUENCE: 24

```
Met Lys Lys Val Thr Val Gly Val Ala Val Val Gly Ala Ala Ala Val
1               5                   10                  15

Cys Ala Val Ala Val Leu Ile Val Asn His Arg Met Arg Lys Ser Ser
```

-continued

```
            20                  25                  30
Lys Trp Gly Arg Ala Met Ala Ile Leu Arg Glu Phe Glu Glu Lys Cys
        35                  40                  45
Lys Thr Gln Asp Ala Lys Leu Lys Gln Val Ala Asp Ala Met Thr Val
 50                  55                  60
Glu Met His Ala Gly Leu Ala Ser Glu Gly Ser Lys Leu Lys Met
 65                  70                  75                  80
Leu Ile Thr Tyr Val Asp Asn Leu Pro Thr Gly Asp Glu Ala Gly Val
                85                  90                  95
Phe Tyr Ala Leu Asp Leu Gly Gly Thr Asn Phe Arg Val Leu Arg Val
            100                 105                 110
Gln Leu Gly Gly Lys Asp Gly Ile Ile His Gln Glu Phe Ala Glu
            115                 120                 125
Ala Ser Ile Pro Pro Ser Leu Met Val Gly Thr Ser Asp Glu Leu Phe
            130                 135                 140
Asp Tyr Ile Ala Ala Glu Leu Ala Lys Phe Val Ala Glu Glu
145                 150                 155                 160
Lys Phe His Gln Pro Pro Gly Lys Gln Arg Glu Leu Gly Phe Thr Phe
                165                 170                 175
Ser Phe Pro Val Met Gln Thr Ser Ile Asn Ser Gly Asn Ile Met Arg
            180                 185                 190
Trp Thr Lys Gly Phe Ser Ile Asp Asp Ala Val Gly Gln Asp Val Val
            195                 200                 205
Gly Glu Leu Thr Lys Ala Met Lys Arg Lys Gly Val Asp Met Arg Val
            210                 215                 220
Ser Ala Leu Val Asn Asp Thr Val Gly Thr Leu Ala Gly Gly Lys Tyr
225                 230                 235                 240
Thr Gln Lys Asp Val Ala Val Ala Val Ile Leu Gly Thr Gly Thr Asn
                245                 250                 255
Ala Ala Tyr Val Glu Arg Val Gln Ala Ile Pro Lys Trp His Gly Pro
            260                 265                 270
Val Pro Lys Ser Gly Glu Met Val Ile Asn Met Glu Trp Gly Asn Phe
            275                 280                 285
Arg Ser Ser His Leu Pro Leu Thr Glu Tyr Asp His Ala Leu Asp Asn
            290                 295                 300
Glu Ser Leu Asn Pro Gly Glu Gln Ile Phe Glu Lys Met Thr Ser Gly
305                 310                 315                 320
Met Tyr Leu Gly Glu Ile Leu Arg Arg Val Leu Leu Arg Val Ala Glu
                325                 330                 335
Glu Ala Gly Val Phe Gly Asp Glu Val Pro Pro Lys Leu Lys Glu Pro
            340                 345                 350
Phe Val Leu Arg Thr Pro Asp Met Ser Ala Met His His Asp Thr Ser
            355                 360                 365
Ser Asp Leu Lys Val Val Gly Glu Lys Leu Lys Asp Ile Leu Glu Ile
            370                 375                 380
Ser Asn Thr Ser Leu Lys Thr Arg Lys Leu Val Val Glu Leu Cys Asn
385                 390                 395                 400
Ile Val Ala Thr Arg Gly Ala Arg Leu Ala Ala Gly Val Leu Gly
                405                 410                 415
Ile Leu Lys Lys Met Gly Arg Asp Thr Pro Lys Gln Gly Gly Ser Glu
            420                 425                 430
Arg Thr Val Ile Ala Met Asp Gly Gly Leu Tyr Glu His Tyr Thr Glu
            435                 440                 445
```

Tyr Arg Met Cys Leu Glu Asn Ser Leu Lys Asp Leu Leu Gly Glu Glu
        450                 455                 460

Leu Ala Thr Ser Ile Val Phe Val His Ser Asn Asp Gly Ser Gly Ile
465                 470                 475                 480

Gly Ala Ala Leu Leu Ala Ala Ser His Ser Met Tyr Leu Glu Asp Gln
                485                 490                 495

Asp Ala

<210> SEQ ID NO 25
<211> LENGTH: 1770
<212> TYPE: DNA
<213> ORGANISM: Solanum lycopersicum
<220> FEATURE:
<221> NAME/KEY: misc_feature
<222> LOCATION: (1329)..(1329)
<223> OTHER INFORMATION: n is a, c, g, or t

<400> SEQUENCE: 25 cttcttttt tcaatgaatt aatcaaatac ataatcttga tctgatctca tttattcata      60
aagaaagaac attattatta ctctaataac aatccttaat taatctgtaa ttttatacga     120
tttcggatag taaaaggatg aagaaggcga cggtgggtgc ggtggtggta ggtacagcgg     180
cggcggtagc tgtggcggcg ctcgtcatgc gccaccgcat gggtaaatcg agcaaatggg     240
cacgtgccag ggcaattctg aaggaattcg aggagaaatg tgccaccca gatgccaagc      300 tgaagcaagt ggctgatgct atgacggtgg agatgcacgc cggactcgcc tctgaaggag     360
gcagcaagct caagatgctt attagctatg tagacaatct ccctactggt gatgaagcag     420 gagtcttta tgcattggat cttggtggaa cgaattttcg agtattgcgg gtacagttgg      480
ggggaaaaga tggtgggatt atgcatcaag aatttgcgga ggcatcaatt cctccaaatt     540
tgatggttgg aacttcagaa gcccttttg actatattgc ggcagaactt gcaaaattcg      600
tagatgaaga aggagaaaaa tttcatccac ctcctggtaa gcagagagaa ttaggcttca     660
ccttctcgtt cccaataatg cagacttcaa tcaattctgg aactcttatc aggtggacga     720
aaggtttctc cattgatgac acggttggca agatgttgt tgcagaactg acaaaagcaa      780
tgcaaaaacg agaaattgat atgagggtgt cagcgcttgt gaatgatact gttggaacat     840
tggctggtgg tagattcacg gataaggatg tatccattgc tgtgatatta ggtactggga     900
caaatgcwgc atatgtggaa cgkgctcagg caatycccaa atggcacggt cctctgccta     960
actctggaga aatggtgatc aatatggaat ggggtaactt taggtcctcc catcttccct    1020
tgacacagta tgataatgct atggataccg atagtttaaa tcccggtgaa cagatatttg    1080
agaagatatg ttctggtatg tacttgggag aaattttacg cagagttcta cttagaatgg    1140
ctaaagaagc tggcatttt ggcgaggaag ttcctccaaa actcaagaat tcattcatat     1200
tgaggacacc tgaaatgtct gctatgcatc atgacacatc ctctgatttg agagtggttg    1260
gcgacaagtt gaaggatatc ttagagatat ccaatacctc cttgaagaca aggagattag    1320
ttgttgagnt gtgtaatatt gttgcaacac gtggcgccag acttgcggca gctggtatct    1380
tgggcattat caaaaagatg ggaaaggata caccgaggga agtggtcca gaaaagattg     1440 tggtagccat ggatggcgga ttgtatgagc actatacaga atacagcaag tgcttggaaa    1500
acacattggt tgaattgctt ggaaaggaaa tggcaacaag cattgtcttc aagcacgcga    1560
atgatggttc tggcattggc gctgcactcc tcgcggcctc caactctgtg tatgttgaag    1620
acaagtgaga gtgatcaaaa tgatatttag ctagaggaaa ctccatttac cttttatatt    1680

```
atgttttttc tctagccttt tctttttgt tcttctaaca attatttcca gatttattat    1740
tcctgggaat gccaacatat ttcttctgga                                    1770
```

<210> SEQ ID NO 26
<211> LENGTH: 496
<212> TYPE: PRT
<213> ORGANISM: Solanum lycopersicum
<220> FEATURE:
<221> NAME/KEY: misc_feature
<222> LOCATION: (398)..(398)
<223> OTHER INFORMATION: Xaa can be any naturally occurring amino acid

<400> SEQUENCE: 26

```
Met Lys Lys Ala Thr Val Gly Ala Val Val Gly Thr Ala Ala Ala
1               5                   10                  15

Val Ala Val Ala Ala Leu Val Met Arg His Arg Met Gly Lys Ser Ser
            20                  25                  30

Lys Trp Ala Arg Ala Arg Ala Ile Leu Lys Glu Phe Glu Glu Lys Cys
        35                  40                  45

Ala Thr Pro Asp Ala Lys Leu Lys Gln Val Ala Asp Ala Met Thr Val
    50                  55                  60

Glu Met His Ala Gly Leu Ala Ser Glu Gly Gly Ser Lys Leu Lys Met
65                  70                  75                  80

Leu Ile Ser Tyr Val Asp Asn Leu Pro Thr Gly Asp Glu Ala Gly Val
                85                  90                  95

Phe Tyr Ala Leu Asp Leu Gly Gly Thr Asn Phe Arg Val Leu Arg Val
            100                 105                 110

Gln Leu Gly Gly Lys Asp Gly Gly Ile Met His Gln Glu Phe Ala Glu
        115                 120                 125

Ala Ser Ile Pro Pro Asn Leu Met Val Gly Thr Ser Glu Ala Leu Phe
    130                 135                 140

Asp Tyr Ile Ala Ala Glu Leu Ala Lys Phe Val Asp Glu Glu Gly Glu
145                 150                 155                 160

Lys Phe His Pro Pro Gly Lys Gln Arg Glu Leu Gly Phe Thr Phe
                165                 170                 175

Ser Phe Pro Ile Met Gln Thr Ser Ile Asn Ser Gly Thr Leu Ile Arg
            180                 185                 190

Trp Thr Lys Gly Phe Ser Ile Asp Asp Thr Val Gly Lys Asp Val Val
        195                 200                 205

Ala Glu Leu Thr Lys Ala Met Gln Lys Arg Glu Ile Asp Met Arg Val
    210                 215                 220

Ser Ala Leu Val Asn Asp Thr Val Gly Thr Leu Ala Gly Gly Arg Phe
225                 230                 235                 240

Thr Asp Lys Asp Val Ser Ile Ala Val Ile Leu Gly Thr Gly Thr Asn
                245                 250                 255

Ala Ala Tyr Val Glu Arg Ala Gln Ala Ile Pro Lys Trp His Gly Pro
            260                 265                 270

Leu Pro Asn Ser Gly Glu Met Val Ile Asn Met Glu Trp Gly Asn Phe
        275                 280                 285

Arg Ser Ser His Leu Pro Leu Thr Gln Tyr Asp Asn Ala Met Asp Thr
    290                 295                 300

Asp Ser Leu Asn Pro Gly Glu Gln Ile Phe Glu Lys Ile Cys Ser Gly
305                 310                 315                 320

Met Tyr Leu Gly Glu Ile Leu Arg Arg Val Leu Leu Arg Met Ala Lys
                325                 330                 335
```

```
Glu Ala Gly Ile Phe Gly Glu Val Pro Pro Lys Leu Lys Asn Ser
                340                 345                 350

Phe Ile Leu Arg Thr Pro Glu Met Ser Ala Met His His Asp Thr Ser
            355                 360                 365

Ser Asp Leu Arg Val Val Gly Asp Lys Leu Lys Asp Ile Leu Glu Ile
        370                 375                 380

Ser Asn Thr Ser Leu Lys Thr Arg Arg Leu Val Val Glu Xaa Cys Asn
385                 390                 395                 400

Ile Val Ala Thr Arg Gly Ala Arg Leu Ala Ala Gly Ile Leu Gly
                405                 410                 415

Ile Ile Lys Lys Met Gly Lys Asp Thr Pro Arg Glu Ser Gly Pro Glu
                420                 425                 430

Lys Ile Val Val Ala Met Asp Gly Gly Leu Tyr Glu His Tyr Thr Glu
                435                 440                 445

Tyr Ser Lys Cys Leu Glu Asn Thr Leu Val Glu Leu Leu Gly Lys Glu
        450                 455                 460

Met Ala Thr Ser Ile Val Phe Lys His Ala Asn Asp Gly Ser Gly Ile
465                 470                 475                 480

Gly Ala Ala Leu Leu Ala Ala Ser Asn Ser Val Tyr Val Glu Asp Lys
                485                 490                 495

<210> SEQ ID NO 27
<211> LENGTH: 2166
<212> TYPE: DNA
<213> ORGANISM: Solanum lycopersicum
<220> FEATURE:
<221> NAME/KEY: misc_feature
<222> LOCATION: (1897)..(1897)
<223> OTHER INFORMATION: n is a, c, g, or t
<220> FEATURE:
<221> NAME/KEY: misc_feature
<222> LOCATION: (1902)..(1902)
<223> OTHER INFORMATION: n is a, c, g, or t
<220> FEATURE:
<221> NAME/KEY: misc_feature
<222> LOCATION: (1947)..(1947)
<223> OTHER INFORMATION: n is a, c, g, or t

<400> SEQUENCE: 27
acatacacca aaaagtttga ttttttcaa gaaagtatgg gaaaattggt tgtaggtgca      60
acagttgtgt gtactgctgc tgtagtatgt ggggtgacag ttttgttaat gaaacatagg    120
gtgaagaatt ctggggagtg gggaaaagtt gaagctttat tgaaagattt tgaggagaag    180
tgtgcaactc cagtggaaaa attaaagcag gtagctgatg ctatgactgt agagatgcaa    240
gctggacttg cttctgaagg tgggagtaag ctcaagatgc ttattagcta tgttgataac    300
cttcctactg gggatgaaaa aggtctgttt tatgcattgg atctaggcgg cacaaacttt    360
cgagtgatgc gtgtacagtt gggtgggaaa gaaaagcgta tagttaaaca tgaagttaaa    420
gaagtttcaa ttccacagaa tgtgatgact ggatcatcat ctgaagtgtt atttgatttt    480
attgccacgg cacttgcaga atttgtagct acagaaggtg atgattttca tcttccacct    540
ggtagacaaa gggagttagg ctttaccttc tctttccctg tgaaacaatt gtcaattgca    600
tcaggaactc ttattaaatg gacaaagggc ttctccatag aagatttggt tgggcaagat    660
gtggttggag aattagcaaa agcaatggaa agggccggcc ttgacgtgcg tgtggctgca    720
ttagtaaatg atactgttgg aacgttagcg ggaggtcggt acaataatcc tgatgtcatt    780
gctgcagtaa ttttgggtac cggaaccaat gcagcatatg ttgaacgggc tcatgcgatt    840
```

```
cccaaatggc atggtctgtt gcctaaatcc ggagaaatgg ttatcaacat ggaatggggt    900
aatttccgct catcacatct tccagtaaca gaatatgacc aaaatcttga tattgagagt    960
ttaaaccccg gtgagcagat ttatgaaaag attatttccg ggatgtatct tggagaaatt   1020
ttgcgtagag tattgtgtag aatggctgaa gaagcttcat tattcggtga ttatgtccca   1080
tccaaactga aagttccttt cgtattgagg actccggaca tggctgctat gcatcacgac   1140
gagtctgctg atctcaaggt tgttggaaat aagctgaagg atatcttaga ggtacctaat   1200
tctaccttga aaatgaggaa aatagttgtg gagctgtgcg atattatcac ctctcgtgga   1260
gctcgtcttt ctgcagcagg aattgtgggc atcctcaaga aattgggaag agacactttt   1320
aaagacggag agaagcagag gtctgtcata gctgtggacg tgcattgtt tgagcattac    1380 accaagttca gaaattgctt gaaggaaact atgaaagagt tactgggaga tgctgcagat   1440
agcacagtca ttgagctttc taatgatggt tcaggcgttg gagctgcact tttggctgcc   1500
tcacattccc aatacacaga tctcgaggaa tcttgatcat ggtcagagtg acacaaccaa   1560
aagtgcctgg tcaagagttc tctacgttta caatcgcccc tcttcttgct aaagggaacc   1620
cacttcttac tttcttctac gagacgattg aaatatttct tgcttccttg tgcactgtgt   1680
catgcaagag tgaactttga agtgagccat agttcaatat accaaaatga gcacatctct   1740
cttcagctaa acaccaatat gctgaccttt tcactcctgg tgcctctaag aaccatcttt   1800
tatcccaagt gttaacttaa attttccct cactagccag aaaataaagt taggatacaa    1860
ataaagttat tctagttgcc acattttgt gtaatcnttt cnaagattta ttgttgccaa    1920
aagttactta ccgggaaaca acctctncat ctctttaagg tagggatagg atttcttac    1980 tctataccct ccctagagtc cacttatgag attacatcag atatgttgtt gtatcgttgc   2040
caaaagtttt ggatttgtgg aattacatcg tatatgttgt tgtatggttg ccaaaagtta   2100
tagtgctgag gtagttcaag cttgtttcta tttttctgga tttttaggaa atctctcctc   2160
cattca                                                              2166
```

<210> SEQ ID NO 28
<211> LENGTH: 499
<212> TYPE: PRT
<213> ORGANISM: Solanum lycopersicum

<400> SEQUENCE: 28

```
Met Gly Lys Leu Val Val Gly Ala Thr Val Val Cys Thr Ala Ala Val
1               5                   10                  15

Val Cys Gly Val Thr Val Leu Leu Met Lys His Arg Val Lys Asn Ser
            20                  25                  30

Gly Glu Trp Gly Lys Val Glu Ala Leu Leu Lys Asp Phe Glu Glu Lys
        35                  40                  45

Cys Ala Thr Pro Val Glu Lys Leu Lys Gln Val Ala Asp Ala Met Thr
    50                  55                  60

Val Glu Met Gln Ala Gly Leu Ala Ser Glu Gly Ser Lys Leu Lys
65                  70                  75                  80

Met Leu Ile Ser Tyr Val Asp Asn Leu Pro Thr Gly Asp Glu Lys Gly
                85                  90                  95

Leu Phe Tyr Ala Leu Asp Leu Gly Gly Thr Asn Phe Arg Val Met Arg
            100                 105                 110

Val Gln Leu Gly Gly Lys Glu Lys Arg Ile Val Lys His Glu Val Lys
        115                 120                 125

Glu Val Ser Ile Pro Gln Asn Val Met Thr Gly Ser Ser Ser Glu Val
```

```
                130                 135                 140
Leu Phe Asp Phe Ile Ala Thr Ala Leu Ala Glu Phe Ala Thr Glu
145                 150                 155                 160

Gly Asp Asp Phe His Leu Pro Pro Gly Arg Gln Arg Glu Leu Gly Phe
                165                 170                 175

Thr Phe Ser Phe Pro Val Lys Gln Leu Ser Ile Ala Ser Gly Thr Leu
                180                 185                 190

Ile Lys Trp Thr Lys Gly Phe Ser Ile Glu Asp Leu Val Gly Gln Asp
                195                 200                 205

Val Val Gly Glu Leu Ala Lys Ala Met Glu Arg Ala Gly Leu Asp Val
        210                 215                 220

Arg Val Ala Ala Leu Val Asn Asp Thr Val Gly Thr Leu Ala Gly Gly
225                 230                 235                 240

Arg Tyr Asn Asn Pro Asp Val Ile Ala Ala Val Ile Leu Gly Thr Gly
                245                 250                 255

Thr Asn Ala Ala Tyr Val Glu Arg Ala His Ala Ile Pro Lys Trp His
                260                 265                 270

Gly Leu Leu Pro Lys Ser Gly Glu Met Val Ile Asn Met Glu Trp Gly
        275                 280                 285

Asn Phe Arg Ser Ser His Leu Pro Val Thr Glu Tyr Asp Gln Asn Leu
290                 295                 300

Asp Ile Glu Ser Leu Asn Pro Gly Glu Gln Ile Tyr Glu Lys Ile Ile
305                 310                 315                 320

Ser Gly Met Tyr Leu Gly Glu Ile Leu Arg Arg Val Leu Cys Arg Met
                325                 330                 335

Ala Glu Glu Ala Ser Leu Phe Gly Asp Tyr Val Pro Ser Lys Leu Lys
                340                 345                 350

Val Pro Phe Val Leu Arg Thr Pro Asp Met Ala Ala Met His His Asp
        355                 360                 365

Glu Ser Ala Asp Leu Lys Val Val Gly Asn Lys Leu Lys Asp Ile Leu
370                 375                 380

Glu Val Pro Asn Ser Thr Leu Lys Met Arg Lys Ile Val Val Glu Leu
385                 390                 395                 400

Cys Asp Ile Ile Thr Ser Arg Gly Ala Arg Leu Ser Ala Ala Gly Ile
                405                 410                 415

Val Gly Ile Leu Lys Lys Leu Gly Arg Asp Thr Phe Lys Asp Gly Glu
                420                 425                 430

Lys Gln Arg Ser Val Ile Ala Val Asp Gly Ala Leu Phe Glu His Tyr
                435                 440                 445

Thr Lys Phe Arg Asn Cys Leu Lys Glu Thr Met Lys Glu Leu Leu Gly
        450                 455                 460

Asp Ala Ala Asp Ser Thr Val Ile Glu Leu Asn Asp Gly Ser Gly
465                 470                 475                 480

Val Gly Ala Ala Leu Leu Ala Ala Ser His Ser Gln Tyr Thr Asp Leu
                485                 490                 495

Glu Glu Ser

<210> SEQ ID NO 29
<211> LENGTH: 1774
<212> TYPE: DNA
<213> ORGANISM: Solanum lycopersicum

<400> SEQUENCE: 29
ggcacgagag atctcactgt tacctaaaat gtcggtcacc gttagctcgc cggccgtccg    60
```

```
atccttccat gtttcacgat cacctcataa aacgatctct aggccacgtg tcattatatc      120
tgccgtccga tctactgaca gcttaggagt agcaccaatt ttgacgaagt tgcagaaaga      180
ttgtgctact cctcttccag ttttgcgcca cgtggcggat gcaatggccg atgatatgag      240
ggccgggctt gccgtcgacg gcggcagtga tctgaagatg atccttagtt atgtcgacac      300
tctaccaact gggaatgaga aaggcttgtt ttatgcgttg gaccttggtg gtacaaattt      360
ccgggtgcta aggtgcagc taggtggtaa agaagagcgt gtagtcgcca ctgagtttga       420
gcaagtctct ataccccaag aactgatgtt tgctacctcc gaggagcttt cgatttcat      480 agcttctgcg ctaggaaaat ttgcacaaaa ggaaggtgg aattttgagt tgcaacaggg       540
acggacaagg gaaataggat tcacgttttc ttttccggtg aaacagactt caataagaac      600
tggaatccta atcaaatgga caaaggtttt gctgtctct ggaactgcgg aaaagatgt        660 tgttgcttgt ctgaatgaag ccatggagag gcggggaatg gatatgcaag tgtctgccct      720
ggtcaatgac actgtgggaa cacttgccgg agcaagatac tgggatgatg atgccatggt      780
tgctgtcatt cttgggactg gaaccaatgc ttgctatgta aacgtgtgg atgctattcc       840 taagctggca aaaaggatgt ctaagtctcc aataacgatt gtgaataccg aatggggagc      900
tttctcaaat ggccttcctt taactgagtt tgatagagaa atggatgccg agagcattaa      960
ccctggtgag cagattttg aaaagaccat ctctggtatg taccttgggg aaattgtgag       1020
acgggtgctg gtcaaaatgg ccaaggttgg gggcttattt ggtagcagct atgttccgga      1080
gaagctagtc actccatttg tgctgaggac acctgtata tgtgccatgc agcaggatac       1140
atcaatagat cttgaagctg ttgagtctgt cctctatgat gtagctgggg taaaatccga      1200
tctaagtgca aggaaaacag tcgtggacat ttgcgatact attgcaaaac gagggggtcg      1260
tctagctggt gcaggaattg ttggtatatt acagaaaatg gaggaagatt ctaaaggtct      1320
catctttggt aaaagaacag ttgtagcaat ggatggaggc ttatatgagc actatcctca      1380
gtacagagga tacctccaag aagctgtcac agagctacta ggctcggaaa tttcgaaaaa      1440
tgtagtgata aacattcaa agatggatc tggtattgga gctgcattat tagctgctgc       1500
aaattcaaag tatgaacatg atgattaagg gaaaagctaa atttcatgtg ttcaaaggtt      1560
tgcttgagga aaaatacatg agcatttgta atttagaatg ttctaaagaa ggattgatga      1620
ttggatttat agaggctctt gtttgtgatg ccatttttg tactcccatt aatgaagtac       1680
gaagaagtga ggatttatat agccaacccc aatttatttg gaatcgaggc gtagttgtaa      1740
ttgtattata tgcagcactg acttatttat gtga                                   1774
```

<210> SEQ ID NO 30
<211> LENGTH: 499
<212> TYPE: PRT
<213> ORGANISM: Solanum lycopersicum

<400> SEQUENCE: 30

Met Ser Val Thr Val Ser Ser Pro Ala Val Arg Ser Phe His Val Ser
1               5                   10                  15

Arg Ser Pro His Lys Thr Ile Ser Arg Pro Arg Val Ile Ile Ser Ala
            20                  25                  30

Val Arg Ser Thr Asp Ser Leu Gly Val Ala Pro Ile Leu Thr Lys Leu
        35                  40                  45

Gln Lys Asp Cys Ala Thr Pro Leu Pro Val Leu Arg His Val Ala Asp
    50                  55                  60

```
Ala Met Ala Asp Asp Met Arg Ala Gly Leu Ala Val Asp Gly Gly Ser
 65                  70                  75                  80

Asp Leu Lys Met Ile Leu Ser Tyr Val Asp Thr Leu Pro Thr Gly Asn
                 85                  90                  95

Glu Lys Gly Leu Phe Tyr Ala Leu Asp Leu Gly Gly Thr Asn Phe Arg
            100                 105                 110

Val Leu Arg Val Gln Leu Gly Gly Lys Glu Glu Arg Val Val Ala Thr
        115                 120                 125

Glu Phe Glu Gln Val Ser Ile Pro Gln Glu Leu Met Phe Ala Thr Ser
    130                 135                 140

Glu Glu Leu Phe Asp Phe Ile Ala Ser Ala Leu Gly Lys Phe Ala Gln
145                 150                 155                 160

Lys Glu Gly Gly Asn Phe Glu Leu Gln Gln Gly Arg Thr Arg Glu Ile
                165                 170                 175

Gly Phe Thr Phe Ser Phe Pro Val Lys Gln Thr Ser Ile Arg Thr Gly
            180                 185                 190

Ile Leu Ile Lys Trp Thr Lys Gly Phe Ala Val Ser Gly Thr Ala Gly
        195                 200                 205

Lys Asp Val Val Ala Cys Leu Asn Glu Ala Met Glu Arg Arg Gly Met
    210                 215                 220

Asp Met Gln Val Ser Ala Leu Val Asn Asp Thr Val Gly Thr Leu Ala
225                 230                 235                 240

Gly Ala Arg Tyr Trp Asp Asp Ala Met Val Ala Val Ile Leu Gly
                245                 250                 255

Thr Gly Thr Asn Ala Cys Tyr Val Glu Arg Val Asp Ala Ile Pro Lys
            260                 265                 270

Leu Ala Lys Arg Met Ser Lys Ser Pro Ile Thr Ile Val Asn Thr Glu
        275                 280                 285

Trp Gly Ala Phe Ser Asn Gly Leu Pro Leu Thr Glu Phe Asp Arg Glu
    290                 295                 300

Met Asp Ala Glu Ser Ile Asn Pro Gly Glu Gln Ile Phe Glu Lys Thr
305                 310                 315                 320

Ile Ser Gly Met Tyr Leu Gly Glu Ile Val Arg Arg Val Leu Val Lys
                325                 330                 335

Met Ala Lys Val Gly Gly Leu Phe Gly Ser Ser Tyr Val Pro Glu Lys
            340                 345                 350

Leu Val Thr Pro Phe Val Leu Arg Thr Pro Asp Ile Cys Ala Met Gln
        355                 360                 365

Gln Asp Thr Ser Ile Asp Leu Glu Ala Val Glu Ser Val Leu Tyr Asp
    370                 375                 380

Val Ala Gly Val Lys Ser Asp Leu Ser Ala Arg Lys Thr Val Val Asp
385                 390                 395                 400

Ile Cys Asp Thr Ile Ala Lys Arg Gly Gly Arg Leu Ala Gly Ala Gly
                405                 410                 415

Ile Val Gly Ile Leu Gln Lys Met Glu Glu Asp Ser Lys Gly Leu Ile
            420                 425                 430

Phe Gly Lys Arg Thr Val Val Ala Met Asp Gly Gly Leu Tyr Glu His
        435                 440                 445

Tyr Pro Gln Tyr Arg Gly Tyr Leu Gln Glu Ala Val Thr Glu Leu Leu
    450                 455                 460

Gly Ser Glu Ile Ser Lys Asn Val Val Ile Glu His Ser Lys Asp Gly
465                 470                 475                 480

Ser Gly Ile Gly Ala Ala Leu Leu Ala Ala Ala Asn Ser Lys Tyr Glu
```

His Asp Asp

<210> SEQ ID NO 31
<211> LENGTH: 1793
<212> TYPE: DNA
<213> ORGANISM: Solanum chacoense

<400> SEQUENCE: 31

| | | | | | |
|---|---|---|---|---|---|
| aatcccaatt | cccttctct | atcattttt | ccttaatcgg | atagtaagga | tgaagaaggc | 60 |
| gacggtggct | gcggtggtgg | taggtacagc | ggcggcggta | gctgtggcgg | cgctcatcat | 120 |
| gcgccaccgc | atgggtaaat | cgagcaaatg | ggcacgtgcc | agggcaattc | tgaaggaatt | 180 |
| cgaggagaaa | tgtgccaccc | cagatggcaa | gctgaagcaa | gtggctgatg | ccatgacggt | 240 |
| ggagatgcac | gccggactcg | cctctgaagg | cggcagcaag | ctcaagatgc | ttattagcta | 300 |
| tgtcgataat | ctccctactg | gcgatgaagg | aggagtcttt | tatgcattgg | atcttggtgg | 360 |
| aacaaatttt | cgagtattgc | gggtgcaatt | gggggaaaa | gatggtggca | ttatccatca | 420 |
| agaatttgcg | gaggcatcaa | ttcctccaaa | tttgatggtt | ggaacttcag | aagcactttt | 480 |
| tgactatatt | gcgcagaac | ttgcaaaatt | cgtagctgaa | gaaggagaag | agtttcatcc | 540 |
| acctcctggt | aggcagagag | aattaggctt | caccttctcg | ttcccaataa | tgcagacttc | 600 |
| aatcaattct | ggaactctta | tcaggtggac | gaaaggtttc | tccattgatg | acacggttgg | 660 |
| caaagatgtt | gttgcagaac | tgacaaaagc | aatgcaaaaa | cgagaaattg | atatgagggt | 720 |
| ctcagcgctt | gtgaatgata | ctgttggaac | attggctggt | ggtagattca | ccaataagga | 780 |
| tgtatccatt | gctgtgatat | taggtactgg | gaccaatgca | gcatatgtgg | aacgggctca | 840 |
| ggcaattccc | aaatggcacg | gtcctctgcc | taaatctgga | gaaatggtga | tcaatatgga | 900 |
| atggggtaac | tttaggtcct | cccaccttcc | cttgacagag | tacgatcatg | ctatggatac | 960 |
| cgatagttta | aatcctggtg | aacagatatt | tgagaagata | tgttctggca | tgtacttggg | 1020 |
| agaaattta | cgcagagttc | tacttagaat | ggctgaagaa | gctggcattt | ttggcgagga | 1080 |
| agttcctcca | aaactcaaga | attcattcat | attgaggaca | cctgaaatgt | ctgctatgca | 1140 |
| tcatgacaca | tcctctgatt | tgagagtggt | tggcgacaag | ttgaaggata | tcttagagat | 1200 |
| atccaatacc | tccttgaaga | caaggagatt | agttgttgag | ctgtgtaata | ttgttgcaac | 1260 |
| acgtggcgcc | agacttgcgg | cagctgggat | cttgggcatt | atcaaaaaga | tgggaaagga | 1320 |
| tacacccagg | gaaagtggtc | cagaaaagat | tgtcgtagcc | atggatggcg | gattgtatga | 1380 |
| acattataca | gaatacagta | agtgcttgga | gaacactttg | gttgaattac | ttggaaagga | 1440 |
| aatggccaca | gtattgtttt | caagcacgc | gaatgatggt | tctggcattg | gcgctgcact | 1500 |
| ccttgcggcc | tctaactccg | tgtatgttga | agacaagtga | gagtgatcaa | aatgatattt | 1560 |
| agctagagga | aactccattt | acctttata | ttatgttttt | tctctggcct | tttctttttg | 1620 |
| gattctctct | ctcctttttg | gttcttctta | caattatttc | cagaattttc | cagcacttgt | 1680 |
| acttggtttt | ctaggatatt | attcctggga | atgccaacat | atttcttctg | gaaaagggtg | 1740 |
| caaagaaatt | atatgaaact | cagcattgct | tattcaaaaa | aaaaaaaaa | aaa | 1793 |

<210> SEQ ID NO 32
<211> LENGTH: 496
<212> TYPE: PRT
<213> ORGANISM: Solanum chacoense

<400> SEQUENCE: 32

```
Met Lys Lys Ala Thr Val Ala Ala Val Val Gly Thr Ala Ala Ala
1               5                   10                  15

Val Ala Val Ala Ala Leu Ile Met Arg His Arg Met Gly Lys Ser Ser
            20                  25                  30

Lys Trp Ala Arg Ala Arg Ala Ile Leu Lys Glu Phe Glu Glu Lys Cys
            35                  40                  45

Ala Thr Pro Asp Gly Lys Leu Lys Gln Val Ala Asp Ala Met Thr Val
            50                  55                  60

Glu Met His Ala Gly Leu Ala Ser Glu Gly Gly Ser Lys Leu Lys Met
65                      70                  75                  80

Leu Ile Ser Tyr Val Asp Asn Leu Pro Thr Gly Asp Glu Gly Gly Val
                85                  90                  95

Phe Tyr Ala Leu Asp Leu Gly Thr Asn Phe Arg Val Leu Arg Val
            100                 105                 110

Gln Leu Gly Gly Lys Asp Gly Gly Ile Ile His Gln Glu Phe Ala Glu
            115                 120                 125

Ala Ser Ile Pro Pro Asn Leu Met Val Gly Thr Ser Glu Ala Leu Phe
            130                 135                 140

Asp Tyr Ile Ala Ala Glu Leu Ala Lys Phe Val Ala Glu Glu Gly Glu
145                 150                 155                 160

Glu Phe His Pro Pro Gly Arg Gln Arg Glu Leu Gly Phe Thr Phe
            165                 170                 175

Ser Phe Pro Ile Met Gln Thr Ser Ile Asn Ser Gly Thr Leu Ile Arg
            180                 185                 190

Trp Thr Lys Gly Phe Ser Ile Asp Asp Thr Val Gly Lys Asp Val Val
            195                 200                 205

Ala Glu Leu Thr Lys Ala Met Gln Lys Arg Glu Ile Asp Met Arg Val
            210                 215                 220

Ser Ala Leu Val Asn Asp Thr Val Gly Thr Leu Ala Gly Gly Arg Phe
225                 230                 235                 240

Thr Asn Lys Asp Val Ser Ile Ala Val Ile Leu Gly Thr Gly Thr Asn
                245                 250                 255

Ala Ala Tyr Val Glu Arg Ala Gln Ala Ile Pro Lys Trp His Gly Pro
            260                 265                 270

Leu Pro Lys Ser Gly Glu Met Val Ile Asn Met Glu Trp Gly Asn Phe
            275                 280                 285

Arg Ser Ser His Leu Pro Leu Thr Glu Tyr Asp His Ala Met Asp Thr
            290                 295                 300

Asp Ser Leu Asn Pro Gly Glu Gln Ile Phe Glu Lys Ile Cys Ser Gly
305                 310                 315                 320

Met Tyr Leu Gly Glu Ile Leu Arg Arg Val Leu Leu Arg Met Ala Glu
            325                 330                 335

Glu Ala Gly Ile Phe Gly Glu Val Pro Pro Lys Leu Lys Asn Ser
            340                 345                 350

Phe Ile Leu Arg Thr Pro Glu Met Ser Ala Met His His Asp Thr Ser
            355                 360                 365

Ser Asp Leu Arg Val Val Gly Asp Lys Leu Lys Asp Ile Leu Glu Ile
            370                 375                 380

Ser Asn Thr Ser Leu Lys Thr Arg Arg Leu Val Val Glu Leu Cys Asn
385                 390                 395                 400

Ile Val Ala Thr Arg Gly Ala Arg Leu Ala Ala Gly Ile Leu Gly
            405                 410                 415
```

```
Ile Ile Lys Lys Met Gly Lys Asp Thr Pro Arg Glu Ser Gly Pro Glu
            420                 425                 430
Lys Ile Val Val Ala Met Asp Gly Gly Leu Tyr Glu His Tyr Thr Glu
        435                 440                 445
Tyr Ser Lys Cys Leu Glu Asn Thr Leu Val Glu Leu Leu Gly Lys Glu
    450                 455                 460
Met Ala Thr Ser Ile Val Phe Lys His Ala Asn Asp Gly Ser Gly Ile
465                 470                 475                 480
Gly Ala Ala Leu Leu Ala Ala Ser Asn Ser Val Tyr Val Glu Asp Lys
                485                 490                 495
```

<210> SEQ ID NO 33
<211> LENGTH: 1619
<212> TYPE: DNA
<213> ORGANISM: Solanum tuberosum

<400> SEQUENCE: 33

```
taaattccgg caaaaaaaat gaagaaagtg acggtgggag ccgccgtggt tggtgcagct      60
gcggtgtgtg cagtggcggc gttaatagtg aaccaccgga tgcggaaatc tagtaaatgg     120
ggtcgtgcta tggctattct tcgtgaattt gaggaaaagt gtaagactca agatgcaaag     180
cttaagcaag ttgctgatgc tatgactgtt gagatgcacg ccggacttgc ttctgaaggc     240
ggccagagct caagatgctt atcacctatg tcgataatct cccaactggt gatgaagctg     300
ggcgtctttt atgcattgga tcttggtgga acaaattttc gagtattgcg agtgcaattg     360
ggtggaaaag atggtggtat tattcatcaa gaatttgctg aggcatcaat tcctccaagt     420
ttgatggttg ggacttcaga tgcactttt gattatattg cggctgagct tgctaaattt     480
gttgctgcgg aagaggaaaa atttcatcaa cctcctggta agcagagaga actaggtttt     540
caccttctca ttcccagtaa tgcagacttc aataactctg gactattat gcggtggaca     600
aaaggcttct caattgatga tgcggttggc caagatgttg ttggagaact cacaaaagct     660
atgaaagaaa aggtgctcga tatgcgggtc tcagctctgg tgaatgatac tgttggaaca     720
ttagctggtg gtaaatatac gcaaaaggat gtagctgttg ctgttatctt aggtacaggg     780
acgaatgcag cttatgtgga gcgggtgcag gcaattccaa gtggcatgg tcctgtgcca     840
aaatctggtg aaatggttat caatatggaa tggggtaatt ttaggtcatc ccatctgccg     900
ttgacagagt atgatcatgc gttggataac gagagtttaa atcctgctga acagatattt     960
gagaagatga cttctggcat gtacttggga gaaattttac gcagagttct cactagggtg    1020
gctgaagaag tcctggcgtt tttggcgatg aggtccctcc aaagcctcaa ggattcattt    1080
gtgttaagga cacctgatat gtctgctatg catcatgaca catcccctga tctgaaagtg    1140
gttggtgaaa agctgaagga tattttagag atatctaata cctccttgaa gacaaggaaa    1200
ttagtgttga gcctgtgcaa tatcgttgca acacgtgggg caagacttga cgctgcaggg    1260
gtattgggca tcttgaaaaa gatgggaaga gatacgccta agcagggtgg ttcagaaagg    1320
acggttatag ccatggatgg cgggttgtat gagcactata cagaatatag aatgtgttta    1380
gagaactctt tgaaggactt gctcggagag gaattggcaa cgagcatcgt ttttgtgcac    1440
tccaatgatg gttctggcat tggtgctgct cttcttcgtg cctctcattc aatgtacctt    1500
gaagatcaag cttaggcgag tgtgatcaaa tccataactt gctagagggg actacctta    1560
gactctatat tttgctctca agcgttttcg gtattttctc tcctttattg taccatcaa    1619
```

<210> SEQ ID NO 34

```
<211> LENGTH: 498
<212> TYPE: PRT
<213> ORGANISM: Solanum tuberosum

<400> SEQUENCE: 34
```

Met Lys Lys Val Thr Val Gly Ala Ala Val Gly Ala Ala Val
1               5                   10                  15

Cys Ala Val Ala Ala Leu Ile Val Asn His Arg Met Arg Lys Ser Ser
                20                  25                  30

Lys Trp Gly Arg Ala Met Ala Ile Leu Arg Glu Phe Glu Lys Cys
            35                  40                  45

Lys Thr Gln Asp Ala Lys Leu Lys Gln Val Ala Asp Ala Met Thr Val
    50                  55                  60

Glu Met His Ala Gly Leu Ala Ser Glu Gly Gly Gln Ser Ser Arg Cys
65                  70                  75                  80

Leu Ser Pro Met Ser Ile Ile Ser Gln Leu Val Met Lys Leu Gly Val
                85                  90                  95

Phe Tyr Ala Leu Asp Leu Gly Gly Thr Asn Phe Arg Val Leu Arg Val
                100                 105                 110

Gln Leu Gly Gly Lys Asp Gly Gly Ile Ile His Gln Glu Phe Ala Glu
            115                 120                 125

Ala Ser Ile Pro Pro Ser Leu Met Val Gly Thr Ser Asp Ala Leu Phe
130                 135                 140

Asp Tyr Ile Ala Ala Glu Leu Ala Lys Phe Val Ala Glu Glu Glu
145                 150                 155                 160

Lys Phe His Gln Pro Pro Gly Lys Gln Arg Glu Leu Gly Phe His Leu
                165                 170                 175

Leu Ile Pro Ser Asn Ala Asp Phe Asn Asn Ser Gly Thr Ile Met Arg
            180                 185                 190

Trp Thr Lys Gly Phe Ser Ile Asp Asp Ala Val Gly Gln Asp Val Val
        195                 200                 205

Gly Glu Leu Thr Lys Ala Met Lys Glu Lys Val Leu Asp Met Arg Val
        210                 215                 220

Ser Ala Leu Val Asn Asp Thr Val Gly Thr Leu Ala Gly Gly Lys Tyr
225                 230                 235                 240

Thr Gln Lys Asp Val Ala Val Ala Val Ile Leu Gly Thr Gly Thr Asn
                245                 250                 255

Ala Ala Tyr Val Glu Arg Val Gln Ala Ile Pro Lys Trp His Gly Pro
            260                 265                 270

Val Pro Lys Ser Gly Glu Met Val Ile Asn Met Glu Trp Gly Asn Phe
    275                 280                 285

Arg Ser Ser His Leu Pro Leu Thr Glu Tyr Asp His Ala Leu Asp Asn
290                 295                 300

Glu Ser Leu Asn Pro Ala Glu Gln Ile Phe Glu Lys Met Thr Ser Gly
305                 310                 315                 320

Met Tyr Leu Gly Glu Ile Leu Arg Arg Val Leu Thr Arg Val Ala Glu
                325                 330                 335

Glu Val Leu Ala Phe Leu Ala Met Arg Ser Leu Gln Ser Leu Lys Asp
            340                 345                 350

Ser Phe Val Leu Arg Thr Pro Asp Met Ser Ala Met His His Asp Thr
        355                 360                 365

Ser Pro Asp Leu Lys Val Val Gly Glu Lys Leu Lys Asp Ile Leu Glu
370                 375                 380

Ile Ser Asn Thr Ser Leu Lys Thr Arg Lys Leu Val Leu Ser Leu Cys

```
                385                 390                 395                 400
Asn Ile Val Ala Thr Arg Gly Ala Arg Leu Asp Ala Ala Gly Val Leu
                405                 410                 415
Gly Ile Leu Lys Lys Met Gly Arg Asp Thr Pro Lys Gln Gly Gly Ser
                420                 425                 430
Glu Arg Thr Val Ile Ala Met Asp Gly Gly Leu Tyr Glu His Tyr Thr
                435                 440                 445
Glu Tyr Arg Met Cys Leu Glu Asn Ser Leu Lys Asp Leu Leu Gly Glu
                450                 455                 460
Glu Leu Ala Thr Ser Ile Val Phe Val His Ser Asn Asp Gly Ser Gly
465                 470                 475                 480
Ile Gly Ala Ala Leu Leu Arg Ala Ser His Ser Met Tyr Leu Glu Asp
                485                 490                 495
Gln Ala
```

<210> SEQ ID NO 35
<211> LENGTH: 1874
<212> TYPE: DNA
<213> ORGANISM: Solanum tuberosum

<400> SEQUENCE: 35

```
ttcggcacga gatcaatccc aattcccctt ctctatcatt ttttccttaa tcggatagta      60
aggatgaaga aggcgacggt gggtgcggtg gtcgtaggta cagcggcggc ggtagctgtg     120
gcggcgctca tcatgcgcca ccgcatgggt aaatcgagca atgggcacg tgccagggca      180
attctgaagg aattcgagga gaaatgtgcc accccagatg gcaagctgaa gcaagtggct     240
gatgccatga cggtggagat gcacgccgga ctcgcctctg aaggcggcag caagctcaag     300
atgcttatta gctatgtcga taatctccct actggcgatg aaggaggagt cttttatgca     360
ttggatcttg gtgaacaaa ttttcgagta ttgcgggtgc aattgggggg aaaagatggt     420
ggcattatcc atcaagaatt tgcggaggca tcaattcctc caaatttgat ggttggaact     480
tcagaagcac ttttgacta tattgcggca gaacttgcaa aattcgtagc tgaagaagga     540
gaagagtttc atccacctcc tggtaggcag agagaattag gcttcacctt ctcgttccca     600
ataatgcaaa cttcaatcaa ttctggaact cttatcaggt ggacgaaagg tttctccatt     660
gatgacacgg ttggcaaaga tgttgttgca gaactgacaa aagcaatgca aaaacgagaa     720
attgatatga gggtctcagc gcttgtgaat gatactgttg gaacattggc tggtggtaga     780
ttcaccaata aggatgtatc cattgctgtg atattaggta ctgggaccaa tgcagcatat     840
gtggaacggg ctcaggcaat tcccaaatgg cacggtcctc tgcctaaatc tggagaaatg     900
gtgatcaata tggaatgggg taactttagg tcctcccacc ttcccttgac agagtacgat     960
catgctatgg ataccaatag tttaaatcct ggtgaacaga tatttgagaa gatatgttct    1020
ggcatgtact tgggagaaat tttacgcaga gttctactta aatggctga agaagctggc    1080
attttggcg aggaagttcc tccaaaactc aagaattcat tcatattgag acacctgaa     1140
atgtctgcta tgcatcatga cacatcctct gatttgagag tggttggcga caagttgaag    1200
gatatcttag agatctccaa ttcctccttg aagacaagga gattagttgt tgagctgtgt    1260
aatattgttg caacacgtgg cgccagactt gcagcagctg ggatcttggg cattatcaaa    1320
aagatgggaa aggatacacc cagggaaagt ggtccagaaa agattgtcgt agccatggat    1380
ggcggattgt atgaacatta tacagaatac agtaagtgct ggagaacac tttggttgaa    1440
ttgcttggaa aggaaatggc cacaagtatt gttttcaagc acgcgaatga tggttctggc    1500
```

```
attggcgcgg cactccttgc ggcctctaac tccgtgtatg ttgaagacaa gtgagagtga    1560
tcaaaatgat atttagctag aggaaactcc atttaccttc tatattatgt tttttctcta    1620
gccttttctt tttggattct ctctcctttt tggttcttct tacaattatt tccagaattt    1680
tccagtactt gtacttggtt ttctaggata ttattcctgg gaatgccaac atatttcttc    1740
tggaaagggg tgcaaagaaa atatatatga aacgcagcac tgcttattct cccctttggt    1800
ctttagtttc caactgcaat taaattttgt agggttgaat aaaatggtgt acttttcaaa    1860
aaaaaaaaaa aaaa                                                      1874
```

<210> SEQ ID NO 36
<211> LENGTH: 496
<212> TYPE: PRT
<213> ORGANISM: Solanum tuberosum

<400> SEQUENCE: 36

```
Met Lys Lys Ala Thr Val Gly Ala Val Val Gly Thr Ala Ala Ala
1               5                  10                  15

Val Ala Val Ala Ala Leu Ile Met Arg His Arg Met Gly Lys Ser Ser
                20                  25                  30

Lys Trp Ala Arg Ala Arg Ala Ile Leu Lys Glu Phe Glu Glu Lys Cys
            35                  40                  45

Ala Thr Pro Asp Gly Lys Leu Lys Gln Val Ala Asp Ala Met Thr Val
        50                  55                  60

Glu Met His Ala Gly Leu Ala Ser Glu Gly Ser Lys Leu Lys Met
65                  70                  75                  80

Leu Ile Ser Tyr Val Asp Asn Leu Pro Thr Gly Asp Glu Gly Gly Val
                85                  90                  95

Phe Tyr Ala Leu Asp Leu Gly Gly Thr Asn Phe Arg Val Leu Arg Val
            100                 105                 110

Gln Leu Gly Gly Lys Asp Gly Gly Ile Ile His Gln Glu Phe Ala Glu
        115                 120                 125

Ala Ser Ile Pro Pro Asn Leu Met Val Gly Thr Ser Glu Ala Leu Phe
    130                 135                 140

Asp Tyr Ile Ala Ala Glu Leu Ala Lys Phe Val Ala Glu Gly Glu
145                 150                 155                 160

Glu Phe His Pro Pro Gly Arg Gln Arg Glu Leu Gly Phe Thr Phe
                165                 170                 175

Ser Phe Pro Ile Met Gln Thr Ser Ile Asn Ser Gly Thr Leu Ile Arg
            180                 185                 190

Trp Thr Lys Gly Phe Ser Ile Asp Asp Thr Val Gly Lys Asp Val Val
        195                 200                 205

Ala Glu Leu Thr Lys Ala Met Gln Lys Arg Glu Ile Asp Met Arg Val
    210                 215                 220

Ser Ala Leu Val Asn Asp Thr Val Gly Thr Leu Ala Gly Gly Arg Phe
225                 230                 235                 240

Thr Asn Lys Asp Val Ser Ile Ala Val Ile Leu Gly Thr Gly Thr Asn
                245                 250                 255

Ala Ala Tyr Val Glu Arg Ala Gln Ala Ile Pro Lys Trp His Gly Pro
            260                 265                 270

Leu Pro Lys Ser Gly Glu Met Val Ile Asn Met Glu Trp Gly Asn Phe
        275                 280                 285

Arg Ser Ser His Leu Pro Leu Thr Glu Tyr Asp His Ala Met Asp Thr
    290                 295                 300
```

```
Asn Ser Leu Asn Pro Gly Glu Gln Ile Phe Glu Lys Ile Cys Ser Gly
305                 310                 315                 320

Met Tyr Leu Gly Glu Ile Leu Arg Arg Val Leu Leu Arg Met Ala Glu
                325                 330                 335

Glu Ala Gly Ile Phe Gly Glu Val Pro Pro Lys Leu Lys Asn Ser
            340                 345                 350

Phe Ile Leu Arg Thr Pro Glu Met Ser Ala Met His His Asp Thr Ser
            355                 360                 365

Ser Asp Leu Arg Val Val Gly Asp Lys Leu Lys Asp Ile Leu Glu Ile
    370                 375                 380

Ser Asn Ser Ser Leu Lys Thr Arg Arg Leu Val Val Glu Leu Cys Asn
385                 390                 395                 400

Ile Val Ala Thr Arg Gly Ala Arg Leu Ala Ala Ala Gly Ile Leu Gly
                405                 410                 415

Ile Ile Lys Lys Met Gly Lys Asp Thr Pro Arg Glu Ser Gly Pro Glu
                420                 425                 430

Lys Ile Val Val Ala Met Asp Gly Gly Leu Tyr Glu His Tyr Thr Glu
                435                 440                 445

Tyr Ser Lys Cys Leu Glu Asn Thr Leu Val Glu Leu Leu Gly Lys Glu
            450                 455                 460

Met Ala Thr Ser Ile Val Phe Lys His Ala Asn Asp Gly Ser Gly Ile
465                 470                 475                 480

Gly Ala Ala Leu Leu Ala Ala Ser Asn Ser Val Tyr Val Glu Asp Lys
                485                 490                 495

<210> SEQ ID NO 37
<211> LENGTH: 2300
<212> TYPE: DNA
<213> ORGANISM: Nicotiana tabacum

<400> SEQUENCE: 37
gtgaattgct acattattac ggcaactatg aatatgaaag taaggaacag tcggtagtta      60
gctaaccata ccttccaacg caacaataac ggcgtacaac agtagtatag taatattcat     120
cgtttaaatc cttacatata tttcatcatt aatttattca aatctaactg ttcgcttacc     180
atcattacga tataaaaaag aaaatttata tagtgttaaa gattcacaac tgtataaaact    240 ctctgtttca gcatcaccat ttattgtctc ttctttttt ctccgtcaca cgttcctttt      300
gatctcactg ttaattatgt cggtcaccgt tagctcgccg gccggccgat ccttccatat     360
ttcacgatca ccttacaaaa agatctccaa gccacgtgtc attatcgctg ccgtccgatc     420
tggtgttagt ttagcggtag caccaatatt gactaagttg cagaaagact gtgcaactcc     480
acttcctgtt ttgcgccacg tggctgatgc catggccgtt gatatgcggg ctggacttgc     540
cgtcgatggt ggcagtgatc tgaagatgat ccttagttat attgacactt taccaactgg     600
gaatgagaaa ggtttgttct atgcattgga ccttggtggt acaaatttcc gagtgttaag     660
agtgcagtta ggtggtaaag aagagcgcgt aatcgccact gagtttgagc aagtctctat     720
acctcaagaa ttgatgtttg caacctctga ggagttgttc gatttcatag cttctgagct     780
aggaaaattt tcacaaagtg aaggcggtaa gtttgagatg caacaaggaa ggactagaga     840 ataggattc acattttctt tcccagtgaa gcagacttca gttaaatctg gcatcctaat      900
caagtggaca aagggttttg cagtctctgg aactgcagga aaagatgtgg ttgcttgttt     960
aaatgaagcc atggaaaggc agggattggg aatgcaagtc tcggccctgg tcaatgacac    1020
```

```
tgtagcaaca cttgctggag cgagatactg ggacaatgat gtcatggttg ctgtcattct    1080
tgggactgga accaatgctt gctacgtaga acgtgtggat gctattccta aactgccaca    1140
aaggatgtcc aactctccag aaacaattgt gaatactgaa tggggagcat tttcaaatgg    1200
ccttccttta actgagtttg atagagaaat ggatgccgag agcattaacc ctggtgagca    1260 gattttgag aaacaatct ctggtatgta ccttggagaa attgtaagac gggtgctggt    1320
caaaatggcc aaggttggcg gcttatttgg cggtggctat gttccagaaa agttagtcac    1380
tccatttgtg ctgaggacac cggatatatg tgcaatgcag caggatacat ccagagatct    1440
tgaagctgtt gagtctgtcc tctatgatat agctggggta aaatctgatc taagtgcaag    1500
gaaaacagtc gtagacattt gcgatactat tgcaaatcga gggggcgtc tagctggtgc    1560 aggaattgtt gggattctcc agaaaatgga agaggattca aaaggcgtaa tcttcggtaa    1620
gagaacagtt gtagcaatgg atggaggttt atatgagcac tatcctcagt acagagaata    1680
cctccaagaa gctgtcacag aacttcttgg atcagaaatt tctaaaaatg tagtgataga    1740
gcattcaaaa gatggatctg gaattggagc tgcattatta gctgctgcaa actcaaagta    1800
tgaacatgat tattaggaaa atggtaattt tcatgtctaa aaatgctggt agagcatttg    1860
taattttgtt tttgcaattt agaatgtatt aagaaggatt gatcattgga tttctcattc    1920
tttaagggct cgtttggtac gagggataag agataattac atccgggatt aaatttgaga    1980
taagtttatc ccacgtttgg ttgggataaa atcgcgtat aactaatccc gggattagtt    2040
attccgggat gtagtgtta ttttttatccc tatgagatgg tgggataact aatcctaaga    2100
taattaattc tgggataatc tgtttcccaa ccaaacgatc cttaagaagt ggcttgttgt    2160 atttttatgcc attttgtat taccataatg cagcagtgaa gtatttatgt gctaaaagca    2220
gatgtatcag taaatataga atatcttgtt tgcttataaa ttgttaaata agcatatttc    2280
tgtggtattt gaggcggccg                                                2300
```

<210> SEQ ID NO 38
<211> LENGTH: 499
<212> TYPE: PRT
<213> ORGANISM: Nicotiana tabacum

<400> SEQUENCE: 38

```
Met Ser Val Thr Val Ser Ser Pro Ala Gly Arg Ser Phe His Ile Ser
1               5                   10                  15

Arg Ser Pro Tyr Lys Lys Ile Ser Lys Pro Arg Val Ile Ile Ala Ala
            20                  25                  30

Val Arg Ser Gly Val Ser Leu Ala Val Ala Pro Ile Leu Thr Lys Leu
        35                  40                  45

Gln Lys Asp Cys Ala Thr Pro Leu Pro Val Leu Arg His Val Ala Asp
    50                  55                  60

Ala Met Ala Val Asp Met Arg Ala Gly Leu Ala Val Asp Gly Ser
65                  70                  75                  80

Asp Leu Lys Met Ile Leu Ser Tyr Ile Asp Thr Leu Pro Thr Gly Asn
                85                  90                  95

Glu Lys Gly Leu Phe Tyr Ala Leu Asp Leu Gly Gly Thr Asn Phe Arg
            100                 105                 110

Val Leu Arg Val Gln Leu Gly Gly Lys Glu Glu Arg Val Ile Ala Thr
        115                 120                 125

Glu Phe Glu Gln Val Ser Ile Pro Gln Glu Leu Met Phe Ala Thr Ser
    130                 135                 140
```

Glu Glu Leu Phe Asp Phe Ile Ala Ser Glu Leu Gly Lys Phe Ser Gln
145                 150                 155                 160

Ser Glu Gly Gly Lys Phe Glu Met Gln Gln Gly Arg Thr Arg Glu Ile
                165                 170                 175

Gly Phe Thr Phe Ser Phe Pro Val Lys Gln Thr Ser Val Lys Ser Gly
                180                 185                 190

Ile Leu Ile Lys Trp Thr Lys Gly Phe Ala Val Ser Gly Thr Ala Gly
                195                 200                 205

Lys Asp Val Val Ala Cys Leu Asn Glu Ala Met Glu Arg Gln Gly Leu
210                 215                 220

Gly Met Gln Val Ser Ala Leu Val Asn Asp Thr Val Ala Thr Leu Ala
225                 230                 235                 240

Gly Ala Arg Tyr Trp Asp Asn Asp Val Met Val Ala Val Ile Leu Gly
                245                 250                 255

Thr Gly Thr Asn Ala Cys Tyr Val Glu Arg Val Asp Ala Ile Pro Lys
                260                 265                 270

Leu Pro Gln Arg Met Ser Asn Ser Pro Glu Thr Ile Val Asn Thr Glu
                275                 280                 285

Trp Gly Ala Phe Ser Asn Gly Leu Pro Leu Thr Glu Phe Asp Arg Glu
                290                 295                 300

Met Asp Ala Glu Ser Ile Asn Pro Gly Glu Gln Ile Phe Glu Lys Thr
305                 310                 315                 320

Ile Ser Gly Met Tyr Leu Gly Glu Ile Val Arg Arg Val Leu Val Lys
                325                 330                 335

Met Ala Lys Val Gly Gly Leu Phe Gly Gly Tyr Val Pro Glu Lys
                340                 345                 350

Leu Val Thr Pro Phe Val Leu Arg Thr Pro Asp Ile Cys Ala Met Gln
                355                 360                 365

Gln Asp Thr Ser Arg Asp Leu Glu Ala Val Glu Ser Val Leu Tyr Asp
                370                 375                 380

Ile Ala Gly Val Lys Ser Asp Leu Ser Ala Arg Lys Thr Val Val Asp
385                 390                 395                 400

Ile Cys Asp Thr Ile Ala Asn Arg Gly Gly Arg Leu Ala Gly Ala Gly
                405                 410                 415

Ile Val Gly Ile Leu Gln Lys Met Glu Glu Asp Ser Lys Gly Val Ile
                420                 425                 430

Phe Gly Lys Arg Thr Val Val Ala Met Asp Gly Gly Leu Tyr Glu His
                435                 440                 445

Tyr Pro Gln Tyr Arg Glu Tyr Leu Gln Glu Ala Val Thr Glu Leu Leu
450                 455                 460

Gly Ser Glu Ile Ser Lys Asn Val Val Ile Glu His Ser Lys Asp Gly
465                 470                 475                 480

Ser Gly Ile Gly Ala Ala Leu Leu Ala Ala Ala Asn Ser Lys Tyr Glu
                485                 490                 495

His Asp Tyr

<210> SEQ ID NO 39
<211> LENGTH: 1494
<212> TYPE: DNA
<213> ORGANISM: Nicotiana tabacum

<400> SEQUENCE: 39
atgaagaaag cgacggtggg agccgccgtg gttggcgccg ctacggtatg tgctgtggcg      60
gcattgatag tgaaccaccg tatgcgcaaa tctagtaaat gggcacgtgc tatggctatt     120

```
cttcgtgaat ttgaggaaaa gtgtgggacc cctgatgcta agctcaagca agtcgctgat    180
gctatgaccg tcgagatgca cgctggactt gcctccgaag gtggtagcaa gctcaagatg    240
cttatcactt acgtcgataa tctccccacc ggtgatgaag ccggcgtctt ttatgcgttg    300
gatcttggtg gaacaaattt tcgagtattg cgggtgcagc ttggtggaaa agatggtggt    360
attattcatc aagaatttgc agaggcatca attcctccaa atttgatggt tgggacttca    420
gaagaacttt ttgattacat tgcggcagaa cttgcaaaat tgtcgctga ggaagaggag     480 aaatttcaac aacctcctgg taagcagaga gaactaggtt tcaccttctc attcccggta    540
atgcagactt caatcaactc tgggactatt atgaggtgga caagggctt ctccatcgat     600 gatgcggttg gccaagatgt tgtcggagaa ctcacaaaag ctatgaaaag aaagggcgtt    660
gatatgcggg tctcagctct ggtgaatgat actgttggga cgttggctgg tggtaaatat    720
acacacaacg acgtagctgt tgctgttatc ttaggtacag ggaccaatgc agcttatgtg    780
gaacgggtgc aggcgattcc aaagtggcat ggtcctatgc caaaatctgg tgaaatggtt    840
atcaacatgg aatggggtaa ttttaggtca tcccatcttc ccttgacaca gtatgatcat    900
gcgttggata ctaatagttt gaatcctggt gatcagatat ttgagaagat gacttctggc    960
atgtacttgg gagaaatttt acgcagagtt ctactcagga tggccgaaga agctggcatt   1020
tttggtgatg aggtccctcc aaagctcaag agtccatttg tattgaggac acctgatatg   1080
tctgctatgc atcatgacac atcatctgat ctgagagtgg ttggtgacaa gctgaaggat   1140
attttagaga tatctaatac ctcattgaag acaaggagga tagtcgttga gctgtgcaac   1200
atcgttgcaa cacgaggggc aaggcttgca gctgcaggtg tattggggat cttgaagaag   1260
atgggaaggg atacgcctag gcaaggtggt ccgcagaaga tggttgtagc catggatggc   1320
ggattgtatg agcactatgc agagtacagg acgtgcttag agaacacatt gaaggaattg   1380
cttggagatg aattggcgac aagcattgtt ttcgagcact ccaatgatgg ttctggcatt   1440
ggtgctgctc ttcttgctgc ctctaactca atgtaccttg aagataagtc ctag          1494

<210> SEQ ID NO 40
<211> LENGTH: 497
<212> TYPE: PRT
<213> ORGANISM: Nicotiana tabacum

<400> SEQUENCE: 40

Met Lys Lys Ala Thr Val Gly Ala Ala Val Val Gly Ala Ala Thr Val
1               5                   10                  15

Cys Ala Val Ala Ala Leu Ile Val Asn His Arg Met Arg Lys Ser Ser
                20                  25                  30

Lys Trp Ala Arg Ala Met Ala Ile Leu Arg Glu Phe Glu Glu Lys Cys
            35                  40                  45

Gly Thr Pro Asp Ala Lys Leu Lys Gln Val Ala Asp Ala Met Thr Val
        50                  55                  60

Glu Met His Ala Gly Leu Ala Ser Glu Gly Ser Lys Leu Lys Met
65                  70                  75                  80

Leu Ile Thr Tyr Val Asp Asn Leu Pro Thr Gly Asp Glu Ala Gly Val
                85                  90                  95

Phe Tyr Ala Leu Asp Leu Gly Gly Thr Asn Phe Arg Val Leu Arg Val
            100                 105                 110

Gln Leu Gly Gly Lys Asp Gly Gly Ile Ile His Gln Glu Phe Ala Glu
        115                 120                 125
```

```
Ala Ser Ile Pro Pro Asn Leu Met Val Gly Thr Ser Glu Glu Leu Phe
        130                 135                 140

Asp Tyr Ile Ala Ala Glu Leu Ala Lys Phe Val Ala Glu Glu Glu
145                 150                 155                 160

Lys Phe Gln Gln Pro Pro Gly Lys Gln Arg Glu Leu Gly Phe Thr Phe
                165                 170                 175

Ser Phe Pro Val Met Gln Thr Ser Ile Asn Ser Gly Thr Ile Met Arg
                180                 185                 190

Trp Thr Lys Gly Phe Ser Ile Asp Asp Ala Val Gly Gln Asp Val Val
                195                 200                 205

Gly Glu Leu Thr Lys Ala Met Lys Arg Lys Gly Val Asp Met Arg Val
        210                 215                 220

Ser Ala Leu Val Asn Asp Thr Val Gly Thr Leu Ala Gly Gly Lys Tyr
225                 230                 235                 240

Thr His Asn Asp Val Ala Val Ala Val Ile Leu Gly Thr Gly Thr Asn
                    245                 250                 255

Ala Ala Tyr Val Glu Arg Val Gln Ala Ile Pro Lys Trp His Gly Pro
                260                 265                 270

Met Pro Lys Ser Gly Glu Met Val Ile Asn Met Glu Trp Gly Asn Phe
        275                 280                 285

Arg Ser Ser His Leu Pro Leu Thr Gln Tyr Asp His Ala Leu Asp Thr
        290                 295                 300

Asn Ser Leu Asn Pro Gly Asp Gln Ile Phe Glu Lys Met Thr Ser Gly
305                 310                 315                 320

Met Tyr Leu Gly Glu Ile Leu Arg Arg Val Leu Leu Arg Met Ala Glu
                325                 330                 335

Glu Ala Gly Ile Phe Gly Asp Glu Val Pro Pro Lys Leu Lys Ser Pro
                340                 345                 350

Phe Val Leu Arg Thr Pro Asp Met Ser Ala Met His His Asp Thr Ser
                355                 360                 365

Ser Asp Leu Arg Val Val Gly Asp Lys Leu Lys Asp Ile Leu Glu Ile
        370                 375                 380

Ser Asn Thr Ser Leu Lys Thr Arg Arg Leu Val Val Glu Leu Cys Asn
385                 390                 395                 400

Ile Val Ala Thr Arg Gly Ala Arg Leu Ala Ala Ala Gly Val Leu Gly
                405                 410                 415

Ile Leu Lys Lys Met Gly Arg Asp Thr Pro Arg Gln Gly Pro Gln
                420                 425                 430

Lys Met Val Val Ala Met Asp Gly Gly Leu Tyr Glu His Tyr Ala Glu
                435                 440                 445

Tyr Arg Thr Cys Leu Glu Asn Thr Leu Lys Glu Leu Leu Gly Asp Glu
450                 455                 460

Leu Ala Thr Ser Ile Val Phe Glu His Ser Asn Asp Gly Ser Gly Ile
465                 470                 475                 480

Gly Ala Ala Leu Leu Ala Ala Ser Asn Ser Met Tyr Leu Glu Asp Lys
                485                 490                 495

Ser

<210> SEQ ID NO 41
<211> LENGTH: 1497
<212> TYPE: DNA
<213> ORGANISM: Helianthus annuus

<400> SEQUENCE: 41
```

```
atgggtaagg tagcagtagc ggccacggtg gtctgcgccg ccgctgtgac cgcggcggcg      60
gtggttgtgg tccggcaccg gatgaagaac tccggcaagt gggcaaaagc tatggagatt     120
ttgaaggagt ttgaggacaa gtgtggaact ccggtttcaa aactccggca ggttgctgac     180
gccatgacgg tggagatgca cgccggactt gcttccgacg gtggtagtaa actcaagatg     240
ttaatcagct atgttgacaa tcttcccact ggggacgaaa cgggaatttt ctatgccctt     300
gatcttggtg gtacaaactt tcgtgttctt cgtgtgaaat taggcggagt aggaaacgtg     360
aaaaaagaat ttaagaagt ttcaatccct ccgaatctca tgatcgggaa atctgaggat      420
ttatttgatt ttattgcggg agaacttgca aaattcgtgg ctactgagga tgaagatatg     480
cagattccac ctggcacgca gcgagaatta gggtttacct tttcgtttcc ggttaaacaa     540
tcatcaattg cgggagggac tcttgtaaga tggacaaaag cttcaatat cgaagatgca      600
gttgggcgg atgttgtaga agagttgaca aaagcgatgg aaagggctgg ccttgatatg      660
cgtgtttcgg ctttggtgaa tgatacagtt ggaacgttag ctggagggcg atatggtaat     720
tccgatgtca ttgctgctgt aatattaggt acaggaacta atgcagcata tgtggagcga     780
gcgaatgcaa tccctaaatg gcaaggtctt cttcctaaat caggagagat ggttataaac     840
atggaatggg gcaacttccg gtcatcacat cttcctttga ccgagtatga tgaaggtctt     900
gatggtgata gcctgaaccc tggagagcag atatatgaga aactgatttc cggaatgtat     960
ttgggggaag ttgtgagacg agtccttgtta aagatggcgg aagaagccga gttttttgga    1020
gatattgtgc catccaaact ccaaaagccc tttatattaa ggacccctga tatgtctgca    1080
atgcatcatg attctactcc ggatctcaaa gtggttgcaa ccaagttgaa agatatcctc    1140
gagatatcca acacttctct aaagatgaga aaagtaattg tggaagtctg tgaccttgtg    1200
gcaactcgtg gtgctcgtct ctcagcggct ggaatcctag gaatcctcaa aaaaattgga    1260
aaagatactt gcaaggaagg agaagaaaac cagaaatcag taatagcaat ggacggcggg    1320
ctgtttgaac actacaccaa gttccgaaaa acaatgcaag ataccatgaa tgaattgtta    1380
ggtgaagaaa tttccaaaaa catcattgtc gagctatcga atgacgggtc gggtctcggt    1440
gcggctcttc ttgcagcgtc tcactcacag tatctcgaat atatagagtc cacataa       1497
```

<210> SEQ ID NO 42
<211> LENGTH: 498
<212> TYPE: PRT
<213> ORGANISM: Helianthus annuus

<400> SEQUENCE: 42

```
Met Gly Lys Val Ala Val Ala Ala Thr Val Cys Ala Ala Val
1               5                   10                  15

Thr Ala Ala Val Val Val Arg His Arg Met Lys Asn Ser Gly
            20                  25                  30

Lys Trp Ala Lys Ala Met Glu Ile Leu Lys Glu Phe Glu Asp Lys Cys
        35                  40                  45

Gly Thr Pro Val Ser Lys Leu Arg Gln Val Ala Asp Ala Met Thr Val
    50                  55                  60

Glu Met His Ala Gly Leu Ala Ser Asp Gly Ser Lys Leu Lys Met
65                  70                  75                  80

Leu Ile Ser Tyr Val Asp Asn Leu Pro Thr Gly Asp Glu Thr Gly Ile
                85                  90                  95

Phe Tyr Ala Leu Asp Leu Gly Gly Thr Asn Phe Arg Val Leu Arg Val
            100                 105                 110
```

```
Lys Leu Gly Gly Val Gly Asn Val Lys Lys Glu Phe Lys Glu Val Ser
            115                 120                 125

Ile Pro Pro Asn Leu Met Ile Gly Lys Ser Glu Asp Leu Phe Asp Phe
        130                 135                 140

Ile Ala Gly Glu Leu Ala Lys Phe Val Ala Thr Glu Asp Gly Asp Met
145                 150                 155                 160

Gln Ile Pro Pro Gly Thr Gln Arg Glu Leu Gly Phe Thr Phe Ser Phe
                165                 170                 175

Pro Val Lys Gln Ser Ser Ile Ala Gly Gly Thr Leu Val Arg Trp Thr
                180                 185                 190

Lys Gly Phe Asn Ile Glu Asp Ala Val Gly Ala Asp Val Val Glu Glu
            195                 200                 205

Leu Thr Lys Ala Met Glu Arg Ala Gly Leu Asp Met Arg Val Ser Ala
        210                 215                 220

Leu Val Asn Asp Thr Val Gly Thr Leu Ala Gly Gly Arg Tyr Gly Asn
225                 230                 235                 240

Ser Asp Val Ile Ala Ala Val Ile Leu Gly Thr Gly Thr Asn Ala Ala
                245                 250                 255

Tyr Val Glu Arg Ala Asn Ala Ile Pro Lys Trp Gln Gly Leu Leu Pro
                260                 265                 270

Lys Ser Gly Glu Met Val Ile Asn Met Glu Trp Gly Asn Phe Arg Ser
            275                 280                 285

Ser His Leu Pro Leu Thr Glu Tyr Asp Glu Gly Leu Asp Gly Asp Ser
        290                 295                 300

Leu Asn Pro Gly Glu Gln Ile Tyr Glu Lys Leu Ile Ser Gly Met Tyr
305                 310                 315                 320

Leu Gly Glu Val Val Arg Arg Val Leu Leu Lys Met Ala Glu Glu Ala
                325                 330                 335

Glu Phe Phe Gly Asp Ile Val Pro Ser Lys Leu Gln Lys Pro Phe Ile
                340                 345                 350

Leu Arg Thr Pro Asp Met Ser Ala Met His His Asp Ser Thr Pro Asp
            355                 360                 365

Leu Lys Val Val Ala Thr Lys Leu Lys Asp Ile Leu Glu Ile Ser Asn
        370                 375                 380

Thr Ser Leu Lys Met Arg Lys Val Ile Glu Val Cys Asp Leu Val
385                 390                 395                 400

Ala Thr Arg Gly Ala Arg Leu Ser Ala Ala Gly Ile Leu Gly Ile Leu
                405                 410                 415

Lys Lys Ile Gly Lys Asp Thr Cys Lys Glu Gly Glu Glu Asn Gln Lys
            420                 425                 430

Ser Val Ile Ala Met Asp Gly Gly Leu Phe Glu His Tyr Thr Lys Phe
        435                 440                 445

Arg Lys Thr Met Gln Asp Thr Met Asn Glu Leu Leu Gly Glu Glu Ile
    450                 455                 460

Ser Lys Asn Ile Ile Val Glu Leu Ser Asn Asp Gly Ser Gly Leu Gly
465                 470                 475                 480

Ala Ala Leu Leu Ala Ala Ser His Ser Gln Tyr Leu Glu Tyr Ile Glu
                485                 490                 495

Ser Thr

<210> SEQ ID NO 43
<211> LENGTH: 1854
<212> TYPE: DNA
<213> ORGANISM: Populus trichocarpa
```

<400> SEQUENCE: 43

```
atggggaagg tggcagtagg agcggcggtt gtttgcgcgg cgacagtgtg tgcggcggcg      60
gcgttggtgg tgaggcacag gatgagatgt tcagggaggt gggccagggc tatggcgata    120
ctaagagagt ttgaggaaaa ttgtgggacc cctattggga agttaagaca ggtggctgat    180
gctatgaccg ttgagatgca tgccggcctt gcatctgagg gtggtagtaa gctcaagatg    240
ttaatcagct atgtagataa tcttccctcc ggagaagaga atgggttgtt ctatgcattg    300
gaccttggcg gaacaaattt tcgagttata cgggtactgc tcggtgggag ggatggaggt    360
gttgtcaaac aagagtttga ggaagtttca attcctccac acttgatgac tggatcttca    420
gatgcactat ttggtttcat tgctacagcg cttgccaatt tgttgccac agaaagtgaa    480
ggtctgcatt gttcacctgg gagacaaagg gagctcggtt ttaccttctc atttccagtt    540
aggcaaacat caatagcatc tggaaatctt ataaaatgga caaaggatt ctccatagat    600
gatgtggttg gagaagatgt ggtgggagaa ttaaccaaag ccatggaaag aattggactt    660
gacatgcgcg tgtcagcttt ggtcaatgat acaattggaa cattagctgg aggtcgatac    720
cacaacccag atgtaattgc tgctgtaata ttgggtactg gaacaaatgc agcatatgta    780
gagcgagcac aagcaattcc taagtggcat ggtcttctac ccaaatctgg agaaatggtt    840
atcaacatgg aatggggtaa tttccggtct tcgcaccttc cactaacaga atatgatcaa    900
gacttggatg ttgagtcttt gaatcctggc gaacagattt ttgaaaagat atttctggt    960
atgtatttgg gagaaattgt acgcagagtt ctactgaaaa tggctgaaga ggctgccttt   1020
tttggtgata ttgttccaca aaaactgaag attccattca tcttaaggac gcctcacatg   1080
tctgcaatgc accatgatga atcttcagat ctgagagttg ttggaagcaa actaaaagat   1140
attttagaga tacctcatac ctcgctgaaa atgaggaaag ctattgttga actatgtgac   1200
attgttgcca ctcgtggtgc ccgcctatct gctgctggga ttgtaggcat catcaagaaa   1260
ttgggtagag acactgtaaa ggatggtgaa aagcagaagt ctgtgatagc aatggatggt   1320
gggttgtatg agcactactc taaatttagt acctgcatgg aaagcactct caaggagtta   1380
ctgggagaag aagtttctga caacattgtc gttgagcagt ctaatgatgg ctcaggcatt   1440
ggagctgctc tcctagcagc ctcgcattcc caatacctgg aggtcgaaga atcttgatga   1500
taacccatta cattaagtag tgttacattt ttgttttttg tatattatct atccctctac   1560
actcgacttc aaatcatctg gagcttttca acctagttct tatgacgatg ccagcgaaat   1620
ccatattttg tggtagtaag ttgagcagta gatcaaatac tcttttgaaa agtgccatta   1680
gtggtcccaa gcttcagtgt gggagtctgt cacactgctc ctctttactt ttctcagtca   1740
tttacatgaa ttcacaaata aagtggggga tgtaaaacaa ttatttgagt tgttacattt   1800
gacggaatat ttttctatg gttccgatgg aaaataaagt gaatttttat gatc          1854
```

<210> SEQ ID NO 44
<211> LENGTH: 498
<212> TYPE: PRT
<213> ORGANISM: Populus trichocarpa

<400> SEQUENCE: 44

```
Met Gly Lys Val Ala Val Gly Ala Ala Val Val Cys Ala Ala Thr Val
1               5                   10                  15
Cys Ala Ala Ala Ala Leu Val Val Arg His Arg Met Arg Cys Ser Gly
            20                  25                  30
```

```
Arg Trp Ala Arg Ala Met Ala Ile Leu Arg Glu Phe Glu Glu Asn Cys
         35                  40                  45

Gly Thr Pro Ile Gly Lys Leu Arg Gln Val Ala Asp Ala Met Thr Val
 50                  55                  60

Glu Met His Ala Gly Leu Ala Ser Glu Gly Ser Lys Leu Lys Met
 65                  70                  75                  80

Leu Ile Ser Tyr Val Asp Asn Leu Pro Ser Gly Glu Asn Gly Leu
                 85                  90                  95

Phe Tyr Ala Leu Asp Leu Gly Gly Thr Asn Phe Arg Val Ile Arg Val
            100                 105                 110

Leu Leu Gly Gly Arg Asp Gly Gly Val Val Lys Gln Glu Phe Glu Glu
            115                 120                 125

Val Ser Ile Pro Pro His Leu Met Thr Gly Ser Ser Asp Ala Leu Phe
    130                 135                 140

Gly Phe Ile Ala Thr Ala Leu Ala Asn Phe Val Ala Thr Glu Ser Glu
145                 150                 155                 160

Gly Leu His Cys Ser Pro Gly Arg Gln Arg Glu Leu Gly Phe Thr Phe
                165                 170                 175

Ser Phe Pro Val Arg Gln Thr Ser Ile Ala Ser Gly Asn Leu Ile Lys
            180                 185                 190

Trp Thr Lys Gly Phe Ser Ile Asp Asp Val Val Gly Glu Asp Val Val
            195                 200                 205

Gly Glu Leu Thr Lys Ala Met Glu Arg Ile Gly Leu Asp Met Arg Val
210                 215                 220

Ser Ala Leu Val Asn Asp Thr Ile Gly Thr Leu Ala Gly Gly Arg Tyr
225                 230                 235                 240

His Asn Pro Asp Val Ile Ala Ala Val Ile Leu Gly Thr Gly Thr Asn
                245                 250                 255

Ala Ala Tyr Val Glu Arg Ala Gln Ala Ile Pro Lys Trp His Gly Leu
            260                 265                 270

Leu Pro Lys Ser Gly Glu Met Val Ile Asn Met Glu Trp Gly Asn Phe
            275                 280                 285

Arg Ser Ser His Leu Pro Leu Thr Glu Tyr Asp Gln Asp Leu Asp Val
    290                 295                 300

Glu Ser Leu Asn Pro Gly Glu Gln Ile Phe Glu Lys Ile Ile Ser Gly
305                 310                 315                 320

Met Tyr Leu Gly Glu Ile Val Arg Arg Val Leu Leu Lys Met Ala Glu
                325                 330                 335

Glu Ala Ala Phe Phe Gly Asp Ile Val Pro Gln Lys Leu Lys Ile Pro
            340                 345                 350

Phe Ile Leu Arg Thr Pro His Met Ser Ala Met His His Asp Glu Ser
            355                 360                 365

Ser Asp Leu Arg Val Val Gly Ser Lys Leu Lys Asp Ile Leu Glu Ile
    370                 375                 380

Pro His Thr Ser Leu Lys Met Arg Lys Ala Ile Val Glu Leu Cys Asp
385                 390                 395                 400

Ile Val Ala Thr Arg Gly Ala Arg Leu Ser Ala Ala Gly Ile Val Gly
                405                 410                 415

Ile Ile Lys Lys Leu Gly Arg Asp Thr Val Lys Asp Gly Glu Lys Gln
            420                 425                 430

Lys Ser Val Ile Ala Met Asp Gly Gly Leu Tyr Glu His Tyr Ser Lys
            435                 440                 445

Phe Ser Thr Cys Met Glu Ser Thr Leu Lys Glu Leu Leu Gly Glu Glu
```

|  |  |  | 450 |  |  |  | 455 |  |  |  | 460 |
|---|---|---|---|---|---|---|---|---|---|---|---|

Val Ser Asp Asn Ile Val Val Glu Gln Ser Asn Asp Gly Ser Gly Ile
465                 470                 475                 480

Gly Ala Ala Leu Leu Ala Ala Ser His Ser Gln Tyr Leu Glu Val Glu
                485                 490                 495

Glu Ser

<210> SEQ ID NO 45
<211> LENGTH: 1971
<212> TYPE: DNA
<213> ORGANISM: Spinacia oleracea

<400> SEQUENCE: 45

| acgagcctta | attagaccac | ctcaaggcaa | agctccgatt | aaaccggtcc | ctccaaaaaa | 60 |
|---|---|---|---|---|---|---|
| aaaactcatc | tgaattttcc | ccaatcaaat | tctcccggat | ctactccttc | tctcccttct | 120 |
| ttctctctct | agattgcatc | ttgtaaagaa | agaaagaaac | caaaatttcc | caacatgcca | 180 |
| aattaatcca | tcttctttcc | attgttgtaa | ttagagagag | aaaatcaaat | tgaagagcac | 240 |
| ccatctgatt | tttttagtg | acgttacat | agagagaaaa | tgaggaaggc | agcggtcgga | 300 |
| gcagcggtgg | tatgtacagc | ggcggtgtgt | gcggcggcag | cggtgttggt | aagacagagg | 360 |
| atgaagagct | caagcaagtg | gggtcgtgta | atggcaatac | tgaaggagtt | agatgacaat | 420 |
| tgtgggaccc | ctttgggtaa | gcttagacag | gtggctgatg | ctatgaccgt | tgagatgcac | 480 |
| gctggtcttg | catctgaggg | tgcttctaag | ctcaagatgc | tcatcagcta | cgttgacaat | 540 |
| ctccccactg | gggacgagca | tggactgttc | tatgcgttag | accttggcgg | caccaacttc | 600 |
| cgagtgcttc | gagtaaagtt | gggtggcaaa | gaaaaacgtg | ttgtcgaaca | agaatttgac | 660 |
| gaagtatcaa | ttccacctga | gttgatggtt | ggtacatcag | aacaactgtt | tgattatatc | 720 |
| gccgaagccc | tagccaaatt | tgttgcaacg | gaaagtgaag | gtcttcatcc | tgaacccaat | 780 |
| aaacagagag | agctgggatt | taccttctct | ttccctgtca | agcagacatc | aatcgcatca | 840 |
| gggactctta | aagatggac | caagggcttt | aatatagaag | atacagttgg | tgaagatgtg | 900 |
| gtggctgaat | tgaccaaggc | catgctaaga | aaaggtgtag | atatgcgtgt | gacagctttg | 960 |
| gtcaacgata | cagttggaac | cctagctgga | ggtaggtact | ataagaaga | tgtaattgct | 1020 |
| gctgttatat | tgggtactgg | aacaaacgca | gcttacgttg | aacgtgctag | tgcaattcac | 1080 |
| aagtggcatg | gtcctttgcc | caaatcaggg | gagatggtaa | ttaacatgga | gtggggtaat | 1140 |
| ttccgttcat | cgtatttacc | tttgactgaa | tatgacatag | cactagatga | agaaagtttg | 1200 |
| aatcctggtg | aacagatatt | tgagaaaatg | atatcaggaa | tgtacttggg | tgagattgtg | 1260 |
| cgaagagtct | tgtataggat | ggcagacgag | gccagccttt | ttggtgatac | agtcccatca | 1320 |
| aaattgaaaa | ctccattcat | cttaaggaca | ccagacatgt | ctgccatgca | tcatgacaca | 1380 |
| tcacctgatc | ttaaagttgt | tgcgagcaaa | ctgaaggatg | tccttgggat | accaaactca | 1440 |
| tcattaaagg | tgcgaaagat | tatagttgac | gtatgtgacg | tcattgcttc | acgtggggcc | 1500 |
| tgcatttctg | cagccgggat | cttgggtatt | attaagaaac | tagggagaga | cacattgaag | 1560 |
| caaggtgaga | accagaagtc | tgtgattgca | ttagatggag | ggttgtttga | gcactacgcc | 1620 |
| aaattccggg | agtgcatgga | ggactctttg | aaggagctcc | taggcgatga | agtcgctgaa | 1680 |
| actattgtaa | ttgagcactc | aaatgatgga | tcaggcattg | gtgctgctct | tctagcagcg | 1740 |
| tcgcattccc | agtacctcga | ggaagatgaa | tcttgatgac | aagatcctac | atcctcaatt | 1800 |
| ttgtataact | ttcttcaagc | tccttagatc | cttagagatc | atggaaattt | tttctttttt | 1860 |

```
tttttctttt tcttttaga ctttgctgcc ccagtgaaga ataaattatg gccaaacggg  1920
ctctgcttgc tgcatgaaaa aatggcatga agctcgctgt tctctcgtgc c           1971

<210> SEQ ID NO 46
<211> LENGTH: 498
<212> TYPE: PRT
<213> ORGANISM: Spinacia oleracea

<400> SEQUENCE: 46

Met Arg Lys Ala Ala Val Gly Ala Ala Val Val Cys Thr Ala Ala Val
1               5                   10                  15

Cys Ala Ala Ala Val Leu Val Arg Gln Arg Met Lys Ser Ser Ser
            20                  25                  30

Lys Trp Gly Arg Val Met Ala Ile Leu Lys Glu Leu Asp Asp Asn Cys
        35                  40                  45

Gly Thr Pro Leu Gly Lys Leu Arg Gln Val Ala Asp Ala Met Thr Val
    50                  55                  60

Glu Met His Ala Gly Leu Ala Ser Glu Gly Ala Ser Lys Leu Lys Met
65                  70                  75                  80

Leu Ile Ser Tyr Val Asp Asn Leu Pro Thr Gly Asp Glu His Gly Leu
                85                  90                  95

Phe Tyr Ala Leu Asp Leu Gly Gly Thr Asn Phe Arg Val Leu Arg Val
            100                 105                 110

Lys Leu Gly Gly Lys Glu Lys Arg Val Val Glu Gln Glu Phe Asp Glu
        115                 120                 125

Val Ser Ile Pro Pro Glu Leu Met Val Gly Thr Ser Glu Gln Leu Phe
    130                 135                 140

Asp Tyr Ile Ala Glu Ala Leu Ala Lys Phe Val Ala Thr Glu Ser Glu
145                 150                 155                 160

Gly Leu His Pro Glu Pro Asn Lys Gln Arg Glu Leu Gly Phe Thr Phe
                165                 170                 175

Ser Phe Pro Val Lys Gln Thr Ser Ile Ala Ser Gly Thr Leu Ile Arg
            180                 185                 190

Trp Thr Lys Gly Phe Asn Ile Glu Asp Thr Val Gly Asp Val Val
        195                 200                 205

Ala Glu Leu Thr Lys Ala Met Leu Arg Lys Gly Val Asp Met Arg Val
    210                 215                 220

Thr Ala Leu Val Asn Asp Thr Val Gly Thr Leu Ala Gly Gly Arg Tyr
225                 230                 235                 240

Tyr Lys Glu Asp Val Ile Ala Ala Val Ile Leu Gly Thr Gly Thr Asn
                245                 250                 255

Ala Ala Tyr Val Glu Arg Ala Ser Ala Ile His Lys Trp His Gly Pro
            260                 265                 270

Leu Pro Lys Ser Gly Glu Met Val Ile Asn Met Glu Trp Gly Asn Phe
        275                 280                 285

Arg Ser Ser Tyr Leu Pro Leu Thr Glu Tyr Asp Ile Ala Leu Asp Glu
    290                 295                 300

Glu Ser Leu Asn Pro Gly Glu Gln Ile Phe Glu Lys Met Ile Ser Gly
305                 310                 315                 320

Met Tyr Leu Gly Glu Ile Val Arg Arg Val Leu Tyr Arg Met Ala Asp
                325                 330                 335

Glu Ala Ser Leu Phe Gly Asp Thr Val Pro Ser Lys Leu Lys Thr Pro
            340                 345                 350
```

```
Phe Ile Leu Arg Thr Pro Asp Met Ser Ala Met His His Asp Thr Ser
            355                 360                 365

Pro Asp Leu Lys Val Val Ala Ser Lys Leu Lys Asp Val Leu Gly Ile
        370                 375                 380

Pro Asn Ser Ser Leu Lys Val Arg Lys Ile Ile Val Asp Val Cys Asp
385                 390                 395                 400

Val Ile Ala Ser Arg Gly Ala Cys Ile Ser Ala Ala Gly Ile Leu Gly
                405                 410                 415

Ile Ile Lys Lys Leu Gly Arg Asp Thr Leu Lys Gln Gly Glu Asn Gln
            420                 425                 430

Lys Ser Val Ile Ala Leu Asp Gly Gly Leu Phe Glu His Tyr Ala Lys
        435                 440                 445

Phe Arg Glu Cys Met Glu Asp Ser Leu Lys Glu Leu Leu Gly Asp Glu
    450                 455                 460

Val Ala Glu Thr Ile Val Ile Glu His Ser Asn Asp Gly Ser Gly Ile
465                 470                 475                 480

Gly Ala Ala Leu Leu Ala Ala Ser His Ser Gln Tyr Leu Glu Glu Asp
                485                 490                 495

Glu Ser

<210> SEQ ID NO 47
<211> LENGTH: 1626
<212> TYPE: DNA
<213> ORGANISM: Oryza sativa

<400> SEQUENCE: 47
ggttcaaagc ttgttcgatt cgttcgcgcg ggaccatggc ggcggcggcg gtggcggcag     60
atcagaaggt ggtgacgatg acgagcctcc gggagggctg cgcttgcgcg gcgcctcctg    120
ctgcagctgc gccgccgatg ccgaagatgg cggcggcgca gagggtggtg gcggagctga    180
gagaagcgtg cgccgacgcc gcggcgaggc tggcggaggt ggccgcgcgc atggccggcg    240
agatggaggc cgggctggcg gtggagggcg gcagcagcga gatgaagatg atcgtgtcgt    300
acgtcgacag cctccccacc ggcggcgagg aggggtcgta ctacgcgctc gacctcggcg    360
gcaccaactt ccgcgtcctc cgcgtgcggc ttgccggcgg cggcgtcgcc gagcgcgtgg    420
cgagggaggt cccgatccct cccggcctca tgtccggcgg cggcgccacc tcggagtgcc    480
tcttcggctt catcgcctcc gcgctagccg agttcgtcgg cgaggaggaa gaagaaggcg    540
gcctcgacgg cggcgagagg gagcttgggt tcaccttctc cttccccgtg caccaaacct    600
ccatcgcgtc ggggacgctc atccggtgga cgaaggcgtt cgccgtcgac gacgcgatcg    660
gcgaggacgt cgtggcggcg ctgcaggcgg ccatgtcgga gcggggctc gacatgcgcg    720 tgtcggcgct catcaacgac accgtcggga cgctcgccgc gggcagctac tacgacgagg    780
acgtcgtggc cgccgtcatc ctcggcaccg gcacgaacgc cgcctacgtc gaggacgcca    840
ccgccatcgc caagctacac ccatcgcagc tgccagcatc gaacaccatg gtgatcaaca    900
ccgagtgggg cagcttcgcc tcgccgtgcc tcccattgac ggagttcgac gaagcactcg    960
atcaggagag cctcaacccc ggcgagcaga cctacgagaa gctcatctcc gggatgtacc   1020
tcggcgagat cgtcaggagg gtcctcctca agatctcctc ccgtgccccc tccctcctcg   1080
gcggcgccgg cgagctcgcg acgccgttcg tcctcaggac acccgacgtg tccgcgatgc   1140
accacgacga cgcccgac ctgagcatcg tcggcgagaa gctggaacgc acgtgggca    1200 tccgcggcac gtcgccggag gcgaggagga tggtcgtcga ggtgtgcgac atcgtcgcca   1260
```

```
cgagggccgc ccggctggcc gcggcgggga tcgtcgggat cctgaagaag atcgggaggg    1320
tcgacggcgg cgaggggcgg aggaggaggt cggtggtcgc cgtggacggc gggctgttcg    1380
agcactacgg caagttccgg cggtgcatgg agagcgcggt gagggagctg ctcggagagg    1440
cggcggcgga gagggtggtc gtcaagctcg ccagcgacgg ctccgggctc ggcgccgccc    1500
tggttgcagc tgctcactcg cagagagcat aatattgaat tgtggtgaaa tatgcgtgtg    1560
tttgaaacaa gcttgaatga tttgaatatt tgatgcgatt tgcaaaacca catatgaaat    1620
agaagc                                                              1626
```

<210> SEQ ID NO 48
<211> LENGTH: 498
<212> TYPE: PRT
<213> ORGANISM: Oryza sativa

<400> SEQUENCE: 48

```
Met Ala Ala Ala Ala Val Ala Ala Asp Gln Lys Val Val Thr Met Thr
1               5                   10                  15

Ser Leu Arg Glu Gly Cys Ala Cys Ala Ala Pro Ala Ala Ala Ala Ala
            20                  25                  30

Pro Pro Met Pro Lys Met Ala Ala Ala Gln Arg Val Val Ala Glu Leu
        35                  40                  45

Arg Glu Ala Cys Ala Thr Pro Ala Ala Arg Leu Ala Glu Val Ala Ala
    50                  55                  60

Ala Met Ala Gly Glu Met Ala Gly Leu Ala Val Glu Gly Gly Ser
65                  70                  75                  80

Ser Glu Met Lys Met Ile Val Ser Tyr Val Asp Ser Leu Pro Thr Gly
                85                  90                  95

Gly Glu Glu Gly Ser Tyr Tyr Ala Leu Asp Leu Gly Gly Thr Asn Phe
            100                 105                 110

Arg Val Leu Arg Val Arg Leu Ala Gly Gly Gly Val Ala Glu Arg Val
        115                 120                 125

Ala Arg Glu Val Pro Ile Pro Pro Gly Leu Met Ser Gly Gly Gly Ala
    130                 135                 140

Thr Ser Glu Cys Leu Phe Gly Phe Ile Ala Ser Ala Leu Ala Glu Phe
145                 150                 155                 160

Val Gly Glu Glu Glu Glu Gly Gly Leu Asp Gly Gly Glu Arg Glu
                165                 170                 175

Leu Gly Phe Thr Phe Ser Phe Pro Val His Gln Thr Ser Ile Ala Ser
            180                 185                 190

Gly Thr Leu Ile Arg Trp Thr Lys Ala Phe Ala Val Asp Asp Ala Ile
        195                 200                 205

Gly Glu Asp Val Val Ala Ala Leu Gln Ala Ala Met Ser Glu Arg Gly
    210                 215                 220

Leu Asp Met Arg Val Ser Ala Leu Ile Asn Asp Thr Val Gly Thr Leu
225                 230                 235                 240

Ala Ala Gly Ser Tyr Tyr Asp Glu Asp Val Val Ala Val Ile Leu
                245                 250                 255

Gly Thr Gly Thr Asn Ala Ala Tyr Val Glu Asp Ala Thr Ala Ile Ala
            260                 265                 270

Lys Leu His Pro Ser Gln Leu Pro Ala Ser Asn Thr Met Val Ile Asn
        275                 280                 285

Thr Glu Trp Gly Ser Phe Ala Ser Pro Cys Leu Pro Leu Thr Glu Phe
    290                 295                 300
```

```
Asp Glu Ala Leu Asp Gln Glu Ser Leu Asn Pro Gly Glu Gln Thr Tyr
305                 310                 315                 320

Glu Lys Leu Ile Ser Gly Met Tyr Leu Gly Glu Ile Val Arg Arg Val
            325                 330                 335

Leu Leu Lys Ile Ser Ser Arg Cys Pro Ser Leu Leu Gly Gly Ala Gly
                340                 345                 350

Glu Leu Ala Thr Pro Phe Val Leu Arg Thr Pro Asp Val Ser Ala Met
            355                 360                 365

His His Asp Glu Thr Pro Asp Leu Ser Ile Val Gly Glu Lys Leu Glu
        370                 375                 380

Arg Thr Leu Gly Ile Arg Gly Thr Ser Pro Glu Ala Arg Arg Met Val
385                 390                 395                 400

Val Glu Val Cys Asp Ile Val Ala Thr Arg Ala Ala Arg Leu Ala Ala
                405                 410                 415

Ala Gly Ile Val Gly Ile Leu Lys Lys Ile Gly Arg Val Asp Gly Gly
            420                 425                 430

Glu Gly Arg Arg Arg Ser Val Val Ala Val Asp Gly Gly Leu Phe
                435                 440                 445

Glu His Tyr Gly Lys Phe Arg Arg Cys Met Glu Ser Ala Val Arg Glu
        450                 455                 460

Leu Leu Gly Glu Ala Ala Ala Glu Arg Val Val Val Lys Leu Ala Ser
465                 470                 475                 480

Asp Gly Ser Gly Leu Gly Ala Ala Leu Val Ala Ala His Ser Gln
                485                 490                 495

Arg Ala

<210> SEQ ID NO 49
<211> LENGTH: 1741
<212> TYPE: DNA
<213> ORGANISM: Oryza sativa

<400> SEQUENCE: 49
atatgtacgt aagggcccca tctcgccgag gagaggctgg gcgaccgcga tgaggaaggc       60
ggcggcggcg gcggtcgcgg cagcggcggc ggtcggcgtg gcgctgctgg tgcgccggca      120
gctgcgggag gcgaagcggt ggggccgggc cgacgcggtg ctgcgggagc tggaggagcg      180
gtgcgcggcg ccgccggggc ggctgcggca ggtggcggac gcgatggccg tcgagatgca      240
cgccgggctc gcctccgagg cgggagcaa actcaagatg atcatcagct acgtcgacgc      300
cctcccttcc ggggaagaga agggggtgtt ttatgcgctt gaccttggag gtacaaattt      360
ccgtgtttta cgggttcaat taggtggcaa ggaagggaga gttatcaagc aagaacatga      420
cgagatttca attcctccgc atctgatgac tggtggttca aatgaactat ttgatttat       480 tgcttcttct ttagcaaaat tgttgcttc agagggtgaa gactttcatc ttgctgaggg      540
gaggcagaga gaacttggct ttacgttctc tttcccagta aagcaaactt caattgcatc      600
tggcactctt attaattgga ctaagggttt ttcgattgat gaaacggttg gtgaagatgt      660
tgtgactgaa ttaaccaagg ctcttgaacg ccaggggctt gatatgaaag tcacagcatt      720
gataaatgat actataggga cattggctgg tgggagatat gatgataatg atgtcattgc      780
tgctgttata ctgggaacag gtactaatgc agcatacgtg gaacgtgcca atgcaattcc      840
taaatggcat gacctcctgc cgaagtcagg agatatggta ataaatatgg aatgggggaa      900
cttcaggtca tccatcttc ctttgactga atttgatcaa gcattagatg ctgaaagttt      960
gaatcctggt gaacaggttt acgaaaagtt gatctctggc atgtatttgg gagaaattgt     1020
```

```
tcgtagagtc ctattaaaga tggctgaaga agcttctctt tttggtgatg aagtaccacc    1080
aaaactcaag attccattta ttatcaggac tccatacatg tcaatgatgc actgcgacag    1140
atcacctgat ctcagaacag ttggagcgaa actgaaagat atcctggggg tccaaaacac    1200
ctcccttaaa acaagaaggc ttgtggtgga tgtctgcgac atcgttgcga acgcgccgc    1260 tcaccttgct gctgcaggga tacacgggat cctgaagaag cttgggcgcg acgtccccaa    1320
caccgacaag cagaggacgg tgatcgccgt cgacggtggg ctctacgagc actacaccat    1380
cttcgccgag tgcgtggaga gcaccctgag ggacatgctt ggggaggatg tgtcctccac    1440
cattgtcatc aagctcgcca aggacgggtc aggcattggc gctgctctcc ttgctgcggc    1500
tcattctcaa taccgtgagg ctgaggagct ctagtggatc tcttctcttg cagctgtta    1560 tgctttagtt gtttggattt tcctgagatt ctgaaccccc aggagcaatt gcattctata    1620
gagttgcacc agcaccgtgc tggtgtttag aactttagat ggaggcacca acctttagta    1680
gcttgcaagt cctgtaaact gtataaacgc agaacacagt attgtccttc aacaaattt    1740 c                                                                    1741

<210> SEQ ID NO 50
<211> LENGTH: 494
<212> TYPE: PRT
<213> ORGANISM: Oryza sativa

<400> SEQUENCE: 50

Met Arg Lys Ala Ala Ala Ala Val Ala Ala Ala Ala Val Gly
1               5                   10                  15

Val Ala Leu Leu Val Arg Arg Gln Leu Arg Glu Ala Lys Arg Trp Gly
                20                  25                  30

Arg Ala Asp Ala Val Leu Arg Glu Leu Glu Glu Arg Cys Ala Ala Pro
            35                  40                  45

Pro Gly Arg Leu Arg Gln Val Ala Asp Ala Met Ala Val Glu Met His
        50                  55                  60

Ala Gly Leu Ala Ser Glu Gly Gly Ser Lys Leu Lys Met Ile Ile Ser
65                  70                  75                  80

Tyr Val Asp Ala Leu Pro Ser Gly Glu Glu Lys Gly Val Phe Tyr Ala
                85                  90                  95

Leu Asp Leu Gly Gly Thr Asn Phe Arg Val Leu Arg Val Gln Leu Gly
            100                 105                 110

Gly Lys Glu Gly Arg Val Ile Lys Gln Glu His Asp Glu Ile Ser Ile
        115                 120                 125

Pro Pro His Leu Met Thr Gly Gly Ser Asn Glu Leu Phe Asp Phe Ile
    130                 135                 140

Ala Ser Ser Leu Ala Lys Phe Val Ala Ser Glu Gly Glu Asp Phe His
145                 150                 155                 160

Leu Ala Glu Gly Arg Gln Arg Glu Leu Gly Phe Thr Phe Ser Phe Pro
                165                 170                 175

Val Lys Gln Thr Ser Ile Ala Ser Gly Thr Leu Ile Asn Trp Thr Lys
            180                 185                 190

Gly Phe Ser Ile Asp Glu Thr Val Gly Glu Asp Val Val Thr Glu Leu
        195                 200                 205

Thr Lys Ala Leu Glu Arg Gln Gly Leu Asp Met Lys Val Thr Ala Leu
    210                 215                 220

Ile Asn Asp Thr Ile Gly Thr Leu Ala Gly Gly Arg Tyr Asp Asp Asn
225                 230                 235                 240
```

```
Asp Val Ile Ala Ala Val Ile Leu Gly Thr Gly Thr Asn Ala Ala Tyr
                245                 250                 255

Val Glu Arg Ala Asn Ala Ile Pro Lys Trp His Asp Leu Leu Pro Lys
            260                 265                 270

Ser Gly Asp Met Val Ile Asn Met Glu Trp Gly Asn Phe Arg Ser Ser
        275                 280                 285

His Leu Pro Leu Thr Glu Phe Asp Gln Ala Leu Asp Ala Glu Ser Leu
    290                 295                 300

Asn Pro Gly Glu Gln Val Tyr Glu Lys Leu Ile Ser Gly Met Tyr Leu
305                 310                 315                 320

Gly Glu Ile Val Arg Arg Val Leu Leu Lys Met Ala Glu Glu Ala Ser
                325                 330                 335

Leu Phe Gly Asp Glu Val Pro Pro Lys Leu Lys Ile Pro Phe Ile Ile
            340                 345                 350

Arg Thr Pro Tyr Met Ser Met Met His Cys Asp Arg Ser Pro Asp Leu
        355                 360                 365

Arg Thr Val Gly Ala Lys Leu Lys Asp Ile Leu Gly Val Gln Asn Thr
    370                 375                 380

Ser Leu Lys Thr Arg Arg Leu Val Val Asp Val Cys Asp Ile Val Ala
385                 390                 395                 400

Lys Arg Ala Ala His Leu Ala Ala Ala Gly Ile His Gly Ile Leu Lys
                405                 410                 415

Lys Leu Gly Arg Asp Val Pro Asn Thr Asp Lys Gln Arg Thr Val Ile
            420                 425                 430

Ala Val Asp Gly Gly Leu Tyr Glu His Tyr Thr Ile Phe Ala Glu Cys
        435                 440                 445

Val Glu Ser Thr Leu Arg Asp Met Leu Gly Glu Asp Val Ser Ser Thr
    450                 455                 460

Ile Val Ile Lys Leu Ala Lys Asp Gly Ser Gly Ile Gly Ala Ala Leu
465                 470                 475                 480

Leu Ala Ala Ala His Ser Gln Tyr Arg Glu Ala Glu Glu Leu
                485                 490

<210> SEQ ID NO 51
<211> LENGTH: 1692
<212> TYPE: DNA
<213> ORGANISM: Oryza sativa

<400> SEQUENCE: 51
tgggattcgt gggtgggttt gggagggagc ggctgcgggg cgggcggggg ggatggcgtg      60
atcgcccgcg cgctctggag gggagggggg agggagaggg ggaggggtgg aggaggagat     120 ggggaggggtg gggctcggcg tggcggtggg gtgcgcggcg gtgacctgcg cgatcgccgc     180
ggcgctcgtg gcgcgcaggg cgtcggcgcg ggcgcggtgg cggcgggcgg tggcgctgct     240
gcgggagttc gaggaggggt gtgccacgcc gcccgcgagg ctgcgccagg tcgtggacgc     300
catggtcgtc gagatgcacg ccggcctcgc gtccgatggc ggcagcaagc tcaagatgct     360
gctcaccttc gtcgacgcgc tccccagcgg gagtgaagaa ggtgtatatt attctattga     420
tcttggagga caaacttcca gagtcttgag ggtacaagtt ggtgcgggat ctgtgatcgt     480
caaccaaaag gttgaacagc aacccatccc tgaggaactg accaaaggca ctactgaggg     540
tttattcaac tttgttgccc tggcactaaa gaatttttctt gaaggagaag atgaccaaga     600
tggaaaaatg gcacttggtt ttacattttc tttccctgtt agacaaattt cagtgtcttc     660
```

```
aggg tcatta attaggtgga caaaaggatt ttccatcaga gacacggttg gcagagatgt    720
tgctcagtgc ttaaatgaag cgcttgccaa ttgtgggcta atgtgcggg tcactgcatt     780 ggtgaatgat acagtgggga cattagctct agggcattac tatgatgaag acacagtggc    840
tgctgtgata attgggtctg gcaccaacgc ttgctacatt gaacgcactg atgcaattat    900
caagtgccag ggtcttctaa cgaactctgg aggcatggta gtaaacatgg agtgggggaa    960
tttctggtca tcacatttgc caaggacgcc atatgacatc ttgctggatg atgaaacaca   1020
caatcgcaat gatcagggct tgagaaaat gatatcagga atgtatcttg gggaaattgc    1080
aagattggta tttcatagaa tggcccagga atcagatgtt tttggtgatg ctgctgatag   1140
tctatccaac cctttcattt tgagcacacc gtttctggcc gcaattcgcg aggacgattc   1200
accagatctg agcgaagtca gaaggatact tcgagaacat ctgaagattc ccgatgctcc   1260
tctgaaaact cgacggctgg tcgtgaaagt ctgcgacatt gtgactcgca gagccgcccg   1320
tctagccgct gcaggcatcg tggggatact gaagaagctg ggagggatg ggagcggcgc    1380 ggcgtcgagc gggagaggta gagggcagcc gaggaggacg gtggtggcga tcagggcgg    1440 gctgtaccag ggttaccgg tgttcaggga gtacctggac gaggccctgg tggagatcct   1500
gggggaggag gtggcgcgga acgtgacgct gagggtgacg gaggatgggt cgggggtcgg   1560
ggctgccctc ctcgccgccg tacattcgtc gaatagacag caacaaggag gtcccatata   1620
gtgagagaga caatgaagat acagctagcc cctcttgttc aaatgtaaaa aagggacatt   1680
gtttgatatc ta                                                        1692
```

<210> SEQ ID NO 52
<211> LENGTH: 500
<212> TYPE: PRT
<213> ORGANISM: Oryza sativa

<400> SEQUENCE: 52

```
Met Gly Arg Val Gly Leu Gly Val Ala Val Gly Cys Ala Ala Val Thr
1               5                   10                  15

Cys Ala Ile Ala Ala Ala Leu Val Ala Arg Arg Ala Ser Ala Arg Ala
                20                  25                  30

Arg Trp Arg Arg Ala Val Ala Leu Arg Glu Phe Glu Glu Gly Cys
            35                  40                  45

Ala Thr Pro Pro Ala Arg Leu Arg Gln Val Val Asp Ala Met Val Val
        50                  55                  60

Glu Met His Ala Gly Leu Ala Ser Asp Gly Gly Ser Lys Leu Lys Met
65                  70                  75                  80

Leu Leu Thr Phe Val Asp Ala Leu Pro Ser Gly Ser Glu Glu Gly Val
                85                  90                  95

Tyr Tyr Ser Ile Asp Leu Gly Gly Thr Asn Phe Arg Val Leu Arg Val
                100                 105                 110

Gln Val Gly Ala Gly Ser Val Ile Val Asn Gln Lys Val Glu Gln Gln
            115                 120                 125

Pro Ile Pro Glu Glu Leu Thr Lys Gly Thr Thr Glu Gly Leu Phe Asn
        130                 135                 140

Phe Val Ala Leu Ala Leu Lys Asn Phe Leu Glu Gly Glu Asp Asp Gln
145                 150                 155                 160

Asp Gly Lys Met Ala Leu Gly Phe Thr Phe Ser Phe Pro Val Arg Gln
                165                 170                 175

Ile Ser Val Ser Ser Gly Ser Leu Ile Arg Trp Thr Lys Gly Phe Ser
                180                 185                 190
```

Ile Arg Asp Thr Val Gly Arg Asp Val Ala Gln Cys Leu Asn Glu Ala
        195                 200                 205

Leu Ala Asn Cys Gly Leu Asn Val Arg Val Thr Ala Leu Val Asn Asp
    210                 215                 220

Thr Val Gly Thr Leu Ala Leu Gly His Tyr Tyr Asp Glu Asp Thr Val
225                 230                 235                 240

Ala Ala Val Ile Ile Gly Ser Gly Thr Asn Ala Cys Tyr Ile Glu Arg
                245                 250                 255

Thr Asp Ala Ile Ile Lys Cys Gln Gly Leu Leu Thr Asn Ser Gly Gly
                260                 265                 270

Met Val Asn Met Glu Trp Gly Asn Phe Trp Ser Ser His Leu Pro
        275                 280                 285

Arg Thr Pro Tyr Asp Ile Leu Leu Asp Asp Glu Thr His Asn Arg Asn
        290                 295                 300

Asp Gln Gly Phe Glu Lys Met Ile Ser Gly Met Tyr Leu Gly Glu Ile
305                 310                 315                 320

Ala Arg Leu Val Phe His Arg Met Ala Gln Glu Ser Asp Val Phe Gly
                325                 330                 335

Asp Ala Ala Asp Ser Leu Ser Asn Pro Phe Ile Leu Ser Thr Pro Phe
                340                 345                 350

Leu Ala Ala Ile Arg Glu Asp Asp Ser Pro Asp Leu Ser Glu Val Arg
            355                 360                 365

Arg Ile Leu Arg Glu His Leu Lys Ile Pro Asp Ala Pro Leu Lys Thr
        370                 375                 380

Arg Arg Leu Val Val Lys Val Cys Asp Ile Val Thr Arg Ala Ala
385                 390                 395                 400

Arg Leu Ala Ala Ala Gly Ile Val Gly Ile Leu Lys Lys Leu Gly Arg
                405                 410                 415

Asp Gly Ser Gly Ala Ala Ser Ser Gly Arg Gly Arg Gly Gln Pro Arg
                420                 425                 430

Arg Thr Val Val Ala Ile Glu Gly Gly Leu Tyr Gln Gly Tyr Pro Val
        435                 440                 445

Phe Arg Glu Tyr Leu Asp Glu Ala Leu Val Glu Ile Leu Gly Glu Glu
        450                 455                 460

Val Ala Arg Asn Val Thr Leu Arg Val Thr Glu Asp Gly Ser Gly Val
465                 470                 475                 480

Gly Ala Ala Leu Leu Ala Ala Val His Ser Ser Asn Arg Gln Gln Gln
                485                 490                 495

Gly Gly Pro Ile
        500

<210> SEQ ID NO 53
<211> LENGTH: 1937
<212> TYPE: DNA
<213> ORGANISM: Oryza sativa

<400> SEQUENCE: 53
tagtacgtgt agtgaggagc atttcttgcc acctttattc gattccacca cttgacacat      60
ccatcgatca ctcctccccc taccaacgat cagctcagct tcagcttctc ctcggcatgt     120
ccgccgccgc cgccatcgcg tcgccgatcc cggcggcgat cgccgtcgtg cagcagcaga     180
ggcgggggag gagccgcggc ggcggctccg gcgctgccgc cgtccgctgc tccgcggtgg     240
ccccgacgtc cgcgatcgcg cccatccttg ccgacctgag gctgcggtgc gccgccccgc     300

```
tccccgtgct gcggcgcgtg gcggacgcca tggcctccgg gatgcgcgcc gggctggccg      360
acgacggcgc cggcgagctc aagatgatcc ccagccacgt ctactcactc cccactggga      420
atgaaacagg actgttttat gctctggacc ttggaggcac caactttaga gtgctgaggg      480
tacaattggg aggaaaagat aagcgcatta tagataccga gtttgagcaa gtctcgatcc      540
caagagaaat catgcatggt ataaccgagg atttgtttga tttcatcgcg agtggcctgt      600
cgagatttgt agcaacggag ggtgataagt ttcatttgcc acaagggaga agagagagt       660 taggcttcac attctccttt ccggtgaatc agacttctat tgattctggc attctgatca      720
agtggacaaa aggttttgct gtctctggaa ctgctgggaa agatgttgtt gcttgtctga      780
atgctgcaat ggagaggcaa ggccttgata tgcgtgtctc tgccttggta atgatactg       840 tgggaacctt agctggagca cgttattggg acgatgacgt aatggtcgcg gtgattttgg      900
gcactggcac caatgcatgc tacattcaac gaactgaagc tattccaaaa ttgcaacacc      960
ttaagcttga acaggaaac acgattatta cactgagtg gggagctttc tcagatggac         1020
ttccattgac tgaatttgac agagaaatgg atgatgagag cataaatcct ggtgaacaga      1080
tattcgagaa gacgatttcc gggatgtatc taggtgaaat tgtccgtagg gtgctggtca      1140
agatggctga agtatctgat ctctttggtc attccttccc caagaaactt gctgaaccat      1200
ttgttctaag gacaccacat ctatgcgcta tgcaacaaga cacctctgac aatcttggag      1260
aagttgagtc catcttgagt gatgtcatcg gcgtgtccca agcttctctg ctggcacgga      1320
gagtcactgt agaagtctcc gactgcatca tcaggagagg aggccggttg gccggggcag      1380
gaatcgtagg gatccttgag aagatggaga atgactccag agggcacatt ttcggacgaa      1440
gaacagtggt cgcgatggac ggtggtctat atgagaagta ccctcagtac aggaggtaca      1500
tgaaggaggc tgtggctgag ctactgggac ccgagcgatc gaatcgtatc gccatcgagc      1560
acacgaaaga cggatcaggg atcggcgctg cgctgttggc agctgcaaac tcaaagtatg      1620
ctgctgctca aatctctaca aggtgatcgc aattgttata attgttgagt tactgggccg      1680
aattaattct ctacaaggtg atctcaattg ttatcattgt tgagctactg ggacctgaac      1740
aatccaagca tatcatcata tggtggcctc ttatctgaag tatggagggg cttcatatat      1800
gctattcttc tgtactacta gtctactata ctatataacg catttgagga aaagaaacac      1860
cagaaattta tcaacttatg ttttgtataa ttcatcaact tatgtgtttg tatagttaca      1920
gttcaccaga aattcat                                                     1937
```

<210> SEQ ID NO 54
<211> LENGTH: 509
<212> TYPE: PRT
<213> ORGANISM: Oryza sativa

<400> SEQUENCE: 54

```
Met Ser Ala Ala Ala Ile Ala Ser Pro Ile Pro Ala Ala Ile Ala
1               5                   10                  15

Val Val Gln Gln Arg Arg Gly Ser Arg Gly Gly Gly Ser Gly
            20                  25                  30

Ala Ala Ala Val Arg Cys Ser Ala Val Ala Pro Thr Ser Ala Ile Ala
        35                  40                  45

Pro Ile Leu Ala Asp Leu Arg Leu Arg Cys Ala Ala Pro Leu Pro Val
    50                  55                  60

Leu Arg Arg Val Ala Asp Ala Met Ala Ser Gly Met Arg Ala Gly Leu
65                  70                  75                  80
```

```
Ala Asp Asp Gly Ala Gly Glu Leu Lys Met Ile Pro Ser His Val Tyr
                85              90              95

Ser Leu Pro Thr Gly Asn Glu Thr Gly Leu Phe Tyr Ala Leu Asp Leu
            100             105             110

Gly Gly Thr Asn Phe Arg Val Leu Arg Val Gln Leu Gly Gly Lys Asp
            115             120             125

Lys Arg Ile Ile Asp Thr Glu Phe Glu Gln Val Ser Ile Pro Arg Glu
            130             135             140

Ile Met His Gly Ile Thr Glu Asp Leu Phe Asp Phe Ile Ala Ser Gly
145             150             155             160

Leu Ser Arg Phe Val Ala Thr Glu Gly Asp Lys Phe His Leu Pro Gln
            165             170             175

Gly Arg Lys Arg Glu Leu Gly Phe Thr Phe Ser Phe Pro Val Asn Gln
            180             185             190

Thr Ser Ile Asp Ser Gly Ile Leu Ile Lys Trp Thr Lys Gly Phe Ala
            195             200             205

Val Ser Gly Thr Ala Gly Lys Asp Val Val Ala Cys Leu Asn Ala Ala
            210             215             220

Met Glu Arg Gln Gly Leu Asp Met Arg Val Ser Ala Leu Val Asn Asp
225             230             235             240

Thr Val Gly Thr Leu Ala Gly Ala Arg Tyr Trp Asp Asp Val Met
            245             250             255

Val Ala Val Ile Leu Gly Thr Gly Thr Asn Ala Cys Tyr Ile Gln Arg
            260             265             270

Thr Glu Ala Ile Pro Lys Leu Gln His Leu Lys Leu Glu Thr Gly Asn
            275             280             285

Thr Ile Ile Asn Thr Glu Trp Gly Ala Phe Ser Asp Gly Leu Pro Leu
290             295             300

Thr Glu Phe Asp Arg Glu Met Asp Asp Glu Ser Ile Asn Pro Gly Glu
305             310             315             320

Gln Ile Phe Glu Lys Thr Ile Ser Gly Met Tyr Leu Gly Glu Ile Val
            325             330             335

Arg Arg Val Leu Val Lys Met Ala Glu Val Ser Asp Leu Phe Gly His
            340             345             350

Ser Phe Pro Lys Lys Leu Ala Glu Pro Phe Val Leu Arg Thr Pro His
            355             360             365

Leu Cys Ala Met Gln Gln Asp Thr Ser Asp Asn Leu Gly Glu Val Glu
            370             375             380

Ser Ile Leu Ser Asp Val Ile Gly Val Ser Gln Ala Ser Leu Leu Ala
385             390             395             400

Arg Arg Val Thr Val Glu Val Ser Asp Cys Ile Ile Arg Arg Gly Gly
            405             410             415

Arg Leu Ala Gly Ala Gly Ile Val Gly Ile Leu Glu Lys Met Glu Asn
            420             425             430

Asp Ser Arg Gly His Ile Phe Gly Arg Arg Thr Val Val Ala Met Asp
            435             440             445

Gly Gly Leu Tyr Glu Lys Tyr Pro Gln Tyr Arg Arg Tyr Met Lys Glu
            450             455             460

Ala Val Ala Glu Leu Leu Gly Pro Glu Arg Ser Asn Arg Ile Ala Ile
465             470             475             480

Glu His Thr Lys Asp Gly Ser Gly Ile Gly Ala Ala Leu Leu Ala Ala
            485             490             495

Ala Asn Ser Lys Tyr Ala Ala Ala Gln Ile Ser Thr Arg
```

<210> SEQ ID NO 55
<211> LENGTH: 2058
<212> TYPE: DNA
<213> ORGANISM: Oryza sativa

<400> SEQUENCE: 55

| | | | | | |
|---|---|---|---|---|---|
| ctctcgtcct | cctttctcct | acgcggccgg | agagaggagg | ggggaagaga | ggatctcgca | 60 |
| gagcgccata | gcctcggatc | cagaagcgga | attcggtgga | ggtctcgggc | acctggatcg | 120 |
| atcggaggaa | gggaaggcgg | agcagcggtg | atggggaagg | cggcggcggt | ggggacggcg | 180 |
| gtggtggtgg | ccgcggcggt | cggggtggcg | gtggtgctgg | cgcggaggcg | gaggaggagg | 240 |
| gacctggagc | tggtggaggg | agccgcggcg | gagaggaaga | ggaaggtggc | ggcggtgatc | 300 |
| gaggacgtgg | agcacgcgct | gtcgaccccg | acggcgctgc | tgcggggcat | ctcggacgcc | 360 |
| atggtcaccg | agatggagcg | aggcctgcgc | ggggacagcc | acgccatggt | taagatgctc | 420 |
| atcacctacg | tcgacaacct | ccccaccgga | aatgaacagg | ggttgtttta | tgcattggat | 480 |
| cttggaggaa | ccaacttccg | cgtcctgcga | gtccaactcg | gtggcaagga | gaaacgtgtc | 540 |
| gtccaacaac | agtacgagga | agtctcaatt | ccaccacatc | tgatggttgg | aacttccatg | 600 |
| gaactgtttg | attttattgc | ttctgcattg | tcaaaatttg | ttgatactga | aggtgatgat | 660 |
| ttccacctcc | cagaagggag | acagagagag | ctgggcttca | cctttccctt | cccagtgagc | 720 |
| cagacatcaa | tatcgtcagg | aacgctcatc | aagtggacaa | agggtttctc | catcaatgac | 780 |
| gcggttggcg | aagatgttgt | atctgagttg | gcaaggcca | tggagaggca | gggattagat | 840 |
| atgaaaattg | cagcattggt | taatgacact | gtcggcacat | tggctggtgg | gaggtatgcg | 900 |
| gataacagtg | ttgttgctgc | tataatattg | ggcactggta | caaatgcagc | atatgttgag | 960 |
| aatgctaatg | caattcctaa | atggaccggt | ttactgccta | ggtccggaaa | tatggtaatc | 1020 |
| aacacagaat | gggggagctt | taaatcagat | aagcttcctc | tttcagaatt | cgataaagca | 1080 |
| atggattttg | aaagcttgaa | tcctggagag | cagatatatg | aaaagttgat | ttctggcatg | 1140 |
| tatcttggag | atagtgtgcg | aagaatcttg | ctgaagcttg | ctcatgatgc | agctttgttt | 1200 |
| ggggatgttg | ttccatctaa | gctagagcaa | ccgtttgtac | taaggacacc | ggatatgtca | 1260 |
| gccatgcatc | atgactcgtc | acatgacctt | aaaactgttg | gagctaagct | aaaggatatc | 1320 |
| gtcggggtcc | cagatacttc | cctggaagta | agatacatta | ccagtcacat | tgtgacata | 1380 |
| gttgcagagc | gtgctgcacg | cttggctgct | gctggcatat | atgggggtcct | aaagaagcta | 1440 |
| ggtcgggaca | agatgccaaa | agacggcagt | aagatgccta | ggactgtcat | tgccttggat | 1500 |
| ggtgggctct | atgaacatta | caagaagttc | agcagttgct | tagaatcaac | tctaacagac | 1560 |
| cttcttgggg | atgatgtctc | gtcttcggtg | gttaccaagc | tggccaacga | tggttctggc | 1620 |
| attggagctg | ctcttctcgc | agcctcgcac | tcccagtatg | ccgagatcga | ctagctttaa | 1680 |
| ggatgatctt | gatgaatgat | gaatcaaact | ccgtttgtag | gttctcattt | ccccccttcaa | 1740 |
| aatccacata | atactcctgg | ctccccccctt | gaaatcttac | catcttttt | tggctattct | 1800 |
| gagggcaaac | ataagtgcct | ctgcagcggg | atatagctag | tatagcgcca | atgagtttgg | 1860 |
| aggttttcta | atggcataaa | acgttggatg | gcagtagcag | actaacaggg | aaatggaggc | 1920 |
| acaggcaatt | tccattcctg | ttctgtcaga | ttcttttccc | ccttaattga | tgttgagaac | 1980 |
| caagattttt | ttgctctgta | ttttctcttc | gtaataaaga | aggggacata | atctaattgc | 2040 |
| tcttgtttga | tctcataa | | | | | 2058 |

<210> SEQ ID NO 56
<211> LENGTH: 507
<212> TYPE: PRT
<213> ORGANISM: Oryza sativa

<400> SEQUENCE: 56

```
Met Gly Lys Ala Ala Val Gly Thr Ala Val Val Ala Ala Ala
1               5                   10                  15

Val Gly Val Ala Val Val Leu Ala Arg Arg Arg Arg Arg Asp Leu
            20                  25                  30

Glu Leu Val Glu Gly Ala Ala Glu Arg Lys Arg Lys Val Ala Ala
        35                  40                  45

Val Ile Glu Asp Val Glu His Ala Leu Ser Thr Pro Thr Ala Leu Leu
    50                  55                      60

Arg Gly Ile Ser Asp Ala Met Val Thr Glu Met Glu Arg Gly Leu Arg
65                  70                  75                  80

Gly Asp Ser His Ala Met Val Lys Met Leu Ile Thr Tyr Val Asp Asn
                85                  90                  95

Leu Pro Thr Gly Asn Glu Gln Gly Leu Phe Tyr Ala Leu Asp Leu Gly
            100                 105                 110

Gly Thr Asn Phe Arg Val Leu Arg Val Gln Leu Gly Gly Lys Glu Lys
        115                 120                 125

Arg Val Val Gln Gln Gln Tyr Glu Glu Val Ser Ile Pro Pro His Leu
    130                 135                 140

Met Val Gly Thr Ser Met Glu Leu Phe Asp Phe Ile Ala Ser Ala Leu
145                 150                 155                 160

Ser Lys Phe Val Asp Thr Glu Gly Asp Phe His Leu Pro Glu Gly
                165                 170                 175

Arg Gln Arg Glu Leu Gly Phe Thr Phe Ser Phe Pro Val Ser Gln Thr
            180                 185                 190

Ser Ile Ser Ser Gly Thr Leu Ile Lys Trp Thr Lys Gly Phe Ser Ile
        195                 200                 205

Asn Asp Ala Val Gly Glu Asp Val Val Ser Glu Leu Gly Lys Ala Met
    210                 215                 220

Glu Arg Gln Gly Leu Asp Met Lys Ile Ala Ala Leu Val Asn Asp Thr
225                 230                 235                 240

Val Gly Thr Leu Ala Gly Gly Arg Tyr Ala Asp Asn Ser Val Val Ala
                245                 250                 255

Ala Ile Ile Leu Gly Thr Gly Thr Asn Ala Ala Tyr Val Glu Asn Ala
            260                 265                 270

Asn Ala Ile Pro Lys Trp Thr Gly Leu Leu Pro Arg Ser Gly Asn Met
        275                 280                 285

Val Ile Asn Thr Glu Trp Gly Ser Phe Lys Ser Asp Lys Leu Pro Leu
    290                 295                 300

Ser Glu Phe Asp Lys Ala Met Asp Phe Glu Ser Leu Asn Pro Gly Glu
305                 310                 315                 320

Gln Ile Tyr Glu Lys Leu Ile Ser Gly Met Tyr Leu Gly Glu Ile Val
                325                 330                 335

Arg Arg Ile Leu Leu Lys Leu Ala His Asp Ala Ala Leu Phe Gly Asp
            340                 345                 350

Val Val Pro Ser Lys Leu Glu Gln Pro Phe Val Leu Arg Thr Pro Asp
        355                 360                 365

Met Ser Ala Met His His Asp Ser Ser His Asp Leu Lys Thr Val Gly
```

```
Ala Lys Leu Lys Asp Ile Val Gly Val Pro Asp Thr Ser Leu Glu Val
            385                 390                 395                 400

Arg Tyr Ile Thr Ser His Ile Cys Asp Ile Val Ala Glu Arg Ala Ala
                405                 410                 415

Arg Leu Ala Ala Ala Gly Ile Tyr Gly Val Leu Lys Lys Leu Gly Arg
                420                 425                 430

Asp Lys Met Pro Lys Asp Gly Ser Lys Met Pro Arg Thr Val Ile Ala
                435                 440                 445

Leu Asp Gly Gly Leu Tyr Glu His Tyr Lys Lys Phe Ser Ser Cys Leu
            450                 455                 460

Glu Ser Thr Leu Thr Asp Leu Leu Gly Asp Asp Val Ser Ser Ser Val
465                 470                 475                 480

Val Thr Lys Leu Ala Asn Asp Gly Ser Gly Ile Gly Ala Ala Leu Leu
                485                 490                 495

Ala Ala Ser His Ser Gln Tyr Ala Glu Ile Asp
            500                 505

<210> SEQ ID NO 57
<211> LENGTH: 2070
<212> TYPE: DNA
<213> ORGANISM: Oryza sativa

<400> SEQUENCE: 57
gaggaaggag gaggagtagg acgctgcagt ggtgggtggc gtagctcccg atccgggaag      60
ccgacccggt ctgggggatt tgctcctggc gcgcgctcga tcgagaggga ggccagggtt     120
gggttggggg gagcgtgaag aagcgcgcgc gcggctatgg ggaagggac ggtagtgggg      180 acggcggtgg tggtgtgcgc tgcagcggcc gggcggttg gggtggcggt ggtggtgtcg      240
cggaggagga ggagcaagcg ggaggcggag gaggagcggc ggaggagggc cgccgctgtg     300
atcgaggagg tggagcagag gttctcgacg cccacggcgc tgctgcgcgg catcgcggac     360
gccatggtgg aggagatgga gcgcggcctc cgcgccgacc ctcacgcccc gctcaagatg     420
ctcatcagct acgtcgacaa cctcccccacc ggggatgagc acggactgtt ctatgctctc    480
gatcttgggg gcaccaattt ccgtgttata cgtgttcagc ttggaggaag ggaaaagcgt     540
gttgttagtc aacagtacga agaggttgcc attccacctc acctgatggt tgggacttct     600
atggaactgt ttgacttcat tgcggctgag ttggaaagtt ttgtcaagac cgagggagag     660
gatttccact tgccagaggg caggcagaga gagttaggct tcaccttttc tttcccagtg     720
caccaaacat caatatcatc aggcactctt attaagtgga caaagggatt ttccatcaat     780
ggcacggtgg gggaagatgt tgtggctgaa ttgagcaggg ctatggaaag gcaagggctt     840
gatatgaaag ttacagctct tgttaatgac actgtaggca cattggctgg cggaagatat     900
gttgataatg acgttgctgc tgctgtaata ttaggcactg gcacaaacgc agcctacgtg     960
gagcatgcaa atgcaattcc aaaatggact ggattactac ctagatcagg aaatatggtg    1020
attaacatgg aatggggaaa cttcaagtca gaaaggcttc ctcgttcaga ttacgataat    1080
gccttggact tgaaagtttt aaacccaggc gagcagatat atgaaaagat gatttccggc    1140
atgtatcttg gagagattgt gcgcagaatc ttgcttaagc ttgctcatga tgcttccttg    1200
tttggagatg ttgttccaac aaagctggag cagcgcttta tactgaggac gccggacatg    1260
tcagcgatgc atcatgatac ctcacatgat ctgaaacacc tggagctaa gctgaaggat    1320 atcctggggg tcgctgatac ttccctggaa gcacgataca tcacccttca tgtctgcgac    1380
```

```
ctcgttgcag agagaggtgc acgcttagct gctgctggta tatatggcat tctaaagaag      1440
ctgggcaggg acagagtgcc aagtgacggt agtcaaaagc agaggactgt cattgctctg      1500
gatggtggtc tctatgagca ttacaagaag ttcagaacct gcctagaagc aacgcttgca      1560
gacctgcttg gagaggaggc tgcctcatca gttgttgtca agttggcaaa cgatggctct      1620
ggcatcggag ctgcacttct tgcagcatct cactcccagt atgctagcgt cgagtagtaa      1680
caggagctca tgggactgag ctcccagtgt agcttgtttt cctcccattt tccccgtttc      1740
tttccaatgg gagttcgttt ccctcctgcg attcgcatct ccttttgcta ttctgcagtc      1800
acataaacga gtgcctgtgc agcgggatgt agctagtatg cgccaaaga gtttgcagtt       1860 atcacatgaa caagcatttg caactgcagg gaagtgaaaa cggggggcttg aatgatgccg      1920 ttcttttcct gcaaattatt ttccccctttt ccctgtaagt ttgtattgtg atgcgatgtc      1980
gcaaaccaat cacagcggtt tcgcgtgtag ccttttgtca ttcagatttc agaataaaga      2040 ggggacata atttcacttt tcgtatgtca                                        2070
```

<210> SEQ ID NO 58
<211> LENGTH: 506
<212> TYPE: PRT
<213> ORGANISM: Oryza sativa

<400> SEQUENCE: 58

```
Met Gly Lys Gly Thr Val Gly Thr Ala Val Val Cys Ala Ala
1               5                  10                  15

Ala Ala Ala Ala Val Gly Val Ala Val Val Ser Arg Arg Arg
            20                  25                  30

Ser Lys Arg Glu Ala Glu Glu Arg Arg Arg Arg Ala Ala Val
        35                  40                  45

Ile Glu Glu Val Glu Gln Arg Phe Ser Thr Pro Thr Ala Leu Leu Arg
    50                  55                  60

Gly Ile Ala Asp Ala Met Val Glu Glu Met Arg Gly Leu Arg Ala
65                  70                  75                  80

Asp Pro His Ala Pro Leu Lys Met Leu Ile Ser Tyr Val Asp Asn Leu
                    85                  90                  95

Pro Thr Gly Asp Glu His Gly Leu Phe Tyr Ala Leu Asp Leu Gly Gly
                100                 105                 110

Thr Asn Phe Arg Val Ile Arg Val Gln Leu Gly Gly Arg Glu Lys Arg
            115                 120                 125

Val Val Ser Gln Gln Tyr Glu Glu Val Ala Ile Pro Pro His Leu Met
    130                 135                 140

Val Gly Thr Ser Met Glu Leu Phe Asp Phe Ile Ala Ala Glu Leu Glu
145                 150                 155                 160

Ser Phe Val Lys Thr Glu Gly Glu Asp Phe His Leu Pro Glu Gly Arg
                    165                 170                 175

Gln Arg Glu Leu Gly Phe Thr Phe Ser Phe Pro Val His Gln Thr Ser
                180                 185                 190

Ile Ser Ser Gly Thr Leu Ile Lys Trp Thr Lys Gly Phe Ser Ile Asn
            195                 200                 205

Gly Thr Val Gly Glu Asp Val Val Ala Glu Leu Ser Arg Ala Met Glu
    210                 215                 220

Arg Gln Gly Leu Asp Met Lys Val Thr Ala Leu Val Asn Asp Thr Val
225                 230                 235                 240

Gly Thr Leu Ala Gly Gly Arg Tyr Val Asp Asn Asp Val Ala Ala Ala
```

```
                245                 250                 255
Val Ile Leu Gly Thr Gly Thr Asn Ala Ala Tyr Val Glu His Ala Asn
            260                 265                 270

Ala Ile Pro Lys Trp Thr Gly Leu Leu Pro Arg Ser Gly Asn Met Val
        275                 280                 285

Ile Asn Met Glu Trp Gly Asn Phe Lys Ser Glu Arg Leu Pro Arg Ser
    290                 295                 300

Asp Tyr Asp Asn Ala Leu Asp Phe Glu Ser Leu Asn Pro Gly Glu Gln
305                 310                 315                 320

Ile Tyr Glu Lys Met Ile Ser Gly Met Tyr Leu Gly Glu Ile Val Arg
                325                 330                 335

Arg Ile Leu Leu Lys Leu Ala His Asp Ala Ser Leu Phe Gly Asp Val
            340                 345                 350

Val Pro Thr Lys Leu Glu Gln Arg Phe Ile Leu Arg Thr Pro Asp Met
        355                 360                 365

Ser Ala Met His His Asp Thr Ser His Asp Leu Lys His Leu Gly Ala
    370                 375                 380

Lys Leu Lys Asp Ile Leu Gly Val Ala Asp Thr Ser Leu Glu Ala Arg
385                 390                 395                 400

Tyr Ile Thr Leu His Val Cys Asp Leu Val Ala Glu Arg Gly Ala Arg
                405                 410                 415

Leu Ala Ala Gly Ile Tyr Gly Ile Leu Lys Lys Leu Gly Arg Asp
            420                 425                 430

Arg Val Pro Ser Asp Gly Ser Gln Lys Gln Arg Thr Val Ile Ala Leu
        435                 440                 445

Asp Gly Gly Leu Tyr Glu His Tyr Lys Lys Phe Arg Thr Cys Leu Glu
    450                 455                 460

Ala Thr Leu Ala Asp Leu Leu Gly Glu Glu Ala Ala Ser Ser Val Val
465                 470                 475                 480

Val Lys Leu Ala Asn Asp Gly Ser Gly Ile Gly Ala Ala Leu Leu Ala
                485                 490                 495

Ala Ser His Ser Gln Tyr Ala Ser Val Glu
            500                 505

<210> SEQ ID NO 59
<211> LENGTH: 1816
<212> TYPE: DNA
<213> ORGANISM: Oryza sativa

<400> SEQUENCE: 59
ctttgatctt gaccaccaat ctcgcatttc ttggatcttc tcgtcttcct cactcctcga     60
tcgatccatc gattggttgc tggtcggaga ccatggtggc ggcggcggtg gcggcggcgg    120
agcaggtggt ggcggcgctg cgggaggagt gcgcgacgcc ggcggcgcgg ctggatgggg    180
tggcggcggc gatggccggc gagatggcgg cggggttggc ggaggagggc ggcagcaaga    240
tcaagatgat cgtttcctac gtcgacaacc tccccaatgg gaccgaagag ggcttgttct    300
acgcgctgga tcttggggga acaaacttcc gagtcctgcg tgtgcagctt gctggaaagg    360
agaaacgggt cgtgaagcgc gagtcgaggg aggtctcgat ccctccccat ctcatgtccg    420
gcaactcctc ggagctgttt ggcttcatcg cttccgcgtt agccaagttc gtcgctgatg    480
aaggacataa tgccgtgttc aacgacaggc aaagggaact ggggttcacc ttctcttttcc    540 ctgtgcggca acatcgatt gcgtctggga ctcttatcaa gtggaccaag gcgttttcta    600
ttgatgatgc tgtaggtgaa gatgtggtgg ccgaattgca gatggccatg gagaagcaag    660
```

```
gtctggacat gcgcgtttcc gcattgacca atgacactgt tgggacattg gcggcaggca     720
gctactacga cgaagatatt gtcgtcggtg tgatcttagg cactggctca aacgccgcat     780
atcttgagaa ggcaaatgct atccctaagt tggaaggcga gttaccaaaa tcaggaaaca     840
tggttattaa tacagaatgg ggtaacttct cctcatcctg tcttccaata acagaatatg     900
atgaagcact agataaagag agcttaaacc ctggagagca gatcttcgag aaattgattt     960
caggaatgta tctaggtgaa atcgtaagga gagtgcttct taaatatct ttgcagtctt    1020 caattttttgg caatctagat cagaccaagc tcaaaacccg ctttattctg aggactcctg    1080
atatttccgt gatgcatcat gatggaacac ctgatctcag aattgtggct gaaaaacttg    1140 cagataaccct gaagatcaca gacacatcct tagaaacaag gaagatggtt gtcgaaatct    1200
gtgacatcgt cacccgaaga tcagcccggc tggctgctgc tgggatcgta gggatcctca    1260
ggaagatcgg cagaggcgtc ccaggcgaca agcgaaagtc ggtcatcgcc atcgatggcg    1320
gtctatatga acattacacc gaattccggc agtgcctgga gaccacgctg acggagttgc    1380
tcggagaaga ggcgtcgaag tcggtggctg tcaagcttgc aaacgacggg tctggccttg    1440
gagctgccct gattgcagct gctcattctc agtacctgaa ttgattcccc atagacagag    1500
ttccaacttt tattagtgac tcagtgctgt tgttatagtt tatagaatgt ggtgaagttc    1560
tgtatgtttc gaaggagcct gatggactct acaaacaaaa ttttcagaaa tgaaatcgaa    1620
gccaaatgtg ttggtggtgt tgcaatttgc agtatctact ctgaattatt ataggagaaa    1680
atagttctga acttttgttg taccggataa agtagttctg aactttgttg tcggttattt    1740
ttggttcagt acttacatca ataattcctt catatcacaa aaaaagttt gtatcaacgg    1800 atttaaattt tgaaat                                                    1816
```

<210> SEQ ID NO 60
<211> LENGTH: 463
<212> TYPE: PRT
<213> ORGANISM: Oryza sativa

<400> SEQUENCE: 60

```
Met Val Ala Ala Val Ala Ala Ala Glu Gln Val Val Ala Ala Leu
1               5                   10                  15

Arg Glu Glu Cys Ala Thr Pro Ala Ala Arg Leu Asp Gly Val Ala Ala
            20                  25                  30

Ala Met Ala Gly Glu Met Ala Ala Gly Leu Ala Glu Glu Gly Gly Ser
        35                  40                  45

Lys Ile Lys Met Ile Val Ser Tyr Val Asp Asn Leu Pro Asn Gly Thr
    50                  55                  60

Glu Glu Gly Leu Phe Tyr Ala Leu Asp Leu Gly Gly Thr Asn Phe Arg
65                  70                  75                  80

Val Leu Arg Val Gln Leu Ala Gly Lys Glu Lys Arg Val Val Lys Arg
                85                  90                  95

Glu Ser Arg Glu Val Ser Ile Pro Pro His Leu Met Ser Gly Asn Ser
            100                 105                 110

Ser Glu Leu Phe Gly Phe Ile Ala Ser Ala Leu Ala Lys Phe Val Ala
        115                 120                 125

Asp Glu Gly His Asn Ala Val Phe Asn Asp Arg Gln Arg Glu Leu Gly
    130                 135                 140

Phe Thr Phe Ser Phe Pro Val Arg Gln Thr Ser Ile Ala Ser Gly Thr
145                 150                 155                 160
```

Leu Ile Lys Trp Thr Lys Ala Phe Ser Ile Asp Asp Ala Val Gly Glu
            165                 170                 175

Asp Val Val Ala Glu Leu Gln Met Ala Met Glu Lys Gln Gly Leu Asp
        180                 185                 190

Met Arg Val Ser Ala Leu Thr Asn Asp Thr Val Gly Thr Leu Ala Ala
            195                 200                 205

Gly Ser Tyr Tyr Asp Glu Asp Ile Val Val Gly Val Ile Leu Gly Thr
        210                 215                 220

Gly Ser Asn Ala Ala Tyr Leu Glu Lys Ala Asn Ala Ile Pro Lys Leu
225                 230                 235                 240

Glu Gly Glu Leu Pro Lys Ser Gly Asn Met Val Ile Asn Thr Glu Trp
                245                 250                 255

Gly Asn Phe Ser Ser Ser Cys Leu Pro Ile Thr Glu Tyr Asp Glu Ala
            260                 265                 270

Leu Asp Lys Glu Ser Leu Asn Pro Gly Glu Gln Ile Phe Glu Lys Leu
        275                 280                 285

Ile Ser Gly Met Tyr Leu Gly Glu Ile Val Arg Arg Val Leu Leu Lys
    290                 295                 300

Ile Ser Leu Gln Ser Ser Ile Phe Gly Asn Leu Asp Gln Thr Lys Leu
305                 310                 315                 320

Lys Thr Arg Phe Ile Leu Arg Thr Pro Asp Ile Ser Val Met His His
                325                 330                 335

Asp Gly Thr Pro Asp Leu Arg Ile Val Ala Glu Lys Leu Ala Asp Asn
            340                 345                 350

Leu Lys Ile Thr Asp Thr Ser Leu Glu Thr Arg Lys Met Val Val Glu
        355                 360                 365

Ile Cys Asp Ile Val Thr Arg Arg Ser Ala Arg Leu Ala Ala Ala Gly
    370                 375                 380

Ile Val Gly Ile Leu Arg Lys Ile Gly Arg Gly Val Pro Gly Asp Lys
385                 390                 395                 400

Arg Lys Ser Val Ile Ala Ile Asp Gly Gly Leu Tyr Glu His Tyr Thr
                405                 410                 415

Glu Phe Arg Gln Cys Leu Glu Thr Thr Leu Thr Glu Leu Leu Gly Glu
            420                 425                 430

Glu Ala Ser Lys Ser Val Ala Val Lys Leu Ala Asn Asp Gly Ser Gly
        435                 440                 445

Leu Gly Ala Ala Leu Ile Ala Ala His Ser Gln Tyr Leu Asn
    450                 455                 460

<210> SEQ ID NO 61
<211> LENGTH: 1835
<212> TYPE: DNA
<213> ORGANISM: Oryza sativa

<400> SEQUENCE: 61
cactgaaagg gatcaactaa actactgatg aaaaaaagtt gagtgcttta gacaaaaaca       60
caaaactttc acgtgcctcc ctccaatccc agattatttt tctatagatc gatcgatcga      120
gccccgtgaa tgcgattctg cgcgcatttc cagagcgtct tttgatcgtg gttgggtttg      180
tctgaaccga actccaaagg tctcgccttt cttgctctga agcttttctt tagcttttcg      240
attcgcctgt cggggaccgg gatcatggcg gcggtggagg cggagaaggt ggtggcggag      300
ctgcgggaga ggtgcgcgac gcgggcgtcg ctgctgcggg atgtggcggc ggcgatggcc      360
ggcgagatgg gcgccggcct ggagaaggag ggtgggagca gggtcaagat gctgctctcc      420

```
tacgtcgaca agctccccac tgggagagag gatggattgt tctatggatt ggacctagga      480
ggaacaaact tccgggtgct caaggttcat cttggtggca gcaagaagca tgtcgtcaac      540
tctgaatcca gggaagtcag catcccacca cacctgatgt cagggacctc ctcggaattg      600
tttggtttca ttgctgggga attaggcaag tttgttgctg aagaggagga gggtactgac      660
atgccaaacg gcaagaagaa agagctagga ttcaccttct cttttcctgt gaggcaacga      720
tctgtggcat cgggtaccct tgtcaagtgg acaaaggcgt tttccattga tgatgcagta      780
ggtgaagatg tggtggctga actacaaacg gctatggtga acaaggtctg gacatgcat      840
gtagctgcat tgattaatga tgctgttgga acattggctg gagcaagata ctacgatgaa      900
gatgttgtcg caggtgtgat atttggtact ggcacaaatg ctgcatatgt tgagaaggca      960
aatgctatac caaatggga aggggagttg cccaattcag gggatatggt catcaatatg     1020
gaatggggta atttctattc atcgcatctt ccagttactg aatacgatga agcattagac     1080
aaggaaagct taaaccctgg agagcagata tatgagaagt taacatcagg aatgtatta      1140
ggtgaaatcg taagaagagt gctgcttaaa ctgtccttgc agtctggaat tttcggttct     1200
atagataact ccaagctcaa aacttgtttc catctgcgga ctccgcacat ttctgcaatg     1260
caccatgatg aaacacctga cctaaagata gtggctgaaa aattgcatca aatcctagag     1320
attacacata catccttaga gataaggaaa atggttgtcg aaatatgcga tatcgtggca     1380
aggagggcag ctcggctggc tgctgctggt gttgcaggga tcctcatgaa gcttggaaga     1440
aatggcggca tcaacaatca gcgctcggtc atcgccattg atggaggttt gttcgaacac     1500
tacaccaaat tcagggaatg tttggagagc acgttgggtg agttgctggg agaggaggct     1560
tccaagtcgg tagccgtcaa gcacgcgaac gacgggtcag ggatagggggc tgcccttatt     1620
gcagcctctc aatctcgatg aaaatttgct agataaatag tagtatatgc cgtccatttt     1680
tgctctggag tgaaaaaat tattgaaaaa acctagcttt gttgtatgtg ctgcttgggc     1740
atggtggaac tggaagcagt ctgtaaccaa aatgaggctt gatatactgt cgccctgcat     1800
agttgtaacc tgaaataaaa ttggaactgc aaaac                                1835

<210> SEQ ID NO 62
<211> LENGTH: 458
<212> TYPE: PRT
<213> ORGANISM: Oryza sativa

<400> SEQUENCE: 62

Met Ala Ala Val Glu Ala Glu Lys Val Val Ala Glu Leu Arg Glu Arg
1               5                   10                  15

Cys Ala Thr Arg Ala Ser Leu Leu Arg Asp Val Ala Ala Met Ala
            20                  25                  30

Gly Glu Met Gly Ala Gly Leu Glu Lys Glu Gly Ser Arg Val Lys
        35                  40                  45

Met Leu Leu Ser Tyr Val Asp Lys Leu Pro Thr Gly Arg Glu Asp Gly
    50                  55                  60

Leu Phe Tyr Gly Leu Asp Leu Gly Gly Thr Asn Phe Arg Val Leu Lys
65                  70                  75                  80

Val His Leu Gly Gly Ser Lys Lys His Val Val Asn Ser Glu Ser Arg
                85                  90                  95

Glu Val Ser Ile Pro Pro His Leu Met Ser Gly Thr Ser Ser Glu Leu
            100                 105                 110

Phe Gly Phe Ile Ala Gly Glu Leu Gly Lys Phe Val Ala Glu Glu Glu
        115                 120                 125
```

Glu Gly Thr Asp Met Pro Asn Gly Lys Lys Glu Leu Gly Phe Thr
130                 135                 140

Phe Ser Phe Pro Val Arg Gln Arg Ser Val Ala Ser Gly Thr Leu Val
145                 150                 155                 160

Lys Trp Thr Lys Ala Phe Ser Ile Asp Asp Ala Val Gly Glu Asp Val
                165                 170                 175

Val Ala Glu Leu Gln Thr Ala Met Val Lys Gln Gly Leu Asp Met His
            180                 185                 190

Val Ala Ala Leu Ile Asn Asp Ala Val Gly Thr Leu Ala Gly Ala Arg
        195                 200                 205

Tyr Tyr Asp Glu Asp Val Val Ala Gly Val Ile Phe Gly Thr Gly Thr
210                 215                 220

Asn Ala Ala Tyr Val Glu Lys Ala Asn Ala Ile Pro Lys Trp Glu Gly
225                 230                 235                 240

Glu Leu Pro Asn Ser Gly Asp Met Val Ile Asn Met Glu Trp Gly Asn
                245                 250                 255

Phe Tyr Ser Ser His Leu Pro Val Thr Glu Tyr Asp Glu Ala Leu Asp
            260                 265                 270

Lys Glu Ser Leu Asn Pro Gly Glu Gln Ile Tyr Glu Lys Leu Thr Ser
        275                 280                 285

Gly Met Tyr Leu Gly Glu Ile Val Arg Arg Val Leu Leu Lys Leu Ser
290                 295                 300

Leu Gln Ser Gly Ile Phe Gly Ser Ile Asp Asn Ser Lys Leu Lys Thr
305                 310                 315                 320

Cys Phe His Leu Arg Thr Pro His Ile Ser Ala Met His His Asp Glu
                325                 330                 335

Thr Pro Asp Leu Lys Ile Val Ala Glu Lys Leu His Gln Ile Leu Glu
            340                 345                 350

Ile Thr His Thr Ser Leu Glu Ile Arg Lys Met Val Val Glu Ile Cys
        355                 360                 365

Asp Ile Val Ala Arg Arg Ala Ala Arg Leu Ala Ala Ala Gly Val Ala
370                 375                 380

Gly Ile Leu Met Lys Leu Gly Arg Asn Gly Ile Asn Asn Gln Arg
385                 390                 395                 400

Ser Val Ile Ala Ile Asp Gly Gly Leu Phe Glu His Tyr Thr Lys Phe
                405                 410                 415

Arg Glu Cys Leu Glu Ser Thr Leu Gly Glu Leu Leu Gly Glu Glu Ala
            420                 425                 430

Ser Lys Ser Val Ala Val Lys His Ala Asn Asp Gly Ser Gly Ile Gly
        435                 440                 445

Ala Ala Leu Ile Ala Ala Ser Gln Ser Arg
450                 455

<210> SEQ ID NO 63
<211> LENGTH: 1844
<212> TYPE: DNA
<213> ORGANISM: Oryza sativa

<400> SEQUENCE: 63
gaactcgcgt tgacctattg actcgtgtcg ccgtctcgcc gagcgaaccc gacgtcgtcg    60
gcgatgagga aggcggcggc gctggcgtcc gcggcgatgg ccgcagcagc agtagcggta   120
gtctccacgg tgttgcacca gaggcaacgt cgggcggcga agcggtcaga gcgcgcggag   180
gccgtgctgc tgcgggacct gcaggagcgg tgcgccgcgc cggtggagct gctgcggcag   240

```
gtggcggacg cgatggccgc ggagatgcgc gcggggctcg ccgccgaggg cgggagcgac    300
ctccagatgc tcgtcaccta cgttgactcc ctcccctccg ggggtgagaa agggatgttt    360
tatgcacttg accttggagg aacaaatttc cgtgttttac gagttcaatt aggaggcaaa    420
gaacgtcgaa ttatcaagca agactcagaa gggatatcca ttccacaaca tttaatgtcc    480
agcagttcac atgagttgtt tgattttgtt gctgtggctt tagcaaaatt tgttgcctct    540
gaaggtgaag actgccatct tcctgagggt acccaaagag aactaggttt tacattctcc    600
tttccagtga acaaaaatc attggcatct ggcactctta tcaagtggac gaagagtttt    660
gcaattgatg aaatggtcgg caaggatgtt gtggctgaat aaacatggc tatcagaagt    720 caaggacttg atatgaaagt cacagcattg gttaatgata cagtagggac attagctgct    780
gggagatatg tgaatcatga tactattgct gctgttatac tgggaacagg tagtaatgca    840
gcgtacatag atcatgcaga tgcaattcca aaatggcatg gatccctgcc caagtctgga    900
aatatggtaa taaacatgga atggggtaac tttaagtcct cacatcttcc acttactgaa    960
tttgatcaag agttggatgc agaaagtttg aaccctggca acaggttta cgagaaatcg    1020 atttctggta tgtatatggg ggaacttgtt cgaagaatct tactaaagat ggctcaagaa    1080
actcgcattt ttggtgataa atacctccca aaacttgaga gaccatacat cttaaggaca    1140
cttgacatgc tgatcatgca tcatgataca tcatctgatc tcagaacagt tgccaacaag    1200
ttgaaagaag tcttggggat cgaatatacc tctttcacga cgaggaaact ggttttggat    1260
gtttgtgagg ccattgcgac acgcggtgca cggcttgctg ctgctgggat atatggcatt    1320
atccaaaagc ttggtcagca ttctgacagc cccagtacga gaaggtccgt gattgctgtg    1380
gatggagggg tctataaata ctacactttc ttcagccagt gcatggagag cactctgagt    1440
gacatgcttg gcaggagct ggcccctct gttatgatca agcatgtcaa tgatggctca    1500
ggcgttgggg cagctctcct ggcagcctct tattctcaat accaccaggc tgaatctgca    1560
gatagttcat aatattctaa aaaaagaag ctgaatctgc agatagctct taatattctg    1620
aaaaaactgt caaaaaataa tattctgaaa aaaaactgtg tattaaggtg ataaacaata    1680
ggttttggag caattttttt tttaagataa tggattaaac cggcctctac atccaaacga    1740
gattctagag caatagcagc tatacagttt gcctaagggc taaatatctt gtattttgca    1800
aatgtcaatt gtacatgaac tctatctgca atatctgttc agtg                     1844
```

<210> SEQ ID NO 64
<211> LENGTH: 502
<212> TYPE: PRT
<213> ORGANISM: Oryza sativa

<400> SEQUENCE: 64

Met Arg Lys Ala Ala Ala Leu Ala Ser Ala Ala Met Ala Ala Ala
1               5                   10                  15

Val Ala Val Val Ser Thr Val Leu His Gln Arg Gln Arg Arg Ala Ala
            20                  25                  30

Lys Arg Ser Glu Arg Ala Glu Ala Val Leu Leu Arg Asp Leu Gln Glu
        35                  40                  45

Arg Cys Ala Ala Pro Val Glu Leu Leu Arg Gln Val Ala Asp Ala Met
    50                  55                  60

Ala Ala Glu Met Arg Ala Gly Leu Ala Ala Glu Gly Gly Ser Asp Leu
65                  70                  75                  80

Gln Met Leu Val Thr Tyr Val Asp Ser Leu Pro Ser Gly Gly Glu Lys

```
                         85                  90                  95
Gly Met Phe Tyr Ala Leu Asp Leu Gly Gly Thr Asn Phe Arg Val Leu
                    100                 105                 110
Arg Val Gln Leu Gly Gly Lys Glu Arg Ile Ile Lys Gln Asp Ser
                    115                 120                 125
Glu Gly Ile Ser Ile Pro Gln His Leu Met Ser Ser Ser His Glu
                    130                 135                 140
Leu Phe Asp Phe Val Ala Val Ala Leu Ala Lys Phe Val Ala Ser Glu
145                     150                 155                 160
Gly Glu Asp Cys His Leu Pro Glu Gly Thr Gln Arg Glu Leu Gly Phe
                        165                 170                 175
Thr Phe Ser Phe Pro Val Lys Gln Lys Ser Leu Ala Ser Gly Thr Leu
                    180                 185                 190
Ile Lys Trp Thr Lys Ser Phe Ala Ile Asp Glu Met Val Gly Lys Asp
                    195                 200                 205
Val Val Ala Glu Leu Asn Met Ala Ile Arg Ser Gln Gly Leu Asp Met
    210                 215                 220
Lys Val Thr Ala Leu Val Asn Asp Thr Val Gly Thr Leu Ala Ala Gly
225                 230                 235                 240
Arg Tyr Val Asn His Asp Thr Ile Ala Ala Val Ile Leu Gly Thr Gly
                        245                 250                 255
Ser Asn Ala Ala Tyr Ile Asp His Ala Asp Ala Ile Pro Lys Trp His
                    260                 265                 270
Gly Ser Leu Pro Lys Ser Gly Asn Met Val Ile Asn Met Glu Trp Gly
                    275                 280                 285
Asn Phe Lys Ser Ser His Leu Pro Leu Thr Glu Phe Asp Gln Glu Leu
    290                 295                 300
Asp Ala Glu Ser Leu Asn Pro Gly Lys Gln Val Tyr Glu Lys Ser Ile
305                 310                 315                 320
Ser Gly Met Tyr Met Gly Glu Leu Val Arg Arg Ile Leu Leu Lys Met
                    325                 330                 335
Ala Gln Glu Thr Arg Ile Phe Gly Asp Asn Ile Pro Pro Lys Leu Glu
                    340                 345                 350
Arg Pro Tyr Ile Leu Arg Thr Leu Asp Met Leu Ile Met His His Asp
                    355                 360                 365
Thr Ser Ser Asp Leu Arg Thr Val Ala Asn Lys Leu Lys Glu Val Leu
    370                 375                 380
Gly Ile Glu Tyr Thr Ser Phe Thr Thr Arg Lys Leu Val Leu Asp Val
385                 390                 395                 400
Cys Glu Ala Ile Ala Thr Arg Gly Ala Arg Leu Ala Ala Ala Gly Ile
                    405                 410                 415
Tyr Gly Ile Ile Gln Lys Leu Gly Gln His Ser Asp Ser Pro Ser Thr
                    420                 425                 430
Arg Arg Ser Val Ile Ala Val Asp Gly Gly Val Tyr Lys Tyr Tyr Thr
                    435                 440                 445
Phe Phe Ser Gln Cys Met Glu Ser Thr Leu Ser Asp Met Leu Gly Gln
                    450                 455                 460
Glu Leu Ala Pro Ser Val Met Ile Lys His Val Asn Asp Gly Ser Gly
465                     470                 475                 480
Val Gly Ala Ala Leu Leu Ala Ala Ser Tyr Ser Gln Tyr His Gln Ala
                        485                 490                 495
Glu Ser Ala Asp Ser Ser
                    500
```

<210> SEQ ID NO 65
<211> LENGTH: 1585
<212> TYPE: DNA
<213> ORGANISM: Oryza sativa

<400> SEQUENCE: 65

```
gtggagtgat cgatcgactc gggcgcgggg aggggagggg gaggggaggt gggggggaat      60
ggaggggagg gcggcggggt gggtgagggt ggcggcggtg gggtgggcgg tggcggcgtg     120
cgcggtggcg gcggggatgg tggcgaggcg aggggcggcg agggtgcggt ggaacagggc     180
ggtggcggtg gtgcgggacc tggaggagcg gtgcgccacg cccgcggagc tgctgcagcg     240
ggtggtcaac tcgctggcca tcgagatgtt cgccggcctc gcctccgacg gcgggagcaa     300
ggtgcggatg ctgctcacct gcgtcgacgc gctccccgac gggagcgagg aaggcatcag     360
ttatgccatt gatcttggag aacaagctt t agagtcctg aaagtagaac ttggcgcagg     420
gtctacaatc atcaatcgaa aagttgaaca tcagcctatc cccgaaaatt tgactaaggg     480
tacaagcgat gatttgttca atttcattgc ctcggcactg aagaatttta ttgaaagaga     540
gggtggggag gttgagggga gggcacttgg ttttacattt tctttccctg tgagacagac     600
ttccatttcc tcggggacat taattcgatg gactaaagaa ttttcaattg aagaggctgt     660
cgggaaagat gttgctcagt gcctaaatga agcccttgct aggaatggac tcaatatgaa     720
ggtcaatgta ttggtgaaca atactgtggg gacattagct ctcgggcatt attatgatga     780
tgacacagta gctgctgtga ttattggagc tggcaccaat gcttgctata ttgaacgcaa     840
cgatgcaatt attaaatctt tgggtcgcgt taccaattct gaacgaacgg tagtaaatgt     900
ggaatggggg agttttcggc ctccacaaat agaattgact ccttatgata tatgcttcaa     960
caacgaaaca tggaattatt atgaccaggg ttttgagaaa atgatctctg gtgtgtatct    1020
tggggaaatt gcaagattgg tgttccaaaa aatggctgaa gagtcagata tatttggtac    1080
tgctgttgat ggtctatcga cccctttcgt cttaagtaca ccaaacttag ctgctatccg    1140
cgaggatgat tccccggact tgagagaagt cggcaagata cttgaggaac atcttaagct    1200
accagatgtt cccctcaaga cccggaagct tgttgccaga gtctccgaca tcatcacccg    1260
gagagctgcc cgcctagcag cggctgcgat tgtcgcgata ctgcaaaaga tcggctgcga    1320
tggaacccct tgtggttcaa ctcaggttcg aacaatgcga ggcgtgcgaa gaagaacggt    1380
ggtcgcgatc gagggcggcc tcttcgaagg ctactcggtc ttcagagagt atctgaatga    1440
agctctagtt gagatccttg gagaggagat tgcagccact gttagtctta gggtgatgga    1500
ggagggatct gggactggtg ctgccctcct tgcagctgca tattcatcgg ctaggcagaa    1560
gaactccgag taggcatgag acaca                                         1585
```

<210> SEQ ID NO 66
<211> LENGTH: 504
<212> TYPE: PRT
<213> ORGANISM: Oryza sativa

<400> SEQUENCE: 66

```
Met Glu Gly Arg Ala Ala Gly Trp Val Arg Val Ala Ala Val Gly Trp
1               5                   10                  15

Ala Val Ala Ala Cys Ala Val Ala Gly Met Val Ala Arg Arg Gly
            20                  25                  30

Ala Ala Arg Val Arg Trp Asn Arg Ala Val Ala Val Val Arg Asp Leu
        35                  40                  45
```

```
Glu Glu Arg Cys Ala Thr Pro Ala Glu Leu Leu Gln Arg Val Val Asn
 50                  55                  60

Ser Leu Ala Ile Glu Met Phe Ala Gly Leu Ala Ser Asp Gly Gly Ser
 65                  70                  75                  80

Lys Val Arg Met Leu Leu Thr Cys Val Asp Ala Leu Pro Asp Gly Ser
             85                  90                  95

Glu Glu Gly Ile Ser Tyr Ala Ile Asp Leu Gly Gly Thr Ser Phe Arg
            100                 105                 110

Val Leu Lys Val Glu Leu Gly Ala Gly Ser Thr Ile Ile Asn Arg Lys
            115                 120                 125

Val Glu His Gln Pro Ile Pro Glu Asn Leu Thr Lys Gly Thr Ser Asp
            130                 135                 140

Asp Leu Phe Asn Phe Ile Ala Ser Ala Leu Lys Asn Phe Ile Glu Arg
145                 150                 155                 160

Glu Gly Gly Glu Val Glu Gly Arg Ala Leu Gly Phe Thr Phe Ser Phe
            165                 170                 175

Pro Val Arg Gln Thr Ser Ile Ser Ser Gly Thr Leu Ile Arg Trp Thr
            180                 185                 190

Lys Glu Phe Ser Ile Glu Glu Ala Val Gly Lys Asp Val Ala Gln Cys
            195                 200                 205

Leu Asn Glu Ala Leu Ala Arg Asn Gly Leu Asn Met Lys Val Asn Val
210                 215                 220

Leu Val Asn Asn Thr Val Gly Thr Leu Ala Leu Gly His Tyr Tyr Asp
225                 230                 235                 240

Asp Asp Thr Val Ala Ala Val Ile Ile Gly Ala Gly Thr Asn Ala Cys
            245                 250                 255

Tyr Ile Glu Arg Asn Asp Ala Ile Ile Lys Ser Leu Gly Arg Val Thr
            260                 265                 270

Asn Ser Glu Arg Thr Val Val Asn Val Glu Trp Gly Ser Phe Arg Pro
            275                 280                 285

Pro Gln Ile Glu Leu Thr Pro Tyr Asp Ile Cys Phe Asn Asn Glu Thr
            290                 295                 300

Trp Asn Tyr Tyr Asp Gln Gly Phe Glu Lys Met Ile Ser Gly Val Tyr
305                 310                 315                 320

Leu Gly Glu Ile Ala Arg Leu Val Phe Gln Lys Met Ala Glu Glu Ser
            325                 330                 335

Asp Ile Phe Gly Thr Ala Val Asp Gly Leu Ser Thr Pro Phe Val Leu
            340                 345                 350

Ser Thr Pro Asn Leu Ala Ala Ile Arg Glu Asp Asp Ser Pro Asp Leu
            355                 360                 365

Arg Glu Val Gly Lys Ile Leu Glu Glu His Leu Lys Leu Pro Asp Val
            370                 375                 380

Pro Leu Lys Thr Arg Lys Leu Val Ala Arg Val Ser Asp Ile Ile Thr
385                 390                 395                 400

Arg Arg Ala Ala Arg Leu Ala Ala Ala Ile Val Ala Ile Leu Gln
                    405                 410                 415

Lys Ile Gly Cys Asp Gly Thr Leu Cys Gly Ser Thr Gln Val Arg Thr
            420                 425                 430

Met Arg Gly Val Arg Arg Thr Val Val Ala Ile Glu Gly Gly Leu
            435                 440                 445

Phe Glu Gly Tyr Ser Val Phe Arg Glu Tyr Leu Asn Glu Ala Leu Val
450                 455                 460
```

Glu Ile Leu Gly Glu Glu Ile Ala Ala Thr Val Ser Leu Arg Val Met
465                 470                 475                 480

Glu Glu Gly Ser Gly Thr Gly Ala Ala Leu Leu Ala Ala Ala Tyr Ser
            485                 490                 495

Ser Ala Arg Gln Lys Asn Ser Glu
        500

<210> SEQ ID NO 67
<211> LENGTH: 1494
<212> TYPE: DNA
<213> ORGANISM: Sorghum bicolor

<400> SEQUENCE: 67

```
atggggcggg tcgggctcgg cgtggcggcg ggctgcgcgg ccgccacgtg cgcgatcgcc      60
gccgcgctgg tggcgcgcag ggcgtcggcg cgggcgcgct ggcgccgcgc cgtcgcgctg     120
ctcagggagt tcgaggaagg ctgcgccacg ccgacgccgc gcctgcgcca ggtcgtcgac     180
gccatggtcg tcgagatgca cgcgggcctc gcctccgacg cggcagcaa gctcaagatg     240
ctgctcacct tcgtcgacgc gctccccgcc ggaaatgaac aaggcacata ttattccatc     300
gatcttggag gaacaaactt tagagtgttg agagttgaag ttggtgctgt gtctgtggtg     360
accagtcggg aggttaaact tcccatccct gaggaattga ccaagggtac aattgaggag     420
ctattcaact tgttgccat gaccctaaag gaatttgtag agacagaaga tgttaaagat     480
gaacaaaggg cgcttggttt cacattttct ttcccagtta gacaaacttc agtgtcttca     540
gggtcattaa ttaggtggac taaaggtttt ttgattgaag atgcggttgg aaagatgtg     600
gctcaatgct aaatgaagc tcttgctagg agtggactaa atgtgcgagt tactgcactg     660
gtgaacgaca ccgtggggac attagctcta ggacattatt atgatgagga tacagtggct     720
gctgtgatca tcggtgctgg caccaatgct tgctatattg aacgcactga tgcaattatt     780
aaatgtcagg gtcttcttac aaactctggt ggcatggtag taaacatgga atggggcaat     840
ttctggtcat cacatttgcc aagaactcct tatgacatct cccttgatga tgagacgcaa     900
aatcgcaatg atcaggggtt tgagaaaatg atctctggga tttatctcgg ggaaattgca     960
aggctggtgc tgcatcgcat ggctctagaa tcagatgttt ttggcgatgc tgctgatcat    1020
ctatctaccc ccttcacatt gagcacacca cttctggctg caattcgcaa ggacgattca    1080
ccagatctga gtgaagtcag aaggatactg caagaacatc tgaagataat ggacactccc    1140
ctgaaaactc gaaggctagt cgtcaaagtc tgcgacattg tcacccgaag agctgcacgc    1200
ctagctgctg ctggtattgt cgggatactg aaaaagctcg gtcgggatgg gagcggcgtg    1260
gcttcaagcg ggagaacacg agggcagctg aggcggacgg tggttgcgat cgagggtggc    1320
ctgtatgagg ctacccagt gttcagggag tacctagatg aagctctggt ggagatcttg    1380
ggggaggagg tggcgcagac ggtggcgcta agggtgacag aggacgggtc tggggctggc    1440
gctgccctcc tcgccgccgt acattcgtcg aatagacagc aaggttccat atag         1494
```

<210> SEQ ID NO 68
<211> LENGTH: 497
<212> TYPE: PRT
<213> ORGANISM: Sorghum bicolor

<400> SEQUENCE: 68

Met Gly Arg Val Gly Leu Gly Val Ala Ala Gly Cys Ala Ala Ala Thr
1               5                   10                  15

Cys Ala Ile Ala Ala Ala Leu Val Ala Arg Arg Ala Ser Ala Arg Ala

```
            20                  25                  30
Arg Trp Arg Arg Ala Val Ala Leu Leu Arg Glu Phe Glu Glu Gly Cys
            35                  40                  45
Ala Thr Pro Thr Pro Arg Leu Arg Gln Val Val Asp Ala Met Val Val
 50                  55                  60
Glu Met His Ala Gly Leu Ala Ser Asp Gly Ser Lys Leu Lys Met
 65                  70                  75                  80
Leu Leu Thr Phe Val Asp Ala Leu Pro Ala Gly Asn Glu Gln Gly Thr
                    85                  90                  95
Tyr Tyr Ser Ile Asp Leu Gly Gly Thr Asn Phe Arg Val Leu Arg Val
                100                 105                 110
Glu Val Gly Ala Val Ser Val Thr Ser Arg Glu Val Lys Leu Pro
                115                 120                 125
Ile Pro Glu Glu Leu Thr Lys Gly Thr Ile Glu Leu Phe Asn Phe
                130                 135                 140
Val Ala Met Thr Leu Lys Glu Phe Val Glu Thr Glu Asp Val Lys Asp
145                 150                 155                 160
Glu Gln Arg Ala Leu Gly Phe Thr Phe Ser Phe Pro Val Arg Gln Thr
                165                 170                 175
Ser Val Ser Ser Gly Ser Leu Ile Arg Trp Thr Lys Gly Phe Leu Ile
                180                 185                 190
Glu Asp Ala Val Gly Lys Asp Val Ala Gln Cys Leu Asn Glu Ala Leu
                195                 200                 205
Ala Arg Ser Gly Leu Asn Val Arg Val Thr Ala Leu Val Asn Asp Thr
                210                 215                 220
Val Gly Thr Leu Ala Leu Gly His Tyr Tyr Asp Glu Asp Thr Val Ala
225                 230                 235                 240
Ala Val Ile Ile Gly Ala Gly Thr Asn Ala Cys Tyr Ile Glu Arg Thr
                245                 250                 255
Asp Ala Ile Ile Lys Cys Gln Gly Leu Leu Thr Asn Ser Gly Gly Met
                260                 265                 270
Val Val Asn Met Glu Trp Gly Asn Phe Trp Ser Ser His Leu Pro Arg
                275                 280                 285
Thr Pro Tyr Asp Ile Ser Leu Asp Asp Glu Thr Gln Asn Arg Asn Asp
                290                 295                 300
Gln Gly Phe Glu Lys Met Ile Ser Gly Ile Tyr Leu Gly Glu Ile Ala
305                 310                 315                 320
Arg Leu Val Leu His Arg Met Ala Leu Glu Ser Asp Val Phe Gly Asp
                325                 330                 335
Ala Ala Asp His Leu Ser Thr Pro Phe Thr Leu Ser Thr Pro Leu Leu
                340                 345                 350
Ala Ala Ile Arg Lys Asp Asp Ser Pro Asp Leu Ser Glu Val Arg Arg
                355                 360                 365
Ile Leu Gln Glu His Leu Lys Ile Met Asp Thr Pro Leu Lys Thr Arg
                370                 375                 380
Arg Leu Val Val Lys Val Cys Asp Ile Val Thr Arg Arg Ala Ala Arg
385                 390                 395                 400
Leu Ala Ala Ala Gly Ile Val Gly Ile Leu Lys Lys Leu Gly Arg Asp
                405                 410                 415
Gly Ser Gly Val Ala Ser Ser Gly Arg Thr Arg Gly Gln Leu Arg Arg
                420                 425                 430
Thr Val Val Ala Ile Glu Gly Gly Leu Tyr Glu Gly Tyr Pro Val Phe
                435                 440                 445
```

Arg Glu Tyr Leu Asp Glu Ala Leu Val Glu Ile Leu Gly Glu Glu Val
       450                 455                 460

Ala Gln Thr Val Ala Leu Arg Val Thr Glu Asp Gly Ser Gly Ala Gly
465                 470                 475                 480

Ala Ala Leu Leu Ala Ala Val His Ser Ser Asn Arg Gln Gln Gly Ser
                485                 490                 495

Ile

<210> SEQ ID NO 69
<211> LENGTH: 2045
<212> TYPE: DNA
<213> ORGANISM: Sorghum bicolor

<400> SEQUENCE: 69

```
cttggtgcta gcctcctttt cccttccccc ttgaatcgaa ctgttgggag ctcttcgctg      60
tcctaccatt cccccctcgc tcttttttag cattttgctt gggctctcga ctcctccgaa     120
aatccagcct tttgtttgct tttctgtctc ctgctgattg tgtcccccgg atccaggatt     180
cttgatttgc tcctcggggg ttggggccat ggcgactgct gcgctggcaa tggcagagca     240
ggtggtggcc gacctccgag cgaagtgtga ggcgccgccg ccgatgctgc gcgaggtggc     300
ggcggagatg gcccgcgaga tgggcgcggg actggagaag gaaggcggga gcagggtcaa     360
gatgctcctc tcctacgttg ataagctccc cacaggggga gaagagggat tattctatgg     420
attggaccta ggagggacga acttccgcgt cttgaaagtg gaactgggtg gaatgagaaa     480
gcacgtcgtg gaccgtgact ccagagaagt cattattcct ccacatttga tgtcagggag     540
ctcctcggag ctttttggtt tcattgcttc tgaattggcc aagtttgttg ttgatgatga     600
gaagttcatc aatgttttga atggaaagaa gcgagaacta gggttcacat tttcattccc     660
agtgaagcag cgttctgttg cttccggtac gcttgtcaag tggacaaagg catttttccat    720
taatgatgct gttggtgaag atgtggtggc taaaactgca acagctatgg agaagcaagg     780
tctggacatg catgtagctg cattgattaa tgatgctgtt gggactctgg ctggagcaag     840
gtactacgac aaagatgttg tcgctggtgt aatatttggc actggcacaa atgcagcata     900
tgttgagaag gcaaatgcta ttccaaaatg ggagggtgag ctgcccaatt caggagatat     960
ggtcatcaac atggaatggg gtaacttctg ctcagcctat ctcccaatca ctgaatatga    1020
ccaagaatta gataaggaga gcttaaatcc aggagaacag atttatgaga agttaacatc    1080
agggatgtat ttgggcgaaa ttgtaaggag ggtgctccct aaaatatcat tgcagtctgc    1140
gattttttggc aatattgacc acactaagct cgaaaccccg ttccttctgc ggactccaca    1200
tatttctgca atgcaccatg atgaaacacc tgatctgaag attgtggcaa aaaaactgga    1260
agaaaaccta gagattacag gcgcatcctt agaggctcga aaattggtgg ttgaaatttg    1320
tgacattgtg caacaagag ctgcccggct ggccgctgca gggcttgcag gatcctcat     1380
gaagctcggg agagattgca gtgtcgagga tcaacgatca gtcatcgcca tcgatggagg    1440
attgttcgag cactacacca aattccgcca atgcttggag accacactgg gcgagctgct    1500
aggagatgag gcgtctaagg cggtggccgt caagcatgca gatgatggtt caggaatagg    1560
tgctgccctg attgcagctt cacaatctct gtacaaaaat gacttagtgg ccgtcaagca    1620
tgcagatgac aagcatgcag atgacaagca tgaagatgca gatgacaagc atgaagatga    1680
cggtaaagga gtcaagcatg cagatgacgg ttcagaaata ggtgctgccc tgattgcagc    1740
ctcgcaatct cagtagagaa atgtcctcga aatctcagta gagaaatttc gagtgatata    1800
```

-continued

```
gtagtatcag ccatgggtgc ttaccataga tgtaggaaag actagctagc aagtagctat    1860
aatgtctttc caacatctta acagtccggc atctgcagtt agcatgctgg acctggatgt    1920
aatctataac caaaacgagg cttggcagct ggatgcaatc tgtaaccaaa acgaggcttg    1980
ggaagtgctg ttcatagttc caaacttcca ataaaagcgg agttgcagat gtctcctaat    2040
tcgac                                                                 2045

<210> SEQ ID NO 70
<211> LENGTH: 515
<212> TYPE: PRT
<213> ORGANISM: Sorghum bicolor

<400> SEQUENCE: 70

Met Ala Thr Ala Ala Leu Ala Met Ala Glu Gln Val Val Ala Asp Leu
1               5                   10                  15

Arg Ala Lys Cys Glu Ala Pro Pro Met Leu Arg Glu Val Ala Ala
                20                  25                  30

Glu Met Ala Arg Glu Met Gly Ala Gly Leu Glu Lys Glu Gly Gly Ser
            35                  40                  45

Arg Val Lys Met Leu Leu Ser Tyr Val Asp Lys Leu Pro Thr Gly Gly
        50                  55                  60

Glu Glu Gly Leu Phe Tyr Gly Leu Asp Leu Gly Gly Thr Asn Phe Arg
65                  70                  75                  80

Val Leu Lys Val Glu Leu Gly Gly Asn Glu Lys His Val Val Asp Arg
                85                  90                  95

Asp Ser Arg Glu Val Ile Ile Pro Pro His Leu Met Ser Gly Ser Ser
            100                 105                 110

Ser Glu Leu Phe Gly Phe Ile Ala Ser Glu Leu Ala Lys Phe Val Val
        115                 120                 125

Asp Asp Glu Lys Phe Ile Asn Val Leu Asn Gly Lys Lys Arg Glu Leu
    130                 135                 140

Gly Phe Thr Phe Ser Phe Pro Val Lys Gln Arg Ser Val Ala Ser Gly
145                 150                 155                 160

Thr Leu Val Lys Trp Thr Lys Ala Phe Ser Ile Asn Asp Ala Val Gly
                165                 170                 175

Glu Asp Val Val Ala Lys Leu Gln Thr Ala Met Glu Lys Gln Gly Leu
            180                 185                 190

Asp Met His Val Ala Ala Leu Ile Asn Asp Ala Val Gly Thr Leu Ala
        195                 200                 205

Gly Ala Arg Tyr Tyr Asp Lys Asp Val Val Ala Gly Val Ile Phe Gly
    210                 215                 220

Thr Gly Thr Asn Ala Ala Tyr Val Glu Lys Ala Asn Ala Ile Pro Lys
225                 230                 235                 240

Trp Glu Gly Glu Leu Pro Asn Ser Gly Asp Met Val Ile Asn Met Glu
                245                 250                 255

Trp Gly Asn Phe Cys Ser Ala Tyr Leu Pro Ile Thr Glu Tyr Asp Gln
            260                 265                 270

Glu Leu Asp Lys Glu Ser Leu Asn Pro Gly Glu Gln Ile Tyr Glu Lys
        275                 280                 285

Leu Thr Ser Gly Met Tyr Leu Gly Glu Ile Val Arg Arg Val Leu Leu
    290                 295                 300

Lys Ile Ser Leu Gln Ser Ala Ile Phe Gly Asn Ile Asp His Thr Lys
305                 310                 315                 320
```

```
Leu Glu Thr Pro Phe Leu Leu Arg Thr Pro His Ile Ser Ala Met His
            325                 330                 335

His Asp Glu Thr Pro Asp Leu Lys Ile Val Ala Lys Lys Leu Glu Glu
        340                 345                 350

Asn Leu Glu Ile Thr Gly Ala Ser Leu Glu Ala Arg Lys Leu Val Val
            355                 360                 365

Glu Ile Cys Asp Ile Val Ala Thr Arg Ala Arg Leu Ala Ala Ala
        370                 375                 380

Gly Leu Ala Gly Ile Leu Met Lys Leu Gly Arg Asp Cys Ser Val Glu
385                 390                 395                 400

Asp Gln Arg Ser Val Ile Ala Ile Asp Gly Gly Leu Phe Glu His Tyr
                405                 410                 415

Thr Lys Phe Arg Gln Cys Leu Glu Thr Thr Leu Gly Glu Leu Leu Gly
            420                 425                 430

Asp Glu Ala Ser Lys Ala Val Ala Val Lys His Ala Asp Asp Gly Ser
        435                 440                 445

Gly Ile Gly Ala Ala Leu Ile Ala Ala Ser Gln Ser Leu Tyr Lys Asn
    450                 455                 460

Asp Leu Val Ala Val Lys His Ala Asp Lys His Ala Asp Lys
465                 470                 475                 480

His Glu Asp Ala Asp Lys His Glu Asp Asp Gly Lys Gly Val Lys
                485                 490                 495

His Ala Asp Asp Gly Ser Glu Ile Gly Ala Ala Leu Ile Ala Ala Ser
            500                 505                 510

Gln Ser Gln
    515

<210> SEQ ID NO 71
<211> LENGTH: 581
<212> TYPE: DNA
<213> ORGANISM: Triticum aestivum

<400> SEQUENCE: 71
gctcaagatg ctcgttagct acgtcgacaa tctgcccacc ggggatgagc atgggctgtt      60
ttatgcactg gatcttggtg ggaccaactt cgtgttcta cgggttcagc ttggaggaaa     120
ggagaaacgt gctgtccaac aatatgaaga ggtgcccatt ccacctcatc tgatggttgg     180
gacttccacc gaactatttg atttcattgc ggctgagcta gaaagatttg ttgagactga     240
aggagacgat ttccacttgc ctgagggcag gcatagggaa ctgggtttca ccttttcttt     300
cccagtacac caaacatcga tatcgtcagg caccctcgtt aagtggacaa aaggattttg     360
catcaatggc acggttgggg aagatgtggt ggctgaattg agcagtgcta tggagaggca     420
ggggcttgat atgaaagtta cagctttggt taatgatact gtgggcacgt ggctggtgg      480
gatatatgct gataatgatg tcgtcgctgc tgtaatattg ggcactggga caaatgcagc     540
gtatgttgag catgctaata caattcccaa atggcatggt c                        581

<210> SEQ ID NO 72
<211> LENGTH: 193
<212> TYPE: PRT
<213> ORGANISM: Triticum aestivum

<400> SEQUENCE: 72

Leu Lys Met Leu Val Ser Tyr Val Asp Asn Leu Pro Thr Gly Asp Glu
1               5                  10                  15

His Gly Leu Phe Tyr Ala Leu Asp Leu Gly Gly Thr Asn Phe Arg Val
```

```
                    20                  25                  30
Leu Arg Val Gln Leu Gly Gly Lys Glu Lys Arg Ala Val Gln Gln Tyr
                35                  40                  45

Glu Glu Val Pro Ile Pro Pro His Leu Met Val Gly Thr Ser Thr Glu
            50                  55                  60

Leu Phe Asp Phe Ile Ala Ala Glu Leu Glu Arg Phe Val Glu Thr Glu
65                  70                  75                  80

Gly Asp Asp Phe His Leu Pro Glu Gly Arg His Arg Glu Leu Gly Phe
                85                  90                  95

Thr Phe Ser Phe Pro Val His Gln Thr Ser Ile Ser Ser Gly Thr Leu
            100                 105                 110

Val Lys Trp Thr Lys Gly Phe Cys Ile Asn Gly Thr Val Gly Glu Asp
            115                 120                 125

Val Val Ala Glu Leu Ser Ser Ala Met Glu Arg Gln Gly Leu Asp Met
        130                 135                 140

Lys Val Thr Ala Leu Val Asn Asp Thr Val Gly Thr Leu Ala Gly Gly
145                 150                 155                 160

Ile Tyr Ala Asp Asn Asp Val Val Ala Val Ile Leu Gly Thr Gly
                165                 170                 175

Thr Asn Ala Ala Tyr Val Glu His Ala Asn Thr Ile Pro Lys Trp His
            180                 185                 190

Gly

<210> SEQ ID NO 73
<211> LENGTH: 3743
<212> TYPE: DNA
<213> ORGANISM: Physcomitrella patens

<400> SEQUENCE: 73
gctctctgag cctcacctcc ctcgctccct tgtcttgctc tgcgatctct cgtcaagctt      60
ttttttcccc cctttctttc ttttttctccc gtcctctgtt gtgcttgcgc cagccgatcg    120
cctacaccta gcagccgcgg ttggagtgct gtgttttag cttttttggag tcctcagatc     180
tggcagacag tttgatgtag ggacgttggt gtaggtttat tcagctgatc gattgagagt    240
gcaaaaggcg aagctgtgtg cgtgtgcgtg tgcgtgtttg ctcgtgagtg tttgggagta    300
ttgctaaagg gtagcaatgg cgatcgggaa ggtactgggg tgtgccgggt tcagcacag     360
tgcagtgcca acgctccgtg aaccagtgcg gctgagggcg caatgcagac gccggggaaa   420
gaccgtgtct atgtcggttc agaagacgtc gaaaacggta cagcaggcgg agaagatgtc   480
gcaggagttc cgtcagtctt cctctactcc cctgcctctt ttgcaccagg tagcggacgc   540
tctcgtgcaa gaaatgtatg ctggattggc gtcggaaggt ggtagtgatc agctgaagat    600
gcttccgacc tatgtcgaaa acttgccttc tgggtgcgct gcttctcaat ccctctcct     660
cgtcgatcct tctttcgttg atgcgaagta gattcttctc ccagacctca gcacccttttg  720
tttgtcgaaa gtgcggcatg caatgctccc tcagtctgtc acggtgtccc gagcaacttc   780
taaaaaaaca catattcact tgttttgcga cgtcaccgcg tagagtgtag cagtcagata   840
tttcaatgac ctggtcgtgg gcgttctctc tttcctgttg ttaaactctc cctatcataa   900
catacggcgc agtttgattg agcttgaaac actgcttgag cacgatcaac gaacattgta   960
ctaagagaac attcgcgatc gctggggaca cgaggccgcg tcttgagaga gatgcctatt  1020
gtgaattttg gcattcttac gaatcccttc gagttttcaa ttgcaggagc gagaaggggc   1080
tgttctatgc cgtggatttg ggcggcacaa acttccgtgt tctgcgagtg gaattgggag  1140
```

```
gcaaaacagg ccaaattttg agccaagagt tcaaggaagt ggtaatccct ccagagctta    1200
tggtgggcac tggtaaggta agacttcata cactcaacac ccatttctaa taactcttcg    1260
tatgaagagc gggacgagtg gcgaatgatt ctctgggcat gatgagaagg gccatgattt    1320
gattcttatg gcgggatgcc gtgcaacagg atcttttcga cttcattgct ggtacactcg    1380
catcatttgt cgacactgaa gacgagtcaa ttaaagctca ctttgttcaa tcgggaaaaa    1440
ccagggagtc cggtttcgct ttctccttcc ccgttcgaca gacctcagtc aaatctggca    1500
ttgtcatcca ctggacgaag ggcttcaaag ttgatgatgc ggtgcgccac ttgtgcaggc    1560
cttttcactc acaaattcac tactcataca cacacattta tcccatgaga ggatgcattt    1620
gccaatttaa atagcgtttt cgatacgagt aagcttagat ttgcatcttc tttcttccct    1680
tgcggagggg cacttttctg aatgtttcag ggacttgagg attatccttt acgaacccct    1740
gttgtatgcg ctgatggtat ttgcaaccca aatttagttc aaacttcctt aatggttcat    1800 cttctggca ggtgggcaaa gacatcgtga agcaatttca ggatgcaatc agcagaagta    1860
accatcagat tatgatctca gccctggtat atctcacttt tcttgaactg cacactctgt    1920
ttggatttaa gttcttacg taatagcgtc catcttctgt ataacctgtg tttgcaatga    1980
tagactgaag gatttcttaa ttttgaatct tttacaggta aacgacaccg ttggcacgtt    2040
ggccggaggc agattcaact tcgacgagga gaccatgatt ggttgcatta ttggaacagg    2100
gacaaacgca tgctatgtcg aacgtgccga tgctgtacat aagtgggacg agccactgcc    2160
caaatcagga gaaatggtaa tcgatttcgc cgcattctc ggtttgtagg cacctgagca    2220
ggaaatcatg ctaacaaacg tcttcaaatg ggtgatttgc tgacgatcat tgagtatatg    2280
agcagttttt tccttacatt ttgttattac gtgtggcagg ttatcaatat ggaatgggga    2340
aatttccgtt caccctacct gccacgaaca tttgctgatg agactgttga caaagacagc    2400
gtcaatccag gggaccaggt gcgaagtcta ccgagagaac tgagtgcatg aggtgttgaa    2460
ttaggtaatt ttcaagagca gacctattca ccctctttgg tggtttttgtg cagtggttcg    2520 agaaaatgat ctctggaatg tacctcggcg agatcgtgcg ccttgttctg gctaggatgg    2580
ccaaagaagc ggaactgttt ggtggcaatg tccccgtgaa gctcttggag cggctcaccc    2640
tagggtaatt ccacggtact tgcagccatt tctcaatgaa ttaatcctca gtaagcctaa    2700
tcgtattcgc tcttggcaaa gcacagatca ttgatccttc actgtttgta cagcaccccca    2760 catgtttcca aaatacatct ggacaattca cctgacctcg acgtggttgc caaagttctc    2820
aaggacgtct tcgaggtgag tgcctatgag caaatgcacg ttcgatgaca ttgaatggaa    2880
tccgaacaat attgacacca cttgcactgg tactaagtac ttgattcatg gccccctttt    2940
gcagatcgaa accaccacac ttgaggaaag aaagatagta cacgaggtgt gtgacatcat    3000
gggcgagcga ggtggaaggt tggctgcagc aggtctctac ggaatcctga gaagatcgg    3060 aagaaccggc aaatctcgaa acggatccaa gaagaagacc gtgattgcaa tggacggtgg    3120
cctgttcgaa caccacgtcc gttaccggtc atacatggag gaggcgctcc aggagttgat    3180
gggttctgac gcagcgtacg aggtggcgtt gagactacag aacgatggtt ctggaatcgg    3240
tgccgctttg cttccgcctt cccactcaca cttcaaatag gataaaacgc acacaaagct    3300 taggggggatc atggcaggtg atgagcatcg cctgttttgc atgcctgtac aatattccga    3360
gtcctgatga tctgtctatc ttctgagatg cacccatcgt ctgtaccatt tgtaccggct    3420
tatcgtaccg caggaagacg ccgttcttca agtcgttgtc tatctggtga ccaaaaccgc    3480
```

-continued

```
agagtttcaa gctgagaggc ctagtagggg tagtgtaggc agagtcaagt tttattgtct   3540
ctggtcagtt acgtagaaca gtttgcggtt gagtctaccc atctcatcta gatctgcact   3600
gcacaccttt caataagctg gtttcacttg aggttgccgt gcgcaagcta gtatctggca   3660
cagagatgag aggttcattg ctgcgcattc tcttagcaat cctcacaatt tccgaggtga   3720
ttgtggggtg atggagctgg gcg                                           3743
```

<210> SEQ ID NO 74
<211> LENGTH: 513
<212> TYPE: PRT
<213> ORGANISM: Physcomitrella patens

<400> SEQUENCE: 74

| Met | Ala | Ile | Gly | Lys | Val | Leu | Gly | Cys | Ala | Gly | Phe | Gln | His | Ser | Ala |
|---|---|---|---|---|---|---|---|---|---|---|---|---|---|---|---|
| 1 | | | | 5 | | | | | 10 | | | | | 15 | |

| Val | Pro | Thr | Leu | Arg | Glu | Pro | Val | Arg | Leu | Arg | Ala | Gln | Cys | Arg | Arg |
| | | | 20 | | | | | 25 | | | | | 30 | | |

| Arg | Gly | Lys | Thr | Val | Ser | Met | Ser | Val | Gln | Lys | Thr | Ser | Lys | Thr | Val |
| | | 35 | | | | | 40 | | | | | 45 | | | |

| Gln | Gln | Ala | Glu | Lys | Met | Ser | Gln | Glu | Phe | Arg | Gln | Ser | Ser | Ser | Thr |
| | 50 | | | | | 55 | | | | | 60 | | | | |

| Pro | Leu | Pro | Leu | Leu | His | Gln | Val | Ala | Asp | Ala | Leu | Val | Gln | Glu | Met |
| 65 | | | | | 70 | | | | | 75 | | | | | 80 |

| Tyr | Ala | Gly | Leu | Ala | Ser | Glu | Gly | Gly | Ser | Asp | Gln | Leu | Lys | Met | Leu |
| | | | | 85 | | | | | 90 | | | | | 95 | |

| Pro | Thr | Tyr | Val | Glu | Asn | Leu | Pro | Ser | Gly | Ser | Glu | Lys | Gly | Leu | Phe |
| | | | 100 | | | | | 105 | | | | | 110 | | |

| Tyr | Ala | Val | Asp | Leu | Gly | Gly | Thr | Asn | Phe | Arg | Val | Leu | Arg | Val | Glu |
| | | 115 | | | | | 120 | | | | | 125 | | | |

| Leu | Gly | Gly | Lys | Thr | Gly | Gln | Ile | Leu | Ser | Gln | Glu | Phe | Lys | Glu | Val |
| | 130 | | | | | 135 | | | | | 140 | | | | |

| Val | Ile | Pro | Pro | Glu | Leu | Met | Val | Gly | Thr | Gly | Lys | Asp | Leu | Phe | Asp |
| 145 | | | | | 150 | | | | | 155 | | | | | 160 |

| Phe | Ile | Ala | Gly | Thr | Leu | Ala | Ser | Phe | Val | Asp | Thr | Glu | Asp | Glu | Ser |
| | | | | 165 | | | | | 170 | | | | | 175 | |

| Ile | Lys | Ala | His | Phe | Val | Gln | Ser | Gly | Lys | Thr | Arg | Glu | Ser | Gly | Phe |
| | | | 180 | | | | | 185 | | | | | 190 | | |

| Ala | Phe | Ser | Phe | Pro | Val | Arg | Gln | Thr | Ser | Val | Lys | Ser | Gly | Ile | Val |
| | | 195 | | | | | 200 | | | | | 205 | | | |

| Ile | His | Trp | Thr | Lys | Gly | Phe | Lys | Val | Asp | Asp | Ala | Val | Gly | Lys | Asp |
| | 210 | | | | | 215 | | | | | 220 | | | | |

| Ile | Val | Lys | Gln | Phe | Gln | Asp | Ala | Ile | Ser | Arg | Ser | Asn | His | Gln | Ile |
| 225 | | | | | 230 | | | | | 235 | | | | | 240 |

| Met | Ile | Ser | Ala | Leu | Val | Asn | Asp | Thr | Val | Gly | Thr | Leu | Ala | Gly | Gly |
| | | | | 245 | | | | | 250 | | | | | 255 | |

| Arg | Phe | Asn | Phe | Asp | Glu | Glu | Thr | Met | Ile | Gly | Cys | Ile | Ile | Gly | Thr |
| | | | 260 | | | | | 265 | | | | | 270 | | |

| Gly | Thr | Asn | Ala | Cys | Tyr | Val | Glu | Arg | Ala | Asp | Ala | Val | His | Lys | Trp |
| | | 275 | | | | | 280 | | | | | 285 | | | |

| Asp | Glu | Pro | Leu | Pro | Lys | Ser | Gly | Glu | Met | Val | Ile | Asn | Met | Glu | Trp |
| | 290 | | | | | 295 | | | | | 300 | | | | |

| Gly | Asn | Phe | Arg | Ser | Pro | Tyr | Leu | Pro | Arg | Thr | Phe | Ala | Asp | Glu | Thr |
| 305 | | | | | 310 | | | | | 315 | | | | | 320 |

| Val | Asp | Lys | Asp | Ser | Val | Asn | Pro | Gly | Asp | Gln | Trp | Phe | Glu | Lys | Met |

```
                325                 330                 335
Ile Ser Gly Met Tyr Leu Gly Glu Ile Val Arg Leu Val Leu Ala Arg
            340                 345                 350

Met Ala Lys Glu Ala Glu Leu Phe Gly Gly Asn Val Pro Val Lys Leu
            355                 360                 365

Leu Glu Arg Leu Thr Leu Gly Thr Pro His Val Ser Lys Ile His Leu
        370                 375                 380

Asp Asn Ser Pro Asp Leu Asp Val Val Ala Lys Val Leu Lys Asp Val
385                 390                 395                 400

Phe Glu Ile Glu Thr Thr Thr Leu Glu Glu Arg Lys Ile Val His Glu
                405                 410                 415

Val Cys Asp Ile Met Gly Glu Arg Gly Gly Arg Leu Ala Ala Ala Gly
            420                 425                 430

Leu Tyr Gly Ile Leu Lys Lys Ile Gly Arg Thr Gly Lys Ser Arg Asn
        435                 440                 445

Gly Ser Lys Lys Lys Thr Val Ile Ala Met Asp Gly Gly Leu Phe Glu
450                 455                 460

His His Val Arg Tyr Arg Ser Tyr Met Glu Glu Ala Leu Gln Glu Leu
465                 470                 475                 480

Met Gly Ser Asp Ala Ala Tyr Glu Val Ala Leu Arg Leu Gln Asn Asp
                485                 490                 495

Gly Ser Gly Ile Gly Ala Ala Leu Leu Ala Ala Ser His Ser His Phe
            500                 505                 510

Lys

<210> SEQ ID NO 75
<211> LENGTH: 2762
<212> TYPE: DNA
<213> ORGANISM: Physcomitrella patens

<400> SEQUENCE: 75 gtttttttgtc atgggctctg ctctgctgcc tttgtggcga agtggcgcag ctggcttctt      60
cttctgcata cttcgcagga agcgctcgaa gctccacgaa tattgagaga gagctggaga     120
agaagaagga attggtacta ctactactac tactactact actacggtga caatgccaat     180
gccagaaacg tccactcttc gggacatagc gcttgtggta aaatctgagg cgctgtcgag     240
gaggagaatt gagtctgtga tttgcaggga gaagtggtga ggaagtgagc gatctgaggg     300
ggagatgatt ttattttttg gtttgttcct cgtgtgagga gtgagtggtg aaggggggtag     360 agagagagag cagagaagag gagaggtttt gagtgagttt gagagagaga gagagagaga     420
gagagagaag cggggaaaga tggcgcaatc gaaagccaga gtgggagtgt gcattgcctg     480
tgcagctgcg acgtgcgctg tagcagctgt gattgtggcg cggcgcgtga agtttcattc     540
tcagaagtgt gctgcgcgga aaattctggt ggagtttcag gaggcatgcg acacgtctct     600
gctgcggttg cgcatggtgg tggatgctat ggcggctgag atgcacgctg tcttgtttc     660 ggaaggcggt agcactctca aaatgcttcc tacctacatt gatcgcttgc cagacgggaa     720
tgagcgagga ctttattatg ctgtggattt aggtggcacc aacttccgag ttctccgtgt     780
tcagctgggt gggttagagg ggagggtaat caaccaagag tatgaggaag tgcccatccc     840
tcctcatgtg atgcttggaa caagtaaaca attatttgat tttattgcca aggaattggt     900
gagctttgtg gcaagagaag gtcaggactt caggctacat gcaggtcagc agcgggaaat     960
agggtttacc ttctcatttc ctgtggacca aacggcagta aatagtggta aacttttgca    1020
```

-continued

```
gtggaccaag gggttcaaag tgaacgatgc tattggccag atgtggttg cagcacttca   1080 gaggagcatt gaatccttag gcacaagat gaggatatct gctttgatca atgatactgt   1140
aggaacgcta gccggcggtc gctactggaa taatgacgtg atgataggtg ttattttggg   1200
taccgggacc aatgcctgtt acgtggagcg agctgaagct gtatcgaagt ggggtggcga   1260
gattccgaag tctggacaga tggtgataaa catggagtgg gggaatttct ggtcatcaca   1320
tttgcctagg acttatgtgg atgaatcctt ggataacgag agtttgaacc aggagaata   1380 cggttttgaa aagatgatct ctggaatgta tttgggcgat tgtgtgaggc gcgtgcttgt   1440
tagaatggca caacaagcag gcatatttgg tccccgtgtt ccacacaggc ttttggaagc   1500
tttctcactt aagacaccgg atatgtcaaa atgcatcag gataataata acgatctaag   1560
agtggttgga gaaattctaa acagtgttta ccagattcaa acaccacat tgggaattcg   1620 aaagattgta gtggaggttt gcgatgtggt gtgtaagaga ggtgctagac tggcaggtgc   1680
gggaattgta ggaatattga agaaaattgg aagggatgga agtgcggcga atggggttat   1740
caagcgtaac ctgtttgaac agagtgacat gaatggttac catgacgacg acctatgca   1800 atatacatca gacgtgaaaa ccgttgttgc tatagacggt ggtttgtatg aacactacac   1860
caagttccga gaatacatgc aagatgctgt gtttgaactt cttggagaag catcaaagaa   1920
tgtctccata cagcttttcca aagatggatc aggcattgga gcagcccttc ttgctgcatc   1980
gcatgccgag catctttctt cttgataacg atgaaaccaa ctacagtctt gtgaaatatg   2040
agtctttgct gattgaaacc tcttagttct aatgttagaa atgtgtatac caatccgtca   2100 aggggggtgcg agttagcttc ctttggagcc cttggtttat cggctcgcca tttctgtaga   2160
aaggttcgct tttttaatc attaatcacg catctcggca gctcatgttt ccaagagtaa   2220
cttgggacaa cagatcccct ggctgcatac gtaagcttat ttgaatacta tggagcaact   2280
actcaaaaat ctatttgctt ttgtaaacac cttaaatcaa aggtgacgct ctttgtctgg   2340
tccagcctag agcccaatag tctagcctaa acctctgatg gctaaagttt ggacgttatg   2400
gttttgagca ccaaacgttc tgcactgttt gcaatgctgc ttttctgtct ttcaatttgt   2460
tgtggaagga ccaacaatgc ctgtagatac gctgggtctt cattgtccaa gtgaaacccc   2520
aaagagctcg ttgaggtttc tattttagtg aatgctgttg tcgtcaatgt gggctagttg   2580
aagtcccaaa ccgcagtatg aggatgcttg cttgcttgct atattttgag aatatggtat   2640
gtagcatcct ctttgctctg ccaaagggtt acttgtcttc aggatcttcc ttagcagttt   2700
aaagaatttt ggatttttgtt aactaaagta gctttcatac ttaaatgcct acttcaaaag   2760
ac                                                                  2762
```

<210> SEQ ID NO 76
<211> LENGTH: 521
<212> TYPE: PRT
<213> ORGANISM: Physcomitrella patens

<400> SEQUENCE: 76

```
Met Ala Gln Ser Lys Ala Arg Val Gly Val Cys Ile Ala Cys Ala Ala
1               5                   10                  15

Ala Thr Cys Ala Val Ala Ala Val Ile Val Ala Arg Arg Val Lys Phe
            20                  25                  30

His Ser Gln Lys Cys Ala Ala Arg Lys Ile Leu Val Glu Phe Gln Glu
        35                  40                  45

Ala Cys Asp Thr Ser Leu Leu Arg Leu Arg Met Val Val Asp Ala Met
    50                  55                  60
```

```
Ala Ala Glu Met His Ala Gly Leu Val Ser Glu Gly Ser Thr Leu
65              70                  75                  80

Lys Met Leu Pro Thr Tyr Ile Asp Arg Leu Pro Asp Gly Asn Glu Arg
                85                  90                  95

Gly Leu Tyr Tyr Ala Val Asp Leu Gly Gly Thr Asn Phe Arg Val Leu
            100                 105                 110

Arg Val Gln Leu Gly Gly Leu Glu Gly Arg Val Ile Asn Gln Glu Tyr
        115                 120                 125

Glu Glu Val Pro Ile Pro Pro His Val Met Leu Gly Thr Ser Lys Gln
130                 135                 140

Leu Phe Asp Phe Ile Ala Lys Glu Leu Val Ser Phe Val Ala Arg Glu
145                 150                 155                 160

Gly Gln Asp Phe Arg Leu His Ala Gly Gln Gln Arg Glu Ile Gly Phe
                165                 170                 175

Thr Phe Ser Phe Pro Val Asp Gln Thr Ala Val Asn Ser Gly Lys Leu
            180                 185                 190

Leu Gln Trp Thr Lys Gly Phe Lys Val Asn Asp Ala Ile Gly Gln Asp
        195                 200                 205

Val Val Ala Ala Leu Gln Arg Ser Ile Glu Ser Leu Gly His Lys Met
210                 215                 220

Arg Ile Ser Ala Leu Ile Asn Asp Thr Val Gly Thr Leu Ala Gly Gly
225                 230                 235                 240

Arg Tyr Trp Asn Asn Asp Val Met Ile Gly Val Ile Leu Gly Thr Gly
                245                 250                 255

Thr Asn Ala Cys Tyr Val Glu Arg Glu Ala Val Ser Lys Trp Gly
            260                 265                 270

Gly Glu Ile Pro Lys Ser Gly Gln Met Val Ile Asn Met Glu Trp Gly
        275                 280                 285

Asn Phe Trp Ser Ser His Leu Pro Arg Thr Tyr Val Asp Glu Ser Leu
    290                 295                 300

Asp Asn Glu Ser Leu Asn Pro Gly Glu Tyr Gly Phe Glu Lys Met Ile
305                 310                 315                 320

Ser Gly Met Tyr Leu Gly Asp Cys Val Arg Arg Val Leu Val Arg Met
                325                 330                 335

Ala Gln Gln Ala Gly Ile Phe Gly Pro Arg Val Pro His Arg Leu Leu
            340                 345                 350

Glu Ala Phe Ser Leu Lys Thr Pro Asp Met Ser Lys Met His Gln Asp
        355                 360                 365

Asn Asn Asn Asp Leu Arg Val Val Gly Glu Ile Leu Asn Ser Val Tyr
    370                 375                 380

Gln Ile Gln Asn Thr Thr Leu Gly Ile Arg Lys Ile Val Glu Val
385                 390                 395                 400

Cys Asp Val Val Cys Lys Arg Gly Ala Arg Leu Ala Gly Ala Gly Ile
                405                 410                 415

Val Gly Ile Leu Lys Lys Ile Gly Arg Asp Gly Ser Ala Ala Asn Gly
            420                 425                 430

Val Ile Lys Arg Asn Leu Phe Glu Gln Ser Asp Met Asn Gly Tyr His
        435                 440                 445

Asp Asp Asp Pro Met Gln Tyr Thr Ser Asp Val Lys Thr Val Val Ala
    450                 455                 460

Ile Asp Gly Gly Leu Tyr Glu His Tyr Thr Lys Phe Arg Glu Tyr Met
465                 470                 475                 480
```

Gln Asp Ala Val Phe Glu Leu Leu Gly Glu Ala Ser Lys Asn Val Ser
            485                 490                 495

Ile Gln Leu Ser Lys Asp Gly Ser Gly Ile Gly Ala Ala Leu Leu Ala
        500                 505                 510

Ala Ser His Ala Glu His Leu Ser Ser
        515                 520

<210> SEQ ID NO 77
<211> LENGTH: 2530
<212> TYPE: DNA
<213> ORGANISM: Physcomitrella patens

<400> SEQUENCE: 77

| | | | | | | |
|---|---|---|---|---|---|---|
| gtgagtgagt | gagtgtgtgt | gtgagtgtga | gagtgttgag | ttgtgttgtc | gccgctgagt | 60 |
| ctggttgtgt | tgctcacgcg | ctgcagagtc | cgggttagcg | agagagagag | agagagcgag | 120 |
| agagctggaa | gcgagagaga | gaaggctcag | atccttggca | atgtaagcga | ggctgacatg | 180 |
| gcggatgtgt | tcaagcgag | gttccacaaa | cataactcaa | atccggaggg | ggagaatttg | 240 |
| gtgcaagaag | cactgggaaa | gttcagttta | agccgcggag | attaagttca | gttgttgcgg | 300 |
| gtgtcgaggg | tgtcgagggt | gtcgaggta | atggtgtttg | gttcggtcga | tcgtctgtgg | 360 |
| attaggaagg | aagagatact | ggcgatctgt | gaaggtgaat | ggttcgggtt | gtgaattgtg | 420 |
| ttaagcaggg | gagggtgttg | ttgttgttgt | tgtggtgtgt | ttgagagagc | gagagagagg | 480 |
| cagaaatggg | acaatcgaag | gtattggtag | gtgtgtacat | tgcttgcgca | gctgcggcat | 540 |
| gcgcaaccgc | agctgtggcg | gtgacgcagc | gactgaaagt | gcgagcgcag | aagtgcactg | 600 |
| cgcggaaaat | tttggtggag | tttcaggagg | cttgcgagac | gcctctgccg | cggttgcggc | 660 |
| aagttgtgga | tgctatggcc | gtcgagatgc | acgctggcct | cgtgtcggaa | ggcggaagca | 720 |
| agcttaagat | gctgcccacc | ttcattgatc | gcttgccgaa | tgggagcgag | aagggccttt | 780 |
| attatgctgt | ggacttgggt | gggacaaact | tccgggtgct | ccgtgtccag | ttgggtggat | 840 |
| tagaaggtag | agtaatcaag | caagagtacg | aggaagttgc | cattccccct | gagctaatgc | 900 |
| ttggaacaag | cgaacaacta | tttcatttta | ttgccaagga | gttggctggc | tttgtggcaa | 960 |
| gagaaggtga | ggaattcagg | ttaggcgacg | gtcagtcacg | ggaaataggg | ttcacctttt | 1020 |
| ccttcccctg | taagcaaacc | gctgtaaatt | ctgggactct | cttgcaatgg | accaagggct | 1080 |
| tcaaagtgaa | cgatgcaatc | ggccaagatg | tggtcgcagc | tcttcaaaag | tgcattgaac | 1140 |
| gactagggtg | caagatgagg | atcgctgctt | tggttaacga | tacagtgggt | actctagctg | 1200 |
| gtggtcgcta | ttggaataac | gacgtgatga | tagctgttat | tttgggtact | ggtaccaatg | 1260 |
| cctgctacgt | tgagcgggct | gaatctatat | cgaagtggac | tggcgagctt | ccgaagtctg | 1320 |
| gccagatggt | gatcaatatg | gagtggggaa | acttttggtc | atcacatttg | cctcggacct | 1380 |
| atgtggatga | gttattggat | agcgagagcc | tccatccagg | agaatatggt | tttgaaaaga | 1440 |
| tgatttctgg | aatgtatttg | ggtgattgtg | tgaggcgagt | gcttgtcagg | atggcacaag | 1500 |
| aagctggcat | cttcggtccc | catgttcctc | acacactctt | ggaatccttc | tcgctccaga | 1560 |
| caccagaaat | gtcaagaatg | caccatgatg | acagtagcga | cctaaaagta | gttgcagaag | 1620 |
| ttctgaaaag | actatatgga | atccagaaca | caacagtagg | gattcgcaaa | atcgtagttg | 1680 |
| ctgtttgcga | cactacgtgc | cagcgagggg | ccaggctggc | agctgctggt | attgtgggaa | 1740 |
| tactaaagaa | aattgggaga | gatggaagta | cagcaaatgg | cttgatgagg | cgaaatgata | 1800 |
| cgaatggtat | ccatgacgag | ctctctgtga | attctacacc | gggaagtggt | aagaccgttg | 1860 |

-continued

```
tggctatgga cggtggcttg tatgagcact acagcaagtt ccgaaattac atgcaagaag    1920
ctgtgcgtga gcttctaggg gacgcatcca aaaacgtctc tatagagctc tccaaggatg    1980
gctcaggcat tggggcagcc cttctagctg catcatatgc cgagtatgtg ccctcctaat    2040
acctcttgaa ctattgatta aaattccagt aggtcaaatt gttaggactg tgctttacca    2100
atgcttctat gaggtatgag tctgtttctt ttggaacatt gggttatctg gctcgtcttg    2160
tcttgtataa agcctcgtag ttcaatcatc agataattgt tctccttgtc agctcataga    2220
ctggagagtg acttagggta gtggctttct aggtagcagt caaagtatta tttgaatact    2280
ttgaaaagta tcaaacccat tccttgtgta ggacattacc ttgatacttc agccacagtt    2340
taagaagtct ggtctttttt ttagtgtagt agacgaggtt gtagttaatg gttgtcagca    2400
gaaatgcctt gcagtctttt agcagttgct ggctctttct tgcaatttat tgctaaacag    2460
ccttttgggg ttatactgtc ccttcatctc aatcaaaatc attttggatt cgcttttccg    2520
gacttttggc                                                           2530
```

<210> SEQ ID NO 78
<211> LENGTH: 517
<212> TYPE: PRT
<213> ORGANISM: Physcomitrella patens

<400> SEQUENCE: 78

```
Met Gly Gln Ser Lys Val Leu Val Gly Val Tyr Ile Ala Cys Ala Ala
1               5                   10                  15

Ala Ala Cys Ala Thr Ala Ala Val Ala Val Thr Gln Arg Leu Lys Val
                20                  25                  30

Arg Ala Gln Lys Cys Thr Ala Arg Lys Ile Leu Val Glu Phe Gln Glu
            35                  40                  45

Ala Cys Glu Thr Pro Leu Pro Arg Leu Arg Gln Val Val Asp Ala Met
        50                  55                  60

Ala Val Glu Met His Ala Gly Leu Val Ser Glu Gly Ser Lys Leu
65                  70                  75                  80

Lys Met Leu Pro Thr Phe Ile Asp Arg Leu Pro Asn Gly Ser Glu Lys
                85                  90                  95

Gly Leu Tyr Tyr Ala Val Asp Leu Gly Gly Thr Asn Phe Arg Val Leu
            100                 105                 110

Arg Val Gln Leu Gly Gly Leu Glu Gly Arg Val Ile Lys Gln Glu Tyr
        115                 120                 125

Glu Glu Val Ala Ile Pro Pro Glu Leu Met Leu Gly Thr Ser Glu Gln
    130                 135                 140

Leu Phe His Phe Ile Ala Lys Glu Leu Ala Gly Phe Val Ala Arg Glu
145                 150                 155                 160

Gly Glu Glu Phe Arg Leu Gly Asp Gly Gln Ser Arg Glu Ile Gly Phe
                165                 170                 175

Thr Phe Ser Phe Pro Cys Lys Gln Thr Ala Val Asn Ser Gly Thr Leu
            180                 185                 190

Leu Gln Trp Thr Lys Gly Phe Lys Val Asn Asp Ala Ile Gly Gln Asp
        195                 200                 205

Val Val Ala Ala Leu Gln Lys Cys Ile Glu Arg Leu Gly Cys Lys Met
    210                 215                 220

Arg Ile Ala Ala Leu Val Asn Asp Thr Val Gly Thr Leu Ala Gly Gly
225                 230                 235                 240

Arg Tyr Trp Asn Asn Asp Val Met Ile Ala Val Ile Leu Gly Thr Gly
                245                 250                 255
```

```
Thr Asn Ala Cys Tyr Val Glu Arg Ala Glu Ser Ile Ser Lys Trp Thr
            260                 265                 270
Gly Glu Leu Pro Lys Ser Gly Gln Met Val Ile Asn Met Glu Trp Gly
        275                 280                 285
Asn Phe Trp Ser Ser His Leu Pro Arg Thr Tyr Val Asp Glu Leu Leu
    290                 295                 300
Asp Ser Glu Ser Leu His Pro Gly Tyr Gly Phe Glu Lys Met Ile
305                 310                 315                 320
Ser Gly Met Tyr Leu Gly Asp Cys Val Arg Arg Val Leu Val Arg Met
                325                 330                 335
Ala Gln Glu Ala Gly Ile Phe Gly Pro His Val Pro His Thr Leu Leu
            340                 345                 350
Glu Ser Phe Ser Leu Gln Thr Pro Glu Met Ser Arg Met His His Asp
        355                 360                 365
Asp Ser Ser Asp Leu Lys Val Val Ala Glu Val Leu Lys Arg Leu Tyr
    370                 375                 380
Gly Ile Gln Asn Thr Thr Val Gly Ile Arg Lys Ile Val Val Ala Val
385                 390                 395                 400
Cys Asp Thr Thr Cys Gln Arg Gly Ala Arg Leu Ala Ala Ala Gly Ile
                405                 410                 415
Val Gly Ile Leu Lys Lys Ile Gly Arg Asp Gly Ser Thr Ala Asn Gly
            420                 425                 430
Leu Met Arg Arg Asn Asp Thr Asn Gly Ile His Asp Glu Leu Ser Val
        435                 440                 445
Asn Ser Thr Pro Gly Ser Gly Lys Thr Val Val Ala Met Asp Gly Gly
    450                 455                 460
Leu Tyr Glu His Tyr Ser Lys Phe Arg Asn Tyr Met Gln Glu Ala Val
465                 470                 475                 480
Arg Glu Leu Leu Gly Asp Ala Ser Lys Asn Val Ser Ile Glu Leu Ser
                485                 490                 495
Lys Asp Gly Ser Gly Ile Gly Ala Ala Leu Leu Ala Ala Ser Tyr Ala
            500                 505                 510
Glu Tyr Val Pro Ser
            515

<210> SEQ ID NO 79
<211> LENGTH: 2087
<212> TYPE: DNA
<213> ORGANISM: Physcomitrella patens

<400> SEQUENCE: 79
gactggcgat ctcgcggacg acggttggaa gggaggttag tagctgccca gggttagaat      60
tgcttatgtc gaagtgacag attctatgat cacaacgact agaagagctt tgtaggattt     120
taacgaactc tgttttctc tcttattctt tctctgtctt caatcttttt ttcaagttgt      180
gcagccgatc ggttgagtgg tttggggatt atcttgcagc ttcagacgat tgcaacatgg     240
aaaatttaaa gaattcggaa tcttgcgatc caagctcttt cctacggcat tttcggaaat     300
cttccgctac gcctgtgatg ctattgcgtc atattgctca ggccatggcg accgagatgc     360
aagagggtct tgaccatcct ggcgagcgca agctgaaaat gctccccacg tatctcgaat     420
gcttgcctac aggaatgaa agagggttgt tttacgccat tgacttggga ggtactaact     480
tccgagtatt gcagtacaa ctagatggga aggaagggcg catcctgaag caggaatcca     540
tacaagttcc cattcctcaa gaagtaatga ctggaagcag taggatcttt tttggcttcc     600
```

```
ttgccaagac tattgttcaa ttcgtatcca gagaagcaga ccttggcttt gagtgtgtag   660
cactcaatca gaaacgggat ataggcttca cgttctcatt tcctgtcaat caaacaaaag   720
tcaacggagg ctctatcaac gcatggacca aaggcttttc catcagtgat ggggttggtg   780
aagatgtagt cgatcaacta gagatagctc ttgcagatat gggctcggtg aatacgaaag   840
ttgtgtgctt ggttaatgat acagtaggga ctttggcaca gtgcagatac tggaacgatg   900
atgcaatggt gggcgtcatt tgggcacag gatcaaatgc ctgctatgtt gagcgtgctg   960
cagccatatc gtgctggagc agtcctccag aagccgatga tttgacggtt gtaaatattg  1020 aatgggcaa ttttgttct gaacttcttc ctcggacgtt tgccgatgag gggttggatg  1080
cagatagttt gaatcctggt caacaggaat cgagaaaat gatcggcggt atgtacttgg  1140
gtgaaattct tcgccgtgtg ctgctcaaga tggccgaaga tacaggcctg ttcggctcgg  1200
aaattccaga aagactgacg aagcctttca gccttctgac tcctcacatg tcgacaatgc  1260
acggtgatga tacttctagc ttggaagtgg tgggttctgt gattgaagaa gccattgggg  1320
tgaaatatac aacgctagct acacggaaag tcgtgtacga cgtgtgtgac atcattgcgg  1380
aaagaggtgc tcgactctca gctgcaggga ttgtgggaat cctgacgaag attaacagat  1440
gtggagattt aatgctcagt tgcctcacta caccaaacga cactgaagta aaaaagacag  1500
ttattgccat agacggtagt ttatatgaga agtaccctaa gtttcggaac tacatggaag  1560
acgccatgaa ggagatgttg ggcgaagact atgccaacaa tgtgacaact acactatcca  1620
aagacgggtc gggagttgga gccgcgcttc ttgcagccgc tatttctact gagctacgat  1680
tgggcgacgt tggagtcacc aagtgataga aaggacattg ttagatacat cctgtacatt  1740
gcgtaaaggt caggcaccct ctaatctgaa caatgcttta gttgagtgaa agtgagcgcc  1800 atttttacacc gtctaggatt gaacatgcca gagctgtttg agcgggaaaa aattggtcag  1860
agttctgatg accacaggaa agaagtccag catgtaatgt gggttaatgc gcaatggtta  1920
catcaaacag gactgtttat gtacgtaatg tgcacttcca gctgcggatt ttcagctgaa  1980
gtgcagtcac agctgatggc ctacatcaca aaagtgaacc cttgaagtta ccgcaagtat  2040
taatgttgaa gcttgagtat ctaactcagc aagtatcttc ttctctt             2087
```

<210> SEQ ID NO 80
<211> LENGTH: 489
<212> TYPE: PRT
<213> ORGANISM: Physcomitrella patens

<400> SEQUENCE: 80

```
Met Glu Asn Leu Lys Asn Ser Glu Ser Cys Asp Pro Ser Ser Phe Leu
1               5                   10                  15

Arg His Phe Arg Lys Ser Ser Ala Thr Pro Val Met Leu Leu Arg His
            20                  25                  30

Ile Ala Gln Ala Met Ala Thr Glu Met Gln Glu Gly Leu Asp His Pro
        35                  40                  45

Gly Glu Arg Lys Leu Lys Met Leu Pro Thr Tyr Leu Glu Cys Leu Pro
    50                  55                  60

Thr Gly Asn Glu Arg Gly Leu Phe Tyr Ala Ile Asp Leu Gly Gly Thr
65                  70                  75                  80

Asn Phe Arg Val Leu Arg Val Gln Leu Asp Gly Lys Glu Gly Arg Ile
                85                  90                  95

Leu Lys Gln Glu Ser Ile Gln Val Pro Ile Pro Gln Glu Val Met Thr
            100                 105                 110
```

Gly Ser Ser Lys Asp Leu Phe Gly Phe Leu Ala Lys Thr Ile Val Gln
              115                 120                 125

Phe Val Ser Arg Glu Ala Asp Leu Gly Phe Glu Cys Val Ala Leu Asn
130                 135                 140

Gln Lys Arg Asp Ile Gly Phe Thr Phe Ser Phe Pro Val Asn Gln Thr
145                 150                 155                 160

Lys Val Asn Gly Gly Ser Ile Asn Ala Trp Thr Lys Gly Phe Ser Ile
                165                 170                 175

Ser Asp Gly Val Gly Glu Asp Val Val Asp Gln Leu Glu Ile Ala Leu
                180                 185                 190

Ala Asp Met Gly Ser Val Asn Thr Lys Val Val Cys Leu Val Asn Asp
                195                 200                 205

Thr Val Gly Thr Leu Ala Gln Cys Arg Tyr Trp Asn Asp Asp Ala Met
                210                 215                 220

Val Gly Val Ile Leu Gly Thr Gly Ser Asn Ala Cys Tyr Val Glu Arg
225                 230                 235                 240

Ala Ala Ala Ile Ser Cys Trp Ser Ser Pro Glu Ala Asp Asp Leu
                245                 250                 255

Thr Val Val Asn Ile Glu Trp Gly Asn Phe Cys Ser Glu Leu Leu Pro
                260                 265                 270

Arg Thr Phe Ala Asp Glu Gly Leu Asp Ala Asp Ser Leu Asn Pro Gly
                275                 280                 285

Gln Gln Glu Phe Glu Lys Met Ile Gly Gly Met Tyr Leu Gly Glu Ile
                290                 295                 300

Leu Arg Arg Val Leu Leu Lys Met Ala Glu Asp Thr Gly Leu Phe Gly
305                 310                 315                 320

Ser Glu Ile Pro Glu Arg Leu Thr Lys Pro Phe Ser Leu Leu Thr Pro
                325                 330                 335

His Met Ser Thr Met His Gly Asp Asp Thr Ser Ser Leu Glu Val Val
                340                 345                 350

Gly Ser Val Ile Glu Glu Ala Ile Gly Val Lys Tyr Thr Thr Leu Ala
                355                 360                 365

Thr Arg Lys Val Val Tyr Asp Val Cys Asp Ile Ile Ala Glu Arg Gly
370                 375                 380

Ala Arg Leu Ser Ala Ala Gly Ile Val Gly Ile Leu Thr Lys Ile Asn
385                 390                 395                 400

Arg Cys Gly Asp Leu Met Leu Ser Cys Leu Thr Thr Pro Asn Asp Thr
                405                 410                 415

Glu Val Lys Lys Thr Val Ile Ala Ile Asp Gly Ser Leu Tyr Glu Lys
                420                 425                 430

Tyr Pro Lys Phe Arg Asn Tyr Met Glu Asp Ala Met Lys Glu Met Leu
                435                 440                 445

Gly Glu Asp Tyr Ala Asn Asn Val Thr Thr Thr Leu Ser Lys Asp Gly
                450                 455                 460

Ser Gly Val Gly Ala Ala Leu Leu Ala Ala Ala Ile Ser Thr Glu Leu
465                 470                 475                 480

Arg Leu Gly Asp Val Gly Val Thr Lys
                485

<210> SEQ ID NO 81
<211> LENGTH: 2177
<212> TYPE: DNA
<213> ORGANISM: Physcomitrella patens

<400> SEQUENCE: 81

```
gcgattaagg gaagaagcaa ccggagcgat gtcgatgacg gtggagcgcg tttcgctctt      60
ttcgcgaggg gcggggtga cgatgcatgg cctgctgagc gcgagggtgc aatgcgtgag     120
gtctccatgg tgggggctgc ccaaagtcgc tggggcgacg ccgaatgcga acagggtggt     180
gcgagtgcac aatgcagatc ggttggtgca cgggttgcgg ctggccgctg cgactccgct     240
cccgctgctg cgccaagtgg cggatgctct ggtgggagaa atgtgcgctg ggctggagga     300
ggaagggggc agcgatcagc tcaagatgct gccatcgtac gtcgagaatt tgcccactgg     360
ggatgaggaa gggctgtttt acgctgtaga ccttggtggc acaaatttc gggtattgcg      420
attacatttg ggcgggaaag gccaagttct gagccaagag tccaaggaga ttgccatacc     480
tcgcgaactt atggtgggca ctggcaagga tcttttcgac ttcattgcca atacgcttgc     540
cacatttgtc gacacggagg acattctgct tgattcaaag tccaacaagc acagggaagc     600
cgggtttgcg ttttcttttc ccgttcgtca aacatcagta aaatctggca atgtcattca     660
atggaccaaa ggctttaaaa tcgatgatgc gataggcaaa gacattgtga agcagttcca     720
ggatgcgatt agtcgcagtg gtcacgatgt tgaaatttct gccttggtga acgatactgt     780
cggtacatta gccggaggta ggtataactt tcaggaagag acaatgatcg gttgcatact     840
tggcacaggg acaaatgctt gttacgtgga acgagctgat gctgtgaaga aatggaaaga     900
ggcacttccc aaatcagggg agatggtcat caacttagag tggggaaatt ttcgatcacc     960
ttggctgccg cgcacatttg ctgatgatga ggtcgacaaa gaaagtgtaa accccggaga    1020
ccagtggttt gaaaaaatgg tgtcaggcat gtaccttggc gaaatcgtac gacacatgct    1080
gctgaggctt gctgaagagg caacgttgtt tggggacact gtccccgaaa aactcagaga    1140
acaacagtct cttgaaacca acatgtttc taaaatccat gctgacattt catcggagct    1200
ccaaacagta gcgactgttc ttcacgaagt tctcaggatc catgacacca ctctcgaaca    1260
gcggaggatt gtgcacagct tatgcgacat ggttggccag cggggtggaa ggttggctgc    1320
tgcaggactc tacgggatac tgaaaaaaat tggtagagct ggaccaaaca agaatggctt    1380
cgccttatct cgacagaaga agacgacggt ggtggcaatg gatggaggtc tttatgaaca    1440
ccaccacccg taccggaaat acatggagga cgctctccaa gagttggtcg gcacaaacgg    1500
accctacgag gtgttttaa gactacaaaa tgacggttca ggaattggag cggcattgct     1560
tgccgcatct cactctcgac acagacaaac cgagtagcga ggcagacgac tcgtcatctg    1620
gctacctctg tagagtggtg tgaataccgc gaatgtgttc ccgaaaagcc agcaatttct    1680
acttagactt catcatatct gggaataagg agctgaactg accaggaaat caacaatttt    1740
cccctttggaa ttccttttg atcggctctt gtggcggttg catcgcggtg aagacgatag    1800
aggtaatcct ctacctcggc aagcattgat atcttccagc acctacacta gtcatatgtc    1860
gcacctgctg gataagatca gagtaacgtg tagaggggtt tggactttac actgagggcg    1920
tagcatggct gtagacgggg cgttgagtgc ttctacctgt ccagctaggt aagtaaattg    1980
tatctctctg agacgtgtct tggttgtgct acacagatca aagaggtct gcatagacaa    2040
ttgatggaca catgtaaacc cgtagaacaa ggcatcgtca actctttcta gcaacctaat    2100
ccaaataatt actatctaga tttgttcgcg aacatttgta aatatactt ttaaacgatg    2160
gaggaaaagt caaaaac                                                   2177
```

<210> SEQ ID NO 82
<211> LENGTH: 522

<212> TYPE: PRT
<213> ORGANISM: Physcomitrella patens

<400> SEQUENCE: 82

```
Met Ser Met Thr Val Glu Arg Val Ser Leu Phe Ser Arg Gly Ala Gly
1               5                   10                  15

Val Thr Met His Gly Leu Leu Ser Ala Arg Val Gln Cys Val Arg Ser
            20                  25                  30

Pro Trp Trp Gly Leu Pro Lys Val Ala Gly Ala Thr Pro Asn Ala Asn
        35                  40                  45

Arg Val Arg Val His Asn Ala Asp Arg Leu Val His Gly Leu Arg
    50                  55                  60

Leu Ala Ala Ala Thr Pro Leu Pro Leu Leu Arg Gln Val Ala Asp Ala
65                  70                  75                  80

Leu Val Gly Glu Met Cys Ala Gly Leu Glu Glu Glu Gly Gly Ser Asp
                85                  90                  95

Gln Leu Lys Met Leu Pro Ser Tyr Val Glu Asn Leu Pro Thr Gly Asp
            100                 105                 110

Glu Glu Gly Leu Phe Tyr Ala Val Asp Leu Gly Gly Thr Asn Phe Arg
        115                 120                 125

Val Leu Arg Leu His Leu Gly Gly Lys Gly Gln Val Leu Ser Gln Glu
130                 135                 140

Ser Lys Glu Ile Ala Ile Pro Arg Glu Leu Met Val Gly Thr Gly Lys
145                 150                 155                 160

Asp Leu Phe Asp Phe Ile Ala Asn Thr Leu Ala Thr Phe Val Asp Thr
                165                 170                 175

Glu Asp Ile Leu Leu Asp Ser Lys Ser Asn Lys His Arg Glu Ala Gly
            180                 185                 190

Phe Ala Phe Ser Phe Pro Val Arg Gln Thr Ser Val Lys Ser Gly Asn
        195                 200                 205

Val Ile Gln Trp Thr Lys Gly Phe Lys Ile Asp Asp Ala Ile Gly Lys
    210                 215                 220

Asp Ile Val Lys Gln Phe Gln Asp Ala Ile Ser Arg Ser Gly His Asp
225                 230                 235                 240

Val Glu Ile Ser Ala Leu Val Asn Asp Thr Val Gly Thr Leu Ala Gly
                245                 250                 255

Gly Arg Tyr Asn Phe Gln Glu Glu Thr Met Ile Gly Cys Ile Leu Gly
            260                 265                 270

Thr Gly Thr Asn Ala Cys Tyr Val Glu Arg Ala Asp Ala Val Lys Lys
        275                 280                 285

Trp Lys Glu Ala Leu Pro Lys Ser Gly Glu Met Val Ile Asn Leu Glu
    290                 295                 300

Trp Gly Asn Phe Arg Ser Pro Trp Leu Pro Arg Thr Phe Ala Asp Asp
305                 310                 315                 320

Glu Val Asp Lys Glu Ser Val Asn Pro Gly Asp Gln Trp Phe Glu Lys
                325                 330                 335

Met Val Ser Gly Met Tyr Leu Gly Glu Ile Val Arg His Met Leu Leu
            340                 345                 350

Arg Leu Ala Glu Glu Ala Thr Leu Phe Gly Asp Thr Val Pro Glu Lys
        355                 360                 365

Leu Arg Glu Gln Gln Ser Leu Glu Thr Lys His Val Ser Lys Ile His
    370                 375                 380

Ala Asp Ile Ser Ser Glu Leu Gln Thr Val Ala Thr Val Leu His Glu
385                 390                 395                 400
```

```
Val Leu Arg Ile His Asp Thr Thr Leu Glu Gln Arg Ile Val His
                405                 410                 415

Ser Leu Cys Asp Met Val Gly Gln Arg Gly Gly Arg Leu Ala Ala Ala
            420                 425                 430

Gly Leu Tyr Gly Ile Leu Lys Lys Ile Gly Arg Ala Gly Pro Asn Lys
        435                 440                 445

Asn Gly Phe Ala Leu Ser Arg Gln Lys Lys Thr Thr Val Val Ala Met
    450                 455                 460

Asp Gly Gly Leu Tyr Glu His His Pro Tyr Arg Lys Tyr Met Glu
465                 470                 475                 480

Asp Ala Leu Gln Glu Leu Val Gly Thr Asn Gly Pro Tyr Glu Val Phe
                485                 490                 495

Leu Arg Leu Gln Asn Asp Gly Ser Gly Ile Gly Ala Ala Leu Leu Ala
                500                 505                 510

Ala Ser His Ser Arg His Arg Gln Thr Glu
            515                 520
```

<210> SEQ ID NO 83
<211> LENGTH: 1569
<212> TYPE: DNA
<213> ORGANISM: Physcomitrella patens

<400> SEQUENCE: 83

```
atgagagcaa tggcgatcgg gtcggtgctg ggttgtgtcg ggttgcagtt ctccgcagtg      60
ccgacgtttc atggatcggg ggtggcgagt ccgaagatga ggacgcaatg cagagcttgg     120
cggagaacta tgtccatgtc ggttcagcag ccgtcgaaac gggtccagcg tgcagagacg     180
ttgctgcatg acttccgtcg gtcgtccgcc actcccctcc ctcttctgca cctggtggcg     240
gatgctctcg tgcacgagat gtacgctgga ttggtctcag aaggggggag tgatcagctg     300
aagatgctcc caacgtacgt cgaggagttg ccttctggga gtgaaaaggg gctgttctac     360
gccgtggact gggcgggac aaactttcgc gttctaaggg tgcaattagg cggccacact     420
ggtgagattt tgagtcagga gttcaaggag gtggccatac ctccagagct catggtgggc     480
accggcaagg atcttttcga cttcattgcg ggtacgctcg cgtcatttgt cgacaccgaa     540
gacgagtcat tgaaagccca ctttgctcag tcgggcaaag tcaggaaatc cggcttcgcg     600
ttctcctttc ctgttcgcca gacgtctgtc aaatccggca ttgtcatcca ctggaccaag     660
ggcttcaaag ttgacgatgc ggtgggcaaa gatatcgtga acagttcca ggatgcaatc     720
agcaggagtg gtcatcagat tgcgatttca gccctggtga cgacaccgt cggtaccttg     780
gccggaggca ggttcaactt tgaggaggag accatgattg gctgcatcat tgggacaggc     840
acgaacgcgt gctacgtgga acgtgctgat agtgttcaaa agtgggcgga tccactgccg     900
aaatcaggac agatggtgat caacatggaa tggggtaatt ttcattcacc cttcctgcca     960
cgcacatttg ctgacgacat tgttgacaaa gacagcgtaa accctggaga ccagtggttt    1020
gagaaaatga tatctgggat gtaccttggc gagatcgtgc gtctcgtgct tgcgaggatg    1080
gctgaagaag cgcagttgtt tggtggcagc ccccccgcca agctgttgga gaaactcagc    1140
ctcggcaccc cacatgtttc gaagatgcat gctgacgctt accggatttt gcaagtcgtt    1200
gccgaagttc tggaggacgt ctacgggatc gaaaccacca cgctcgagga gaggaagatt    1260
gtacgcgagg tgtgtgacat cttgggcaaa cgaggaggaa ggctagctgc agcaggtctt    1320
tacggcatac tgaagaagat aggcagaacg gagagatctc agaacggatt ccaacaaaag    1380
```

```
aagaagacgg tgattgcaat ggacggaggt ctgttcgagc atcacgagcc ttaccgggcc    1440
tacatggagg aggcactcca cgagttgatg ggctccgaag ccctttacga ggtgtcttta    1500
aggctgcaaa acgatgggtc cggtgtaggt gctgcgttgc ttgctgcttc ccattcacaa    1560
tttaaatag                                                            1569
```

```
<210> SEQ ID NO 84
<211> LENGTH: 522
<212> TYPE: PRT
<213> ORGANISM: Physcomitrella patens

<400> SEQUENCE: 84
```

| | | | | | | | | | | | | | | |
|---|---|---|---|---|---|---|---|---|---|---|---|---|---|---|
| Met | Arg | Ala | Met | Ala | Ile | Gly | Ser | Val | Leu | Gly | Cys | Val | Gly | Leu | Gln |
| 1 | | | | 5 | | | | | 10 | | | | | 15 | |
| Phe | Ser | Ala | Val | Pro | Thr | Phe | His | Gly | Ser | Gly | Val | Ala | Ser | Pro | Lys |
| | | | 20 | | | | | 25 | | | | | 30 | | |
| Met | Arg | Thr | Gln | Cys | Arg | Ala | Trp | Arg | Arg | Thr | Met | Ser | Met | Ser | Val |
| | | | 35 | | | | | 40 | | | | | 45 | | |
| Gln | Gln | Pro | Ser | Lys | Arg | Val | Gln | Arg | Ala | Glu | Thr | Leu | Leu | His | Asp |
| | 50 | | | | | 55 | | | | | 60 | | | | |
| Phe | Arg | Arg | Ser | Ser | Ala | Thr | Pro | Leu | Pro | Leu | His | Leu | Val | Ala | |
| 65 | | | | | 70 | | | | | 75 | | | | | 80 |
| Asp | Ala | Leu | Val | His | Glu | Met | Tyr | Ala | Gly | Leu | Val | Ser | Glu | Gly | Gly |
| | | | | 85 | | | | | 90 | | | | | 95 | |
| Ser | Asp | Gln | Leu | Lys | Met | Leu | Pro | Thr | Tyr | Val | Glu | Glu | Leu | Pro | Ser |
| | | | 100 | | | | | 105 | | | | | 110 | | |
| Gly | Ser | Glu | Lys | Gly | Leu | Phe | Tyr | Ala | Val | Asp | Leu | Gly | Gly | Thr | Asn |
| | | 115 | | | | | 120 | | | | | 125 | | | |
| Phe | Arg | Val | Leu | Arg | Val | Gln | Leu | Gly | Gly | His | Thr | Gly | Glu | Ile | Leu |
| | 130 | | | | | 135 | | | | | 140 | | | | |
| Ser | Gln | Glu | Phe | Lys | Glu | Val | Ala | Ile | Pro | Pro | Glu | Leu | Met | Val | Gly |
| 145 | | | | | 150 | | | | | 155 | | | | | 160 |
| Thr | Gly | Lys | Asp | Leu | Phe | Asp | Phe | Ile | Ala | Gly | Thr | Leu | Ala | Ser | Phe |
| | | | | 165 | | | | | 170 | | | | | 175 | |
| Val | Asp | Thr | Glu | Asp | Glu | Ser | Leu | Lys | Ala | His | Phe | Ala | Gln | Ser | Gly |
| | | | 180 | | | | | 185 | | | | | 190 | | |
| Lys | Val | Arg | Glu | Ser | Gly | Phe | Ala | Phe | Ser | Phe | Pro | Val | Arg | Gln | Thr |
| | | 195 | | | | | 200 | | | | | 205 | | | |
| Ser | Val | Lys | Ser | Gly | Ile | Val | Ile | His | Trp | Thr | Lys | Gly | Phe | Lys | Val |
| | 210 | | | | | 215 | | | | | 220 | | | | |
| Asp | Asp | Ala | Val | Gly | Lys | Asp | Ile | Val | Lys | Gln | Phe | Gln | Asp | Ala | Ile |
| 225 | | | | | 230 | | | | | 235 | | | | | 240 |
| Ser | Arg | Ser | Gly | His | Gln | Ile | Ala | Ile | Ser | Ala | Leu | Val | Asn | Asp | Thr |
| | | | | 245 | | | | | 250 | | | | | 255 | |
| Val | Gly | Thr | Leu | Ala | Gly | Gly | Arg | Phe | Asn | Phe | Glu | Glu | Thr | Met | |
| | | | 260 | | | | | 265 | | | | | 270 | | |
| Ile | Gly | Cys | Ile | Ile | Gly | Thr | Gly | Thr | Asn | Ala | Cys | Tyr | Val | Glu | Arg |
| | | 275 | | | | | 280 | | | | | 285 | | | |
| Ala | Asp | Ser | Val | Gln | Lys | Trp | Ala | Asp | Pro | Leu | Pro | Lys | Ser | Gly | Gln |
| | 290 | | | | | 295 | | | | | 300 | | | | |
| Met | Val | Ile | Asn | Met | Glu | Trp | Gly | Asn | Phe | His | Ser | Pro | Phe | Leu | Pro |
| 305 | | | | | 310 | | | | | 315 | | | | | 320 |
| Arg | Thr | Phe | Ala | Asp | Asp | Ile | Val | Asp | Lys | Asp | Ser | Val | Asn | Pro | Gly |
| | | | | 325 | | | | | 330 | | | | | 335 | |

```
Asp Gln Trp Phe Glu Lys Met Ile Ser Gly Met Tyr Leu Gly Glu Ile
                340                 345                 350

Val Arg Leu Val Leu Ala Arg Met Ala Glu Glu Ala Gln Leu Phe Gly
        355                 360                 365

Gly Ser Pro Pro Ala Lys Leu Leu Glu Lys Leu Ser Leu Gly Thr Pro
    370                 375                 380

His Val Ser Lys Met His Ala Asp Ala Ser Pro Asp Leu Gln Val Val
385                 390                 395                 400

Ala Glu Val Leu Glu Asp Val Tyr Gly Ile Glu Thr Thr Thr Leu Glu
                405                 410                 415

Glu Arg Lys Ile Val Arg Glu Val Cys Asp Ile Leu Gly Lys Arg Gly
            420                 425                 430

Gly Arg Leu Ala Ala Ala Gly Leu Tyr Gly Ile Leu Lys Lys Ile Gly
        435                 440                 445

Arg Thr Glu Arg Ser Gln Asn Gly Phe Gln Gln Lys Lys Lys Thr Val
    450                 455                 460

Ile Ala Met Asp Gly Gly Leu Phe Glu His His Glu Pro Tyr Arg Ala
465                 470                 475                 480

Tyr Met Glu Glu Ala Leu His Glu Leu Met Gly Ser Glu Ala Leu Tyr
                485                 490                 495

Glu Val Ser Leu Arg Leu Gln Asn Asp Gly Ser Gly Val Gly Ala Ala
            500                 505                 510

Leu Leu Ala Ala Ser His Ser Gln Phe Lys
        515                 520

<210> SEQ ID NO 85
<211> LENGTH: 2446
<212> TYPE: DNA
<213> ORGANISM: Physcomitrella patens

<400> SEQUENCE: 85
gttttatagc aaagagtgtg tgtgtgggcg tgcatgtatg tgtgtgtgtg cttctgtgct    60
tggaagtgaa gcgtgctgga agcattccaa ccttcacgag attgagagcc ggaaggaagg   120
gattggaacc gattgatggc aatgtgagtg gcgcctggcc atggcggatg cgttcaaggc   180
gaggtacagc agcggagctc agattcggac agggaaaatt cggagcggtg aggggaggga   240
aaattatttg tagagggaga ggagtgattt cggaggaagg aggtcattga ttgattgatt   300
gattgattga ttgcgagact ttttagaaga ggtgaggagg cgaagaaagt gagcttttat   360
ttttatttgt gtgtgtgtga gagagaggga ggggtagaga cagaggagag gaaaaatgac   420
acaatcgaag gtaatgacgg gcgtgtacat cgcctgcgca gctgcggcgt gcgctgctgc   480
ggctgtgatt gtatcacggc gcttgaaggt tcgatcacag aaatgcactg cgcggaaaat   540
tctgctggag tttcaggagg cctgttacac gcctttggcg cgcctgcgcc aggtggtgga   600
tgctatggcg gtcgagatgc acgctggtct tgtttcggaa ggtggaagca aacttaagat   660
gcttcccacc tacattgatc gcttgcctga cgggcatgag agggtctat actatgctgt   720 ggatttgggt ggtaccaact tccgagtact ccgcgttcaa ttgggtggac tggagggtag   780
ggtgatcaaa caagagtatg aggaagtggc tattcctcct gagctcatgc ttggaacaag   840
tgaacagttg tttgatttca ttgccaagga gttggtgagt tttgtagcaa gggaaggtca   900
ggacttcaga ttgcatgctg gtcaaaatcg agaaatagga tttacttttt cattccccgt   960
gaagcaaact gcagtgaact ctggcactct tctgcagtgg actaaagggt tcaaagtgaa  1020
cgatgctgtt ggcgaggatg tagttgcagc gcttcagagg ggtattgagc gaagagggta  1080
```

```
caagatgagg attgctgctt tggtcaacga taccgtagga accctagctg gcggacggta    1140
ttggaacaat gacgtaatga taggtgttat cttgggtact gggaccaacg cctgctatgt    1200
ggagagagct gaagctgtat cgaagtgggc tggcgacatt ccaaagtccg gggagatggt    1260
tataaacatg gagtggggga atttctggtc atctcacttg cctcggacct atgtggatga    1320
gtcattggac aacgagagtt tgaatccagg agaatatggt ttcgagaaaa tgatctctgg    1380
aatgtatttg ggtgattgtg tgaggcgcgt gcttgttaga atggcacaag aagcctgcat    1440
ttttggcacc cctgtcccac acaagctttt ggaagcattt tctcttatga ctccagacat    1500
gtcgaaaatg catcatgatg atagttctga tttaaaggtg gttgctgaag ttctgaaaag    1560
agtttacggg atccagaaca ctacagtagg aatccgcaaa atcgttgttg cagtttgtga    1620
tacggtgtgc cagcgagggg caagactagc tgctgctggc attgtgggaa tattgaagaa    1680
aattggaaga gatggaagtg cggcaaatgg tgttattaag cggaatacct tcgaacagag    1740
tgatatgaat ggttttcatg acgaagttcc tgtgcattac acatcgggcg gcagaactgt    1800
tgtggctatg gacggtggtt tgtatgaaca ctacaccaag tttcgaaact acatgcaaga    1860
agctgtggtc gagctcctag gagaaggatc taagaacgtc gtcattgagc tttctaaaga    1920
cggatcaggc attggagcag ctcttcttgc tgcatcacat gcagagtacg tcatttcctg    1980
ataatgatga gaaaaactac attgtcttat gaaacctgag gctttgttga ttagaaattc    2040
ttagttctga tcgtgagggc tgtgtacttg actaatgcat caaggatgta cgagtttgct    2100
tcttttgaag cacatggttt gttggctcgt catttctcct gtataaagtc tcttcagtct    2160
tcatcattag ttatcctcat agtttcgaga gtcactcagg acgttacatt tcttggtaac    2220
aaattaggtt ttatttgagt actttggagc aagtactcaa gcgattttct tctgtacatc    2280
gtcttgaaac aaaggtcact tcttaagtct ggtccagcat agagcggaat agttctgtac    2340
taatcaacct ctggtaccca agggttggag gcaatgcttt tcagcataaa atgtttgcag    2400
tcttctactg cgactgttca attctaaact tctgttttgg aaggtc                   2446
```

<210> SEQ ID NO 86
<211> LENGTH: 521
<212> TYPE: PRT
<213> ORGANISM: Physcomitrella patens

<400> SEQUENCE: 86

Met Thr Gln Ser Lys Val Met Thr Gly Val Tyr Ile Ala Cys Ala Ala
1               5                   10                  15

Ala Ala Cys Ala Ala Ala Ala Val Ile Val Ser Arg Arg Leu Lys Val
                20                  25                  30

Arg Ser Gln Lys Cys Thr Ala Arg Lys Ile Leu Leu Glu Phe Gln Glu
            35                  40                  45

Ala Cys Tyr Thr Pro Leu Ala Arg Leu Arg Gln Val Val Asp Ala Met
        50                  55                  60

Ala Val Glu Met His Ala Gly Leu Val Ser Glu Gly Gly Ser Lys Leu
65                  70                  75                  80

Lys Met Leu Pro Thr Tyr Ile Asp Arg Leu Pro Asp Gly His Glu Arg
                85                  90                  95

Gly Leu Tyr Tyr Ala Val Asp Leu Gly Gly Thr Asn Phe Arg Val Leu
                100                 105                 110

Arg Val Gln Leu Gly Gly Leu Glu Gly Arg Val Ile Lys Gln Glu Tyr
            115                 120                 125

Glu Glu Val Ala Ile Pro Pro Glu Leu Met Leu Gly Thr Ser Glu Gln
130                 135                 140

Leu Phe Asp Phe Ile Ala Lys Glu Leu Val Ser Phe Val Ala Arg Glu
145                 150                 155                 160

Gly Gln Asp Phe Arg Leu His Ala Gly Gln Asn Arg Glu Ile Gly Phe
                165                 170                 175

Thr Phe Ser Phe Pro Val Lys Gln Thr Ala Val Asn Ser Gly Thr Leu
            180                 185                 190

Leu Gln Trp Thr Lys Gly Phe Lys Val Asn Asp Ala Val Gly Glu Asp
        195                 200                 205

Val Val Ala Ala Leu Gln Arg Gly Ile Glu Arg Gly Tyr Lys Met
210                 215                 220

Arg Ile Ala Ala Leu Val Asn Asp Thr Val Gly Thr Leu Ala Gly Gly
225                 230                 235                 240

Arg Tyr Trp Asn Asn Asp Val Met Ile Gly Val Ile Leu Gly Thr Gly
                245                 250                 255

Thr Asn Ala Cys Tyr Val Glu Arg Ala Glu Ala Val Ser Lys Trp Ala
            260                 265                 270

Gly Asp Ile Pro Lys Ser Gly Glu Met Val Ile Asn Met Glu Trp Gly
        275                 280                 285

Asn Phe Trp Ser Ser His Leu Pro Arg Thr Tyr Val Asp Glu Ser Leu
290                 295                 300

Asp Asn Glu Ser Leu Asn Pro Gly Glu Tyr Gly Phe Glu Lys Met Ile
305                 310                 315                 320

Ser Gly Met Tyr Leu Gly Asp Cys Val Arg Arg Val Leu Val Arg Met
                325                 330                 335

Ala Gln Glu Ala Cys Ile Phe Gly Thr Pro Val Pro His Lys Leu Leu
            340                 345                 350

Glu Ala Phe Ser Leu Met Thr Pro Asp Met Ser Lys Met His His Asp
        355                 360                 365

Asp Ser Ser Asp Leu Lys Val Val Ala Glu Val Leu Lys Arg Val Tyr
370                 375                 380

Gly Ile Gln Asn Thr Thr Val Gly Ile Arg Lys Ile Val Val Ala Val
385                 390                 395                 400

Cys Asp Thr Val Cys Gln Arg Gly Ala Arg Leu Ala Ala Gly Ile
                405                 410                 415

Val Gly Ile Leu Lys Lys Ile Gly Arg Asp Gly Ser Ala Ala Asn Gly
            420                 425                 430

Val Ile Lys Arg Asn Thr Phe Glu Gln Ser Asp Met Asn Gly Phe His
        435                 440                 445

Asp Glu Val Pro Val His Tyr Thr Ser Gly Gly Arg Thr Val Val Ala
450                 455                 460

Met Asp Gly Gly Leu Tyr Glu His Tyr Thr Lys Phe Arg Asn Tyr Met
465                 470                 475                 480

Gln Glu Ala Val Val Glu Leu Leu Gly Glu Gly Ser Lys Asn Val Val
                485                 490                 495

Ile Glu Leu Ser Lys Asp Gly Ser Gly Ile Gly Ala Ala Leu Leu Ala
            500                 505                 510

Ala Ser His Ala Glu Tyr Val Ile Ser
        515                 520

<210> SEQ ID NO 87
<211> LENGTH: 1829
<212> TYPE: DNA

<213> ORGANISM: Physcomitrella patens

<400> SEQUENCE: 87

```
actggttcgt gttccagtgt tgacgttcga tgaagtcgat gttttgagga ttcgaagggt      60
aatacattgg cgatctgcgg gaggtgagtg ttttgtgagg gttggagttg aggcaaggag     120
agaaggaagg aaggcaggaa gggagaacag ttttgtgagg aggagagaga tggggcaatc     180
gaaagcaatg gcggggtgt atatcgcctg tgcagctgcg gcgtgcgctg ctgcagctgt      240
ggtgttgacg cagcgagtga agtccgatc gcaaaagtac acagcgcgga aaattttagt      300
ggagtttcag gaggcttgtg agacgcctct gccgcggttg aggcaggttg tggatgctat     360
ggcagtcgag atgcatgctg gtcttgtttc ggaaggtggt agcaagctta agatgctgcc     420
tacatttatt gaccacttgc cagacgggaa tgagaaaggc ctttattatg ctgtggattt     480
gggtggcaca aacttccggg tgctccgtac ccaattgggt gggctggagg gtagagtaat     540
taaacaagaa tatgaggagg ttgccattcc tcctgagctg atgcttggaa caagcgaaca     600
attgtttgat ttattgcca aggagttggt tagctttgtg caagagaag gtgaggattt       660
tagattgcac gaaggtcagt cacgggagat agggttcacc ttttcctttc cctgtaagca     720
aaccgctgtg aactctggta ctctcttgca gtggaccaag ggctttaaag tcaacgatgc     780
aatcggccag gatgtggttg cagctctaca agggagcatt gaacggcgag gtacaagat     840
gaggattgct gctttggtta cgacacggt aggaactcta gctggtggtc gctattggaa      900
taacgacgtc atgatagctg ttatttttggg tactggcacc aacgcctgct atgtggagcg     960
agctgaatct atatcgaagt gggtggcga gcttccgaag tctggccaga tggtgatcaa     1020
tatggagtgg ggaaatttt ggtcgtcaca tttgcctcgg acctacgtgg acgagctatt     1080
ggataacgag agtctgaatc caggagaata cggcttcgag aaaatgattt cgggaatgta     1140
tttgggtgat tgtgtgaggc gtgtacttgt tagaatggct cagcaagctg gcatcttcgg     1200
tccccatgtt ccacacaagc tcttggaagc cttcacactt caaacaccag atatgtcgaa     1260
aatgcatcat gatgacagta gtgaccctcaa atggttgca gaagttctga agacagtata     1320
tgggatccat aacacaacac tgggattcg caaaattgta cttgctgttt gcgatattgt     1380
gtgccagcga ggggccagat tagcagctgc tggtattgtg gaatattaa agaaaattgg     1440
aagggatgga agtacagcaa atggttttat caggcgaaat gacgtgaatg gtattcacga     1500
tgagctcacc gtgaattcca ttgggggaag cgggaaaacc gtcgtggcta tggacggtgg     1560
tttgtatgag cactacagta agttccggaa ctacatgcaa caagctgtac gtgaactcct     1620
agggacgca gccaaaaacg tcttcataga gctttcgaag gatggctcag gcattggagc     1680
agccattctt gctgcatcac atgccgagta tgtaccaacc taatatcaac ccgataccgc     1740
ttaaattaat aacatttaat tatggaaccc aaggccttgt tgattaaaac cctttagttc     1800
ttatcgttag gactgtactc tacttatgc                                       1829
```

<210> SEQ ID NO 88
<211> LENGTH: 517
<212> TYPE: PRT
<213> ORGANISM: Physcomitrella patens

<400> SEQUENCE: 88

```
Met Gly Gln Ser Lys Ala Met Ala Gly Val Tyr Ile Ala Cys Ala Ala
1               5                   10                  15

Ala Ala Cys Ala Ala Ala Ala Val Val Leu Thr Gln Arg Val Lys Val
            20                  25                  30
```

```
Arg Ser Gln Lys Tyr Thr Ala Arg Lys Ile Leu Val Glu Phe Gln Glu
            35                  40                  45

Ala Cys Glu Thr Pro Leu Pro Arg Leu Arg Gln Val Val Asp Ala Met
 50                  55                  60

Ala Val Glu Met His Ala Gly Leu Val Ser Glu Gly Gly Ser Lys Leu
 65                  70                  75                  80

Lys Met Leu Pro Thr Phe Ile Asp His Leu Pro Asp Gly Asn Glu Lys
                85                  90                  95

Gly Leu Tyr Tyr Ala Val Asp Leu Gly Gly Thr Asn Phe Arg Val Leu
               100                 105                 110

Arg Thr Gln Leu Gly Gly Leu Glu Gly Arg Val Ile Lys Gln Glu Tyr
           115                 120                 125

Glu Glu Val Ala Ile Pro Pro Glu Leu Met Leu Gly Thr Ser Glu Gln
       130                 135                 140

Leu Phe Asp Phe Ile Ala Lys Glu Leu Val Ser Phe Val Ala Arg Glu
145                 150                 155                 160

Gly Glu Asp Phe Arg Leu His Glu Gly Gln Ser Arg Glu Ile Gly Phe
                165                 170                 175

Thr Phe Ser Phe Pro Cys Lys Gln Thr Ala Val Asn Ser Gly Thr Leu
            180                 185                 190

Leu Gln Trp Thr Lys Gly Phe Lys Val Asn Asp Ala Ile Gly Gln Asp
        195                 200                 205

Val Val Ala Ala Leu Gln Gly Ser Ile Glu Arg Arg Gly Tyr Lys Met
    210                 215                 220

Arg Ile Ala Ala Leu Val Asn Asp Thr Val Gly Thr Leu Ala Gly Gly
225                 230                 235                 240

Arg Tyr Trp Asn Asn Asp Val Met Ile Ala Val Ile Leu Gly Thr Gly
                245                 250                 255

Thr Asn Ala Cys Tyr Val Glu Arg Ala Glu Ser Ile Ser Lys Trp Gly
            260                 265                 270

Gly Glu Leu Pro Lys Ser Gly Gln Met Val Ile Asn Met Glu Trp Gly
        275                 280                 285

Asn Phe Trp Ser Ser His Leu Pro Arg Thr Tyr Val Asp Glu Leu Leu
    290                 295                 300

Asp Asn Glu Ser Leu Asn Pro Gly Glu Tyr Gly Phe Glu Lys Met Ile
305                 310                 315                 320

Ser Gly Met Tyr Leu Gly Asp Cys Val Arg Arg Val Leu Val Arg Met
                325                 330                 335

Ala Gln Gln Ala Gly Ile Phe Gly Pro His Val Pro His Lys Leu Leu
            340                 345                 350

Glu Ala Phe Thr Leu Gln Thr Pro Asp Met Ser Lys Met His His Asp
        355                 360                 365

Asp Ser Ser Asp Leu Lys Met Val Ala Glu Val Leu Lys Thr Val Tyr
370                 375                 380

Gly Ile His Asn Thr Thr Leu Gly Ile Arg Lys Ile Val Leu Ala Val
                390                 395                 400
385

Cys Asp Ile Val Cys Gln Arg Gly Ala Arg Leu Ala Ala Ala Gly Ile
            405                 410                 415

Val Gly Ile Leu Lys Lys Ile Gly Arg Asp Gly Ser Thr Ala Asn Gly
        420                 425                 430

Phe Ile Arg Arg Asn Asp Val Asn Gly Ile His Asp Glu Leu Thr Val
    435                 440                 445
```

-continued

```
Asn Ser Ile Gly Gly Ser Gly Lys Thr Val Val Ala Met Asp Gly Gly
    450                 455                 460
Leu Tyr Glu His Tyr Ser Lys Phe Arg Asn Tyr Met Gln Gln Ala Val
465                 470                 475                 480
Arg Glu Leu Leu Gly Asp Ala Ala Lys Asn Val Phe Ile Glu Leu Ser
                485                 490                 495
Lys Asp Gly Ser Gly Ile Gly Ala Ala Ile Leu Ala Ala Ser His Ala
            500                 505                 510
Glu Tyr Val Pro Thr
        515

<210> SEQ ID NO 89
<211> LENGTH: 1929
<212> TYPE: DNA
<213> ORGANISM: Physcomitrella patens

<400> SEQUENCE: 89
```

| | | | | | |
|---|---|---|---|---|---|
| gctcttgata | atggctggtg | gactatgacg | atattctgat | gttacgattg | cggtcctaga | 60 |
| gtagtaaatc | aagaagggag | gattcaatta | tggaaaggaa | catggaggtc | ctctagcgag | 120 |
| caacaagctt | gtgcaggata | gcttgtcgag | aacatcccct | gatggcagat | aataaggcgt | 180 |
| ggattaacgc | cctcacagca | ggtacggcag | tggttgctgt | tgccactgtt | gtttgtgtgt | 240 |
| ggcagaggat | gcaggggagc | acacaaacaa | cgagaactac | tcgccaccaa | gcgctcgggc | 300 |
| ttttacatga | atttcagcat | gctgcagcga | ccccttgta | cgttttgcga | cagatctcgg | 360 |
| agcacatggc | ggtagagatg | cgtgccggcc | taatgacaga | gggcaagagc | agcctgctca | 420 |
| tgctgccaac | tttcgtggaa | atcttccgg | acggaaatga | gacaggtctg | ttctacgcct | 480 |
| tggatttagg | cggaaccaac | tttcgggttc | tgcgctgtct | ccttggggga | agagaaggca | 540 |
| gagtactgaa | acaggagtac | gaggaggtcc | ctattcccaa | aatactcatg | tttggcacaa | 600 |
| gtgaggaact | tttcgacttc | atagccaaga | agctggtcga | cttcgtcaac | cgagaggggg | 660 |
| atgagtacaa | gccgcgcggt | ggccgacaac | aaacagtccg | cgaactcggg | ctgacgtttt | 720 |
| ctttcccctgt | gaagcaaaca | tcagtaagat | ctggtgttct | catccagtgg | agcaaaggct | 780 |
| tcttagttgc | tgacggggtt | ggagcagatg | tggtggcgct | gttgcagcgt | gcgatcaatc | 840 |
| gccagcatgg | accaaagatt | gaggtggttg | tgctggtgaa | cgacacggtg | ggcactttgg | 900 |
| caggagggcg | ctattggaac | gaagatgcga | tggtttggat | gattctgggg | acaggtacca | 960 |
| acgcttgcta | tgtggagcgt | gatctgcctg | cccatgccaa | ttccagcacg | ggtgaaatgg | 1020 |
| ttatcaacat | ggagtgggct | gggttctggt | cgtcacatct | gccacgcact | tatgccgatg | 1080 |
| agcagcttga | cagtgagagc | gtcaaccctg | gtcaagcggg | attcgagaaa | atgattggag | 1140 |
| gcatgtactt | gggagaaatc | gtccgtcgtg | tattgttcaa | aatggcgggg | gaggctgcgt | 1200 |
| tgttcgggga | tgaaataccg | cacaaattga | agagccgtt | tgtcttaatg | acttcggaga | 1260 |
| tgtcgaaaat | gcatgctgat | gaatccagcg | acttacgggt | ggtgggcaca | attttgagag | 1320 |
| atgtgtttgg | gattcaaaaa | accgagttgc | ctacgcgtag | gattgtgcac | gacgtgtgcg | 1380 |
| acactgtaac | cttgcgcagt | gcaaggctgg | cggcagctgg | aattgtgggc | atcttcaaga | 1440 |
| aaattggcgg | ggactcgtgg | gactcccccac | atctgagcgg | gacctccaaa | gcagtccacc | 1500 |
| accactcccg | agtgactagc | acaggagtag | gagccggaaa | gaccatggtg | gccatggacg | 1560 |
| gaggactctt | cgagcattac | atccagtacc | ggatctacat | gcaagccgct | gttagtgagc | 1620 |
| tactgagtga | agccgcagcg | agtcgcctgg | tgatccagtt | ggctaaagat | ggatctggta | 1680 |

-continued

```
ttggagcgag cattcttgca gcctgtcact ccaagtacag gtaacaggta ctcgatcagt    1740
catatgctga gctgatgatg cttttccgga gctgagtgct cagccaattg aatctctatg    1800
ctttgcaaca caccccaca tcgcagacag tcaaatttct ttttggtcgt ggtgctgaat     1860
atcataagta gttggcaaaa cgaatgtgcg tttctcattc accaagagag tgcgttatcc    1920
atccttgaa                                                            1929
```

<210> SEQ ID NO 90
<211> LENGTH: 520
<212> TYPE: PRT
<213> ORGANISM: Physcomitrella patens

<400> SEQUENCE: 90

```
Met Ala Asp Asn Lys Ala Trp Ile Asn Ala Leu Thr Ala Gly Thr Ala
1               5                   10                  15

Val Val Ala Val Ala Thr Val Val Cys Val Trp Gln Arg Met Gln Gly
            20                  25                  30

Ser Thr Gln Thr Thr Arg Thr Arg His Gln Ala Leu Gly Leu Leu
        35                  40                  45

His Glu Phe Gln His Ala Ala Thr Pro Leu Tyr Val Leu Arg Gln
    50                  55                  60

Ile Ser Glu His Met Ala Val Glu Met Arg Ala Gly Leu Met Thr Glu
65                  70                  75                  80

Gly Lys Ser Ser Leu Leu Met Leu Pro Thr Phe Val Glu Asn Leu Pro
                85                  90                  95

Asp Gly Asn Glu Thr Gly Leu Phe Tyr Ala Leu Asp Leu Gly Gly Thr
            100                 105                 110

Asn Phe Arg Val Leu Arg Cys Leu Leu Gly Gly Arg Glu Gly Arg Val
        115                 120                 125

Leu Lys Gln Glu Tyr Glu Glu Val Pro Ile Pro Lys Ile Leu Met Phe
    130                 135                 140

Gly Thr Ser Glu Glu Leu Phe Asp Phe Ile Ala Lys Lys Leu Val Asp
145                 150                 155                 160

Phe Val Asn Arg Glu Gly Asp Glu Tyr Lys Pro Arg Gly Gly Arg Gln
                165                 170                 175

Gln Thr Val Arg Glu Leu Gly Leu Thr Phe Ser Phe Pro Val Lys Gln
            180                 185                 190

Thr Ser Val Arg Ser Gly Val Leu Ile Gln Trp Ser Lys Gly Phe Leu
        195                 200                 205

Val Ala Asp Gly Val Gly Ala Asp Val Val Ala Leu Leu Gln Arg Ala
    210                 215                 220

Ile Asn Arg Gln His Gly Pro Lys Ile Glu Val Val Val Leu Val Asn
225                 230                 235                 240

Asp Thr Val Gly Thr Leu Ala Gly Gly Arg Tyr Trp Asn Glu Asp Ala
                245                 250                 255

Met Val Gly Met Ile Leu Gly Thr Gly Thr Asn Ala Cys Tyr Val Glu
            260                 265                 270

Arg Asp Leu Pro Ala His Ala Asn Ser Ser Thr Gly Glu Met Val Ile
        275                 280                 285

Asn Met Glu Trp Ala Gly Phe Trp Ser Ser His Leu Pro Arg Thr Tyr
    290                 295                 300

Ala Asp Glu Gln Leu Asp Ser Glu Ser Val Asn Pro Gly Gln Ala Gly
305                 310                 315                 320

Phe Glu Lys Met Ile Gly Gly Met Tyr Leu Gly Glu Ile Val Arg Arg
```

```
                    325                 330                 335
Val Leu Phe Lys Met Ala Gly Glu Ala Ala Leu Phe Gly Asp Glu Ile
            340                 345                 350

Pro His Lys Leu Lys Glu Pro Phe Val Leu Met Thr Ser Glu Met Ser
            355                 360                 365

Lys Met His Ala Asp Glu Ser Ser Asp Leu Arg Val Val Gly Thr Ile
        370                 375                 380

Leu Arg Asp Val Phe Gly Ile Gln Lys Thr Glu Leu Pro Thr Arg Arg
385                 390                 395                 400

Ile Val His Asp Val Cys Asp Thr Val Thr Leu Arg Ser Ala Arg Leu
                405                 410                 415

Ala Ala Ala Gly Ile Val Gly Ile Phe Lys Lys Ile Gly Gly Asp Ser
            420                 425                 430

Trp Asp Ser Pro His Leu Ser Gly Thr Ser Lys Ala Val His His His
            435                 440                 445

Ser Arg Val Thr Ser Thr Gly Val Gly Ala Gly Lys Thr Met Val Ala
        450                 455                 460

Met Asp Gly Gly Leu Phe Glu His Tyr Ile Gln Tyr Arg Ile Tyr Met
465                 470                 475                 480

Gln Ala Ala Val Ser Glu Leu Leu Ser Glu Ala Ala Ser Arg Leu
                485                 490                 495

Val Ile Gln Leu Ala Lys Asp Gly Ser Gly Ile Gly Ala Ser Ile Leu
            500                 505                 510

Ala Ala Cys His Ser Lys Tyr Arg
            515                 520

<210> SEQ ID NO 91
<211> LENGTH: 1557
<212> TYPE: DNA
<213> ORGANISM: Physcomitrella patens

<400> SEQUENCE: 91
atgccggaat tggagaatag gatatggatg aacatgctca tagcaggtgc tgcggtggct      60
gccattacta ccgtggtgat tgcctggaat agtacacaga aggcccctct cgtgaaaact     120
cgcaaccggg cactagagct tttatacgag tttcagcatg cggctgcaac tcctttacac     180
gctttgcggc agattgcgga gcacatggcc attgagatgc gtgcaggact gaggagggc      240
ggcaagagca accttctcat gcttcctact tacgtggaga atcttccgga cggagacgag     300
gaaggactgt tctatgcttt ggatttgggg ggtaccaact tcgggtcct gcgctgtctg      360
cttggaggga agatggcag gtattgaaa caggaatttg aggaggtctc cataccaaaa       420
gcgctgatgt tgggcacaag tgcggagctc ttcgacttca tagcgagag actggtcgat      480
tttgtgagcc gagaaggaga agggtttaag acgagaaacg gcatgcaaca aacagttcgc     540
gaaatgggtt taacgttctc atttcctgtc aaacaacaat ctgtgaaatc ggggccata      600
attcagtgga gcaagggctt cgacattgct gatgggttg agcagatgt cgtggcgctg       660
ttgcaaagtg caataaaccg ccagcgtgga ccgaagattg aggtggctgt cttggtcaat     720
gacacggtgg gtactctggc tggtgggcgc tactggaacg aagatgtgat ggtgggaatg     780
attttgggga caggcaccaa cgcttgctac gtagagcatg atttgcccag ccacgtccaa     840
tctggatcgg gcgagatgat aatcaacatg gagtggggtg ggttctggtc gtcacatttg     900
ccacggactt cgccgatga gcagcttgac aaggagagcc tcaaccccgg tcaggcgggt     960
tacgaaaaaa tgatcggcgg tatgtacctg ggagaaatag ttcgtcgagt gttgttgagg   1020
```

```
atggaaaagg aggcttcact atttggtggt ccagtacctt ctaaattaaa agagcccttc    1080
agtttgataa ctccagagat tgccaagatg catgccgatg agtcaaagaa cttgcgggtg    1140
gtggccaaag ttttgaggga cgtgtttggg gttcaaaaaa ccgatttggc agcaaggagg    1200
atcgtgcacg atgtttgtga cattgtaatc atgcgcagtg caaggttggc ggcagcggga    1260
atcgtgggca ttttcaaaaa aattgggggc gaggcttteg actcgacgga ttcaaggaca    1320
ctcacaaatc tgcactggga ctcccaagag cctcaacaac ttgacacaaa cgaattgtg     1380 gtggccgtgg acggagggct gtatgagcac tgcacccaat accgggtcta tatgcgggct    1440
gctgtgaatg agcttctgag cgaagcaggg gcaaagcgat tgcaaatcgt gttgtccaag    1500
gatgggtcgg gcattggagc aagcatcctt gcagcacgtc actcccagca taggtaa      1557
```

<210> SEQ ID NO 92
<211> LENGTH: 518
<212> TYPE: PRT
<213> ORGANISM: Physcomitrella patens

<400> SEQUENCE: 92

```
Met Pro Glu Leu Glu Asn Arg Ile Trp Met Asn Met Leu Ile Ala Gly
1               5                   10                  15

Ala Ala Val Ala Ala Ile Thr Thr Val Val Ile Ala Trp Asn Ser Thr
            20                  25                  30

Gln Lys Ala Pro Leu Val Lys Thr Arg Asn Arg Ala Leu Glu Leu Leu
        35                  40                  45

Tyr Glu Phe Gln His Ala Ala Ala Thr Pro Leu His Ala Leu Arg Gln
    50                  55                  60

Ile Ala Glu His Met Ala Ile Glu Met Arg Ala Gly Leu Arg Arg Gly
65                  70                  75                  80

Gly Lys Ser Asn Leu Leu Met Leu Pro Thr Tyr Val Glu Asn Leu Pro
                85                  90                  95

Asp Gly Asp Glu Glu Gly Leu Phe Tyr Ala Leu Asp Leu Gly Gly Thr
            100                 105                 110

Asn Phe Arg Val Leu Arg Cys Leu Leu Gly Gly Lys Asp Gly Arg Val
        115                 120                 125

Leu Lys Gln Glu Phe Glu Val Ser Ile Pro Lys Ala Leu Met Leu
    130                 135                 140

Gly Thr Ser Ala Glu Leu Phe Asp Phe Ile Ala Glu Arg Leu Val Asp
145                 150                 155                 160

Phe Val Ser Arg Glu Gly Glu Gly Phe Lys Thr Arg Asn Gly Met Gln
                165                 170                 175

Gln Thr Val Arg Glu Met Gly Leu Thr Phe Ser Phe Pro Val Lys Gln
            180                 185                 190

Gln Ser Val Lys Ser Gly Ala Ile Ile Gln Trp Ser Lys Gly Phe Asp
        195                 200                 205

Ile Ala Asp Gly Val Gly Ala Asp Val Val Ala Leu Leu Gln Ser Ala
    210                 215                 220

Ile Asn Arg Gln Arg Gly Pro Lys Ile Glu Val Ala Val Leu Val Asn
225                 230                 235                 240

Asp Thr Val Gly Thr Leu Ala Gly Gly Arg Tyr Trp Asn Glu Asp Val
                245                 250                 255

Met Val Gly Met Ile Leu Gly Thr Gly Thr Asn Ala Cys Tyr Val Glu
            260                 265                 270

His Asp Leu Pro Ser His Val Gln Ser Gly Ser Gly Glu Met Ile Ile
```

```
            275                 280                 285
Asn Met Glu Trp Gly Gly Phe Trp Ser Ser His Leu Pro Arg Thr Phe
    290                 295                 300

Ala Asp Glu Gln Leu Asp Lys Glu Ser Leu Asn Pro Gly Gln Ala Gly
305                 310                 315                 320

Tyr Glu Lys Met Ile Gly Gly Met Tyr Leu Gly Ile Val Arg Arg
                325                 330                 335

Val Leu Leu Arg Met Glu Lys Glu Ala Ser Leu Phe Gly Gly Pro Val
                340                 345                 350

Pro Ser Lys Leu Lys Glu Pro Phe Ser Leu Ile Thr Pro Glu Ile Ala
                355                 360                 365

Lys Met His Ala Asp Glu Ser Lys Asn Leu Arg Val Val Ala Lys Val
    370                 375                 380

Leu Arg Asp Val Phe Gly Val Gln Lys Thr Asp Leu Ala Ala Arg Arg
385                 390                 395                 400

Ile Val His Asp Val Cys Asp Ile Val Ile Met Arg Ser Ala Arg Leu
                405                 410                 415

Ala Ala Ala Gly Ile Val Gly Ile Phe Lys Lys Ile Gly Gly Glu Ala
                420                 425                 430

Phe Asp Ser Thr Asp Ser Arg Thr Leu Thr Asn Leu His Trp Asp Ser
        435                 440                 445

Gln Glu Pro Gln Gln Leu Asp Thr Lys Arg Ile Val Val Ala Val Asp
    450                 455                 460

Gly Gly Leu Tyr Glu His Cys Thr Gln Tyr Arg Val Tyr Met Arg Ala
465                 470                 475                 480

Ala Val Asn Glu Leu Leu Ser Glu Ala Gly Ala Lys Arg Leu Gln Ile
                485                 490                 495

Val Leu Ser Lys Asp Gly Ser Gly Ile Gly Ala Ser Ile Leu Ala Ala
                500                 505                 510

Arg His Ser Gln His Arg
        515

<210> SEQ ID NO 93
<211> LENGTH: 1906
<212> TYPE: DNA
<213> ORGANISM: Physcomitrella patens

<400> SEQUENCE: 93
aagttgtaaa gtaatctctc cgtgctcggt tggtttctag aggttaagta tgatatgaga      60
gtctcgttga gcattcgatt gtagcatgca caatcgaact ctaaacaggg atctgccaat     120
tagtccaaat cgacgaagaa ataaggttcc tcccttcga tgattctgat gccttgtagg      180
agcagatgac acagatgctg ttaagcacgg ctgtggcatg tgcaacggtg gcagccgtgg     240
cggcagccgt catggtctgg cagaaattcc acaagcatag tcattgcgat caggcgctcg     300
tcttactgta cgaatttcga catgcctgcg ctaccccttt gtatgtcttg cgccacatct     360
cggagcatgt ggctcttgaa atgcaggccg gtctcaatca gcctggaggc agtcagctca     420
tgatgctccc cactttcatt gaaaaactgc caaatgggtg tgagaagggg cttttctatg     480
cattggattt gagtgggacc aattttcgcg tgttgcgatg ccttttaggt gggcctaatg     540
cgcgagtgat aaaacaagag tatgaagtgg tcgccattcc gcgtgcactc ttgctgggaa     600
caagcgagga gctcttcgac ttcatcgcac agagattgat ctcgtttatt aagctggagg     660
gaccggagtt tcagcgggga cataactgga atggacatca aattcgtgaa ttagggttga     720
```

```
caatctcttt tcccatctgc cagacctcac acaacacggg cattctcatc aagtggactg      780
aaggattcaa gattgccgac ggggttggca agatgtagt ggcaatgctc caaagtgcaa      840
tggaccggca gaaaggattt cagattaggg tggctgtgtt gattaatgac acagttggaa     900
caatggcggg tgggcactat tggaatgatg atgtgatggt aggcgtgatt ctagggacta    960
acaccaatgc ctgctacgtt gagtgcaact tgcccgagga catccagacg aagagcggca    1020
agatggtgat ctatatggaa tggggtaggt tttggtcatc acacctccca cgcacttaca    1080
ttgacgagca gcttgacaat gagagtgtga atccaggcga taggggattt gagaagatga    1140 cagggggccat gtacttaggt gagatagttc gtcgcgttct ggcgaggatg cacaggaag     1200 caaatttatt cggagactcc gtaccaacaa aattaaaaca accttttcatt tgttaacac    1260 tggagatgtc caaatgcac gcagatgagt caccagattt acgaattgtg acaaagttt      1320 tgaaagatgt cttttgatatc aaacggaccg agttgtcaga gcggaggatt gtgcacagcg   1380
tctgcgacac agtgaccatg cgggctgctc ggctagcagc agcattcatt gtgggtatct    1440
tgaagaaaat cgggcgggat ggttgggatg cgacaggtgt tagtagcaga ctaatggcat    1500
taccacgaga ctcggagcat agagccaggc tcgaattgaa gagaccgtc gttgctatgg     1560 atggaattct atacgagcat tatcaccgct ttagaatcta catgcaagca gccgtctatg    1620
agttgttaag tgaagccgct gccaggaaac ttgtgattga gctttcgaaa gatggggcag    1680
gtactggagc cagtattctt gctgcttgtc attcagagtt tgctccctct tattcatgag    1740
ttatgactgc cgcatcgaaa ttaattgtgt cttcttttg tgtaaatatc catcaacgat     1800
tggtacaacc cctttggcaa tcaagtgttg attccccagg tagtatttg ttcacaacct     1860 cttttttgaac tttagaatgt gagctatcat cggtccagta caacat                  1906
```

<210> SEQ ID NO 94
<211> LENGTH: 517
<212> TYPE: PRT
<213> ORGANISM: Physcomitrella patens

<400> SEQUENCE: 94

```
Met Thr Gln Met Leu Leu Ser Thr Ala Val Ala Cys Ala Thr Val Ala
1               5                   10                  15

Ala Val Ala Ala Ala Val Met Val Trp Gln Lys Phe His Lys His Ser
            20                  25                  30

His Cys Asp Gln Ala Leu Val Leu Leu Tyr Glu Phe Arg His Ala Cys
        35                  40                  45

Ala Thr Pro Leu Tyr Val Leu Arg His Ile Ser Glu His Val Ala Leu
    50                  55                  60

Glu Met Gln Ala Gly Leu Asn Gln Pro Gly Gly Ser Gln Leu Met Met
65                  70                  75                  80

Leu Pro Thr Phe Ile Glu Lys Leu Pro Asn Gly Cys Glu Lys Gly Leu
                85                  90                  95

Phe Tyr Ala Leu Asp Leu Ser Gly Thr Asn Phe Arg Val Leu Arg Cys
            100                 105                 110

Leu Leu Gly Gly Pro Asn Ala Arg Val Ile Lys Gln Glu Tyr Glu Val
        115                 120                 125

Val Ala Ile Pro Arg Ala Leu Leu Gly Thr Ser Glu Glu Leu Phe
    130                 135                 140

Asp Phe Ile Ala Gln Arg Leu Ile Ser Phe Ile Lys Leu Glu Gly Pro
145                 150                 155                 160

Glu Phe Gln Arg Gly His Asn Trp Asn Gly His Gln Ile Arg Glu Leu
```

```
                    165                 170                 175
Gly Leu Thr Ile Ser Phe Pro Ile Cys Gln Thr Ser His Asn Thr Gly
                180                 185                 190

Ile Leu Ile Lys Trp Thr Glu Gly Phe Lys Ile Ala Asp Gly Val Gly
            195                 200                 205

Lys Asp Val Val Ala Met Leu Gln Ser Ala Met Asp Arg Gln Lys Gly
210                 215                 220

Phe Gln Ile Arg Val Ala Val Leu Ile Asn Asp Thr Val Gly Thr Met
225                 230                 235                 240

Ala Gly Gly His Tyr Trp Asn Asp Val Met Val Gly Val Ile Leu
                245                 250                 255

Gly Thr Asn Thr Asn Ala Cys Tyr Val Glu Cys Asn Leu Pro Glu Asp
                260                 265                 270

Ile Gln Thr Lys Ser Gly Lys Met Val Ile Tyr Met Glu Trp Gly Arg
            275                 280                 285

Phe Trp Ser Ser His Leu Pro Arg Thr Tyr Ile Asp Glu Gln Leu Asp
        290                 295                 300

Asn Glu Ser Val Asn Pro Gly Asp Arg Gly Phe Glu Lys Met Thr Gly
305                 310                 315                 320

Ala Met Tyr Leu Gly Glu Ile Val Arg Arg Val Leu Ala Arg Met Ala
                325                 330                 335

Gln Glu Ala Asn Leu Phe Gly Asp Ser Val Pro Thr Lys Leu Lys Gln
                340                 345                 350

Pro Phe Ile Leu Leu Thr Leu Glu Met Ser Lys Met His Ala Asp Glu
            355                 360                 365

Ser Pro Asp Leu Arg Ile Val Asp Lys Val Leu Lys Asp Val Phe Asp
370                 375                 380

Ile Lys Arg Thr Glu Leu Ser Glu Arg Ile Val His Ser Val Cys
385                 390                 395                 400

Asp Thr Val Thr Met Arg Ala Ala Arg Leu Ala Ala Ala Phe Ile Val
                405                 410                 415

Gly Ile Leu Lys Lys Ile Gly Arg Asp Gly Trp Asp Ala Thr Gly Val
                420                 425                 430

Ser Ser Arg Leu Met Ala Leu Pro Arg Asp Ser Glu His Arg Ala Arg
            435                 440                 445

Leu Glu Leu Lys Arg Thr Val Val Ala Met Asp Gly Ile Leu Tyr Glu
        450                 455                 460

His Tyr His Arg Phe Arg Ile Tyr Met Gln Ala Ala Val Tyr Glu Leu
465                 470                 475                 480

Leu Ser Glu Ala Ala Ala Arg Lys Leu Val Ile Glu Leu Ser Lys Asp
                485                 490                 495

Gly Ser Gly Thr Gly Ala Ser Ile Leu Ala Ala Cys His Ser Glu Phe
                500                 505                 510

Ala Pro Ser Tyr Ser
            515

<210> SEQ ID NO 95
<211> LENGTH: 2642
<212> TYPE: DNA
<213> ORGANISM: Arabidopsis thaliana

<400> SEQUENCE: 95
atattattca cgcttctcgt aattaatcat ttggtgaatt atataattcg aagtatcttt      60
tgacagctct agttcgagat attatacaat aaaatcaact agctactcta tttattttat     120
```

```
tgtgttcgat aatgagacat ttcatgtcgg ttttgtttaa ttttataaga agagacatta    180
ttgagcgagt tttcttttg ggttcctgca tgaacaatgg caaattgtgg gaactttaca    240
tatcgcttct ctcagactct gagcacttct ataaagctac actttctgac caagacacta    300
gtctgactct ttggttcggc catttccaac cagcaccagt tgctggacca cttgcttctc    360
catcttaatg aagccacaaa tgaacacatt ctcctcaaag cttcctctca aattttgca    420 aaatatttga aaaccatttt cttgttttcc tattaaaatt tgtaatatat agtaaacttt    480
taacagtaat aaagaaaaaa gattagtaag ttctcttttt taattcatat acgtgtagtc    540
ttttttccac gatattttta ggattgggtc ccaataaaca aatggataaa cggtaagagt    600
ctaacgagag gccgtctcta gataacgtaa gaaagctaca aaaattcaac atgtgaatat    660
ttgagggaaa gtttgagtgg atggacaaag aatatacct ctctattatg aatcatttta    720
aggcaaaaaa agggagaaag atgacaaaga gaagtgagtc aatttaattt aaaacgtata    780
aagcaaacaa aagagacact tgattattct cattcatctg caaaagtaac catattttt    840 aagcaaaatt tctaaatttc gttatgtagc catttaattc catttaatca tttttggaaa    900
cattaaccaa tgatgacaat ttcttgctgg ttatgaacct ttcccattat ttcctttatt    960
tgatgcgttc atcttcacaa atatttagtc ctcatttagc atttgctttt aattcattgc    1020
attaatcttt catgacgaca acacacaact cttctttgtc ctcattctta tctacatata    1080
tcatctaagg tgttatttta attgttccat tctcactaca ataatttttt gcaaaaacgt    1140
ttctaatgct ctagtaaata tttggttttg atccgtgtac gatacacgta tgatgtaatc    1200
ctatatcttt atacgacggc tcgctgattt ttctgggttg aaagatttta aaattgatct    1260
tctaataaat cacaacaaat ttatacatta gacataaatt gagaattact ctttctcttg    1320
acaaaaaaaa cattcaaaaa gctttgggga atcacttttt caataaatca cacatcccaa    1380
tagcttcaaa cagttgtagt aaaatgtacg tcaggttcac ttggtgacat atataattaa    1440
gagagaaaaa aaacacatgc acatcatcat tagcaaagag atatccttgt cacagaccaa    1500
aatattttaa agagcacaca ttgctccaaa ctctcgtcga ctttgataca ttattaagaa    1560
ctcttaccaa tttatatgtg gaatccatct ttccatcaat tataatctta ataaactcta    1620
cactcttctc gcagctgatt tactaataaa aaataaaaat aaaaaaaact ttttgtttcg    1680
atgctttctc tcactcggac aaatactaac gatcatttta gaataagtca accatattga    1740
aaacgactct caactaatta cgtaaactta tattttgaag tagtcattct tacattgttg    1800
taaacacttt tccataaatg catgaagttt ataattataa aatatttaga catattccta    1860 tcaattttt atagatcacg atttacatga atctccgaaa agagaaacat caaaagaata    1920
tggaaaaatt tccgaaataa aaactctaga agaattgctg aggtcacgcc ggttttggct    1980
gtgtagagtg attcgtaaca tcttttaggc tgaacatgaa tgagcatgtc tccactactt    2040
agactcacat aattttagct ctataaaaga aataattttc ggtgattgtt tgaaattaat    2100
atatatcgat catactttg tcgtagcgtt tgaacgtatg atcataatgg gtccatttag    2160
agatgacgaa tgtatgatga ttagagtgat gtaaaaggtt taaaaaacta ctacatgaac    2220
tccatttctt aaccttaact ttcttaccat tggtgcgagc cgatccgacg tggaccaatc    2280
aaattgtttc tacaaagctg aaaaaaattt acacactttt gcaactttc tctcaatcct    2340 tttttaaaaa gaagatttag aaaaggaaaa tagtagtaaa agagagcata aaattcaaca    2400
aacccttctg aagaaagtga cttttcttag ttctattaat actctctctc tctgcagatc    2460
```

| tgttacttca ttatctcttc cttttttca ttagattcca ttaaccttca aaagttttc | 2520 |
| taatacattc tctctgctca caactttttt ttctttcaat acttgtaaag aaaaaataga | 2580 |
| gctttcttct tcttctcttt tactgttagc tttgcacagc attgcagctg tgaataacta | 2640 |
| aa | 2642 |

<210> SEQ ID NO 96
<211> LENGTH: 1694
<212> TYPE: DNA
<213> ORGANISM: Arabidopsis thaliana

<400> SEQUENCE: 96

| gctcctgctc ttcctcaaga ccttccttga ttcgccgccg gtatgttctc cgtctgtggt | 60 |
| agcgcctttg gaacactcta ccaacgccgc catgaaagga tctctcatgg ccgcagggga | 120 |
| cgtgttcttc ttacatctgg tgttagggct atggttactc cagtgaggag ggagaggcaa | 180 |
| gaggttgctt aatgattcgt tttccggtg atacgagaac tctttaggtt taccgggaag | 240 |
| cttttcccat gaaatggga tgccaagtgg atggagagga gttgccggag agttgccgga | 300 |
| gaataggagg gaattggagg aggaggaaga gagtgatcgc cgggttgaaa tgttaaccgt | 360 |
| cgaggagaat ttgaccgagt tggatcgtct agtaggtaca attcgggtcc ttggcgaagt | 420 |
| atccattcaa aatagtgttt agttttggac ttgagaactt gttgtctctt tgatctcttt | 480 |
| tatataaaac tttggacgtg taggacaaac ttgtcaacat aagaaacaaa atggttgcaa | 540 |
| cagagaggat gaatttataa gttttcaaca ccgcttttct tattagacgg acaacaatct | 600 |
| atagtggagt aaatttttat ttttggtaaa atggttagtg aattcaaata tctaaatttt | 660 |
| gtgactcact aacattaaca aatatgcata agacataaaa aaagaaaga ataattctta | 720 |
| tgaaacaaga aaaaaaacct atacaatcaa tcttttaggaa ttgacgatgt agaattgtag | 780 |
| atgataaatt ttctcaaata tagatgggcc taatgaaggg tgccgcttat tggatctgac | 840 |
| ccatttgag gacattaata tttcattgg ttataagcct tttaatcaaa attgtcatta | 900 |
| aattgatgtc tccctctcgg gtcattttcc tttctccctc acaattaatg tagactttag | 960 |
| caatttgcac gctgtgcttt gtctttata ttagtaacac aaacattttg acttgtcttg | 1020 |
| tagagttttt ctcttttatt tttctatcca atatgaaaac taaagtgtt ctcgtataca | 1080 |
| tatattaaaa ttaagaaaac ctatgaaaac accaatacaa atgcgatatt gttttcagtt | 1140 |
| cgacgtttca tgtttgttag aaaatttcta atgacgtttg tataaaatag acaattaaac | 1200 |
| gccaaacact acatctgtgt tttcgaacaa tattgcgtct gcgtttcctt catctatctc | 1260 |
| tctcagtgtc acaatgtctg aactaagaga cagctgtaaa ctatcattaa gacataaact | 1320 |
| accaaagtat caagctaatg taaaaattac tctcatttcc acgtaacaaa ttgagttagc | 1380 |
| ttaagatatt agtgaaacta ggtttgaatt ttcttcttct tcttccatgc atcctccgaa | 1440 |
| aaaagggaac caatcaaaac tgtttgcata tcaaactcca acactttaca gcaaatgcaa | 1500 |
| tctataatct gtgatttatc caataaaaac ctgtgattta tgtttggctc cagcgatgaa | 1560 |
| agtctatgca tgtgatctct atccaacatg agtaattgtt cagaaaataa aaagtagctg | 1620 |
| aaatgtatct atataaagaa tcatccacaa gtactatttt cacacactac ttcaaaatca | 1680 |
| ctactcaaga aata | 1694 |

<210> SEQ ID NO 97
<211> LENGTH: 1292
<212> TYPE: DNA
<213> ORGANISM: Arabidopsis thaliana

<400> SEQUENCE: 97

```
catatggtat gatgatatgc tttgtttctc tgcttctctt actaatttga agctgttgga    60
ttgatttgtc tcttcttacg ttcccttctt ttttttttcg ttttctttg tcgtatagac    120
caggcagggg ctagggccta gtgatgggta ttggcccaat actattgggt tatttgcctg   180
gtttattatt tcgattttag gttaattcaa ttttaagaat acgtagattt gtttggttta   240
gtttggtttg gttgcactaa gttcggtttt acataaatag aatctaacac tactaattgt   300
tatacgtaaa atacaacaac aataacagat ttttcgtttc aattttcgtt taagagggta   360
gacattttgg tttggtttgg ttcattttt ttttcccttt caaattcaca tccttcacgt   420
agatgacaaa ataagaaaa acatgaatga agttgtaac ttgtaagcat caacatggaa    480
atcatatcac aaagaacaca aatctaacta atgggtcttt tcacatattg gtataattat   540
aagttgtaag aatattagtt aaacagaggc aacgagagat gcgtgatata tgaaaagttg   600
aaaacaaaag acatggatct aaagagtcaa gcaaaatgta atatctttt ttcttctaaa    660
cttgaggatg tccaagttgc agtgaatgat tcccttaat catggagaaa ttcaatgaaa   720
taattgtgtt tcttcccaca ctttatcttt atttatttc ttaccacaat tacaactatt    780
atcacaaaaa tgtaagtaac atagcttgtg actcttcttc catttatgag ttgattatca   840
ctatatttat aagtaattac caacgaatgt tccaaattaa gcaaatatt gtaatcgata    900
cactatgtat tcatctacaa tatgttaacg agctccttt atggaaatat ttcgattgaa    960
aaaacatttg atggatcgtt cactaaataa ataatccagt aacgttttct taagggagat  1020
atacatattc gtgtggagat caacatatct tcgttaattg actacgcaaa atagttaatg  1080
gaaaaggcag agtgactcgt gagcttggca gatccaaaag aggttgtcaa gaaaaagcag  1140
atttaaaagt tcttccctct tctttaagtc acccattaat ttcacatata tgtacataca  1200
tgttgcattt aactcatata catacatatt ctcacatcta taaagagagc ataagactca  1260
gagagatcta gaggaagaga gagagagaaa ga                                1292
```

<210> SEQ ID NO 98
<211> LENGTH: 2174
<212> TYPE: DNA
<213> ORGANISM: Vitis vinifera

<400> SEQUENCE: 98

```
gtgattaaat ttttattcat attcttgaat atcccaaatt aatcaagata actcatattt    60
gtttaaaaaa aaattaaatt ttaggtttaa aaactaaaat tacctatta ccectctaac    120
taaaattgtt tctttgactc ttttaagaga gtagtcaatt tgaaggcacc tccccattca   180
ttggtcaaaa ctaatgactt aaatgctttt cacattgctt aaatcaacaa ttttaatttt   240
aagataatcg tcatactcaa gagcacgaaa caaaaaaag agtataatgg tgaaactctc   300
tctctcctca caattatagt aacacactct aaaaaaacaa aactctaaat cataaaaata   360
ttaaatatat aataagagta aaatcgtcgt tgctcaaata aataaacaaa caaaaaattc   420
aaaaaacgct actccttcaa cctttgtgag ctgtttggac aacctattcc tcacaagttc   480
aacgaaaaac tccacccocta atatttctta caaagcacaca ctaaattaat ttaaacttca   540
taaatattca atgttaattt ataacatctg caagaagaat atgcttttat atcatctctc   600
tctctctaaa agataacatt cataggaaag taaaaatagt cacataactt ataagaacca   660
cattccatta acttggatct tactttaaaa ctattatttc attttccta attttggtaa    720
```

```
aattcctcat aaacaagact aatccatccc atcattaaaa ttttcagtgc tttctttgct    780
ttctaacgcc aacacccttt ctttatttttt aattttttttt ttcttttata gcaaatttaa   840
ggaaaagtga aaatttcatt gttcttacac ggaattgctt ttcttcaaaa ctaagacaac    900
aaaaattgaa gttaaaaaaa aaaaataaaa atcatgagtg ataatggaat ccaaagatat    960
aaataataag aaatatgaga aaatgtttat tttaaaaaag gattttttttt tttaaatgat   1020
acctctataa atgtgtgaag aagtttggta agacacctct ataaatacaa catagctcta   1080
aaattttaat attaagatgt tttaaaatta aaattctcaa tatctattgc taggattaat   1140
tttaagtttc ttacaatgaa atcatagaat aatttaagga aaaaaagcta aagttttgag   1200
taagagacaa attaatttttt tcatagcgtt aattaagtac ttaagtctta ttttcatata   1260
tttcttatga acacaaaaaa aagttttaaa aaaaaaatt tatctagtaa ttaataatat    1320
ttttatacat gtatttctat tttaatttct aacaaatttg aacttattca gacttcaaat   1380
aaaaaaacaa tctccacctt ctaactcacg tggtccaata tttatcataa gatagtagtc   1440
tcatgcttag atgtttcatc tgaatacaaa aaagtcaaaa attttaactt gattttttatt   1500
taaatttcaa acaaaccctta acccattcat acttcgaata ttaaacaata aataaaagaa   1560
aaattttcat atttgatgaa accaaatttg atgcatgaga tttcaatgtg tgacctgatc   1620
ccaagatagt aaaaaattga attcagatct caatcttctt ccaaattaac taaattaaaa   1680
tatatatata aaagagaata taaaatgttg tgtccatgaa atgatgaata gcatggctta   1740
aatgcatggt gtcaacccac ctaaacccat tactgaaata agaggcttag aagaagtgaa   1800
ataaatacga tgactatgaa gtttcctatt agctttgttg gtgaagtgct gtggcatgtg   1860
agtgtacaac agaaaagaga ctcacagaag gaattcaact ccatacttct gactttggtt   1920
ctctctgtgg atatcaacca agctatattt ataataaagt tgagaaaaag gcaaggtaga   1980
tcaatggaaa tgggtgaaaa aaagagaggt tttatgagtc actcttagta tataaacacc   2040
ctcacatggt gatatgctac tatttgaaag gcacgaagag atagatagat agagagagag   2100
agagagagag acagagagag agagagagag agagagagag agagagagag agagtttggg   2160
atgaaaacaa gcca                                                     2174
```

<210> SEQ ID NO 99
<211> LENGTH: 3001
<212> TYPE: DNA
<213> ORGANISM: Arabidopsis thaliana

<400> SEQUENCE: 99

```
aaccaaaaaa tcgggttagg gcgggttaaa attttaggaa atttccttat tgggtagagt     60
tttactaaac ccgtggatat ccgattggac cggaaattat ccgttatcta aaaagagtat    120
tcaaaaaccc aaacattaat ttaatatcca aaatattaat tatatgatat tattttattt    180
gattttaaat atatagtaaa ctgcgagttg tatatgtttt cttgatatta tttatattgt    240
ttagtgttta aaattataca cttgtatttt gattgttaat tttagagttt cacctgtagt    300
ataccatctt atattaatat cgatttaaac ccgtcaattc taggattttc cagcttgtat    360
taaaaattga atcacatcat acacataaaa aaatctaata tgttattaat tattgttgta    420
tataagatta taaattctta aaataatatg catgaaattg aatataaata tttaaattat    480
gacccagtac ttagtaataa attttcttaa atctattttt gacccgttat aatatttttt    540
catgtattga acagtttata ttcgttttta aaagtttaaa ttatggcata tgcgaaaaaa    600
ctctaattat ttttttataa cgatgatatt attttttcgc aaaaatagaa tcatataaag    660
```

```
atgagaggtg aactataata attaataaaa aattaatatg ataatttaga tatcaaatct    720
tatttgttga ttttaattgg ttaatttttt gaaaattaat aatgtatttc gttttttaat    780
gaaatttaat taattaaatt agtatttgac tttttaattt ttaaagaaat gaattaattt    840
actctttaaa ttttatttct aatggcatac ctatgtaatt acttacaaaa aataaggtta    900
catttaaaat gtacttccca aataatatag aaggatgtga aactagataa aaaaacgttg    960
tattatcggt cagattttc ttttacgttt tatttatttt cctttttatt aacgttttcg    1020
tcatgtttca acttcaggca gttacaactt acaacagttt ttaacaaaat agaaataaat    1080
tagaaagcga tttccagcta cacaagtaac aaaaatttga agattatact taaaagaga    1140 gagagatatt catctcccca aatttaaaga gacatttcaa aattgaacta gcgaatgcaa    1200
taaatactag gaaatatatt cgtagctcct ttaccctatg ataattaata ttcagtcatc    1260
tactattcta ctttctttgt tattataaga agaagtagaa ttacattaaa atctgtgaac    1320
atttgagtgt taaataaagt gaagcttcgt taagtttacc taccattcct atttctttgt    1380
ttttcatgac attttactag ttgaatgcta accaaaattc tttgatcaga tctaaactaa    1440
atataatatt tgtaaccgta aaatataatg tgaagagagt actgtacata gtgaatatat    1500
tcatattcct tttcaagaaa atactagaac attcatacac atctttaaaa attactagat    1560
tctagtcact tggcataagc aaaccaagct atccagccaa ataattagtg ttgggctagt    1620
ggtgaacgtc atgcgaatag tctggatacc ctagtttgag tttaagttga gagggtttct    1680
aaacgatttt tggaaataca ttaactttgg ttcagacttt ctcgattaat taccattaaa    1740
aatcaaaagg tcaatgttgt cgaaaatgta aaagtatagg cttcaaatag tacaatggta    1800
caatcaatgc ccaacgaaac gaacgaagca tatgaaacaa atatagtggt agatacatgt    1860
gatcgtgtat gattagaatt tgctactctc gaattatttc tgtttagttt ctagagagtt    1920
tggttggttt actatttgca gatagatcat ggagaatgct acttcgacct caatctctgg    1980
gaaccatata ctcactaatc atcttcaaac gatttgtccc aaaacaacgt atattactaa    2040
ctgcgtttga tgttttgaat atgtatgata aggttaaaca tatagagcgt atagattttc    2100
aaaagcatgg tagctgttgg tgaaaatgca tggcttatta gtgtttcttt tagagaagct    2160
aacgttgtat atagcattaa tttacatatc taattttgtc aattgtaatg agactttgga    2220
tacaacaaca tccggctgcg aaataattgt gactttatat gtattttaa taaattaat    2280 ggtccaacta acacagaaaa cgtacgagta cactgtctca atatttgttt ctcattggtc    2340
cacgtccaac ttggccagcc actgaccact tcaactacaa tttaaaatga actgacaaat    2400
ctccaaccaa acactgaccc gtaataaatt ctatctatct ttagagactt cgagtccttt    2460
cccttttcta ctttcctctt ttggattcat taattaacta cacaaatcaa tttgaggaaa    2520
atcacatgat tctaacacac ttctttcagg taaagtgtca aaagtttcac agaccatatc    2580
aattcaaata ctccatgcga aattaattta ttaatgctat gaaagtgtgc aaccggtgca    2640
cccatgggaa acaatcataa cacaaataat tggtatacat attttgtaat aaacatggta    2700
acaattagaa tggttaaaat gtttaaacag tgaattgaga taagttttaa ctcgtgatca    2760
gaactatttt tatgctcttt tgtttaaaat ggtcgtattc atgtgttctt atacgtataa    2820
agtcacaaaa agacgaccat tttttaaaag tgcgttcacc tatttgtaca acttgcggta    2880
acgattttgt gttttaataa acggtaacct taaaacgcag accacatttt ccgcggcaca    2940
aacgcgctta acgccatctc tataaattaa aacccaccca atgcccaata ttttctcata    3000
``` t                                                                3001

<210> SEQ ID NO 100
<211> LENGTH: 1256
<212> TYPE: DNA
<213> ORGANISM: Arabidopsis thaliana

<400> SEQUENCE: 100
aaggtaacac atgtatatat atgtcacata gacattacta gtatatatta tgtacttcta      60
tcatatattt atgatattgc agttgcagcg tacacaagtc agctcctttt gactttaca     120 tctcatgaat gcattgccat gacatctaat cttactcgag atttgtgcat gcacattatt    180 cactttttgtc ttttgcaatt tttgttattg taaaaaaagg aaaaacaaat gtaaaagaga   240
gagagaccag aaaggtctaa ctaaacctaa agagtcaatg aaatgtgttt ctttcttgtg    300
ggattaatca attcactctt taacacttct ttataccatt gaagaaatta gatgaaagag    360
tcacgagttg cttaccaaat ccctcacaag aattgagaac tgataaacca aattgagaag    420
attaaatatc acgtctcctt tgatctcta ttataattaa tcgaaaataa aaataagagt     480
tttcaacaaa acgtgatcat tggtttacga tcacttgcaa agtcaaacct aaaacgtagc    540
attagtacac taaccttaaa tactaattat atcatgcaaa ccctaatgtc attacctaac    600
tatacatgtg taatgtgttc aacagatctt cttaacccac attagatcaa tattaaacaa    660
taaaaagatt cttatatatt ctactactta cttcttctta ttcccatcca tatttttctg    720
tgcctttagg ttctcaacta atctcattta atttagctag cacacagaga aacacacacg    780
tatataaata atatgataac acacaaaaag actcatatat ataaataatt agagtcatta    840
aatgtggatt catcattaaa tgaaacaact cttcttctct gtacaatttc tcttcacacc    900
ttcaccaaat tctttgactt caaaaatctt ataaaattta tatatctcca aaaccataaa    960
accaaaacga gttttcacaa ataaattact tagttgaaat ttcaaatctc attcaattag   1020
ggtacactct ctcaacaatc cacattaatg agggttgctg cttctgatgg ctagcagtaa   1080
cagttttatc gcctccactt cttaatgcca tcttttttcct cttccctctc cttctctata   1140 tatatttttct gactctgcaa aaccttaatt catccatctc tcaaacacca ttttttggaaa 1200 caccatttca tattccttaa acttttccat tttagtatca tttcatattc attgat       1256

<210> SEQ ID NO 101
<211> LENGTH: 1219
<212> TYPE: DNA
<213> ORGANISM: Solanum tuberosum

<400> SEQUENCE: 101
aagcttttaa acatcgataa ttcatcactt ttattttttg tactcttctt cttcttcctt      60
cctttctttt ttttttttg tgtgaaattt gatatttttt gtcttaaatg attaatctat     120
tgtgtagaaa atagattttc ttgttagtgt ataaattta taaataaat ttaaagacct      180 cttaatataa ttttcgctta ggccacgaga tttgttgagc cgccctgatt atcataaatt    240
atttgaagat tttggtctgc aattgtcagc taatctccaa ctaaataatg tccaacataa    300
tttggaccct accaaatatt taacgggcaa agattaatat aacactatag tatataaaat    360
gacattcatg agtgtgaaat tgtatatagt gttcatgtgc atatttact attttcttgc     420 aaatcatatg gttcatatac aataataaca atggaaaaga caggtgtttg gcctgtaatg    480
ggtctctatt gtccagatct tggtggaccc tacacactat gacgtctgtc aaataatctt    540
ggaaaaataa cttgttgcac gactcttcga gtctaatttt cagtgattta tttaataatg    600

```
actaagtttt atcgctttta taatgacaaa aggatttct tattattact atctctgttc    660
tatattaatt gaatcgatga gccaattata tgaaatttta tcaaatattc attttaaatt    720
ttgaacgata aaaaaagcct catgagaatt ttatcaaagt aaaatatgaa aaaaatgatt    780
atcaagtaaa aatgaacaaa gagaataata tgaaggtttt atcaaacatt catcttaaat    840
tttgaacgat aaaaaagct tcgtaaagaa tattttatca tagtaaaaca tgattatcaa    900 gtaaagtga acaagggag taatatgaag atttatcatg tatttaaaag ctcaatagtg    960
attataattt gagggactaa ataaatttaa ggagttgtta atatattccg agaaaataaa   1020
atattgttta agtagaaaag ttatggggtg tataagttaa ataataatat tttgtaaata   1080
gggatatgga aatgagtata aatagaaaga tagcaaggtt tctcgtgaga gttcacaagc   1140
caataaagct gatcacactc ccctttgtat gtccactcaa caacacaact tcttgtgatt   1200
cactttcaat tctagatct                                                 1219

<210> SEQ ID NO 102
<211> LENGTH: 3430
<212> TYPE: DNA
<213> ORGANISM: Arabidopsis thaliana

<400> SEQUENCE: 102
aaaaacaaat ctcatataaa tcatgccgac attacacaaa caaatcact tatgcagtgt    60 ctatgactcg tttatcatgt tgttcttgta ccgttgatat tgtggaaaat tatcttgttt    120
ttatttgtgt taaatcagat ctttctcctc ttagtagcat gagaaagagg atcaacccgg    180
gacgatattc catccataac gactataatt acagttaatg ttaaactgtt tttatttata    240
agacacaatt ataatacatc cattaagatt ttaagttt tcataacaaa aaaaataaaa    300
aatataataa ttagacgcat tttgataata gaaaaactct aaattttcaa taaaagtctc    360
aactgccttt acagtctaat atgatcatga gaagggttaa gaatagaata gttgactttt    420
aacttaatgg aagatttact ggaaaatgtc tctatctgtt atctagtatt ggacccgtta    480
ataatgtgca acgtataatg tagggtacta aatcccaaga aaaatctaga ttttctagat    540
aacatattta accagaaaag aaaaaaaatt gtagtggaat agaccagcat ggttcaatct    600
ggtcgttact aaaactacca atccaaaacc taccaactat aatacaatat gactacaaat    660
acggttttga agattaattc gcggctaacc atcaaaaat aatgtttgac gatggctcat    720
ggttccactc gccaaccata tacagtttat attctctttt gagacctcaa aatcaagtta    780
ctagaactcg atgatcttac atgaatataa aatgaaaatc agctccaatg tagttttgaag    840 aaggtataaa acaggtttag accaaccgat tccaagactt atgatggccc acaacaacaa    900
aaataactaa caaattttta gaccctacac tactcttagc atgcatgtga cagcttaaac    960
ttaaatttaa acagttaaca tgaacaaccc cacttgcact aggaagacag caaatagcaa   1020
acttaaagca gtttacgatt tctggtcttt taaggcaagg tttagtaacc cagtaattcc   1080
ttttgatttg aaatatatga ataaccgaaa ttaaaaaaca aaaaaaaat cacaaaatac   1140 taaaatttga aagccgaaat aattcatttt tcaatagtta taatcatctt ttaaaaagta   1200
agttagatca taaaacctaa tataaaactt ttattggcaa aactaattaa tcacgagaaa   1260
ataatattaa agttagctca tgttatgttt atattaggaa tctctcattt actttatttt   1320
gttttgtttt gtttctataa tgatattagg attcaggaag acaataaaca aaatatcaac   1380
aaggaatcat gaaagataca ttcgaacggg ctcagatcga cgcagaaaca aaaagctttg   1440
```

| | |
|---|---|
| gaatgattta ataatacaaa tttggcggaa aggtttgaag aatttatact tggcattcta | 1500 |
| tactagcgaa cgaaaacaaa agtttagtca aatatttagg attaccaaaa aatcaatatt | 1560 |
| cgtatacaaa tgtgttttat tataaaccat gattttcat aactttattc ttagttgttt | 1620 |
| caatttgttt tctctcattt ctcgttccta ttgtagaaaa aattcctgat tctttttct | 1680 |
| tttcttttgt tttcccatgt caattataac cgcattagaa aaggttagca catgttcatt | 1740 |
| tgcacagaat gtagtcaatg tacaattcat ctataattta tcacctttt gttaaaaata | 1800 |
| tttatagcca tgttatatat attttatcat gttgtgtttt aaactctaga tttgttcttt | 1860 |
| cacagtttat gggatttatc atttcatata tttcctccta tgagtaagat gtcattttta | 1920 |
| aattcttaat taagaattta gaaatcaagt ttattatttt gttaaaattt ataaattacg | 1980 |
| tattttcct ttattagtga gattaagata taaagagtct agcacactag agaaatgaaa | 2040 |
| acatacatat atctagaaag ggtttataag aaattagtaa atggaatcag aacatgaagg | 2100 |
| agaagggagg ggccaccata ccgacgggaa tgagaagtat gggacggaca agaaatcaag | 2160 |
| tgtacacaca tgaaaaaacc caccacgtga agatctccta ttggtgtgtc ttctcctaag | 2220 |
| tactaagtat aaaccaaagt caaaacacaa caaagacata ttgcttgcga gccagcgagt | 2280 |
| gtgtccgagt gagaagagag tttgggactt cactgtttag agagcctcat tcgctaccta | 2340 |
| gattcggttt atccacgtgg agagttcacg tagcttctat aataataata cattatataa | 2400 |
| gctgtttcgg taaaataatc ttagagtttc acttcccatg caaaaagatt aaatggacta | 2460 |
| ctatatttc tatatgagtg ttttggaaat aatcttccaa gtttatggct atttagtaaa | 2520 |
| actcaatcca aaatgagaac aataactttt ttttttttt ttttgcaatg agtacaataa | 2580 |
| acttatgatt ggttttgggg actagaaaat aaaatagaga catatacttt aagaatagtt | 2640 |
| gatgagaaaa taaaacttt ttcgaagaaa gaaaaaaaa tatactctgg ccccttacat | 2700 |
| attctgtcaa atgccatttt attttcttta ttttgcttgg tccatttctg gattcctgaa | 2760 |
| atgaacacac cataattttc atgcccattt ttgtcctccc attaacactt accaaacacc | 2820 |
| aaacgtacct tccttccttt atatgtgtct ctatgtctat atatcactcc caccttcaaa | 2880 |
| tgctaggaaa gtggacatca caccatagtc tgatagtcat gaatctcatc aagtagaaac | 2940 |
| ctccaaagaa acagattgcg tttcctcttc ttcttcctcc tctttcgaat cttatatttt | 3000 |
| cgtgtcaaaa aagaaacaaa atatgatgat atctaccgca aaagctcaat gtttgccact | 3060 |
| taaattctgt ctcatctctc aagattttg atcatctcac acttactccg ttccgcattt | 3120 |
| tacgcctttt cttcaccatt gttgcttctc gaatcgaaac catattggtt ttgcagcatt | 3180 |
| aatggtgcac tgagtcttct taaagccgtt aacctttccc tgccaaattc tcaaccaaaa | 3240 |
| agaaaaaaag ataacaaatg ggtcacaaca agttgccata aaggtcccaa cagaagaaga | 3300 |
| aaagagaagt ttccccgtgt tgctttgtca caagcttcat cactatttat aactaccttg | 3360 |
| ccaagaagaa agcctaaaaa ggtataacag tttctttgtc tttagagatc atcaaaaaga | 3420 |
| tgtcgatctc | 3430 |

<210> SEQ ID NO 103
<211> LENGTH: 2630
<212> TYPE: DNA
<213> ORGANISM: Arabidopsis thaliana

<400> SEQUENCE: 103

| | |
|---|---|
| ttggatccac caattattaa caaggagaag tgttatagga acatgagaaa gcaagaagga | 60 |
| agctaagatc atcttttcat atgcccaaaa ttccctagtt agtcttgttt agttcatatt | 120 |

```
ttcttgtacc taattgcttt atttcatgta agcaatatcg catgtacgta tacgatgtat      180
ttttatataa ccctagttct taaatatttg taatgcttat taaaaatcac aggttttcat      240
cttaaaacaa attggcaata agtaaaaaaa tttaatgttg aatttatcaa acttccaatg      300
tgggacaatt tccctatcta ataagtcttt gagaatttgt gagaaacggt ctaacaagaa      360
caatccaaac ttaatatatt ggaaatacca taacaagacg gatcacttat acgaaccgca      420
gaggtgagaa accccttat ttggaaaagt gtcagtggg tcaatctggc tctgatacca       480
tattagaaat tataggcttt caactcaaaa ccaattgaca atgagaggag aatattagtg      540
tagaatttac tacaagcatt atataatatt aatatatatc aaattacaac tttaaaatat      600
aaagtatcat attttgtttt attcctaata tgatctaatt taggaaataa aaactctaat      660
acatgtatag tacgtacact gatatgtgcc ctcttgggag gaaaattgcg gaaccgcatt      720
tttgcgggaa aaatattgac tcacgttttt gtggaaacta tacggaatca catattttg       780 cgagaaaaat tcattctctt attttttagct ggaaattatg aaccgtattg ttagcaaaga     840
actatagaat tatgttttga cgctaaaaag cgaactcgca ttttttgcgg aaaaatggtg     900
agatcgtgta tttgacagaa attttgattt tgagagagaa tgagagatcg atgatgaaag     960
atgtgagaaa tttgtgtttg cttctgttta ctaaaattgg tttaaacatt ttattcagtt    1020
atatttggtt tacacatttg gttattttgt caatttggtt atgggtaatc cactaatcta    1080
tttcaaccaa ttattccaac ccaaatcatt acactcatta atccattgat tcattaatta    1140
tcaaatttcc aacaactcat tagatccatg agttggattg gtttgggttg agttgaaaaa    1200
ttaacttcaa ttcattttga catacctata atatggtata tcatacgaac cacctaaaat    1260
atgtgatgca tgcacttatt aaattgcatt ttacaccatg ttttgtttta agtacgtcaa     1320
cattgaatta gcacaatgta tacgtacaaa aaagactact ttcatggtaa tttaatattc     1380
taactcaaca agatatcata gaatgcaata agaagttgtc attgcaatga ggtactatca    1440
aaattctaaa agtctcaatt gtgtaatttt ccctaagaaa tagggaaaat accatttaaa    1500
tatcaaacat ttacaaaatg ctaaacaatg ttcaaattt ctttctatac ttcttaagtt     1560
ttaaatacga aatttctttc acagtaccaa attaaaactt tgttaatatc atcggatatt    1620
tctaaaaaag gaaataattt acatgatcct caatccccga aaaaagtat ggaagataac      1680 agttctgcat atgataaagc acctccaatt ttaataacga ttaaaaaaaa gcaaagggt      1740 ggttggttta tatttattgt cttttggata gagagtctct agtttcatgt gataaagtat    1800
cgatcgccca aaatccattc atacgagata tgctgtgctg tgaggtgtga gcggtaaggc    1860
tcgtgatgaa tggcaaacga ttcatgtaac tatttttcttt tattatctta acaaagtcgt    1920
tgttactcta aatttaacac ttgatcatat ttctaatatg tatattctga ataatggcat    1980
ggcgtcaatt ctaacttatg agactttaaa cttataatgt tcactttctc ggtagcaaaa    2040
acgcttctct ttgcccctta agtagaagga caagaaatct attttttgtt tcattgctcc    2100
cgtttcctca catctgcact tgctaagcca accttggctt acttatgacc acctcgagaa    2160
gaacctattt gaaacagtc taatgccaca aaccaatctt gatgcatgga cttctagttt      2220
tgcgagaacg tttaatacat attatactgt atgactgttg accaatcaat tgaaaatgtg    2280
acttagtttg tgctgcaagt cgtgttccgt atgaggataa catgagataa cgatagtaat    2340
taacagttca caactgagta aaagaatgca acacattaaa atgatcaatt gaaaagcaaa    2400
gcagtccgaa aagtgtaaac aaacatttaa aaataaaaaa ttgttacatt caggtagagt    2460
```
aagcaatccc acgggattca tgtcacctta acctcccaaa atatcatgac gctaagacaa    2520
ggtaatgtat acgtcactct tctctaacaa aggctatata aaccctagat tggcactagg    2580
cttccatgca acacaaaaac atacacacta ctaataaacc atgaagcttc               2630

<210> SEQ ID NO 104
<211> LENGTH: 2001
<212> TYPE: DNA
<213> ORGANISM: Arabidopsis thaliana

<400> SEQUENCE: 104
tcaatcttat gagttgattt cggaattgtt ttggcttcat cttttttttt tttttatgtt      60
tgttttgttg ttgtttaaac tgtttcgatg actctttgta tatggtggga gttttctttt     120
gattatgtaa tgttttttt ataattactt ttcttctttt ggattaatga ttattcctga      180
ggtggagact ttactatata tagagagaat gagttggaag atggaacttg ggaacaaatc     240
gtcgtggaat acgaggtgta ttagactttc agttgtgcaa agggacaaaa caacatgatc     300
tgttaaaatt tctttgttta tacaccacaa attaatgcat acacacacag tatacatgtg     360
taacgttttt gatgttcccg tgaaaataga tgtgtattta gagcctagat ggatagatta     420
tgattggatg aaacatttgt aatattttga caaaagttta ccatttacgt taaatgtaat     480
agaatgaaca ttcctctaaa aaaaaactcc ctaagcaaaa aattactata aggatgaatg     540
gtatatcgct tagtcacgtt ttcaaacgct atttttttac attcaaaata tttatcaaat     600 tttttttcgat ttcacgtttt cgaaaagtaa ttcggctgta tactactagg ctactagcat    660
gtcaatatac ctagaaaaaa acatgattaa tccactagaa ctatattttc atccattaaa     720
ctaatttatt cagttcaatt cattccacta ataattattc agttattccg tcatttcact     780
ataattataa gttatagaca agttttttttt actaacatgt tatagctatc cttcaaaaat    840
ggtacttagc aataacatct tatagctatt ctgaacatcc ataatgtttt gtcatccaat     900
tttgttcttc aaaataaaca agttaaaatt aatttctcgt cttcaattct aaataattgg     960
ctccactgat gaaagcccat aacccatatg gaaaaacgtg catttcagca tttgtgtaga    1020
tagcgatatt tgttcgact acacagaaag tttttttttct ttttgactac caaagaaatt    1080
tgattcatag tatcttcgag ttaggtacca aaacatgtaa aacagtctcg tcttaaaccg    1140
tccaatacga cttcatgacc gacaaaatta aatcacacgg ccagttttga cgcgtgagac    1200
aacaacctac tattgaggat ttggctaaac actcgccaca atgcttctat tgtattgaca    1260
atatttgtgt ttatttcatt tgttattaat aaagacaaat atcataagta ataattgact    1320
actactaatc cataatttaa aatgttattt ttttgaacc aaggactaca taactaacaa     1380
cttgtgacta aagattacaa aacatgtttt agtcgttatt tttaatcatt atagtttata    1440
gtaatcgcta ttattcgttg ttattgctaa ctatgaaatg aacatggttg tacattttgt    1500
cccatcacta ccaccaaaat ttttggattt tgttgaaaaa agggagacta accatggttt    1560
acaaagaatc tatgaaatac taacgaaact atacacaatt atcgacttta ttattaagag    1620
acatcgtcta caatatatga aggtcagcgt gtaacatatt tttgttttg gggcgttttt     1680 agtattttag acaaatatag ggatttatcg taatttcgat aatcttgtgg ttttttttagt   1740 tataagtctc ctcttgtcat attcacgagc cgtataaaaa agttgtttct tcttctctg     1800 ttttttttgct ttcgtcttca agagagagag agagagagat acaaagagag aaatttggtt   1860
gtttgttgac ggaagcttct tcggtctctc ttctccgtct tacgattgtc aacgcgtggt    1920
tccatcttca attttgtttc tatttttagca gaagtttctc gagcttcaaa tactgtttca    1980

```
gatcaatcaa tcagtcaatc a                                              2001

<210> SEQ ID NO 105
<211> LENGTH: 2519
<212> TYPE: DNA
<213> ORGANISM: Arabidopsis thaliana

<400> SEQUENCE: 105
ttttggggat tcaaaggac tctcttatcg acgactttt ttttttgttt tgttctcgtc        60
tatatttgga acatgtgata tagttcaagt atgaagaaga tatgtgaaga aatttatagg    120
caaaaattat aaatgtattg gtttgaagat tcaaaaaagt aattatgttg ttacttgtaa    180
ttttggtgca tctcacgtgt gactagacct tgagtggaag tatttggttt ttttttttt    240 tcttatgata tttgttttt tagtagaaaa tttaaaaacc attagatttt gggtgctata    300
attagaaacc atctatgtct ttgaattgtt catgtttaca ataaagtata gaaagtaaaa    360
atctactcaa aaacaatttg tggttgctat aactcattct tatcagtttt atttcaagca    420
aaactaataa cataaattta gtattgagaa gaaaaaaga aacaactcgt ctcacagacg    480
gaaattgcaa actaaaataa gagtggctta tcaccgaagc aggaatcatg tgagtcaaac    540
gtgggacgcg agagatgggc gttgacaaat gctgcgtcgg cgtggatggg ttttacaagt    600
gcaaccaaat tgacacgtat ctatgacttc tcatatattc caaagtattt cgatataagt    660
tggcaatatt ttcattaaat agagctgttg attttccaa gaagtggtat ctcaattctg    720
cttggtattt acgactttcc taactttta tctagtttag attgttcgtc aagtttgaaa    780
taaaactgtt gataatagct atgactatca tatacagtat gaaaaaatta agagttagat    840
tgtggcaaag agacatctga aattgtagaa ataaaggatc taaagcagtg gactgcctcg    900
aagatgctat aaattttgta atcacacttt atttcgacca tttcatggtt aagtaattat    960
gtatgtttgt ggtttaagat taatataatg atcacacggt tttctattag atgttttgga   1020
gcgttagtta cttttgtgca tattatctta aggatctctc aaatccgatt gacgcgataa   1080
aaaggtcacc aaaagttata gactcgaaat ccatattttc tgacctacct aatggtcgaa   1140
atattagtcc aagacacata tccaatggaa aaaaacttat ttaaatttt taagagaaac   1200 tacgtcaatc atattacttt ttaaaagttt agatagtggg agaattcaca agaatactga   1260
ttacaaaaaa aaaaaaaaa aaaaaaaaaa aactgaaaat cacgaggcga tcgttatttc   1320
atttcccttt ctatgaaata gatttggact tttcatgaag gcaagccaaa agtgccaaac   1380
aagtggtcct ccaaattttg aggaacagtt agttcaaaac atagcaagtt tggtctcacc   1440 catcttttt tacattacag ctcaaagata gaacattaaa aaaaaaaaga aaaaaaaga   1500 tttatagaga agattcatga atctagctag actattgtac cttaaattgc agctcaaagt   1560
catattttgc atgttgatca gatatgtcat aagagttatg tcaaatacac ttgttgtatc   1620
tctttgtaga aaataagatt gctaatccta ataattttgt tgacaaaaaa aagaaagaaa   1680
agaatacatc ctcaatttat aaagacacta tagctttgac attgacgact cacacgccca   1740
aataaggtcg gcagagtgaa attgtctgtg aaatcatggt gttttaagtt gtactggaac   1800
ttgtgtatga acagtctat agcaataata atgaaaaaga aacaacacat tttgctccat   1860
agcttttgta tttgtgtaaa tcggaaagaa aagtggttta ttattcatgg tcgaaaaaat   1920
cagaaaaatg ggtcgattag agaaaaaagt aattttcagt ggctacagta taagtacagc   1980
gaactgttct aggtagagag tcccattata caacaacaac tcattataaa atttgacttc   2040
```

| | | | | |
|---|---|---|---|---|
| agtaacgact | gattgagaat | atgttaatgt | acactaaact | attgacattg | atgtaattgt | 2100 |
| atattttttgt | acaattacgt | tagtaatatg | gcgattgcac | ctgattggtg | aagaatctat | 2160 |
| attctcttcc | agttacccta | cactagaatt | tttcaatgaa | gttatcactt | gacataatca | 2220 |
| atttaaaaat | ttgatttcga | gacttcgacg | ataaattttg | ttgggccact | acaaaaggtt | 2280 |
| ttactgagtg | ctgactactt | attataatag | gcccaaacaa | aacatatatg | ttgggccact | 2340 |
| acattattag | ccaaaagatt | ttactgtaac | ttattatgag | cccatacgga | gcatttcaca | 2400 |
| gggaaaattt | aactaaacgc | gaaagtggcg | ttacgattat | tagaatgatt | tcgtaataaa | 2460 |
| cagaggatta | gttaaatcac | gtttcgatta | ctgtatatga | ttaaaaatta | aagttgaag | 2519 |

<210> SEQ ID NO 106
<211> LENGTH: 3497
<212> TYPE: DNA
<213> ORGANISM: Artificial sequence
<220> FEATURE:
<223> OTHER INFORMATION: A construct sequence consisting KST1 promoter,
      AtHXK1 cDNA and a terminator
<220> FEATURE:
<221> NAME/KEY: misc_feature
<222> LOCATION: (1)..(682)
<223> OTHER INFORMATION: KST1 promoter
<220> FEATURE:
<221> NAME/KEY: misc_feature
<222> LOCATION: (701)..(2670)
<223> OTHER INFORMATION: AtHXK1 cDNA
<220> FEATURE:
<221> NAME/KEY: misc_feature
<222> LOCATION: (2713)..(3497)
<223> OTHER INFORMATION: Terminator

<400> SEQUENCE: 106

| | | | | | |
|---|---|---|---|---|---|---|
| gtcgactaga | aaatgaaatg | aaaaacacct | atctgttttt | tcactcaaat | tccatccttg | 60 |
| caataaaatg | cttattctta | aaatttctat | cttggtggag | atcccaccac | cattaccatt | 120 |
| ttccccaaaa | atcttacaac | attatttcca | ttttctttct | cttaattctc | tcaacaaatt | 180 |
| ccccttgcac | ctgaattatt | atcaaagaaa | atcatgtttg | ccacttcaac | aactttataa | 240 |
| ctcatatctc | gcctcgtttg | ttgtttattg | tgtttcaata | ttgctatgtt | ttcttctatt | 300 |
| ttgtacttgc | atttgctcac | tcgagctttt | ggtaacaatc | tctctacttc | tactagatct | 360 |
| gcgtacagtc | taccttctcc | agaccccact | tgtgggaaga | tactatagaa | gtaggcaagt | 420 |
| agcaatgtca | cgttcttaaa | gctaaatgct | ttttcaaaag | aatcacaata | aagaaacact | 480 |
| tgacccgtgt | atcaccccaa | ctacttcttc | atctacatcc | tctatatata | aacacgctaa | 540 |
| aaataactag | ttagtatttt | taatatttac | acattgcctt | tccaagaaac | tcgaaaaaaa | 600 |
| aaaaaaaaaa | aaaacccac | atcaacaaaa | aagaagcagc | aatatataat | actgcagacg | 660 |
| cgtctcgagg | aattcggtac | cccggggtcg | aaatcgataa | gcttggatcc | cgccagtgtg | 720 |
| agtaatttag | gtttctctaa | tttctctcaa | ttcactccaa | aattttgatt | atttcttctt | 780 |
| tctggcttgt | caattttagt | catttgtaat | ccttgctttt | gcgatcggaa | tcgtaaaaat | 840 |
| ccgatctttc | ttttagattc | gttttgtttt | tgattccaaa | tcggaaaaat | gggtaaagta | 900 |
| gctgttggag | cgactgttgt | ttgcacggcg | gcggtttgtg | cggtggctgt | tttggttgtt | 960 |
| cgacgacgga | tgcagagctc | agggaagtgg | ggacgtgttg | tggctatcct | caaggccttt | 1020 |
| gaagaggatt | gtgcgactcc | gatctcgaaa | ctgagacaag | tggctgatgc | tatgaccgtt | 1080 |
| gagatgcatg | ctggtcttgc | atccgacggt | ggtagcaaac | tcaagatgct | tatcagctac | 1140 |
| gttgataatc | ttccttccgg | ggatgaaaag | ggtctctttt | atgcattgga | cctaggggggg | 1200 |

```
acaaacttcc gtgtcatgcg tgtgcttctt ggcgggaagc aagagcgtgt tgttaaacaa    1260
gaattcgaag aagtttcgat tcctcctcat ttgatgactg gtggttcaga tgagttgttc    1320
aattttatag ctgaagctct tgcgaagttt gtcgctacag aatgcgaaga ctttcatctt    1380
ccagaaggta gacagaggga attaggtttc actttctcgt ttcctgttaa gcagacttct    1440
ctgtcctctg gtagtctcat caaatggaca aaaggctttt ccatcgaaga agcagttgga    1500
caagatgttg ttggagcact taataaggct ctggaaagag ttggtcttga catgcgaatc    1560
gcagcacttg ttaatgatac cgttggaaca ctagccggtg gtagatacta taacccggat    1620
gttgttgctg ctgttatttt aggcactggg acaaacgcag cctatgttga gcgtgcaacc    1680
gcgatcccta aatggcatgg tctgcttcca aaatcaggag aaatggttat aaacatggaa    1740
tggggaaact tcaggtcatc acatcttcca ttaaccgagt ttgatcacac gctggatttc    1800
gagagtctga atccaggcga acagattctt gagaaaatca tttccggtat gtacttggga    1860
gagattttgc gaaagttct tctaaagatg gctgaagatg ctgctttctt tggcgataca    1920
gtcccatcta agctgagaat accattcatc attaggactc ctcacatgtc ggctatgcac    1980
aacgacactt ctccagactt gaagattgtt gggagcaaga ttaaggatat attggaggtc    2040
cctacaactt ctctgaaaat gagaaaagtt gtgatcagtc tctgcaacat catagcaacc    2100
cgaggagctc gtctctctgc tgctggaatc tatggtattc tgaagaaact gggaagagat    2160
actactaaag acgaggaggt gcagaaatcg gttatagcca tggatggtgg attgtttgag    2220
cattacactc agtttagtga gtgtatggag agctcactaa aagagttgct tggagatgaa    2280
gcttcaggaa gcgttgaagt cactcactcc aatgatggat caggcattgg agctgcgctt    2340
cttgctgctt ctcactctct ctaccttgaa gactcttaaa acctacccaa agagcgccat    2400
ttttcggtaa tttactgaaa gcttttcgct atcagaaaac gcctaagcca agttctaagg    2460
cgtcataaaa gaaagcattc catgttttta ctcttcccca agactttctt tgtagcaaat    2520
aagtttcctt gggagaaata tttgttttca tgttcttcaa aaataaaaga ctcagttctt    2580
cagattctgg gattttatta taaccagata tgttgtaaaa actacaaatt caaagctcac    2640
ttcactggaa ttctgagtat ataaagattt cattttttcct aaaaaaaaaa ctaaattact    2700
cacactagcg ggatccatgc tagagtcctg ctttaatgag atatgcgaga cgcctatgat    2760
cgcatgatat ttgctttcaa ttctgttgtg cacgttgtaa aaaacctgag catgtgtagc    2820
tcagatcctt accgccggtt tcggttcatt ctaatgaata tatcacccgt tactatcgta    2880
tttttatgaa taatattctc cgttcaattt actgattgta ccctactact tatatgtaca    2940
atattaaaat gaaaacaata tattgtgctg aataggttta tagcgacatc tatgatagag    3000
cgccacaata acaaacaatt gcgttttatt attacaaatc caattttaaa aaaagcggca    3060
gaaccggtca aacctaaaag actgattaca taaatcttat tcaaatttca aaaggcccca    3120
ggggctagta tctacgacac accgagcggc gaactaataa cgttcactga agggaactcc    3180
ggttccccgc cggcgcgcat gggtgagatt ccttgaagtt gagtattggc cgtccgctct    3240
accgaaagtt acgggcacca ttcaacccgg tccagcacgg cggccgggta accgacttgc    3300
tgccccgaga attatgcagc attttttttgg tgtatgtggg ccccaaatga agtgcaggtc    3360
aaaccttgac agtgacgaca aatcgttggg cgggtccagg gcgaattttg cgacaacatg    3420
tcgaggctca gcaggacctg caggcatgca agctagctta ctagtgatgc atattctata    3480
gtgtcaccta aatctgc                                                   3497
```

```
<210> SEQ ID NO 107
<211> LENGTH: 2280
<212> TYPE: DNA
<213> ORGANISM: Artificial sequence
<220> FEATURE:
<223> OTHER INFORMATION: A construct sequence consisting KST1 promoter,
      GFP cDNA and a terminator
<220> FEATURE:
<221> NAME/KEY: misc_feature
<222> LOCATION: (51)..(736)
<223> OTHER INFORMATION: KST1 promoter
<220> FEATURE:
<221> NAME/KEY: misc_feature
<222> LOCATION: (761)..(1487)
<223> OTHER INFORMATION: GFP coding sequence
<220> FEATURE:
<221> NAME/KEY: misc_feature
<222> LOCATION: (1488)..(2266)
<223> OTHER INFORMATION: Terminator

<400> SEQUENCE: 107
```

| | | | | | |
|---|---|---|---|---|---|
| attcctgcag | cccggggat | ccactagttc | tagagcggcc | gcatgcatat | gtcgactaga | 60 |
| aaatgaaatg | aaaaacacct | atctgttttt | tcactcaaat | tccatccttg | caataaaatg | 120 |
| cttattctta | aaatttctat | cttggtggag | atcccaccac | cattaccatt | ttccccaaaa | 180 |
| atcttacaac | attatttcca | ttttctttct | cttaattctc | tcaacaaatt | ccccttgcac | 240 |
| ctgaattatt | atcaaagaaa | atcatgtttg | ccacttcaac | aactttataa | ctcatatctc | 300 |
| gcctcgtttg | ttgttttattg | tgtttcaata | ttgctatgtt | ttcttctatt | ttgtacttgc | 360 |
| atttgctcac | tcgagctttt | ggtaacaatc | tctctacttc | tactagatct | gcgtacagtc | 420 |
| taccttctcc | agaccccact | tgtgggaaga | tactatagaa | gtaggcaagt | agcaatgtca | 480 |
| cgttcttaaa | gctaaatgct | ttttcaaaag | aatcacaata | agaaacact | tgacccgtgt | 540 |
| atcaccccaa | ctacttcttc | atctacatcc | tctatatata | aacacgctaa | aaataactag | 600 |
| ttagtatttt | taaatattac | acattgcctt | tccaagaaac | tcgaaaaaaa | aaaaaaaaa | 660 |
| aaaaacccac | atcaacaaaa | aagaagcagc | aatatataat | actgcagacg | cgtctcgagg | 720 |
| aattcggtac | cccgggttcg | aaatcgataa | gcttggatcc | atggtgagca | agggcgagga | 780 |
| gctgttcacc | ggggtggtgc | ccatcctggt | cgagctggac | ggcgacgtaa | acggccacaa | 840 |
| gttcagcgtg | tccggcgagg | gcgagggcga | tgccacctac | ggcaagctga | ccctgaagtt | 900 |
| catctgcacc | accggcaagc | tgcccgtgcc | ctggcccacc | ctcgtgacca | ccttcaccta | 960 |
| cggcgtgcag | tgcttcagcc | gctaccccga | ccacatgaag | cagcacgact | tcttcaagtc | 1020 |
| cgccatgccc | gaaggctacg | tccaggagcg | caccatcttc | ttcaaggacg | acggcaacta | 1080 |
| caagacccgc | gccgaggtga | agttcgaggg | cgacaccctg | gtgaaccgca | tcgagctgaa | 1140 |
| gggcatcgac | ttcaaggagg | acggcaacat | cctggggcac | aagctggagt | acaactacaa | 1200 |
| caggccacaa | cgtctatatc | atggccgaca | agcagaagaa | cggcatcaag | gtgaacttca | 1260 |
| agatccgcca | caacatcgag | gacggcagcg | tgcagctcgc | cgaccactac | cagcagaaca | 1320 |
| cccccatcgg | cgacggcccc | gtgctgctgc | ccgacaacca | ctacctgagc | acccagtccg | 1380 |
| ccctgagcaa | agaccccaac | gagaagcgcg | atcacatggt | cctgctggag | ttcgtgaccg | 1440 |
| ccgccgggat | cactcacggc | atggacgagc | tgtacaagta | atctagagtc | ctgctttaat | 1500 |
| gagatatgcg | agacgcctat | gatcgcatga | tatttgcttt | caattctgtt | gtgcacgttg | 1560 |
| taaaaaacct | gagcatgtgt | agctcagatc | cttaccgccg | gtttcggttc | attctaatga | 1620 |
| atatatcacc | cgttactatc | gtattttat | gaataatatt | ctccgttcaa | tttactgatt | 1680 |
| gtaccctact | acttatatgt | acaatattaa | aatgaaaaca | atatattgtg | ctgaataggt | 1740 |

```
ttatagcgac atctatgata gagcgccaca ataacaaaca attgcgtttt attattacaa      1800
atccaatttt aaaaaaagcg gcagaaccgg tcaaacctaa aagactgatt acataaatct      1860
tattcaaatt tcaaaaggcc ccaggggcta gtatctacga cacaccgagc ggcgaactaa      1920
taacgttcac tgaagggaac tccggttccc cgccggcgcg catgggtgag attccttgaa      1980
gttgagtatt ggccgtccgc tctaccgaaa gttacgggca ccattcaacc cggtccagca      2040
cggcggccgg gtaaccgact tgctgccccg agaattatgc agcattttt tggtgtatgt      2100 gggcccaaa tgaagtgcag gtcaaacctt gacagtgacg acaaatcgtt gggcgggtcc       2160
agggcgaatt ttgcgacaac atgtcgaggc tcagcaggac ctgcaggcat gcaagctagc      2220
ttactagtga tgcatattct atagtgtcac ctaaatctgc ggccgccacc gcggtggagc      2280

<210> SEQ ID NO 108
<211> LENGTH: 686
<212> TYPE: DNA
<213> ORGANISM: Artificial sequence
<220> FEATURE:
<223> OTHER INFORMATION: KST1 promoter

<400> SEQUENCE: 108
gtcgactaga aaatgaaatg aaaaacacct atctgttttt tcactcaaat tccatccttg        60
caataaaatg cttattctta aaatttctat cttggtggag atcccaccac cattaccatt       120
ttccccaaaa atcttacaac attatttcca ttttctttct cttaattctc tcaacaaatt       180
ccccttgcac ctgaattatt atcaaagaaa atcatgtttg ccacttcaac aactttataa       240
ctcatatctc gcctcgtttg ttgtttattg tgtttcaata ttgctatgtt ttcttctatt       300
ttgtacttgc atttgctcac tcgagctttt ggtaacaatc tctctacttc tactagatct       360
gcgtacagtc taccttctcc agacccact  tgtgggaaga tactatagaa gtaggcaagt        420
agcaatgtca cgttcttaaa gctaaatgct ttttcaaaag aatcacaata aagaaacact       480 tgaccegtgt atcacccaa  ctacttcttc atctacatcc tctatatata aacacgctaa       540
aaataactag ttagtatttt taaatattac acattgcctt tccaagaaac tcgaaaaaaa       600 aaaaaaaaa aaaacccac atcaacaaaa aagaagcagc aatatataat actgcagacg        660
cgtctcgagg aattcggtac cccggg                                             686
```